United States Patent
Beaulieu et al.

(10) Patent No.: US 8,476,257 B2
(45) Date of Patent: Jul. 2, 2013

(54) VIRAL POLYMERASE INHIBITORS

(75) Inventors: Pierre L. Beaulieu, Rosemere (CA);
Pasquale Forgione, Montreal (CA);
Alexandre Gagnon, Cambridge, MA
(US); Cedrickx Godbout, Laval (CA);
Marc-Andre Joly, Terrebonne (CA);
Montse Llinas-Brunet,
Dollard-des-Ormeaux (CA); Julie Naud,
Blainville (CA); Martin Poirier,
Blainville (CA); Jean Rancourt, Laval
(CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/808,220

(22) PCT Filed: Dec. 3, 2008

(86) PCT No.: PCT/CA2008/002107
§ 371 (c)(1),
(2), (4) Date: Sep. 2, 2010

(87) PCT Pub. No.: WO2009/076747
PCT Pub. Date: Jun. 25, 2009

(65) Prior Publication Data
US 2011/0021486 A1    Jan. 27, 2011

Related U.S. Application Data

(60) Provisional application No. 61/015,123, filed on Dec. 19, 2007.

(51) Int. Cl.
| | | |
|---|---|---|
| *A61K 31/397* | (2006.01) | |
| *A61K 31/444* | (2006.01) | |
| *A61K 31/44* | (2006.01) | |
| *A61K 31/5377* | (2006.01) | |
| *A61K 31/4439* | (2006.01) | |
| *A61K 31/4545* | (2006.01) | |
| *A61K 31/497* | (2006.01) | |
| *A61K 31/4353* | (2006.01) | |
| *A61K 31/5355* | (2006.01) | |
| *A61K 31/506* | (2006.01) | |
| *A61K 31/551* | (2006.01) | |
| *C07D 401/12* | (2006.01) | |
| *C07D 401/04* | (2006.01) | |
| *C07D 213/643* | (2006.01) | |
| *C07D 413/04* | (2006.01) | |
| *C07D 417/04* | (2006.01) | |
| *C07D 471/04* | (2006.01) | |
| *A61P 31/14* | (2006.01) | |

(52) U.S. Cl.
USPC ............ 514/210.2; 514/218; 514/228.8; 514/235.5; 514/255.05; 514/300; 514/318; 514/335; 514/340; 514/342; 514/351; 540/575; 544/131; 544/331; 544/405; 544/63; 546/113; 546/194; 546/262; 546/268.1; 546/268.4; 546/270.4; 546/300

(58) Field of Classification Search
None
See application file for complete search history.

(56) References Cited

U.S. PATENT DOCUMENTS

| | | | |
|---|---|---|---|
| 4,062,682 A | 12/1977 | Laridon et al. | |
| 4,740,519 A | 4/1988 | Shroot et al. | |
| 5,633,388 A | 5/1997 | Diana et al. | |
| 6,434,489 B1 | 8/2002 | Lesburg et al. | |
| 6,448,281 B1 | 9/2002 | Beaulieu et al. | |
| 6,479,508 B1 | 11/2002 | Beaulieu et al. | |
| 6,794,404 B2 | 9/2004 | Beaulieu et al. | |
| 6,878,727 B2 | 4/2005 | Borchardt et al. | |
| 6,927,225 B2 | 8/2005 | Ricks et al. | |
| 7,074,784 B2 | 7/2006 | Goldmann et al. | |
| 7,112,600 B1 | 9/2006 | Hashimoto et al. | |
| 7,157,486 B2 | 1/2007 | Beaulieu et al. | |
| 7,223,785 B2 | 5/2007 | Beaulieu et al. | |
| 7,238,725 B2 | 7/2007 | Balasubramanian et al. | |
| 7,386,398 B2 | 6/2008 | Coulombe et al. | |
| 7,816,348 B2 | 10/2010 | Coulombe et al. | |
| 7,897,622 B2 | 3/2011 | Beaulieu et al. | |
| 8,003,819 B2 | 8/2011 | Olhava et al. | |

(Continued)

FOREIGN PATENT DOCUMENTS

| | | |
|---|---|---|
| CA | 2412718 A1 | 1/2002 |
| CA | 2450033 A1 | 2/2003 |

(Continued)

OTHER PUBLICATIONS

HCV, 2011, http://www.idph.state.il.us/public/hb/hbhepc.htm.*

(Continued)

*Primary Examiner* — Sun Jae Loewe
(74) *Attorney, Agent, or Firm* — Michael P. Morris; David A. Dow

(57) ABSTRACT

Compounds of formula I:

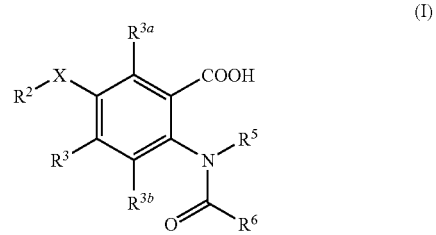

(I)

wherein X, $R^2$, $R^3$, $R^{3a}$, $R^{3b}$, $R^5$ and $R^6$ are defined herein, are useful as inhibitors of the hepatitis C virus NS5B polymerase.

35 Claims, No Drawings

U.S. PATENT DOCUMENTS

| | | |
|---|---|---|
| 2003/0236251 A1 | 12/2003 | Beaulieu et al. |
| 2004/0038993 A1 | 2/2004 | Shipps et al. |
| 2004/0082635 A1 | 4/2004 | Hashimoto et al. |
| 2004/0106627 A1 | 6/2004 | Gardelli et al. |
| 2004/0110126 A1 | 6/2004 | Kukolj et al. |
| 2004/0224955 A1 | 11/2004 | Beaulieu et al. |
| 2005/0003348 A1 | 1/2005 | Coulombe et al. |
| 2006/0004197 A1 | 1/2006 | Thrash et al. |
| 2006/0052418 A1 | 3/2006 | Beaulieu et al. |
| 2006/0160798 A1 | 7/2006 | Beaulieu et al. |
| 2006/0189672 A1 | 8/2006 | Poupart et al. |
| 2006/0264389 A1 | 11/2006 | Bhat et al. |
| 2006/0293306 A1 | 12/2006 | Beaulieu et al. |
| 2007/0219176 A1 | 9/2007 | Coulombe et al. |
| 2008/0045516 A1 | 2/2008 | Beaulieu et al. |
| 2008/0114068 A1 | 5/2008 | Simoneau et al. |
| 2008/0146539 A1 | 6/2008 | Priepke et al. |
| 2010/0190779 A1 | 7/2010 | Beaulieu et al. |
| 2010/0273651 A1 | 10/2010 | Dietz et al. |
| 2010/0286131 A1 | 11/2010 | Beaulieu et al. |
| 2010/0311581 A1 | 12/2010 | Dietz et al. |
| 2010/0317515 A1 | 12/2010 | Dietz et al. |
| 2011/0021486 A1 | 1/2011 | Beaulieu et al. |

FOREIGN PATENT DOCUMENTS

| | | |
|---|---|---|
| CA | 2511301 A1 | 8/2004 |
| EP | 1256628 A2 | 11/2002 |
| EP | 1688420 A1 | 8/2006 |
| WO | 9118591 A1 | 12/1991 |
| WO | 9827108 A2 | 6/1998 |
| WO | 9907733 A2 | 2/1999 |
| WO | 9907734 A2 | 2/1999 |
| WO | 9949830 A2 | 10/1999 |
| WO | 0009543 A2 | 2/2000 |
| WO | 0009558 A1 | 2/2000 |
| WO | 0059929 A1 | 10/2000 |
| WO | 0114339 A2 | 3/2001 |
| WO | 0147883 | 7/2001 |
| WO | 0177113 A2 | 10/2001 |
| WO | 0181325 A2 | 11/2001 |
| WO | 0204425 | 1/2002 |
| WO | 0208187 A1 | 1/2002 |
| WO | 0208198 A2 | 1/2002 |
| WO | 0208244 A2 | 1/2002 |
| WO | 0208256 A2 | 1/2002 |
| WO | 0248172 A2 | 6/2002 |
| WO | 02060926 A2 | 8/2002 |
| WO | 03000254 | 1/2003 |
| WO | 03004458 A1 | 1/2003 |
| WO | 03007945 A1 | 1/2003 |
| WO | 03010140 A2 | 2/2003 |
| WO | 03010141 A2 | 2/2003 |
| WO | 03026587 | 4/2003 |
| WO | 03053349 A2 | 7/2003 |
| WO | 03062228 A1 | 7/2003 |
| WO | 03062265 A2 | 7/2003 |
| WO | 03064416 A1 | 8/2003 |
| WO | 03064455 A2 | 8/2003 |
| WO | 03064456 A1 | 8/2003 |
| WO | 03099274 A1 | 12/2003 |
| WO | 03099316 A1 | 12/2003 |
| WO | 03101993 | 12/2003 |
| WO | 2004030670 A1 | 4/2004 |
| WO | 2004032827 A2 | 4/2004 |
| WO | 2004037855 A1 | 5/2004 |
| WO | 2004039833 A1 | 5/2004 |
| WO | 2004043339 A2 | 5/2004 |
| WO | 2004064925 A1 | 8/2004 |
| WO | 2004065367 A1 | 8/2004 |
| WO | 2004072243 A2 | 8/2004 |
| WO | 2004087714 | 10/2004 |
| WO | 2004093798 A2 | 11/2004 |
| WO | 2004094452 A2 | 11/2004 |
| WO | 2004099241 A1 | 11/2004 |
| WO | 2004101602 A2 | 11/2004 |
| WO | 2004101605 A1 | 11/2004 |
| WO | 2004103996 A1 | 12/2004 |
| WO | 2004113365 A2 | 12/2004 |
| WO | 2005010029 A1 | 2/2005 |
| WO | 2005012288 A1 | 2/2005 |
| WO | 2005014543 | 2/2005 |
| WO | 2005021584 A2 | 3/2005 |
| WO | 2005028501 A1 | 3/2005 |
| WO | 2005030796 A1 | 4/2005 |
| WO | 2005037214 A2 | 4/2005 |
| WO | 2005046712 A1 | 5/2005 |
| WO | 2005049622 A1 | 6/2005 |
| WO | 2005051410 A1 | 6/2005 |
| WO | 2005051980 A1 | 6/2005 |
| WO | 2005054430 A2 | 6/2005 |
| WO | 2005058821 A1 | 6/2005 |
| WO | 2005070955 A1 | 8/2005 |
| WO | 2005080388 A1 | 9/2005 |
| WO | 2005085197 A1 | 9/2005 |
| WO | 2005085242 A1 | 9/2005 |
| WO | 2005085275 A1 | 9/2005 |
| WO | 2005087721 A2 | 9/2005 |
| WO | 2005087725 A2 | 9/2005 |
| WO | 2005087730 A1 | 9/2005 |
| WO | 2005087731 A1 | 9/2005 |
| WO | 2005107745 A1 | 11/2005 |
| WO | 2005113581 A1 | 12/2005 |
| WO | 2005121132 A1 | 12/2005 |
| WO | 2006000085 A1 | 1/2006 |
| WO | 2006007693 A1 | 1/2006 |
| WO | 2006007700 A1 | 1/2006 |
| WO | 2006007708 A1 | 1/2006 |
| WO | 2006014405 A2 | 2/2006 |
| WO | 2006049304 A1 | 5/2006 |
| WO | 2007014922 A1 | 2/2007 |
| WO | 2007087717 A1 | 8/2007 |
| WO | 2008019477 A1 | 2/2008 |
| WO | 2009010783 A1 | 1/2009 |
| WO | 2009018656 A1 | 2/2009 |
| WO | 2009018657 A1 | 2/2009 |
| WO | 2009076747 A1 | 6/2009 |
| WO | 2009077443 A2 | 6/2009 |
| WO | 2009077471 A2 | 6/2009 |
| WO | 2009077497 A2 | 6/2009 |
| WO | 2009077500 A2 | 6/2009 |
| WO | 2009077608 A1 | 6/2009 |
| WO | 2009080637 A1 | 7/2009 |
| WO | 2009085230 A1 | 7/2009 |
| WO | 2009085584 A1 | 7/2009 |
| WO | 2009085816 A1 | 7/2009 |
| WO | 2009085983 A1 | 7/2009 |
| WO | 2010037210 A1 | 4/2010 |

OTHER PUBLICATIONS

HCV Drugs, http://hcvdrugs.com (2012).*

Beaulieu et al., caplus an 2008:222767, 2008.*

International Search Report, Form PCT/ISA/210, for corresponding PCT/CA2008/002107; date of mailing:Mar. 4, 2009.

Abdel-Magid, A.F., et al., "Reductive Amination of Aldehydes and Ketones with Sodium Triacetoxyborohydride. Studies on Direct and Indirect Reductive Amination Procedures", J. Org. Chem., 1996, vol. 61, p. 3849.

Abstract in English for WO1999049830 which is in the German language. Publication date: 1999.

Abstract in English for WO2009077497 which is in the German language. Publication Date: 2009.

Ago, H.,et al. "Crystal Structure of the RNA-dependent RNA Polymerase of Hepatitis C Virus", Structure, vol. 7, No. 11, pp. 1417-1426, USA, Nov. 1999.

Beaulieu et al., Inhibitors of the HCV NS5B polymerase: New hope for the treatment of hepatitis C infections, "Current Opinion in Investigational Drugs" vol. 5 (8) pp. 838-850, 2004 (abstract and discussion).

Beaulieu et al., Non-nucleoside inhibitors of the hepatitis C virus NS5B polymerase: discovery of benzimidazole 5-carboxylic amide derivatives with low-nanomolar potency, "Biorganic & Medicinal Chemistry Letters" vol. 14 (4) pp. 967-971 (2004) (abstract and discussion).

Beaulieu, P. L., "Finger loop inhibitors of the HCV NS5B polymerase: Discovery and prospects for new HCV therapy", Curr. Opin. Drug Discovery & Development, 2006, vol. 9, No. 5, p. 618.

Beaulieu, P. L., "Non-nucleoside inhibitors of the HCV NS5B polymerase: Progress in the discovery and development of novel agents for the treatment of HCV infections", Curr. Opin. Investigational Drugs, 2007, vol. 8, No. 8, p. 614.

Beaulieu, P. L., "The discover of finger loop inhibitors of the hepatitis C virus NS5B polymerase: Status and prospects for novel HCV therapeutics", IDRUGS, 2006, vol. 9, No. 1, p. 39.

Berge, S. M., et al., "Pharmaceutical Salts", Journal of Pharmaceutical Sciences, 1977, vol. 66, No. 1, p. 1.

Bowie, et al., "Deciphering the message in protein sequences: tolerance to amino acide substitutions". Science, vol. 247, No. 4948, Mar. 1990, pp. 1306-1310.

Bressanelli, S., et al. "Crystal Structure of the RNA-dependent RNA Polymerase of Hepatitis C Virus", PNAS, vol. 96, No. 23, pp. 13034-13039, USA, Nov. 1999.

Bressanelli, S., et al. "Structural Analysis of the Hepatitis C Virus RNA Polymerase in Complex with Ribonucleotides", J. Virology. Vol. 76, No. 7, pp. 3482-3492, USA, Apr. 2002.

Buck, E., et al., "Preparation of 1-Methoxy-2-(4-Methoxyphenoxy) Benzene", Org. Syntheses, 2005, vol. 82, p. 69.

Caplus: Hemalatha, R. et al., "QSAR Analysis of 5-substituted-2-Benzoylaminobenzoic acids as PPAR Modulator", E-Journal of Chemistry, 2004, vol. 1, No. 5, p. 243-2508.

Di Marco, S., et al., "Interdomain Communication in Hepatitis C Virus Polymerase Abolished by Small Molecule Inhibitors Bound to a Novel Allosteric Site", J. Biological Chemistry, 2005, vol. 280, No. 33, p. 29765.

Faucher et al., Synthesis of BILN 2061, an HCV NS3 Protease Inhibitor with Proven Antiviral Effect in Humans, "Organic Letters" vol. 6 (17) pp. 2901-2904, 2004 (abstract and discussion).

Giuliano, C. et al., "Preclinical pharmacokinetics and metabolism of a potent non-nucleoside inhibitor of the hepatitis C virus NS5B polymerase" Xenobiotica, 2005, vol. 35, No. 10, p. 1035.

Harper, S. et al., "Development and Preliminary Optimization of Indole-N-Acetamide Inhibitors of Hepatitis C Virus NS5B Polymerase", J. Medicinal Chemistry, 2005, vol. 48, p. 1314.

Harper, S., et al., "Potent Inhibitors of Subgenomic Hepatitis C Virus RNA Replication through Optimization of Indole-N-Acetamide Allosteric inhibitors of the Viral NS5B polymerase", J. Medicinal Chemistry, 2005, vol. 48, p. 454.

Hemalatha, et al., "QSAR Analysis of 5-substituted-2-benzoylaminobenzoic acids as PPAR Modulator," E-Journal of Chemistry, vol. 1, No. 5, 2004, pp. 243-250.

Hennessy, E.J., et al., "A General and Mild Copper-Catalyzed Arylation of Diethyl Malonate", Organic Letters, 2002, vol. 4, No. 2, p. 269.

International Search Report for PCT/CA2009/001346 mailed Jan. 26, 2010.

International Search Report PCT/CA2008/002107 mailed Mar. 4, 2009.

Khoshtariya, T.E. et al., "Condensed Tetracyclic Systems with an ISATIN Fragment in the Molecule". Chemistry of Heterocyclic Compounds, vol. 43, No. 9, 2007, p. 1111-1117.

Kolykhalov, A.A., et al., "Hepatitis C Virus-Encoded Enzymatic Activities and Conserved RNA Elements in the 3' Nontranslated Region are Essential for Virus Replication in Vivo", J. Virology, 2000, vol. 74, No. 4, p. 2046.

Labonte, P. et al. "Modulation of Hepatitis C Virus RNA-dependent RNA Polymerase Activity by Structure-based Site-directed Mutagenesis", J. Bio. Chem. vol. 277, No. 41, Issue of Oct. 11, pp. 38838-38846, USA, 2002.

Lesburg, C. A., et al. "Crystal Structure of the RNA-dependent RNA Polymerase from Hepatitis C Virus Reveals a Fully Encircled Active Site", Nature Structural Biology, vol. 6, No. 10, pp. 937-943, USA, Oct. 1999.

Llinas-Brunet et al., Highly Potent and Selective Peptide-Based Inhibitors of the Hepatitis C virus Serine Protease: Towards Smaller Inhibitors, "Bioorganic & Medicinal Chemistry Letters" vol. 10 (20) pp. 2267-2270, 2000 (abstract and discussion).

Lohmann, V. et al., "Replication of Subgenomic Hepatitis C Virus RNAa i a Hepatoma Cell Line". Science, vol. 285, 1999, p. 110-113.

McKercher, G., et al., "Specific inhibitors of HCV polymerase identified using an NS5B with lower affinity for template/primer substrate", Nucleic Acids Res., 2004, vol. 32, No. 2, p. 422.

Oestberg, T. et al., "A New Class of Peroxisome Proliferator-activated Receptor Agonists with a novel Binding Epitope Shows Antidiabetic Effects", J. Biological Chemistry, 2004, vol. 279, No. 39, p. 41124.

Still, W.C.,et al., "Rapid Chromatographic Technique for Preparative Separations with Moderate Resolution", J. Org. Chem., 1978, vol. 43, No. 14, p. 2923.

Takagi, K., "Synthesis of Aromatic Thiols from Aryl Iodides and Thiourea by Means of Nickel Catalyst", Chemistry Letters, 1985, p. 1307.

Tanaka, K. et al., "Synthesis and Reaction of 5-Amino-3-trifluoromethylisoxazole and -pyrazole-4-carboxylic Acids", J. Heterocyclic Chem., 1986, vol. 23, p. 1535.

Thor, M., et al., "Synthesis and Pharmacological Evaluation of a New Class of Peroxisome Proliferator-Activated Receptor Modulators", Bioorganic and Medicinal Chemistry Letters, 2002, vol. 12, p. 3565.

Tomei, L., et al. "Mechanism of Action and Antiviral Activity of Benzimidazole-Based Allosteric Inhibitors of the Hepatitis C Virus RNA-Dependent RNA Polymerase" Journal of Virology, vol. 77, No. 24, pp. 13225-13231, USA, Dec. 2003.

Zurawski, et al., "Definition and spatial locatin of mouse interleukin-2-residues that interact with its heterotrimeric receptor." The EMBO Journal, vol. 12, No. 13, Dec. 1993, pp. 5113-5119.

Chilean International Search Report for Chilean Patent Appln 03819-2008 issued on Jul. 6, 2011.

Coulombe et al.; CAS 147:234873; WO2007087717; PCT International Appl.; 2007.

Response filed Mar. 23, 2012 for U.S. Appl. No. 12/671,765. Inventor: Pierre L. Beaulieu.

Office Action for U.S. Appl. No. 12/671,765 mailed Dec. 28, 2011. Inventor: Pierre L. Beaulieu.

Chan, Laval Discovery of thiophene-2-carboxylic acids as potent inhibitors of HCV NS5B polymerase and HCV subgenomic RNA replication. Part 2: Tertiary amides. Bioorganic & Medicinal Chemistry Letters, (2004) 14, 797-800.

* cited by examiner

VIRAL POLYMERASE INHIBITORS

RELATED APPLICATIONS

This application claims benefit of U.S. Ser. No. 61/015,123, filed Dec. 19, 2007, which is herein incorporated by reference.

FIELD OF THE INVENTION

The present invention relates to compounds, compositions and methods for the treatment of hepatitis C virus (HCV) infection. In particular, the present invention provides novel inhibitors of the hepatitis C virus NS5B polymerase, pharmaceutical compositions containing such compounds and methods for using these compounds in the treatment of HCV infection.

BACKGROUND OF THE INVENTION

It is estimated that at least 170 million persons worldwide are infected with the hepatitis C virus (HCV). Acute HCV infection progresses to chronic infection in a high number of cases, and, in some infected individuals, chronic infection leads to serious liver diseases such as cirrhosis and hepatocellular carcinoma.

Currently, standard treatment of chronic hepatitis C infection involves administration of pegylated interferon-alpha in combination with ribavirin. However, this therapy is not effective in reducing HCV RNA to undetectable levels in many infected patients and is associated with often intolerable side effects such as fever and other influenza-like symptoms, depression, thrombocytopenia and hemolytic anemia. Furthermore, some HCV-infected patients have co-existing conditions which contraindicate this treatment.

Therefore, a need exists for alternative treatments for hepatitis C viral infection. One possible strategy to address this need is the development of effective antiviral agents which inactivate viral or host cell factors which are essential for viral replication.

HCV is an enveloped positive strand RNA virus in the genus *Hepacivirus* in the Flaviviridae family. The single strand HCV RNA genome is approximately 9500 nucleotides in length and has a single open reading frame (ORF), flanked by 5' and 3' non-translated regions. The HCV 5' non-translated region is 341 nucleotides in length and functions as an internal ribosome entry site for cap-independent translation initiation. The open reading frame encodes a single large polyprotein of about 3000 amino acids which is cleaved at multiple sites by cellular and viral proteases to produce the mature structural and non-structural (NS2, NS3, NS4A, NS4B, NS5A, and NS5B) proteins. The viral NS2/3 protease cleaves at the NS2-NS3 junction; while the viral NS3 protease mediates the cleavages downstream of NS3, at the NS3-NS4A, NS4A-NS4B, NS4B-NS5A and NS5A-NS5B cleavage sites. The NS3 protein also exhibits nucleoside triphosphatase and RNA helicase activities. The NS4A protein acts as a cofactor for the NS3 protease and may also assist in the membrane localization of NS3 and other viral replicase components. Although NS4B and the NS5A phosphoprotein are also likely components of the replicase, their specific roles are unknown. The NS5B protein is the elongation subunit of the HCV replicase possessing RNA-dependent RNA polymerase (RdRp) activity.

The development of new and specific anti-HCV treatments is a high priority, and virus-specific functions essential for replication are the most attractive targets for drug development. The absence of RNA dependent RNA polymerases in non-human mammals, and the fact that this enzyme appears to be essential to viral replication, would suggest that the NS5B polymerase is an ideal target for anti-HCV therapeutics. It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046-2051).

WO 2007/087717 discloses compounds of the general formula (A):

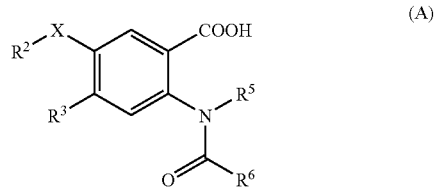

wherein $R^2$ is an optionally substituted aryl and $R^6$ is an optionally substituted $(C_{5-7})$cycloalkyl or aryl which are useful for the treatment of Hepatitis C virus infections.

SUMMARY OF THE INVENTION

The present invention provides a novel series of compounds having inhibitory activity against HCV polymerase. In particular compounds according to this invention inhibit RNA synthesis by the RNA dependent RNA polymerase of HCV, especially the enzyme NS5B encoded by HCV. A further advantage of compounds provided by this invention is their low to very low or even non-significant activity against other polymerases. Further objects of this invention arise for the one skilled in the art from the following description and the examples.

One aspect of the invention provides compounds of formula (I):

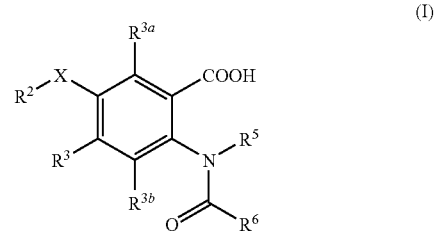

wherein:
X is selected from O and S;
$R^2$ is Het or aryl, optionally substituted with 1 to 5 $R^{20}$ substituents, wherein $R^{20}$ in each case is independently selected from:
  a) halo, cyano or nitro;
  b) $R^7$, —C(=O)—$R^7$, —C(=O)—O—$R^7$, —O—$R^7$, —S—$R^7$, —SO—$R^7$, —SO$_2$—$R^7$, —(C$_{1-6}$)alkylene-$R^7$, —(C$_{1-6}$)alkylene-C(=O)—$R^7$, —(C$_{1-6}$)alkylene-C(=O)—O—$R^7$, —(C$_{1-6}$)alkylene-O—$R^7$, —(C$_{1-6}$)alkylene-S—$R^7$, —(C$_{1-6}$)alkylene-SO—$R^7$ or —(C$_{1-6}$)alkylene-SO$_2$—$R^7$;
    wherein $R^7$ is in each instance independently selected from H, (C$_{1-6}$)alkyl, (C$_{2-6}$)alkenyl, (C$_{2-6}$)alkynyl, (C$_{1-6}$)haloalkyl, (C$_{3-7}$)cycloalkyl, (C$_{3-7}$)cycloalkyl-(C$_{1-6}$)alkyl, aryl and Het;

wherein the $(C_{1-6})$alkyl, $(C_{2-6})$alkenyl, $(C_{2-6})$alkynyl, $(C_{1-6})$haloalkyl, $(C_{3-7})$cycloalkyl, $(C_{3-7})$cycloalkyl-$(C_{1-6})$alkyl, and $(C_{1-6})$alkylene are optionally substituted with 1 or 2 substituents each independently selected from —OH, —$(C_{1-6})$alkyl (optionally substituted with —O—$(C_{1-6})$alkyl), halo, —$(C_{1-6})$haloalkyl, $(C_{3-7})$cycloalkyl, —O—$(C_{1-6})$alkyl, cyano, COOH, —NH$_2$, —NH$(C_{1-4})$alkyl, —NH$(C_{3-7})$cycloalkyl, —N($(C_{1-4})$alkyl)$(C_{3-7})$cycloalkyl, —N($(C_{1-4})$alkyl)$_2$, aryl, —$(C_{1-6})$alkyl-aryl, Het, —$(C_{1-6})$alkyl-Het; and wherein each of the aryl and Het is optionally substituted with 1 to 3 substituents each independently selected from:

i) halo, cyano, oxo, thioxo, imino, —OH, —O—$(C_{1-6})$alkyl, —O—$(C_{1-6})$haloalkyl, $(C_{3-7})$cycloalkyl, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N($(C_{1-4})$alkyl)$_2$, —C(=O)—NH$(C_{3-7})$cycloalkyl, —C(=O)—N($(C_{1-4})$alkyl)$(C_{3-7})$cycloalkyl, —NH$_2$, —NH$(C_{1-4})$alkyl, —N($(C_{1-4})$alkyl)$_2$, —NH$(C_{3-7})$cycloalkyl, —N($(C_{1-4})$alkyl)$(C_{3-7})$cycloalkyl or —NH—C(=O)$(C_{1-4})$alkyl;

ii) $(C_{1-6})$alkyl optionally substituted with —OH, —O—$(C_{1-6})$haloalkyl, or —O—$(C_{1-6})$alkyl; and iii) aryl or Het, wherein each of the aryl and Het is optionally substituted with halo or $(C_{1-6})$alkyl; and c) —N(R$^8$)R$^9$, —C(=O)—N(R$^8$)R$^9$, —O—C(=O)—N(R$^8$)R$^9$, —SO$_2$—N(R$^8$)R$^9$, —$(C_{1-6})$alkylene-N(R$^8$)R$^9$, —$(C_{1-6})$alkylene-C(=O)—N(R$^8$)R$^9$, —$(C_{1-6})$alkylene-O—C(=O)—N(R$^8$)R$^9$, or —$(C_{1-6})$alkylene-SO$_2$—N(R$^8$)R$^9$;

wherein the $(C_{1-6})$alkylene is optionally substituted with 1 or 2 substituents each independently selected from —OH, —$(C_{1-6})$alkyl, halo, —$(C_{1-6})$haloalkyl, $(C_{3-7})$cycloalkyl, —O—$(C_{1-6})$alkyl, cyano, COOH, —NH$_2$, —NH$(C_{1-4})$alkyl, —NH$(C_{3-7})$cycloalkyl, —N($(C_{1-4})$alkyl)$(C_{3-7})$cycloalkyl and —N($(C_{1-4})$alkyl)$_2$;

R$^8$ is in each instance independently selected from H, $(C_{1-6})$alkyl and $(C_{3-7})$cycloalkyl; and R$^9$ is in each instance independently selected from R$^7$, —O—$(C_{1-6})$alkyl, —$(C_{1-6})$alkylene-R$^7$, —SO$_2$—R$^7$, —C(=O)—R$^7$, —C(=O)OR$^7$ and —C(=O)N(R$^8$)R$^7$; wherein R$^7$ and R$^8$ are as defined above;

or R$^8$ and R$^9$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;

wherein the heterocycle is optionally substituted with 1 to 3 substituents each independently selected from $(C_{1-6})$alkyl, $(C_{1-6})$haloalkyl, halo, oxo, —OH, SH, —O$(C_{1-6})$alkyl, —S$(C_{1-6})$alkyl, $(C_{3-7})$cycloalkyl, —NH$_2$, —NH$(C_{1-6})$alkyl, —N($(C_{1-6})$alkyl)$_2$, —NH$(C_{3-7})$cycloalkyl, —N($(C_{1-4})$alkyl)$(C_{3-7})$cycloalkyl, —C(=O)$(C_{1-6})$alkyl and —NHC(=O)—$(C_{1-6})$alkyl;

R$^3$, R$^{3a}$ and R$^{3b}$ are selected from H, halo, CN, $(C_{1-4})$alkyl, —OH, —O—$(C_{1-4})$alkyl, —S—$(C_{1-4})$alkyl, —NH$_2$, —NH$(C_{1-4})$alkyl, —NH$(C_{3-7})$cycloalkyl, —N($(C_{1-4})$alkyl)$(C_{3-7})$cycloalkyl) and —N($(C_{1-4})$alkyl)$_2$;

R$^5$ is R$^{51}$ mono-, di-, or tri-substituted with O—R$^{52}$, wherein R$^{51}$ is $(C_{1-6})$alkyl, $(C_{3-7})$cycloalkyl, $(C_{1-6})$alkyl-$(C_{3-7})$cycloalkyl, aryl, $(C_{1-6})$alkyl-aryl, Het or $(C_{1-6})$alkyl-Het, each R$^{51}$ being optionally substituted with $(C_{1-6})$alkyl, $(C_{3-7})$cycloalkyl or $(C_{1-6})$alkyl-$(C_{3-7})$cycloalkyl; and R$^{52}$ is $(C_{1-6})$alkyl, $(C_{3-7})$cycloalkyl, $(C_{1-6})$alkyl-$(C_{3-7})$cycloalkyl, aryl, $(C_{1-6})$alkyl-aryl, Het or $(C_{1-6})$alkyl-Het, said aryl and Het being optionally substituted with $(C_{1-6})$alkyl or O—$(C_{1-6})$alkyl;

R$^6$ is $(C_{3-7})$cycloalkyl, $(C_{1-6})$alkyl-$(C_{3-7})$cycloalkyl, aryl, $(C_{1-6})$alkyl-aryl, Het or $(C_{1-6})$alkyl-Het; being optionally substituted with 1 to 5 substituents each independently selected from halo, $(C_{1-6})$alkyl, $(C_{1-6})$haloalkyl, $(C_{3-7})$cycloalkyl, —OH, —SH, —O—$(C_{1-4})$alkyl, —S—$(C_{1-4})$alkyl and —N(R$^8$)R$^9$; wherein R$^8$ and R$^9$ are as defined above; and Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;

or a salt or ester thereof.

Another aspect of this invention provides a compound of formula (I), or a pharmaceutically acceptable salt or ester thereof, as a medicament.

Still another aspect of this invention provides a pharmaceutical composition comprising a therapeutically effective amount of a compound of formula (I) or a pharmaceutically acceptable salt or ester thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described hereinabove for the treatment of a hepatitis C viral infection in a mammal having or at risk of having the infection.

A further aspect of the invention involves a method of treating a hepatitis C viral infection in a mammal having or at risk of having the infection, the method comprising administering to the mammal a therapeutically effective amount of a compound of formula (I), a pharmaceutically acceptable salt or ester thereof, or a composition thereof as described hereinabove.

Another aspect of the invention involves a method of treating a hepatitis C viral infection in a mammal having or at risk of having the infection, the method comprising administering to the mammal a therapeutically effective amount of a combination of a compound of formula (I) or a pharmaceutically acceptable salt or ester thereof, and at least one other antiviral agent; or a composition thereof.

Also within the scope of this invention is the use of a compound of formula (I) as described herein, or a pharmaceutically acceptable salt or ester thereof, for the treatment of a hepatitis C viral infection in a mammal having or at risk of having the infection.

Another aspect of this invention provides the use of a compound of formula (I) as described herein, or a pharmaceutically acceptable salt or ester thereof, for the manufacture of a medicament for the treatment of a hepatitis C viral infection in a mammal having or at risk of having the infection.

An additional aspect of this invention refers to an article of manufacture comprising a composition effective to treat a hepatitis C viral infection; and packaging material comprising a label which indicates that the composition can be used to treat infection by the hepatitis C virus; wherein the composition comprises a compound of formula (I) according to this invention or a pharmaceutically acceptable salt or ester thereof.

Still another aspect of this invention relates to a method of inhibiting the replication of hepatitis C virus comprising exposing the virus to an effective amount of the compound of formula (I), or a salt or ester thereof, under conditions where replication of hepatitis C virus is inhibited.

Further included in the scope of the invention is the use of a compound of formula (I), or a salt or ester thereof, to inhibit the replication of hepatitis C virus.

DETAILED DESCRIPTION OF THE INVENTION

Definitions

As used herein, the following definitions apply unless otherwise noted:

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

The term "$(C_{1-n})$alkyl" as used herein, wherein n is an integer, either alone or in combination with another radical, is intended to mean acyclic, straight or branched chain alkyl radicals containing from 1 to n carbon atoms, and includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tert-butyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "$(C_{1-n})$alkylene" as used herein, wherein n is an integer, either alone or in combination with another radical, is intended to mean acyclic, straight or branched chain divalent alkyl radicals containing from 1 to n carbon atoms and includes, but is not limited to, —CH$_2$—, —CH$_2$CH$_2$—,

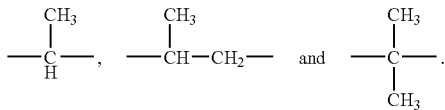

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$ alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{3-m})$cycloalkyl" as used herein, wherein m is an integer, either alone or in combination with another radical, is intended to mean a cycloalkyl substituent containing from 3 to m carbon atoms and includes, but is not limited to, cyclopropyl, cyclobutyl, cyclopentyl, cyclohexyl and cycloheptyl.

The term "$(C_{3-m})$cycloalkyl-$(C_{1-n})$alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above, and includes, but is not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl- group is substituted, it is understood that substituents may be attached to either the cycloalkyl or the alkyl portion thereof or both, unless specified otherwise.

The term "aryl" as used herein, either alone or in combination with another radical, is intended to mean a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, 1-naphthyl, 2-naphthyl, tetrahydronaphthyl and dihydronaphthyl.

The term "aryl-$(C_{1-n})$alkyl-" as used herein, wherein n is an integer, either alone or in combination with another radical, is intended to mean an alkyl radical having 1 to n carbon atoms as defined above which is itself substituted with an aryl radical as defined above. Examples of aryl-$(C_{1-n})$alkyl-include, but are not limited to, phenylmethyl (benzyl), 1-phenylethyl, 2-phenylethyl and phenylpropyl. When an aryl-$(C_{1-n})$alkyl- group is substituted, it is understood that substituents may be attached to either the aryl or the alkyl portion thereof or both, unless specified otherwise.

The term "Het" as used herein, either alone or in combination with another radical, is intended to mean a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$, unless specified otherwise. When a Het group is substituted, it is understood that substituents may be attached to any carbon atom or heteroatom thereof which would otherwise bear a hydrogen atom, unless specified otherwise.

The term "Het-($C_{1-n}$)alkyl-" as used herein and unless specified otherwise, wherein n is an integer, either alone or in combination with another radical, is intended to mean an alkyl radical having 1 to n carbon atoms as defined above which is itself substituted with a Het substituent as defined above. Examples of Het-($C_{1-n}$)alkyl-include, but are not limited to, thienylmethyl, furylmethyl, piperidinylethyl, 2-pyridinylmethyl, 3-pyridinylmethyl, 4-pyridinylmethyl, quinolinylpropyl, and the like. When a Het-($C_{1-n}$)alkyl-group is substituted, it is understood that substituents may be attached to either the Het or the alkyl portion thereof or both, unless specified otherwise.

The term "heteroatom" as used herein is intended to mean O, S or N.

The term "heterocycle" as used herein and unless specified otherwise, either alone or in combination with another radical, is intended to mean a 4- to 7-membered saturated, unsaturated or aromatic heterocycle containing from 1 to 4 heteroatoms each independently selected from O, N and S; or a monovalent radical derived by removal of a hydrogen atom therefrom. Examples of such heterocycles include, but are not limited to, azetidine, pyrrolidine, tetrahydrofuran, tetrahydrothiophene, thiazolidine, oxazolidine, pyrrole, thiophene, furan, pyrazole, imidazole, isoxazole, oxazole, isothiazole, thiazole, triazole, tetrazole, piperidine, piperazine, azepine, diazepine, pyran, 1,4-dioxane, 4-morpholine, 4-thiomorpholine, pyridine, pyridine-N-oxide, pyridazine, pyrazine, pyrimidine, and the following heterocycles:

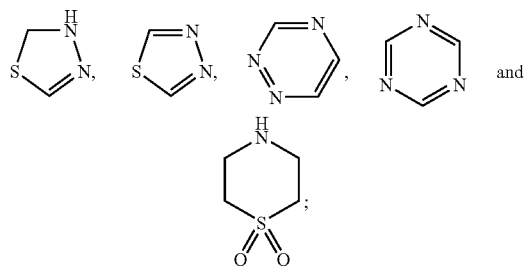

and saturated, unsaturated and aromatic derivatives thereof.

The term "heteropolycycle" as used herein and unless specified otherwise, either alone or in combination with another radical, is intended to mean a heterocycle as defined above fused to one or more other cycle, including a carbocycle, a heterocycle or any other cycle; or a monovalent radical derived by removal of a hydrogen atom therefrom. Examples of such heteropolycycles include, but are not limited to, indole, isoindole, benzimidazole, benzothiophene, benzofuran, benzodioxole, benzothiazole, quinoline, isoquinoline, naphthyridine, and the following heteropolycycles:

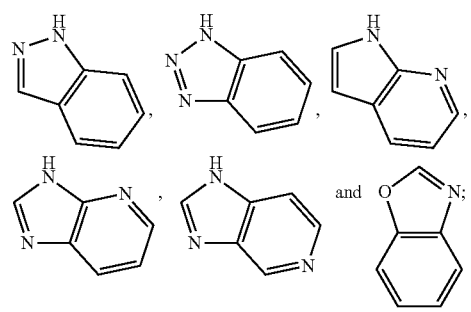

and saturated, unsaturated and aromatic derivatives thereof.

The term "halo" as used herein is intended to mean a halogen substituent selected from fluoro, chloro, bromo or iodo.

The term "($C_{1-n}$)haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of ($C_{1-n}$)haloalkyl include but are not limited to chloromethyl, chloroethyl, dichloroethyl, bromomethyl, bromoethyl, dibromoethyl, fluoromethyl, difluoromethyl, trifluoromethyl, fluoroethyl and difluoroethyl.

The terms "—O—($C_{1-n}$)alkyl" or "($C_{1-n}$)alkoxy" as used herein interchangeably, wherein n is an integer, either alone or in combination with another radical, is intended to mean an oxygen atom further bonded to an alkyl radical having 1 to n carbon atoms as defined above. Examples of —O—($C_{1-n}$) alkyl include but are not limited to methoxy ($CH_3O$—), ethoxy ($CH_3CH_2O$—), propoxy ($CH_3CH_2CH_2O$—), 1-methylethoxy (iso-propoxy; $(CH_3)_2CH$—O—) and 1,1-dimethylethoxy (tert-butoxy; $(CH_3)_3C$—O—). When an —O—($C_{1-n}$)alkyl radical is substituted, it is understood to be substituted on the ($C_{1-n}$)alkyl portion thereof.

The terms "—S—($C_{1-n}$)alkyl" or "($C_{1-n}$)alkylthio" as used herein interchangeably, wherein n is an integer, either alone or in combination with another radical, is intended to mean an sulfur atom further bonded to an alkyl radical having 1 to n carbon atoms as defined above. Examples of —S—($C_{1-n}$) alkyl include but are not limited to methylthio ($CH_3S$—), ethylthio ($CH_3CH_2S$—), propylthio ($CH_3CH_2CH_2S$—), 1-methylethylthio (isopropylthio; $(CH_3)_2CH$—S—) and 1,1-dimethylethylthio (tert-butylthio; $(CH_3)_3C$—S—). When —S—($C_{1-n}$)alkyl radical, or an oxidized derivative thereof, such as an —SO—($C_{1-n}$)alkyl radical or an —$SO_2$—($C_{1-n}$) alkyl radical, is substituted, each is understood to be substituted on the ($C_{1-n}$)alkyl portion thereof.

The term "oxo" as used herein is intended to mean an oxygen atom attached to a carbon atom as a substituent by a double bond (=O).

The term "thioxo" as used herein is intended to mean a sulfur atom attached to a carbon atom as a substituent by a double bond (=S).

The term "imino" as used herein is intended to mean a NH group attached to a carbon atom as a substituent by a double bond (=NH).

The term "cyano" or "CN" as used herein is intended to mean a nitrogen atom attached to a carbon atom by a triple bond (C≡N).

The term "COOH" as used herein is intended to mean a carboxyl group (—C(=O)—OH). It is well known to one skilled in the art that carboxyl groups may be substituted by functional group equivalents. Examples of such functional group equivalents contemplated in this invention include, but are not limited to, esters, amides, imides, boronic acids, phosphonic acids, phosphoric acids, tetrazoles, triazoles, N-acylsulfamides ($RCONHSO_2NR_2$), and N-acylsulfonamides ($RCONHSO_2R$).

The term "functional group equivalent" as used herein is intended to mean an atom or group that may replace another atom or group which has similar electronic, hybridization or bonding properties.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof, herein incorporated by reference.

The following designation $\dashv$ is used in sub-formulas to indicate the bond which is connected to the rest of the molecule as defined.

The term "salt thereof" as used herein is intended to mean any acid and/or base addition salt of a compound according to the invention, including but not limited to a pharmaceutically acceptable salt thereof.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Berge et al., J. Pharm. Sci., 1977, 66, pp. 1-19, herein incorporated by reference.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The term "ester thereof" as used herein is intended to mean any ester of a compound according to the invention in which any of the —COOH substituents of the molecule is replaced by a —COOR substituent, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl, each of which being optionally further substituted. The term "ester thereof" includes but is not limited to pharmaceutically acceptable esters thereof.

The term "pharmaceutically acceptable ester" as used herein is intended to mean esters of the compound according to the invention in which any of the COOH substituents of the molecule are replaced by a —COOR substituent, in which the R moiety of the ester is selected from alkyl (including, but not limited to, methyl, ethyl, propyl, 1-methylethyl, 1,1-dimethylethyl, butyl); alkoxyalkyl (including, but not limited to methoxymethyl); acyloxyalkyl (including, but not limited to acetoxymethyl); arylalkyl (including, but not limited to, benzyl); aryloxyalkyl (including, but not limited to, phenoxymethyl); and aryl (including, but not limited to phenyl) optionally substituted with halogen, $(C_{1-4})$alkyl or $(C_{1-4})$alkoxy. Other suitable esters can be found in Design of Prodrugs, Bundgaard, H. Ed. Elsevier (1985), herein incorporated by reference. Such pharmaceutically acceptable esters are usually hydrolyzed in vivo when injected into a mammal and transformed into the acid form of the compound according to the invention. With regard to the esters described above, unless otherwise specified, any alkyl moiety present preferably contains 1 to 16 carbon atoms, more preferably 1 to 6 carbon atoms. Any aryl moiety present in such esters preferably comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "mammal" as used herein is intended to encompass humans, as well as non-human mammals which are susceptible to infection by hepatitis C virus. Non-human mammals include but are not limited to domestic animals, such as cows, pigs, horses, dogs, cats, rabbits, rats and mice, and non-domestic animals.

The term "treatment" as used herein is intended to mean the administration of a compound or composition according to the present invention to alleviate or eliminate symptoms of the hepatitis C disease and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood.

The term "antiviral agent" as used herein is intended to mean an agent that is effective to inhibit the formation and/or replication of a virus in a mammal, including but not limited to agents that interfere with either host or viral mechanisms necessary for the formation and/or replication of a virus in a mammal.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Preferred Embodiments

In the following preferred embodiments, groups and substituents of the compounds of formula (I):

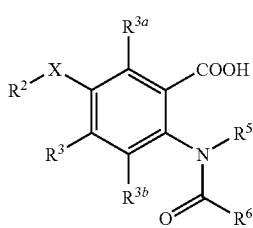

are described in detail.

X:

X-A: In one embodiment, X is O.

X-B: In another embodiment, X is S.

X-C: In another embodiment, X is O or S.

Any and each individual definition of X as set out herein may be combined with any and each individual definition of $R^2$, $R^{20}$, $R^3$, $R^{3a}$, $R^{3b}$, $R^5$ and $R^6$ as set out herein.

$R^2$:

$R^2$-A: In one embodiment, $R^2$ is Het or aryl, optionally substituted with 1 to 5 $R^{20}$ substituents, wherein $R^{20}$ is as defined herein.

$R^2$-B: In another embodiment, $R^2$ is Het wherein Het is a 5- or 6-membered heterocycle containing 1 to 3 heteroatoms each independently selected from O, N and S, or a 9- or 10-membered bicyclic heteropolycycle containing 1 to 3 heteroatoms each independently selected from O, N and S; wherein Het is optionally substituted with 1 to 5 $R^{20}$ substituents, wherein $R^{20}$ is as defined herein.

$R^2$-C: In another embodiment, $R^2$ is Het wherein Het is a 5- or 6-membered aromatic heterocycle containing 1 or 2 N heteroatoms, or a 9- or 10-membered bicyclic heteropolycycle containing 1 or 2 N heteroatoms; wherein Het is optionally substituted with 1 to 3 $R^{20}$ substituents, wherein $R^{20}$ is as defined herein.

$R^2$-D: In another embodiment, $R^2$ is Het selected from the following formulas:

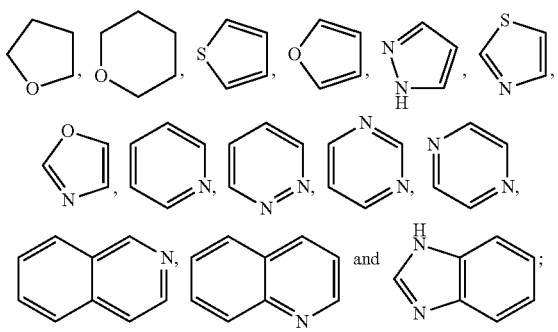

wherein Het is optionally substituted with 1 to 3 $R^{20}$ substituents, wherein $R^{20}$ is as defined herein.

$R^2$-E: In another embodiment, $R^2$ is Het selected from the following formulas:

wherein Het is optionally substituted with 1 to 3 $R^{20}$ substituents, wherein $R^{20}$ is as defined herein.

$R^2$-F: In another embodiment, $R^2$ is Het of the formula:

wherein Het is optionally substituted with 1 to 3 $R^{20}$ substituents, wherein $R^{20}$ is as defined herein.

$R^2$-G: In another embodiment, $R^2$ is of the formula:

wherein $R^{21}$ is as defined:

$R^{21}$-A: In this embodiment, $R^{21}$ is selected from H, halo, $(C_{1-6})$alkyl, $(C_{1-6})$haloalkyl, $(C_{3-7})$cycloalkyl and —O—$(C_{1-6})$haloalkyl.

$R^{21}$-B: In this embodiment, $R^{21}$ is selected from H, Cl, Br, $CH_3$, $CHF_2$, $CF_3$, cyclopropyl, cyclobutyl and —$OCF_3$.

$R^{21}$-C: In this embodiment, $R^{21}$ is H, $CHF_2$, $CF_3$ or cyclopropyl.
$R^{21}$-D: In this embodiment, $R^{21}$ is H or $CF_3$.
$R^{21}$-E: In this embodiment, $R^{21}$ is $CHF_2$ or $CF_3$.
$R^{21}$-F: In this embodiment, $R^{21}$ is $CF_3$;
and $R^{20}$ is as defined herein.
Any and each individual definition of $R^{21}$ as set out herein may be combined with any and each individual definition of X, $R^{20}$, $R^3$, $R^{3a}$, $R^{3b}$, $R^5$ and $R^6$ as set out herein.

$R^2$-H: In another embodiment, $R^2$ is a group of the formula:

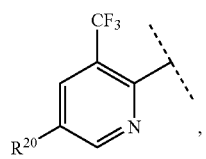

wherein $R^{20}$ is as defined herein.

$R^2$-I: In another embodiment, $R^2$ is naphthyl or phenyl, the phenyl being optionally substituted with 1 to 3 $R^{20}$ wherein $R^{20}$ is as defined herein.

$R^2$-J: In yet another embodiment, $R^2$ is phenyl optionally substituted with 1 to 3 $R^{20}$ wherein $R^{20}$ is as defined herein.

$R^2$-K: In an alternative embodiment, $R^2$ is a group of formula:

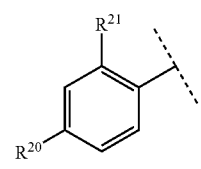

wherein $R^{21}$ and $R^{20}$ are as defined herein.

$R^2$-L: In another embodiment, $R^2$ is a group of the formula:

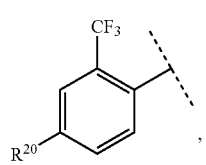

wherein $R^{20}$ is as defined herein.

$R^2$-M: In another embodiment, $R^2$ is phenyl or Het, all being optionally substituted with 1 to 3 $R^{20}$ substituents, wherein $R^{20}$ is as defined herein; and Het is a 5- or 6-membered aromatic heterocycle containing 1 or 2 N heteroatoms, or a 9- or 10-membered bicyclic heteropolycycle containing 1 or 2 N heteroatoms.

$R^2$-N: In another embodiment, $R^2$ is phenyl or Het wherein Het is selected from the following formulas:

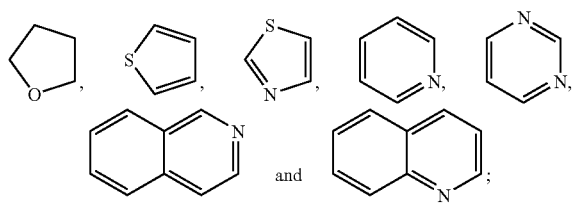

wherein $R^2$ is optionally substituted with 1 to 3 $R^{20}$ substituents, wherein $R^{20}$ is as defined herein.

$R^2$-O: In another embodiment, $R^2$ is phenyl or Het wherein Het is selected from the following formulas:

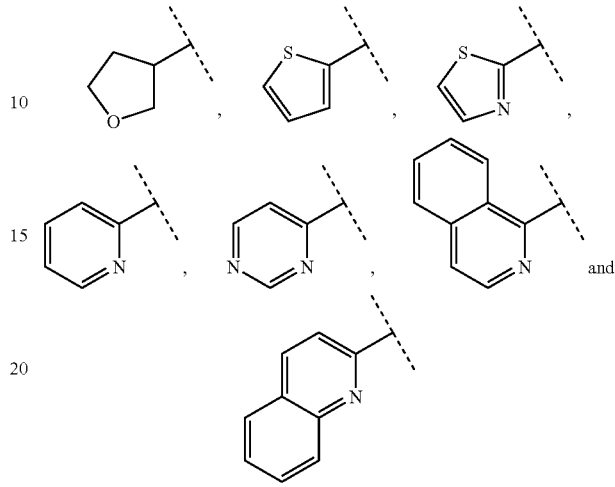

wherein $R^2$ is optionally substituted with 1 to 3 $R^{20}$ substituents, wherein $R^{20}$ is as defined herein.

$R^2$-P: In yet another alternative embodiment, $R^2$ is selected from the group:

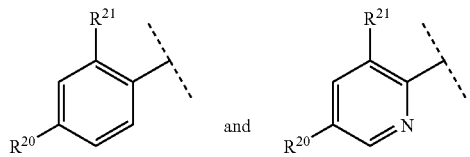

wherein $R^{21}$ and $R^{20}$ are as defined herein.

$R^2$-Q: In yet another alternative embodiment, $R^2$ is selected from the group:

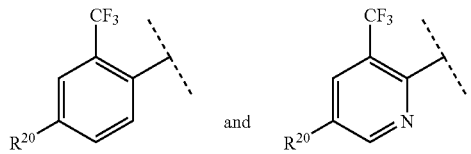

wherein $R^{20}$ is as defined herein.

Any and each individual definition of $R^2$ as set out herein may be combined with any and each individual definition of X, $R^{20}$, $R^3$, $R^{3a}$, $R^{3b}$, $R^5$ and $R^6$ as set out herein.

$R^{20}$-A:

$R^{20}$-A: In one embodiment, $R^{20}$ is selected from:
a) halo, cyano or nitro;
b) $R^7$, —C(=O)—$R^7$, —C(=O)—O—$R^7$, —O—$R^7$, —S—$R^7$, —SO—$R^7$, —$SO_2$—$R^7$, —$(C_{1-6})$alkylene-$R^7$, —$(C_{1-6})$alkylene-C(=O)—$R^7$, —$(C_{1-6})$alkylene-C(=O)—O—$R^7$, —$(C_{1-6})$alkylene-O—$R^7$, —$(C_{1-6})$alkylene-S—$R^7$, —$(C_{1-6})$alkylene-SO—$R^7$ or —$(C_{1-6})$alkylene-$SO_2$—$R^7$;
wherein $R^7$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, $(C_{3-7})$cycloalkyl-$(C_{1-6})$alkyl, aryl and Het;

wherein the $(C_{1-6})$alkyl, $(C_{2-6})$alkenyl, $(C_{2-6})$alkynyl, $(C_{1-6})$haloalkyl, $(C_{3-7})$cycloalkyl, $(C_{3-7})$cycloalkyl-$(C_{1-6})$alkyl, and $(C_{1-6})$alkylene are optionally substituted with 1 or 2 substituents each independently selected from —OH, —$(C_{1-6})$alkyl optionally substituted with —O—$(C_{1-6})$alkyl, halo, —$(C_{1-6})$haloalkyl, $(C_{3-7})$cycloalkyl, —O—$(C_{1-6})$alkyl, cyano, COOH, —$NH_2$, —NH$(C_{1-4})$alkyl, —NH$(C_{3-7})$cycloalkyl, —N$((C_{1-4})$alkyl$)(C_{3-7})$cycloalkyl, —N$((C_{1-4})$alkyl$)_2$, aryl, —$(C_{1-6})$alkyl-aryl, Het, —$(C_{1-6})$alkyl-Het; and wherein each of the aryl and Het is optionally substituted with 1 to 3 substituents each independently selected from:

i) halo, cyano, oxo, thioxo, imino, —OH, —O—$(C_{1-6})$alkyl, —O—$(C_{1-6})$haloalkyl, $(C_{3-7})$cycloalkyl, $(C_{1-6})$haloalkyl, —C(=O)—$(C_{1-6})$alkyl, —$SO_2(C_{1-6})$alkyl, —C(=O)—$NH_2$, —C(=O)—NH$(C_{1-4})$alkyl, —C(=O)—N$((C_{1-4})$alkyl$)_2$, —C(=O)—NH$(C_{3-7})$cycloalkyl, —C(=O)—N$((C_{1-4})$alkyl$)(C_{3-7})$cycloalkyl, —$NH_2$, —NH$(C_{1-4})$alkyl, —N$((C_{1-4})$alkyl$)_2$, —NH$(C_{3-7})$cycloalkyl, —N$((C_{1-4})$alkyl$)(C_{3-7})$cycloalkyl or —NH—C(=O)$(C_{1-4})$alkyl;

ii) $(C_{1-6})$alkyl optionally substituted with —OH, —O—$(C_{1-6})$haloalkyl, or —O—$(C_{1-6})$alkyl; and iii) aryl or Het, wherein each of the aryl and Het is optionally substituted with halo or $(C_{1-6})$alkyl; and c) —N($R^8$)$R^9$, —C(=O)—N($R^8$)$R^9$, —O—C(=O)—N($R^8$)$R^9$, —$SO_2$—N($R^8$)$R^9$, —$(C_{1-6})$alkylene-N($R^8$)$R^9$, —$(C_{1-6})$alkylene-C(=O)—N($R^8$)$R^9$, —$(C_{1-6})$alkylene-O—C(=O)—N($R^8$)$R^9$, or —$(C_{1-6})$alkylene-$SO_2$—N($R^8$)$R^9$;

wherein the $(C_{1-6})$alkylene is optionally substituted with 1 or 2 substituents each independently selected from —OH, —$(C_{1-6})$alkyl, halo, —$(C_{1-6})$haloalkyl, $(C_{3-7})$cycloalkyl, —O—$(C_{1-6})$alkyl, cyano, COOH, —$NH_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$;

$R^8$ is in each instance independently selected from H, $(C_{1-6})$alkyl and $(C_{3-7})$cycloalkyl; and $R^9$ is in each instance independently selected from $R^7$, —O—$(C_{1-6})$alkyl, —$(C_{1-6})$alkylene-$R^7$, —$SO_2$—$R^7$, —C(=O)—$R^7$, —C(=O)O$R^7$ and —C(=O)N($R^8$)$R^7$; wherein $R^7$ and $R^8$ are as defined above;

or $R^8$ and $R^9$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or $SO_2$;

wherein the heterocycle is optionally substituted with 1 to 3 substituents each independently selected from $(C_{1-6})$alkyl, $(C_{1-6})$haloalkyl, halo, oxo, —OH, SH, —O$(C_{1-6})$alkyl, —S$(C_{1-6})$alkyl, $(C_{3-7})$cycloalkyl, —$NH_2$, —NH$(C_{1-6})$alkyl, —N$((C_{1-6})$alkyl$)_2$, —NH$(C_{3-7})$cycloalkyl, —N$((C_{1-4})$alkyl$)(C_{3-7})$cycloalkyl, —C(=O)$(C_{1-6})$alkyl and —NHC(=O)—$(C_{1-6})$alkyl.

$R^{20}$-B: In another embodiment, $R^{20}$ is selected from:

b) $R^7$, —C(=O)—$R^7$, —C(=O)—O—$R^7$, —$(C_{1-6})$alkylene-$R^7$, —$(C_{1-6})$alkylene-C(=O)—$R^7$, —$(C_{1-6})$alkylene-C(=O)—O—$R^7$, —$(C_{1-6})$alkylene-O—$R^7$, —$(C_{1-6})$alkylene-S—$R^7$;

wherein $R^7$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, $(C_{3-7})$cycloalkyl-$(C_{1-6})$alkyl, aryl and Het;

wherein the $(C_{1-6})$alkyl, $(C_{2-6})$alkenyl, $(C_{2-6})$alkynyl, $(C_{1-6})$haloalkyl, $(C_{3-7})$cycloalkyl, $(C_{3-7})$cycloalkyl-$(C_{1-6})$alkyl, and $(C_{1-6})$alkylene are optionally substituted with 1 or 2 substituents each independently selected from —OH, —$(C_{1-6})$alkyl optionally substituted with —O—$(C_{1-6})$alkyl, halo, —$(C_{1-6})$haloalkyl, $(C_{3-7})$cycloalkyl, —O—$(C_{1-6})$alkyl, cyano, COOH, —$NH_2$, —NH$(C_{1-4})$alkyl, —NH$(C_{3-7})$cycloalkyl, —N$((C_{1-4})$alkyl$)(C_{3-7})$cycloalkyl, —N$((C_{1-4})$alkyl$)_2$, aryl, —$(C_{1-6})$alkyl-aryl, Het, —$(C_{1-6})$alkyl-Het; and wherein each of the aryl and Het is optionally substituted with 1 to 3 substituents each independently selected from:

i) halo, cyano, oxo, thioxo, imino, —OH, —O—$(C_{1-6})$alkyl, —O—$(C_{1-6})$haloalkyl, $(C_{3-7})$cycloalkyl, $(C_{1-6})$haloalkyl, —C(=O)—$(C_{1-6})$alkyl, —$SO_2(C_{1-6})$alkyl, —C(=O)—$NH_2$, —C(=O)—NH$(C_{1-4})$alkyl, —C(=O)—N$((C_{1-4})$alkyl$)_2$, —C(=O)—NH$(C_{3-7})$cycloalkyl, —C(=O)—N$((C_{1-4})$alkyl$)(C_{3-7})$cycloalkyl, —$NH_2$, —NH$(C_{1-4})$alkyl, —N$((C_{1-4})$alkyl$)_2$, —NH$(C_{3-7})$cycloalkyl, —N$((C_{1-4})$alkyl$)(C_{3-7})$cycloalkyl or —NH—C(=O)$(C_{1-4})$alkyl;

ii) $(C_{1-6})$alkyl optionally substituted with —OH, —O—$(C_{1-6})$haloalkyl, or —O—$(C_{1-6})$alkyl; and iii) aryl or Het, wherein each of the aryl and Het is optionally substituted with halo or $(C_{1-6})$alkyl; and c) —N($R^8$)$R^9$, —$(C_{1-6})$alkylene-N($R^8$)$R^9$, —$(C_{1-6})$alkylene-C(=O)—N($R^8$)$R^9$, or —$(C_{1-6})$alkylene-O—C(=O)—N($R^8$)$R^9$; wherein the $(C_{1-6})$alkylene is optionally substituted with 1 or 2 substituents each independently selected from —OH, —$(C_{1-6})$alkyl, halo, —$(C_{1-6})$haloalkyl, $(C_{3-7})$cycloalkyl, —O—$(C_{1-6})$alkyl, cyano, COOH, —$NH_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$;

$R^8$ is in each instance independently selected from H, $(C_{1-6})$alkyl and $(C_{3-7})$cycloalkyl; and $R^9$ is defined as $R^7$, wherein $R^7$ is as defined above;

or $R^8$ and $R^9$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or $SO_2$;

wherein the heterocycle is optionally substituted with 1 to 3 substituents each independently selected from $(C_{1-6})$alkyl, $(C_{1-6})$haloalkyl, halo, oxo, —OH, SH, —O$(C_{1-6})$alkyl, —S$(C_{1-6})$alkyl, $(C_{3-7})$cycloalkyl, —$NH_2$, —NH$(C_{1-6})$alkyl, —N$((C_{1-6})$alkyl$)_2$, —NH$(C_{3-7})$cycloalkyl, —N$((C_{1-4})$alkyl$)(C_{3-7})$cycloalkyl, —C(=O)$(C_{1-6})$alkyl and —NHC(=O)—$(C_{1-6})$alkyl.

$R^{20}$-C: In another embodiment, $R^{29}$ is selected from:

b) $R^7$, —$(C_{1-6})$alkylene-$R^7$, —$(C_{1-6})$alkylene-O—$R^7$, —$(C_{1-6})$alkylene-S—$R^7$;

wherein $R^7$ is in each instance independently selected from H, $(C_{1-6})$alkyl, $(C_{1-6})$haloalkyl, $(C_{3-7})$cycloalkyl, $(C_{3-7})$cycloalkyl-$(C_{1-6})$alkyl, aryl and Het;

wherein the $(C_{1-6})$alkyl, $(C_{1-6})$haloalkyl, $(C_{3-7})$cycloalkyl, $(C_{3-7})$cycloalkyl-$(C_{1-6})$alkyl, and $(C_{1-6})$ alkylene are optionally substituted with 1 or 2 substituents each independently selected from —OH, —(C$_{1-6}$)alkyl optionally substituted with —O—(C$_{1-6}$)alkyl, halo, —(C$_{1-6}$)haloalkyl, (C$_{3-7}$)cycloalkyl, —O—(C$_{1-6}$)alkyl, cyano, COOH, —NH$_2$, —NH(C$_{1-4}$)alkyl, —NH(C$_{3-7}$)cycloalkyl, —N((C$_{1-4}$)alkyl)(C$_{3-7}$)cycloalkyl, —N((C$_{1-4}$)alkyl)$_2$, Het, —(C$_{1-6}$)alkyl-Het; and wherein each of the aryl and Het is optionally substituted with 1 to 3 substituents each independently selected from:
  i) halo, (C$_{3-7}$)cycloalkyl, (C$_{1-6}$)haloalkyl, —C(=O)—NH$_2$, —C(=O)—NH(C$_{1-4}$)alkyl, —C(=O)—N((C$_{1-4}$)alkyl)$_2$, —C(=O)—NH(C$_{3-7}$)cycloalkyl, —C(=O)—N((C$_{1-4}$)alkyl)(C$_{3-7}$)cycloalkyl, —NH$_2$, —NH(C$_{1-4}$)alkyl, —N((C$_{1-4}$)alkyl)$_2$, —NH(C$_{3-7}$)cycloalkyl, —N((C$_{1-4}$)alkyl)(C$_{3-7}$)cycloalkyl or —NH—C(=O)(C$_{1-4}$)alkyl;
  ii) (C$_{1-6}$)alkyl optionally substituted with —OH, —O—(C$_{1-6}$)haloalkyl, or —O—(C$_{1-6}$)alkyl; and
  iii) aryl or Het, wherein each of the aryl and Het is optionally substituted with halo or (C$_{1-6}$)alkyl; and
c) —N(R$^8$)R$^9$ or —(C$_{1-6}$)alkylene-N(R$^8$)R$^9$; wherein the (C$_{1-6}$)alkylene is optionally substituted with 1 or 2 substituents each independently selected from —OH, —(C$_{1-6}$)alkyl, halo, —(C$_{1-6}$)haloalkyl, (C$_{3-7}$)cycloalkyl, —O—(C$_{1-6}$)alkyl, —NH$_2$, —NH(C$_{1-4}$)alkyl, —NH(C$_{3-7}$)cycloalkyl, —N((C$_{1-4}$)alkyl)(C$_{3-7}$)cycloalkyl and —N((C$_{1-4}$)alkyl)$_2$;
R$^8$ is in each instance independently selected from H, (C$_{1-6}$)alkyl and (C$_{3-7}$)cycloalkyl; and
R$^9$ is defined as R$^7$, wherein R$^7$ is as defined above.

R$^{20}$-D: In another embodiment, R$^{20}$ is selected from:
b) R$^7$ or —(C$_{1-6}$)alkylene-R$^7$
  wherein R$^7$ is in each instance independently selected from H, (C$_{1-6}$)alkyl, (C$_{3-7}$)cycloalkyl, (C$_{3-7}$)cycloalkyl-(C$_{1-6}$)alkyl, phenyl and Het;
  wherein each of the phenyl and Het are optionally substituted with 1 to 3 substituents each independently selected from:
  i) halo, (C$_{3-7}$)cycloalkyl, (C$_{1-6}$)haloalkyl, —C(=O)—NH$_2$, —C(=O)—NH(C$_{1-4}$)alkyl, —C(=O)—N((C$_{1-4}$)alkyl)$_2$, —C(=O)—NH(C$_{3-7}$)cycloalkyl, —C(=O)—N((C$_{1-4}$)alkyl)(C$_{3-7}$)cycloalkyl, —NH$_2$, —NH(C$_{1-4}$)alkyl, —N((C$_{1-4}$)alkyl)$_2$, —NH(C$_{3-7}$)cycloalkyl, —N((C$_{1-4}$)alkyl)(C$_{3-7}$)cycloalkyl or —NH—C(=O)(C$_{1-4}$)alkyl; and
  ii) (C$_{1-6}$)alkyl optionally substituted with —OH, —O—(C$_{1-6}$)haloalkyl, or —O—(C$_{1-6}$)alkyl; and
c) —N(R$^8$)R$^9$ or —(C$_{1-6}$)alkylene-N(R$^8$)R$^9$;
R$^8$ is in each instance independently selected from H, (C$_{1-6}$)alkyl and (C$_{3-7}$)cycloalkyl; and
R$^9$ is defined as R$^7$, wherein R$^7$ is as defined above.

R$^{20}$-E: In another embodiment, R$^{20}$ is selected from:
b) R$^7$ or —(C$_{1-6}$)alkylene-R$^7$
  wherein R$^7$ is in each instance independently selected from H, (C$_{1-6}$)alkyl, (C$_{3-7}$)cycloalkyl, (C$_{3-7}$)cycloalkyl-(C$_{1-6}$)alkyl, phenyl and Het;
  wherein each of the phenyl and Het are optionally substituted with 1 to 3 substituents each independently selected from:
  i) halo, (C$_{3-7}$)cycloalkyl, (C$_{1-6}$)haloalkyl, —C(=O)—NH$_2$, —C(=O)—NH(C$_{1-4}$)alkyl, —C(=O)—N((C$_{1-4}$)alkyl)$_2$, —C(=O)—NH(C$_{3-7}$)cycloalkyl, —C(=O)—N((C$_{1-4}$)alkyl)(C$_{3-7}$)cycloalkyl, —NH$_2$, —NH(C$_{1-4}$)alkyl, —N((C$_{1-4}$)alkyl)$_2$, —NH(C$_{3-7}$)cycloalkyl, —N((C$_{1-4}$)alkyl)(C$_{3-7}$)cycloalkyl or —NH—C(=O)(C$_{1-4}$)alkyl; and
  ii) (C$_{1-6}$)alkyl optionally substituted with —OH, —O—(C$_{1-6}$)haloalkyl, or —O—(C$_{1-6}$)alkyl;

wherein the Het is selected from:

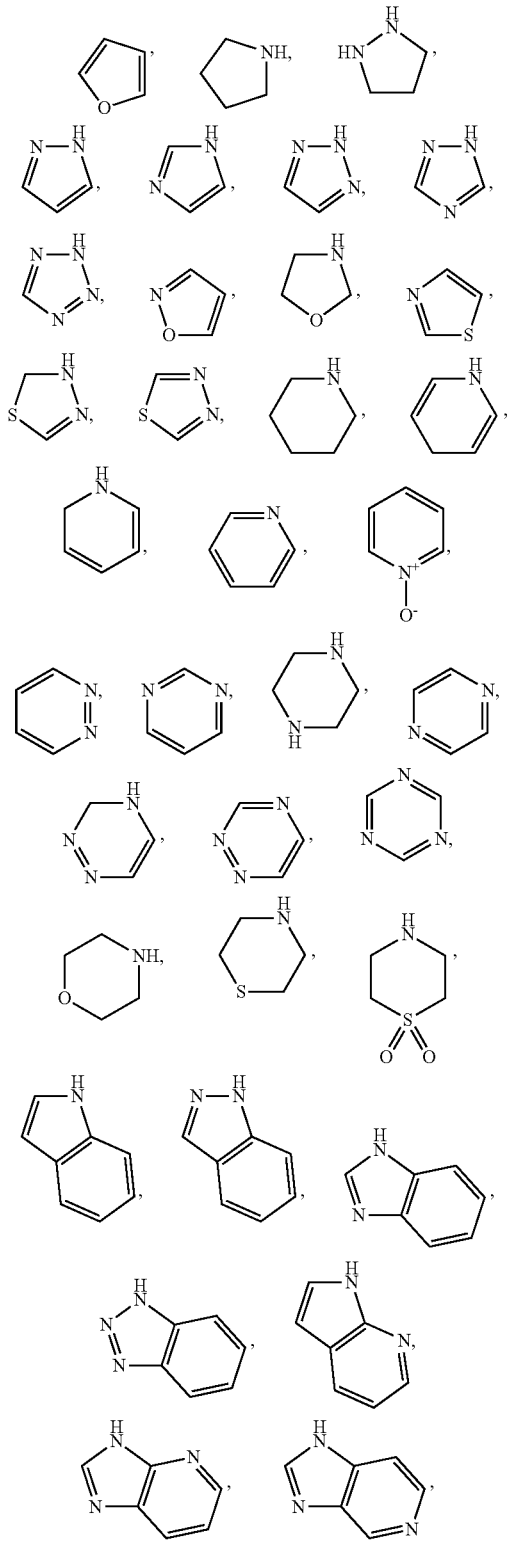

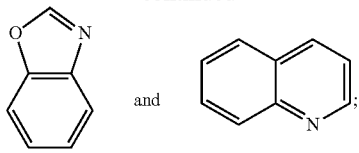 [SMILES: c1ccc2ocnc2c1 ; c1ccc2ncccc2c1]

and c) —N(R⁸)R⁹ or —(C₁₋₆)alkylene-N(R⁸)R⁹;
R⁸ is in each instance independently selected from H, (C₁₋₆)alkyl and (C₃₋₇)cycloalkyl; and
R⁹ is defined as R⁷, wherein R⁷ is as defined above.

R²⁰-F: In another embodiment, R²⁹ is selected from:

b) —(C₁₋₃)alkylene-R⁷;
wherein R⁷ is Het; wherein the Het is a 5- or 6-membered heterocycle containing 1 to 4 heteroatoms, each independently selected from N, O and S, or Het is a 9- or 10-membered heteropolycycle containing 1 to 4 heteroatoms, each independently selected from N, O and S;
wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO₂;
wherein the Het is optionally substituted with 1 to 3 substituents each independently selected from halo, cyano, oxo, imino, —OH, —O—(C₁₋₆)alkyl, —O—(C₁₋₆)haloalkyl, (C₃₋₇)cycloalkyl, —NH₂, —NH(C₁₋₄)alkyl, —NH(C₃₋₇)cycloalkyl, —N((C₁₋₄)alkyl)(C₃₋₇)cycloalkyl, —N((C₁₋₄)alkyl)₂, —NH—C(=O)(C₁₋₄)alkyl, (C₁₋₆)alkyl and Het, wherein the Het is a 5- or 6-membered heterocycle containing 1 to 4 heteroatoms, each independently selected from N, O and S.

R²⁰-G: In another embodiment, R²⁹ is selected from:

b) —CH₂—R⁷, —CH₂CH₂—R⁷,
wherein R⁷ is Het; wherein the Het is selected from:

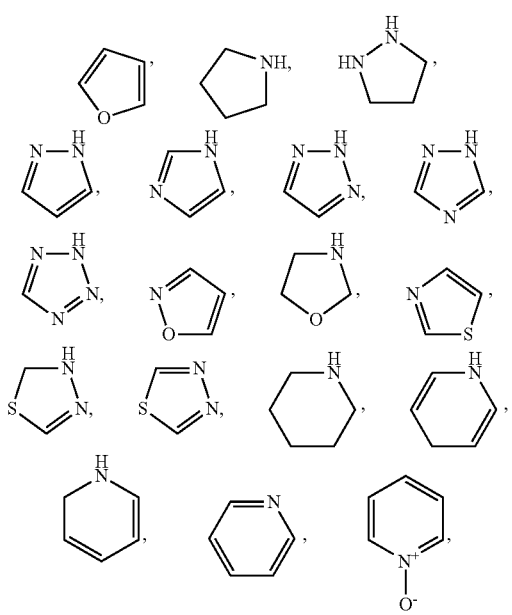

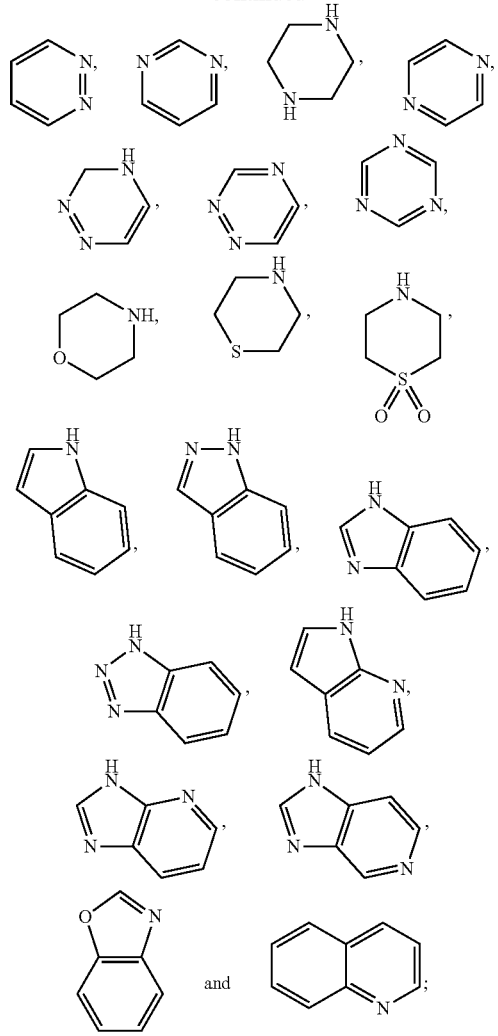

and
wherein the Het is optionally substituted with 1 to 3 substituents each independently selected from halo, cyano, oxo, imino, —OH, —O—(C₁₋₆)alkyl, —NH₂, —NH(C₁₋₄)alkyl, —N((C₁₋₄)alkyl)₂, —NH—C(=O)(C₁₋₄)alkyl and (C₁₋₆)alkyl.

R²⁰-H: In another embodiment, R²⁰ is selected from:

b) —CH₂—R⁷, —CH₂CH₂—R⁷,
wherein R⁷ is Het; wherein the Het is selected from:

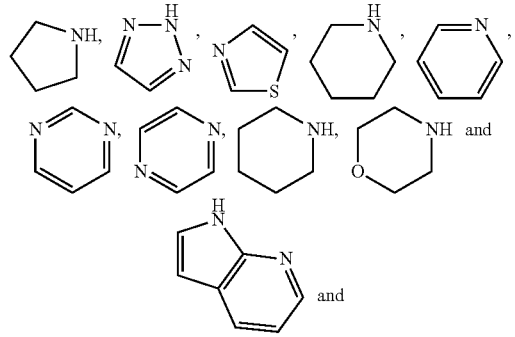

wherein the Het is optionally substituted with 1 to 3 substituents each independently selected from halo, —($C_{1-6}$)alkyl, —O—($C_{1-6}$)alkyl, —$NH_2$, —NH($C_{1-4}$)alkyl, —N(($C_{1-4}$)alkyl)$_2$ and ($C_{1-6}$)alkyl.
$R^{20}$—I: In another embodiment, $R^{20}$ is selected from:
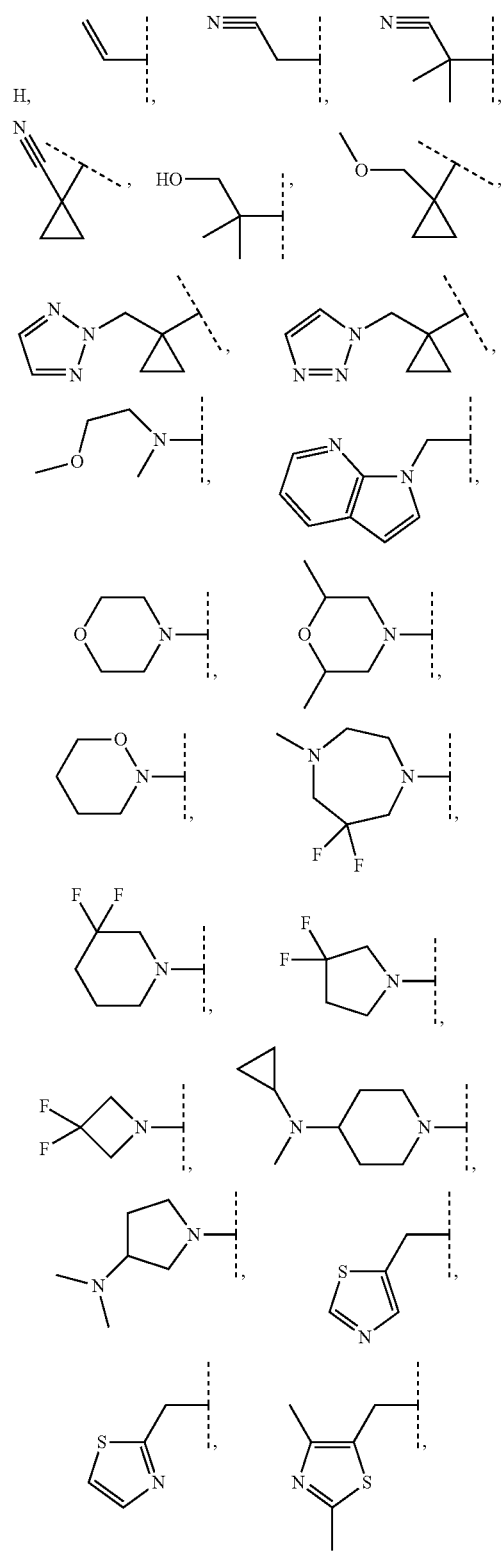
-continued
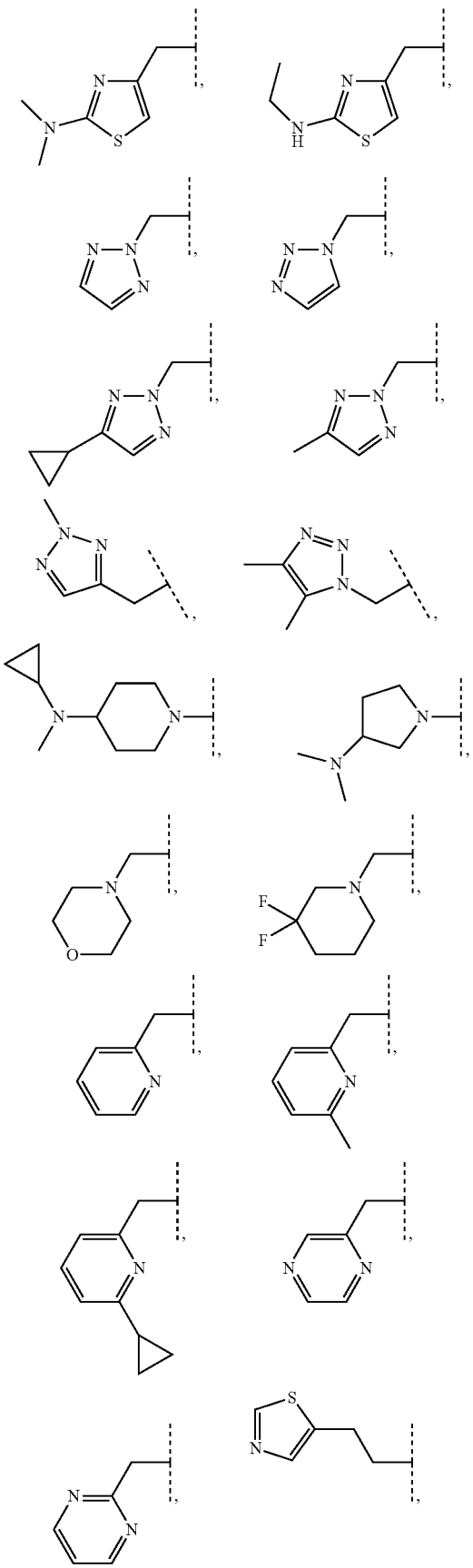

-continued
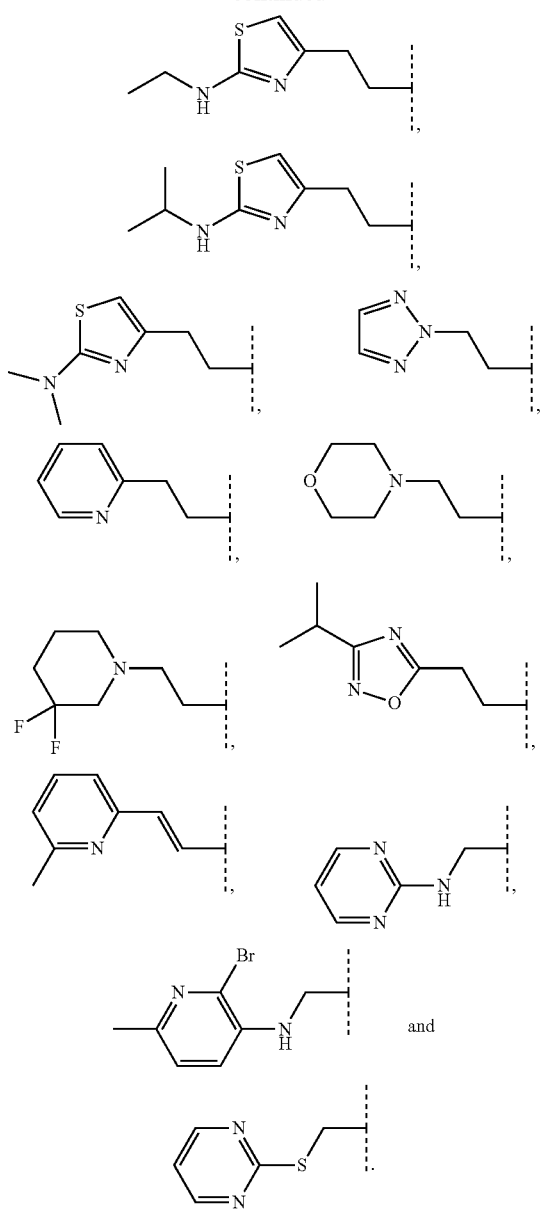
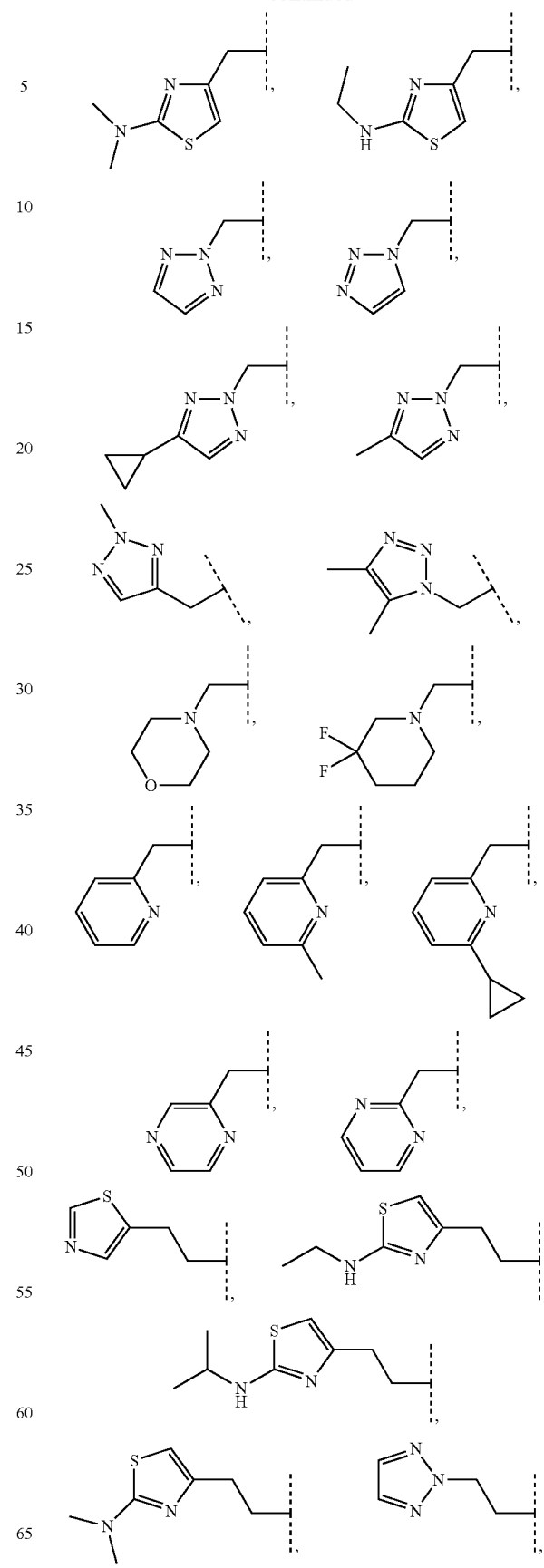
$R^{20}$-J: In another embodiment, $R^{20}$ is selected from:
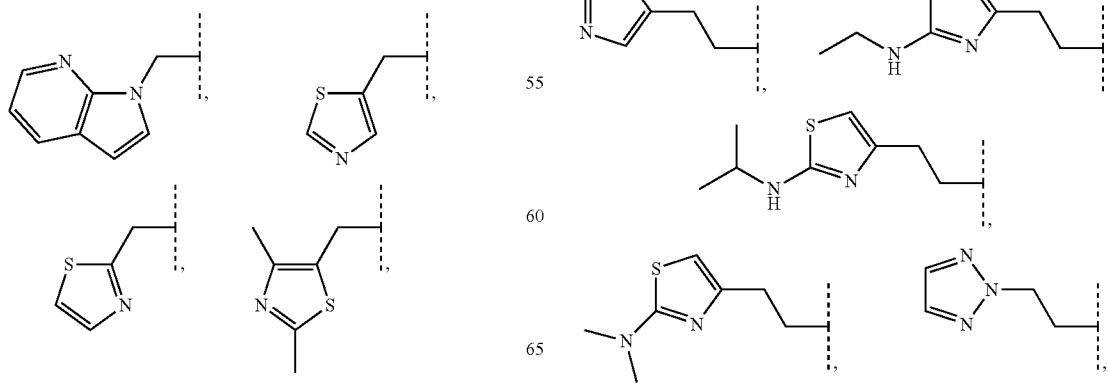

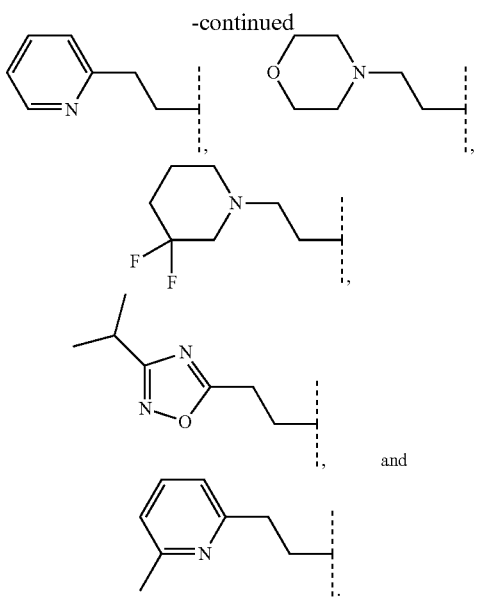

and

Any and each individual definition of $R^{20}$ as set out herein may be combined with any and each individual definition of X, $R^2$, $R^3$, $R^{3a}$, $R^{3b}$, $R^5$ and $R^6$ as set out herein.

$R^3$:

$R^3$-A: In one embodiment, $R^3$ is selected from H, halo, CN, $(C_{1-4})$alkyl, —OH, —O—$(C_{1-4})$alkyl, —S—$(C_{1-4})$alkyl, —NH$_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$.

$R^3$-B: In another embodiment, $R^3$ is selected from H, halo, CN, $(C_{1-4})$alkyl, —O—$(C_{1-4})$alkyl and —N$((C_{1-4})$alkyl$)_2$.

$R^3$-C: In another embodiment, $R^3$ is selected from H, halo, $(C_{1-4})$alkyl and CN.

$R^3$-D: In another embodiment, $R^3$ is selected from H, F, Cl, CH$_3$ and CN.

$R^3$-E: In another embodiment, $R^3$ is selected from H, F, C$_1$ and CH$_3$.

$R^3$-F: In another embodiment, $R^3$ is selected from H, F and CH$_3$.

$R^3$-G: In another embodiment, $R^3$ is H or F.

$R^3$-H: In another embodiment, $R^3$ is H.

Any and each individual definition of $R^3$ as set out herein may be combined with any and each individual definition of X, $R^{20}$, $R^2$, $R^{3a}$, $R^{3b}$, $R^5$ and $R^6$ as set out herein.

$R^{3a}$:

$R^{3a}$-A: In one embodiment, $R^{3a}$ is selected from H, halo, CN, $(C_{1-4})$alkyl, —OH, —O—$(C_{1-4})$alkyl, —S—$(C_{1-4})$alkyl, —NH$_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$.

$R^{3a}$-B: In another embodiment, $R^{3a}$ is selected from H, halo, CN, $(C_{1-4})$alkyl, —O—$(C_{1-4})$alkyl and —N$((C_{1-4})$alkyl$)_2$.

$R^{3a}$-C: In another embodiment, $R^{3a}$ is selected from H, halo, $(C_{1-4})$alkyl and CN.

$R^{3a}$-D: In another embodiment, $R^{3a}$ is selected from H, F, Cl, CH$_3$ and CN.

$R^{3a}$-E: In another embodiment, $R^{3a}$ is selected from H, F, Cl and CH$_3$.

$R^{3a}$-F: In another embodiment, $R^{3a}$ is selected from H, F and CH$_3$.

$R^{3a}$-G: In another embodiment, $R^{3a}$ is H or F.

$R^{3a}$-H: In another embodiment, $R^{3a}$ is H.

Any and each individual definition of $R^{3a}$ as set out herein may be combined with any and each individual definition of X, $R^{20}$, $R^2$, $R^3$, $R^{3b}$, $R^5$ and $R^6$ as set out herein.

$R^{3b}$:

$R^{3b}$-A: In one embodiment, $R^{3b}$ is selected from H, halo, CN, $(C_{1-4})$alkyl, —OH, —O—$(C_{1-4})$alkyl, —S—$(C_{1-4})$alkyl, —NH$_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$.

$R^{3b}$-B: In another embodiment, $R^{3b}$ is selected from H, halo, CN, $(C_{1-4})$alkyl, —O—$(C_{1-4})$alkyl and —N$((C_{1-4})$alkyl$)_2$.

$R^{3b}$-C: In another embodiment, $R^{3b}$ is selected from H, halo, $(C_{1-4})$alkyl and CN.

$R^{3b}$-D: In another embodiment, $R^{3b}$ is selected from H, F, Cl, CH$_3$ and CN.

$R^{3b}$-E: In another embodiment, $R^{3b}$ is selected from H, F, Cl and CH$_3$.

$R^{3b}$-F: In another embodiment, $R^{3b}$ is selected from H, F and CH$_3$.

$R^{3b}$-G: In another embodiment, $R^{3b}$ is H or F.

$R^{3b}$-H: In another embodiment, $R^{3b}$ is H.

Any and each individual definition of $R^{3b}$ as set out herein may be combined with any and each individual definition of X, $R^{20}$, $R^2$, $R^3$, $R^{3a}$, $R^5$ and $R^6$ as set out herein.

$R^5$:

$R^5$-A: In one embodiment, $R^5$ is $R^{51}$ being mono-, di-, or tri-substituted with O—$R^{52}$, wherein $R^{51}$ is $(C_{1-6})$alkyl, $(C_{3-7})$cycloalkyl, $(C_{1-6})$alkyl-$(C_{3-7})$cycloalkyl, aryl, $(C_{1-6})$alkyl-aryl, Het or $(C_{1-6})$alkyl-Het, each $R^{51}$ being optionally substituted with $(C_{1-6})$alkyl, $(C_{3-7})$cycloalkyl or $(C_{1-6})$alkyl-$(C_{3-7})$cycloalkyl; and $R^{52}$ is $(C_{1-6})$alkyl, $(C_{3-7})$cycloalkyl, $(C_{1-6})$alkyl-$(C_{3-7})$cycloalkyl, aryl, $(C_{1-6})$alkyl-aryl, Het or $(C_{1-6})$alkyl-Het, said aryl and Het being optionally substituted with $(C_{1-6})$alkyl or O—$(C_{1-6})$alkyl.

$R^5$-B: In one embodiment, $R^5$ is $R^{51}$ being mono-, di-, or tri-substituted with O—$R^{52}$, wherein $R^{51}$ is $(C_{1-6})$alkyl, $(C_{3-7})$cycloalkyl, $(C_{1-6})$alkyl-$(C_{3-7})$cycloalkyl, aryl or $(C_{1-6})$alkyl-aryl, each $R^{51}$ being optionally substituted with $(C_{1-6})$alkyl, $(C_{3-7})$cycloalkyl or $(C_{1-6})$alkyl-$(C_{3-7})$cycloalkyl; and $R^{52}$ is $(C_{1-6})$alkyl, $(C_{3-7})$cycloalkyl, $(C_{1-6})$alkyl-$(C_{3-7})$cycloalkyl, aryl or $(C_{1-6})$alkyl-aryl, said aryl being optionally substituted with $(C_{1-6})$alkyl or O—$(C_{1-6})$alkyl.

$R^5$-C: In one embodiment, $R^5$ is $R^{51}$ being mono- or di-substituted with O—$R^{52}$, wherein $R^{51}$ is $(C_{1-6})$alkyl, $(C_{3-7})$cycloalkyl, $(C_{1-6})$alkyl-$(C_{3-7})$cycloalkyl, aryl or $(C_{1-6})$alkyl-aryl, each $R^{51}$ being optionally substituted with $(C_{1-6})$alkyl, $(C_{3-7})$cycloalkyl or $(C_{1-6})$alkyl-$(C_{3-7})$cycloalkyl; and $R^{52}$ is $(C_{1-6})$alkyl, $(C_{3-7})$cycloalkyl, $(C_{1-6})$alkyl-$(C_{3-7})$cycloalkyl, aryl or $(C_{1-6})$alkyl-aryl, said aryl being optionally substituted with $(C_{1-6})$alkyl or O—$(C_{1-6})$alkyl.

$R^5$-D: In one embodiment, $R^5$ is $R^{51}$ being mono- or di-substituted with O—$R^{52}$, wherein $R^{51}$ is $(C_{1-6})$alkyl, $(C_{3-7})$cycloalkyl or $(C_{1-6})$alkyl-$(C_{3-7})$cycloalkyl, each $R^{51}$ being optionally substituted with $(C_{1-6})$alkyl, $(C_{3-7})$cycloalkyl or $(C_{1-6})$alkyl-$(C_{3-7})$cycloalkyl; and $R^{52}$ is $(C_{1-6})$alkyl, $(C_{3-7})$cycloalkyl, $(C_{1-6})$alkyl-$(C_{3-7})$cycloalkyl, aryl or $(C_{1-6})$alkyl-aryl, said aryl being optionally substituted with $(C_{1-6})$alkyl or O—$(C_{1-6})$alkyl.

$R^5$-E: In one embodiment, $R^5$ is $R^{51}$ being mono- or di-substituted with O—$R^{52}$, wherein $R^{51}$ is $(C_{1-6})$alkyl, being optionally substituted with $(C_{1-6})$alkyl, $(C_{3-7})$cycloalkyl or $(C_{1-6})$alkyl-$(C_{3-7})$cycloalkyl; and $R^{52}$ is $(C_{1-6})$alkyl, aryl or $(C_{1-6})$alkyl-aryl, said aryl being optionally substituted with $(C_{1-6})$alkyl or O—$(C_{1-6})$alkyl.

$R^5$-F: In one embodiment, $R^5$ is $R^{51}$ being mono- or di-substituted with O—$R^{52}$, wherein $R^{51}$ is $(C_{1-6})$alkyl, being optionally substituted with $(C_{1-6})$alkyl, and $R^{52}$ is $(C_{1-6})$alkyl, aryl or $(C_{1-6})$alkyl-aryl, said aryl being optionally substituted with $(C_{1-6})$alkyl or $O$—$(C_{1-6})$alkyl.
$R^5$-G: In one embodiment, $R^5$ is $R^{51}$ being mono- or di-substituted with $O$—$R^{52}$, wherein $R^{51}$ is $(C_{1-6})$alkyl, being optionally substituted with $(C_{1-6})$alkyl, and $R^{52}$ is $(C_{1-6})$alkyl.
$R^5$-H: In another embodiment, $R^5$ is selected from:
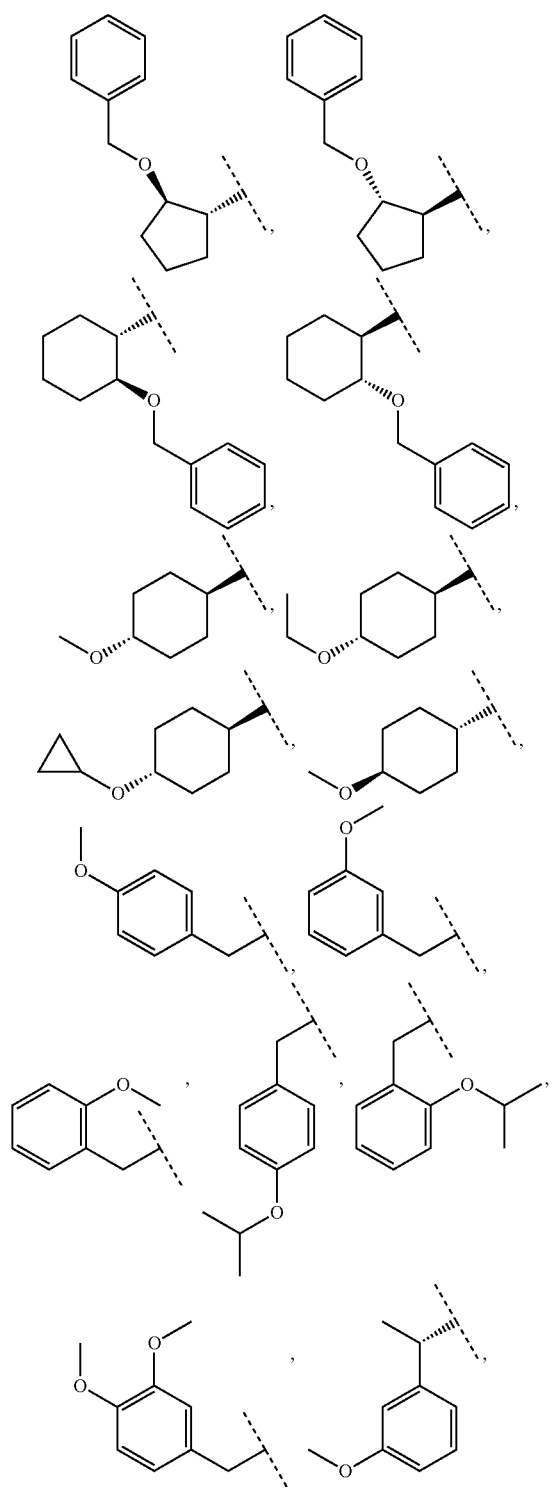
-continued
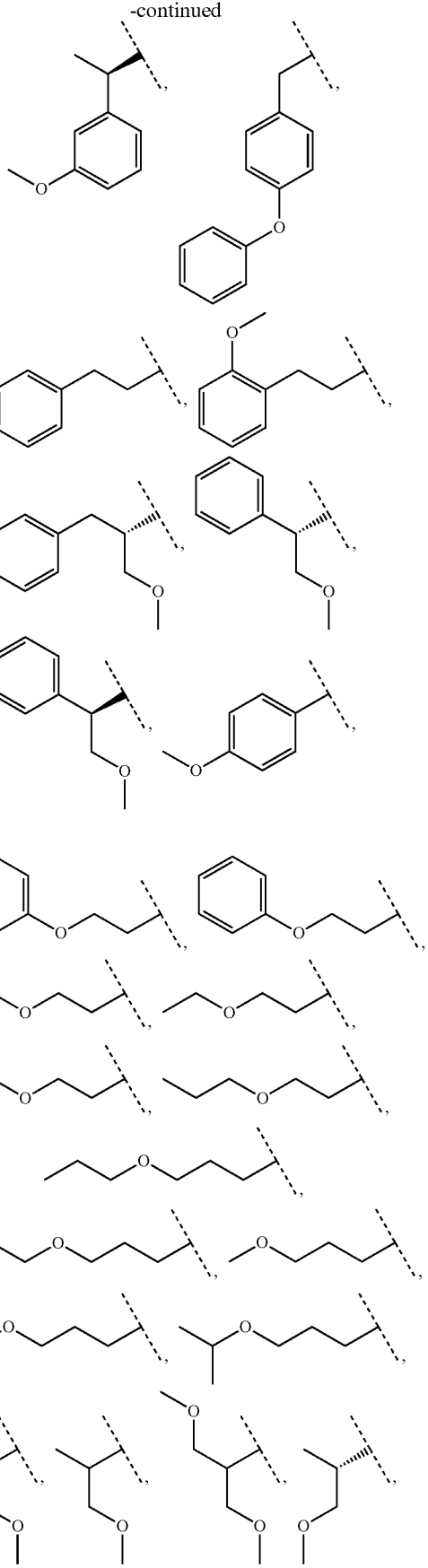

-continued

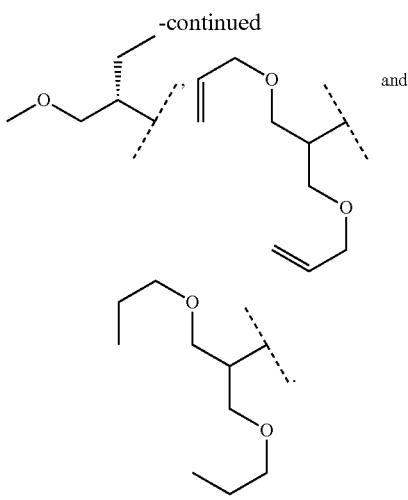

R$^5$-I: In one embodiment, R$^5$ is R$^{51}$ being mono- or di-substituted with O—R$^{52}$, wherein R$^{51}$ is (C$_{1-6}$)alkyl, being optionally substituted with (C$_{1-6}$)alkyl, (C$_{3-7}$)cycloalkyl or (C$_{1-6}$)alkyl-(C$_{3-7}$)cycloalkyl; and R$^{52}$ is (C$_{1-6}$)alkyl, (C$_{3-7}$)cycloalkyl, (C$_{1-6}$)alkyl-(C$_{3-7}$)cycloalkyl, aryl or (C$_{1-6}$)alkyl-aryl, said aryl being optionally substituted with (C$_{1-6}$)alkyl or O—(C$_{1-6}$)alkyl.

Any and each individual definition of R$^5$ as set out herein may be combined with any and each individual definition of X, R$^{20}$, R$^2$, R$^3$, R$^{3a}$, R$^{3b}$ and R$^6$ as set out therein.

R$^6$:

R$^6$-A: In one embodiment, R$^6$ is (C$_{3-7}$)cycloalkyl, (C$_{1-6}$) alkyl-(C$_{3-7}$)cycloalkyl, aryl, (C$_{1-6}$)alkyl-aryl, Het or (C$_{1-6}$) alkyl-Het; being optionally substituted with 1 to 5 substituents each independently selected from halo, (C$_{1-6}$)alkyl, (C$_{1-6}$)haloalkyl, (C$_{3-7}$)cycloalkyl, —OH, —SH, —O—(C$_{1-4}$)alkyl, —S—(C$_{1-4}$)alkyl and —N(R$^8$)R$^9$; wherein R$^8$ is in each instance independently selected from H, (C$_{1-6}$) alkyl and (C$_{3-7}$)cycloalkyl; and R$^9$ is in each instance independently selected from R$^7$, —O—(C$_{1-6}$)alkyl, —(C$_{1-6}$)alkylene-R$^7$, —SO$_2$—R$^7$, —C(=O)—R$^7$, —C(=O)OR$^7$ and —C(=O)N(R$^8$)R$^7$; wherein R$^7$ and R$^8$ are as defined above;

or R$^8$ and R$^9$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;

wherein the heterocycle is optionally substituted with 1 to 3 substituents each independently selected from (C$_{1-6}$) alkyl, (C$_{1-6}$)haloalkyl, halo, oxo, —OH, SH, —O(C$_{1-6}$) alkyl, —S(C$_{1-6}$)alkyl, (C$_{3-7}$)cycloalkyl, —NH$_2$, —NH (C$_{1-6}$)alkyl, —N((C$_{1-6}$)alkyl)$_2$, —NH(C$_{3-7}$)cycloalkyl, —N((C$_{1-4}$)alkyl)(C$_{3-7}$)cycloalkyl, —C(=O)(C$_{1-6}$) alkyl and —NHC(=O)—(C$_{1-6}$)alkyl.

R$^6$-B: In yet another alternative embodiment, R$^6$ is (C$_{3-7}$) cycloalkyl, aryl or Het, being optionally substituted with 1 to 3 substituents each independently selected from halo, (C$_{1-6}$)alkyl and (C$_{1-6}$)haloalkyl.

R$^6$-C: In still another embodiment, R$^6$ is (C$_{3-7}$)cycloalkyl, phenyl or Het, optionally substituted with 1 to 3 substituents each independently selected from halo, (C$_{1-6}$)alkyl and (C$_{1-6}$)haloalkyl;

wherein the Het is selected from:

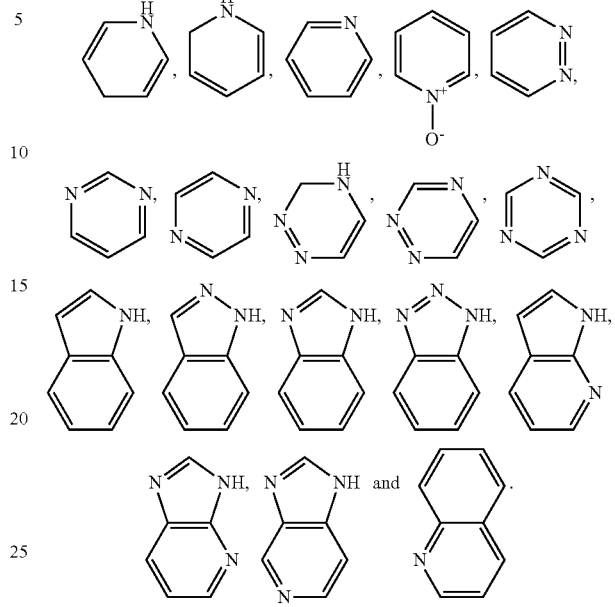

R$^6$-D: In another alternative embodiment, R$^6$ is (C$_{5-6}$)cycloalkyl, phenyl or Het optionally substituted with 1 to 3 substituents each independently selected from halo, (C$_{1-4}$) alkyl and (C$_{1-4}$)haloalkyl; wherein Het is a 4- to 7-membered saturated, unsaturated or aromatic heterocycle having 1 to 3 nitrogen heteroatoms.

R$^6$-E: In still another embodiment, R$^6$ is phenyl, cyclohexyl or pyridine optionally substituted with 1 to 3 substituents each independently selected from halo, (C$_{1-4}$)alkyl and (C$_{1-4}$)haloalkyl.

R$^6$-F: In still another embodiment, R$^6$ is phenyl, optionally substituted with 1 to 3 substituents each independently selected from halo and (C$_{1-4}$)alkyl.

R$^6$-G: In still another embodiment, R$^6$ is

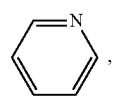

optionally substituted with 1 to 3 substituents each independently selected from halo.

R$^6$-H: In still another embodiment, R$^6$ is

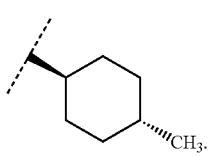

R⁶-I: In still another embodiment, R⁶ is selected from:

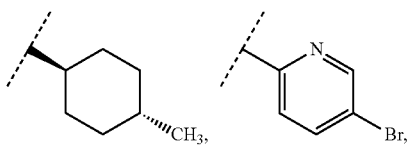
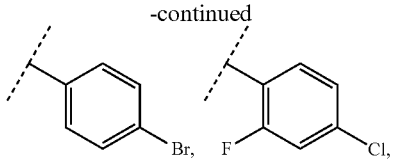
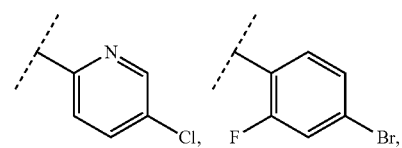
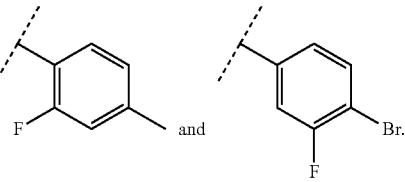
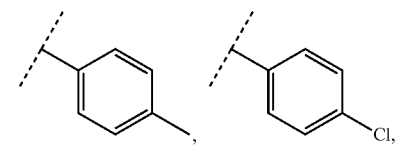

Any and each individual definition of R⁶ as set out herein may be combined with any and each individual definition of X, $R^2$, $R^{20}$, $R^3$, $R^{3a}$, $R^{3b}$ and $R^5$ as set out herein.

Examples of preferred subgeneric embodiments of the present invention are set forth in the following table, wherein each substituent group of each embodiment is defined according to the definitions set forth above:

| Embodiment | X | $R^2$ | $R^{20}$ | $R^3$ | $R^{3a}$ | $R^{3b}$ | $R^5$ | $R^6$ |
|---|---|---|---|---|---|---|---|---|
| E-1 | X-A | $R^2$-A | $R^{20}$-D | $R^3$-F | $R^{3a}$-D | $R^{3b}$-H | $R^5$-A | $R^6$-I |
| E-2 | X-A | $R^2$-A | $R^{20}$-D | $R^3$-F | $R^{3a}$-D | $R^{3b}$-H | $R^5$-A | $R^6$-A |
| E-3 | X-A | $R^2$-A | $R^{20}$-I | $R^3$-A | $R^{3a}$-F | $R^{3b}$-A | $R^5$-A | $R^6$-F |
| E-4 | X-A | $R^2$-A | $R^{20}$-B | $R^3$-E | $R^{3a}$-H | $R^{3b}$-C | $R^5$-B | $R^6$-G |
| E-5 | X-A | $R^2$-A | $R^{20}$-H | $R^3$-H | $R^{3a}$-H | $R^{3b}$-H | $R^5$-C | $R^6$-I |
| E-6 | X-A | $R^2$-A | $R^{20}$-A | $R^3$-G | $R^{3a}$-H | $R^{3b}$-H | $R^5$-D | $R^6$-H |
| E-7 | X-A | $R^2$-A | $R^{20}$-J | $R^3$-B | $R^{3a}$-B | $R^{3b}$-G | $R^5$-H | $R^6$-E |
| E-8 | X-A | $R^2$-B | $R^{20}$-H | $R^3$-G | $R^{3a}$-H | $R^{3b}$-H | $R^5$-H | $R^6$-F |
| E-9 | X-A | $R^2$-B | $R^{20}$-H | $R^3$-G | $R^{3a}$-H | $R^{3b}$-H | $R^5$-H | $R^6$-G |
| E-10 | X-A | $R^2$-B | $R^{20}$-H | $R^3$-G | $R^{3a}$-H | $R^{3b}$-H | $R^5$-H | $R^6$-I |
| E-11 | X-B | $R^2$-B | $R^{20}$-H | $R^3$-G | $R^{3a}$-H | $R^{3b}$-H | $R^5$-A | $R^6$-I |
| E-12 | X-A | $R^2$-C | $R^{20}$-F | $R^3$-A | $R^{3a}$-D | $R^{3b}$-D | $R^5$-A | $R^6$-A |
| E-13 | X-A | $R^2$-C | $R^{20}$-A | $R^3$-A | $R^{3a}$-G | $R^{3b}$-A | $R^5$-C | $R^6$-F |
| E-14 | X-A | $R^2$-C | $R^{20}$-B | $R^3$-B | $R^{3a}$-A | $R^{3b}$-B | $R^5$-D | $R^6$-G |
| E-15 | X-A | $R^2$-C | $R^{20}$-G | $R^3$-F | $R^{3a}$-F | $R^{3b}$-E | $R^5$-H | $R^6$-H |
| E-16 | X-A | $R^2$-C | $R^{20}$-E | $R^3$-D | $R^{3a}$-E | $R^{3b}$-F | $R^5$-H | $R^6$-G |
| E-17 | X-A | $R^2$-C | $R^{20}$-B | $R^3$-B | $R^{3a}$-H | $R^{3b}$-B | $R^5$-H | $R^6$-E |
| E-18 | X-A | $R^2$-D | $R^{20}$-D | $R^3$-C | $R^{3a}$-F | $R^{3b}$-G | $R^5$-E | $R^6$-C |
| E-19 | X-A | $R^2$-D | $R^{20}$-E | $R^3$-G | $R^{3a}$-E | $R^{3b}$-A | $R^5$-G | $R^6$-C |
| E-20 | X-B | $R^2$-D | $R^{20}$-E | $R^3$-G | $R^{3a}$-E | $R^{3b}$-G | $R^5$-G | $R^6$-C |
| E-21 | X-A | $R^2$-D | $R^{20}$-J | $R^3$-H | $R^{3a}$-E | $R^{3b}$-H | $R^5$-H | $R^6$-D |
| E-22 | X-A | $R^2$-E | $R^{20}$-D | $R^3$-F | $R^{3a}$-D | $R^{3b}$-H | $R^5$-A | $R^6$-I |
| E-23 | X-A | $R^2$-E | $R^{20}$-D | $R^3$-F | $R^{3a}$-D | $R^{3b}$-H | $R^5$-A | $R^6$-A |
| E-24 | X-A | $R^2$-E | $R^{20}$-H | $R^3$-G | $R^{3a}$-H | $R^{3b}$-H | $R^5$-D | $R^6$-F |
| E-25 | X-A | $R^2$-E | $R^{20}$-H | $R^3$-G | $R^{3a}$-H | $R^{3b}$-H | $R^5$-E | $R^6$-G |
| E-26 | X-B | $R^2$-E | $R^{20}$-H | $R^3$-G | $R^{3a}$-H | $R^{3b}$-H | $R^5$-C | $R^6$-F |
| E-27 | X-C | $R^2$-E | $R^{20}$-H | $R^3$-A | $R^{3a}$-H | $R^{3b}$-H | $R^5$-D | $R^6$-F |
| E-28 | X-C | $R^2$-E | $R^{20}$-A | $R^3$-G | $R^{3a}$-H | $R^{3b}$-H | $R^5$-E | $R^6$-F |
| E-29 | X-A | $R^2$-F | $R^{20}$-C | $R^{20}$-I | $R^3$-H | $R^{3a}$-H | $R^{3b}$-H | $R^6$-G |
| E-30 | X-A | $R^2$-F | $R^{20}$-D | $R^3$-F | $R^{3a}$-D | $R^{3b}$-H | $R^5$-A | $R^6$-I |
| E-31 | X-A | $R^2$-F | $R^{20}$-J | $R^3$-B | $R^{3a}$-B | $R^{3b}$-G | $R^5$-A | $R^6$-E |
| E-32 | X-A | $R^2$-F | $R^{20}$-I | $R^3$-G | $R^{3a}$-H | $R^{3b}$-H | $R^5$-A | $R^6$-I |
| E-33 | X-A | $R^2$-F | $R^{20}$-B | $R^3$-E | $R^{3a}$-H | $R^{3b}$-C | $R^5$-B | $R^6$-G |
| E-34 | X-A | $R^2$-F | $R^{20}$-H | $R^3$-G | $R^{3a}$-H | $R^{3b}$-H | $R^5$-E | $R^6$-C |
| E-35 | X-A | $R^2$-F | $R^{20}$-H | $R^3$-H | $R^{3a}$-H | $R^{3b}$-H | $R^5$-F | $R^6$-D |
| E-36 | X-A | $R^2$-G | $R^{20}$-A | $R^3$-G | $R^{3a}$-H | $R^{3b}$-H | $R^5$-A | $R^6$-H |
| E-37 | X-A | $R^2$-G | $R^{20}$-H | $R^3$-G | $R^{3a}$-H | $R^{3b}$-H | $R^5$-C | $R^6$-H |
| E-38 | X-A | $R^2$-G | $R^{20}$-H | $R^3$-H | $R^{3a}$-H | $R^{3b}$-H | $R^5$-H | $R^6$-H |
| E-39 | X-A | $R^2$-G | $R^{20}$-I | $R^3$-G | $R^{3a}$-H | $R^{3b}$-H | $R^5$-H | $R^6$-I |
| E-40 | X-A | $R^2$-G | $R^{20}$-H | $R^3$-G | $R^{3a}$-H | $R^{3b}$-H | $R^5$-H | $R^6$-H |
| E-41 | X-A | $R^2$-G | $R^{20}$-H | $R^3$-H | $R^{3a}$-H | $R^{3b}$-H | $R^5$-F | $R^6$-I |
| E-42 | X-A | $R^2$-H | $R^{20}$-A | $R^3$-E | $R^{3a}$-A | $R^{3b}$-D | $R^5$-A | $R^6$-E |
| E-43 | X-A | $R^2$-H | $R^{20}$-F | $R^3$-A | $R^{3a}$-E | $R^{3b}$-B | $R^5$-B | $R^6$-F |
| E-44 | X-A | $R^2$-H | $R^{20}$-B | $R^3$-F | $R^{3a}$-C | $R^{3b}$-H | $R^5$-C | $R^6$-G |
| E-45 | X-A | $R^2$-H | $R^{20}$-F | $R^3$-B | $R^{3a}$-G | $R^{3b}$-F | $R^5$-D | $R^6$-A |
| E-46 | X-A | $R^2$-H | $R^{20}$-D | $R^3$-F | $R^{3a}$-H | $R^{3b}$-H | $R^5$-H | $R^6$-G |

-continued

| Embodiment | X | $R^2$ | $R^{20}$ | $R^3$ | $R^{3a}$ | $R^{3b}$ | $R^5$ | $R^6$ |
|---|---|---|---|---|---|---|---|---|
| E-47 | X-A | $R^2$-H | $R^{20}$-H | $R^3$-G | $R^{3a}$-H | $R^{3b}$-H | $R^5$-H | $R^6$-E |
| E-48 | X-A | $R^2$-H | $R^{20}$-H | $R^3$-G | $R^{3a}$-H | $R^{3b}$-H | $R^5$-H | $R^6$-F |
| E-49 | X-A | $R^2$-I | $R^{20}$-I | $R^3$-H | $R^{3a}$-H | $R^{3b}$-H | $R^5$-A | $R^6$-G |
| E-50 | X-A | $R^2$-I | $R^{20}$-B | $R^3$-E | $R^{3a}$-H | $R^{3b}$-C | $R^5$-B | $R^6$-G |
| E-51 | X-A | $R^2$-I | $R^{20}$-J | $R^3$-B | $R^{3a}$-B | $R^{3b}$-G | $R^5$-H | $R^6$-E |
| E-52 | X-A | $R^2$-J | $R^{20}$-D | $R^3$-F | $R^{3a}$-D | $R^{3b}$-H | $R^5$-A | $R^6$-I |
| E-53 | X-A | $R^2$-J | $R^{20}$-H | $R^3$-H | $R^{3a}$-H | $R^{3b}$-H | $R^5$-A | $R^6$-H |
| E-54 | X-A | $R^2$-J | $R^{20}$-H | $R^3$-G | $R^{3a}$-H | $R^{3b}$-H | $R^5$-B | $R^6$-H |
| E-55 | X-A | $R^2$-J | $R^{20}$-F | $R^3$-A | $R^{3a}$-E | $R^{3b}$-B | $R^5$-B | $R^6$-F |
| E-56 | X-C | $R^2$-J | $R^{20}$-H | $R^3$-H | $R^{3a}$-H | $R^{3b}$-H | $R^5$-C | $R^6$-H |
| E-57 | X-A | $R^2$-J | $R^{20}$-H | $R^3$-G | $R^{3a}$-D | $R^{3b}$-H | $R^5$-H | $R^6$-A |
| E-58 | X-A | $R^2$-J | $R^{20}$-I | $R^3$-G | $R^{3a}$-H | $R^{3b}$-H | $R^5$-H | $R^6$-I |
| E-59 | X-B | $R^2$-J | $R^{20}$-H | $R^3$-G | $R^{3a}$-D | $R^{3b}$-H | $R^5$-H | $R^6$-A |
| E-60 | X-A | $R^2$-K | $R^{20}$-A | $R^3$-E | $R^{3a}$-A | $R^{3b}$-D | $R^5$-A | $R^6$-G |
| E-61 | X-B | $R^2$-K | $R^{20}$-A | $R^3$-E | $R^{3a}$-A | $R^{3b}$-D | $R^5$-A | $R^6$-E |
| E-62 | X-A | $R^2$-K | $R^{20}$-F | $R^3$-A | $R^{3a}$-C | $R^{3b}$-B | $R^5$-B | $R^6$-F |
| E-63 | X-A | $R^2$-K | $R^{20}$-B | $R^3$-D | $R^{3a}$-C | $R^{3b}$-H | $R^5$-C | $R^6$-G |
| E-64 | X-C | $R^2$-K | $R^{20}$-F | $R^3$-C | $R^{3a}$-G | $R^{3b}$-F | $R^5$-D | $R^6$-A |
| E-65 | X-A | $R^2$-K | $R^{20}$-F | $R^3$-B | $R^{3a}$-G | $R^{3b}$-F | $R^5$-F | $R^6$-A |
| E-66 | X-A | $R^2$-K | $R^{20}$-A | $R^3$-G | $R^{3a}$-H | $R^{3b}$-H | $R^5$-H | $R^6$-D |
| E-67 | X-A | $R^2$-K | $R^{20}$-H | $R^3$-H | $R^{3a}$-H | $R^{3b}$-H | $R^5$-A | $R^6$-I |
| E-68 | X-A | $R^2$-K | $R^{20}$-B | $R^3$-E | $R^{3a}$-H | $R^{3b}$-D | $R^5$-C | $R^6$-A |
| E-69 | X-A | $R^2$-L | $R^{20}$-A | $R^3$-C | $R^{3a}$-H | $R^{3b}$-F | $R^5$-C | $R^6$-G |
| E-70 | X-A | $R^2$-L | $R^{20}$-D | $R^3$-D | $R^{3a}$-D | $R^{3b}$-H | $R^5$-C | $R^6$-A |
| E-71 | X-C | $R^2$-L | $R^{20}$-A | $R^3$-C | $R^{3a}$-H | $R^{3b}$-F | $R^5$-C | $R^6$-G |
| E-72 | X-A | $R^2$-L | $R^{20}$-G | $R^3$-G | $R^{3a}$-A | $R^{3b}$-E | $R^5$-H | $R^6$-E |
| E-73 | X-A | $R^2$-L | $R^{20}$-H | $R^3$-G | $R^{3a}$-H | $R^{3b}$-H | $R^5$-H | $R^6$-H |
| E-74 | X-A | $R^2$-L | $R^{20}$-G | $R^3$-G | $R^{3a}$-E | $R^{3b}$-H | $R^5$-H | $R^6$-I |
| E-75 | X-A | $R^2$-M | $R^{20}$-D | $R^3$-F | $R^{3a}$-D | $R^{3b}$-H | $R^5$-A | $R^6$-I |
| E-76 | X-A | $R^2$-M | $R^{20}$-B | $R^3$-E | $R^{3a}$-H | $R^{3b}$-C | $R^5$-B | $R^6$-G |
| E-77 | X-A | $R^2$-M | $R^{20}$-J | $R^3$-D | $R^{3a}$-B | $R^{3b}$-G | $R^5$-H | $R^6$-E |
| E-78 | X-A | $R^2$-M | $R^{20}$-A | $R^3$-G | $R^{3a}$-H | $R^{3b}$-H | $R^5$-D | $R^6$-H |
| E-79 | X-A | $R^2$-M | $R^{20}$-H | $R^3$-H | $R^{3a}$-H | $R^{3b}$-H | $R^5$-E | $R^6$-I |
| E-80 | X-A | $R^2$-M | $R^{20}$-J | $R^3$-A | $R^{3a}$-F | $R^{3b}$-A | $R^5$-F | $R^6$-F |
| E-81 | X-B | $R^2$-M | $R^{20}$-I | $R^3$-A | $R^{3a}$-F | $R^{3b}$-A | $R^5$-F | $R^6$-F |
| E-82 | X-C | $R^2$-M | $R^{20}$-I | $R^3$-A | $R^{3a}$-F | $R^{3b}$-A | $R^5$-F | $R^6$-F |
| E-83 | X-A | $R^2$-N | $R^{20}$-D | $R^3$-F | $R^{3a}$-D | $R^{3b}$-H | $R^5$-A | $R^6$-A |
| E-84 | X-A | $R^2$-N | $R^{20}$-A | $R^3$-E | $R^{3a}$-A | $R^{3b}$-D | $R^5$-A | $R^6$-E |
| E-85 | X-A | $R^2$-N | $R^{20}$-C | $R^3$-C | $R^{3a}$-H | $R^{3b}$-F | $R^5$-C | $R^6$-F |
| E-86 | X-A | $R^2$-N | $R^{20}$-F | $R^3$-B | $R^{3a}$-G | $R^{3b}$-F | $R^5$-D | $R^6$-A |
| E-87 | X-A | $R^2$-N | $R^{20}$-G | $R^3$-G | $R^{3a}$-A | $R^{3b}$-C | $R^5$-H | $R^6$-A |
| E-88 | X-A | $R^2$-N | $R^{20}$-H | $R^3$-G | $R^{3a}$-H | $R^{3b}$-H | $R^5$-F | $R^6$-B |
| E-89 | X-A | $R^2$-N | $R^{20}$-J | $R^3$-G | $R^{3a}$-H | $R^{3b}$-H | $R^5$-F | $R^6$-I |
| E-90 | X-A | $R^2$-O | $R^{20}$-A | $R^3$-E | $R^{3a}$-A | $R^{3b}$-D | $R^5$-A | $R^6$-E |
| E-91 | X-A | $R^2$-O | $R^{20}$-F | $R^3$-A | $R^{3a}$-E | $R^{3b}$-B | $R^5$-B | $R^6$-F |
| E-92 | X-A | $R^2$-O | $R^{20}$-B | $R^3$-F | $R^{3a}$-C | $R^{3b}$-H | $R^5$-C | $R^6$-G |
| E-93 | X-A | $R^2$-O | $R^{20}$-C | $R^3$-C | $R^{3a}$-H | $R^{3b}$-F | $R^5$-C | $R^6$-F |
| E-94 | X-A | $R^2$-O | $R^{20}$-D | $R^3$-D | $R^{3a}$-D | $R^{3b}$-H | $R^5$-C | $R^6$-A |
| E-95 | X-A | $R^2$-O | $R^{20}$-F | $R^3$-B | $R^{3a}$-G | $R^{3b}$-F | $R^5$-D | $R^6$-A |
| E-96 | X-A | $R^2$-O | $R^{20}$-G | $R^3$-G | $R^{3a}$-A | $R^{3b}$-C | $R^5$-H | $R^6$-E |
| E-97 | X-A | $R^2$-O | $R^{20}$-H | $R^3$-G | $R^{3a}$-H | $R^{3b}$-H | $R^5$-H | $R^6$-H |
| E-98 | X-A | $R^2$-O | $R^{20}$-H | $R^3$-H | $R^{3a}$-H | $R^{3b}$-H | $R^5$-H | $R^6$-H |
| E-99 | X-A | $R^2$-O | $R^{20}$-I | $R^3$-G | $R^{3a}$-H | $R^{3b}$-H | $R^5$-H | $R^6$-H |
| E-100 | X-A | $R^2$-O | $R^{20}$-I | $R^3$-H | $R^{3a}$-H | $R^{3b}$-H | $R^5$-H | $R^6$-H |
| E-101 | X-A | $R^2$-O | $R^{20}$-J | $R^3$-G | $R^{3a}$-H | $R^{3b}$-H | $R^5$-A | $R^6$-H |
| E-102 | X-A | $R^2$-O | $R^{20}$-J | $R^3$-H | $R^{3a}$-H | $R^{3b}$-H | $R^5$-C | $R^6$-H |
| E-103 | X-A | $R^2$-O | $R^{20}$-H | $R^3$-G | $R^{3a}$-H | $R^{3b}$-H | $R^5$-D | $R^6$-F |
| E-104 | X-A | $R^2$-O | $R^{20}$-H | $R^3$-G | $R^{3a}$-H | $R^{3b}$-H | $R^5$-E | $R^6$-G |
| E-105 | X-A | $R^2$-O | $R^{20}$-H | $R^3$-G | $R^{3a}$-H | $R^{3b}$-H | $R^5$-F | $R^6$-I |
| E-106 | X-A | $R^2$-O | $R^{20}$-I | $R^3$-G | $R^{3a}$-H | $R^{3b}$-H | $R^5$-F | $R^6$-F |
| E-107 | X-A | $R^2$-O | $R^{20}$-I | $R^3$-G | $R^{3a}$-H | $R^{3b}$-H | $R^5$-F | $R^6$-G |
| E-108 | X-A | $R^2$-O | $R^{20}$-I | $R^3$-G | $R^{3a}$-H | $R^{3b}$-H | $R^5$-F | $R^6$-I |
| E-109 | X-A | $R^2$-O | $R^{20}$-J | $R^3$-G | $R^{3a}$-H | $R^{3b}$-H | $R^5$-H | $R^6$-F |
| E-110 | X-A | $R^2$-O | $R^{20}$-J | $R^3$-G | $R^{3a}$-H | $R^{3b}$-H | $R^5$-H | $R^6$-G |
| E-111 | X-A | $R^2$-O | $R^{20}$-J | $R^3$-G | $R^{3a}$-H | $R^{3b}$-H | $R^5$-H | $R^6$-I |
| E-112 | X-A | $R^2$-O | $R^{20}$-H | $R^3$-G | $R^{3a}$-H | $R^{3b}$-H | $R^5$-A | $R^6$-H |
| E-113 | X-A | $R^2$-P | $R^{20}$-A | $R^3$-E | $R^{3a}$-A | $R^{3b}$-D | $R^5$-A | $R^6$-E |
| E-114 | X-A | $R^2$-P | $R^{20}$-F | $R^3$-A | $R^{3a}$-E | $R^{3b}$-B | $R^5$-B | $R^6$-F |
| E-115 | X-A | $R^2$-P | $R^{20}$-B | $R^3$-F | $R^{3a}$-C | $R^{3b}$-H | $R^5$-C | $R^6$-G |
| E-116 | X-A | $R^2$-P | $R^{20}$-C | $R^3$-C | $R^{3a}$-H | $R^{3b}$-F | $R^5$-C | $R^6$-F |
| E-117 | X-A | $R^2$-P | $R^{20}$-D | $R^3$-D | $R^{3a}$-D | $R^{3b}$-H | $R^5$-C | $R^6$-A |
| E-118 | X-B | $R^2$-P | $R^{20}$-C | $R^3$-C | $R^{3a}$-H | $R^{3b}$-F | $R^5$-C | $R^6$-F |
| E-119 | X-B | $R^2$-P | $R^{20}$-C | $R^3$-C | $R^{3a}$-H | $R^{3b}$-F | $R^5$-C | $R^6$-E |
| E-120 | X-A | $R^2$-P | $R^{20}$-F | $R^3$-B | $R^{3a}$-G | $R^{3b}$-F | $R^5$-D | $R^6$-A |
| E-121 | X-A | $R^2$-P | $R^{20}$-G | $R^3$-G | $R^{3a}$-A | $R^{3b}$-C | $R^5$-H | $R^6$-E |
| E-122 | X-A | $R^2$-P | $R^{20}$-H | $R^3$-G | $R^{3a}$-H | $R^{3b}$-H | $R^5$-C | $R^6$-H |
| E-123 | X-A | $R^2$-P | $R^{20}$-H | $R^3$-H | $R^{3a}$-H | $R^{3b}$-H | $R^5$-D | $R^6$-H |
| E-124 | X-A | $R^2$-P | $R^{20}$-I | $R^3$-G | $R^{3a}$-H | $R^{3b}$-H | $R^5$-E | $R^6$-H |

-continued

| Embodiment | X | $R^2$ | $R^{20}$ | $R^3$ | $R^{3a}$ | $R^{3b}$ | $R^5$ | $R^6$ |
|---|---|---|---|---|---|---|---|---|
| E-125 | X-A | $R^2$-P | $R^{20}$-I | $R^3$-G | $R^{3a}$-H | $R^{3b}$-H | $R^5$-F | $R^6$-I |
| E-126 | X-A | $R^2$-P | $R^{20}$-J | $R^3$-G | $R^{3a}$-H | $R^{3b}$-H | $R^5$-F | $R^6$-F |
| E-127 | X-A | $R^2$-P | $R^{20}$-J | $R^3$-G | $R^{3a}$-H | $R^{3b}$-H | $R^5$-F | $R^6$-G |
| E-128 | X-A | $R^2$-P | $R^{20}$-J | $R^3$-G | $R^{3a}$-H | $R^{3b}$-H | $R^5$-F | $R^6$-I |
| E-129 | X-A | $R^2$-P | $R^{20}$-H | $R^3$-G | $R^{3a}$-H | $R^{3b}$-H | $R^5$-F | $R^6$-H |
| E-130 | X-A | $R^2$-Q | $R^{20}$-A | $R^3$-E | $R^{3a}$-A | $R^{3b}$-D | $R^5$-A | $R^6$-E |
| E-131 | X-A | $R^2$-Q | $R^{20}$-F | $R^3$-A | $R^{3a}$-E | $R^{3b}$-B | $R^5$-B | $R^6$-F |
| E-132 | X-A | $R^2$-Q | $R^{20}$-B | $R^3$-F | $R^{3a}$-C | $R^{3b}$-H | $R^5$-C | $R^6$-G |
| E-133 | X-A | $R^2$-Q | $R^{20}$-C | $R^3$-C | $R^{3a}$-H | $R^{3b}$-F | $R^5$-C | $R^6$-F |
| E-134 | X-A | $R^2$-Q | $R^{20}$-D | $R^3$-D | $R^{3a}$-D | $R^{3b}$-H | $R^5$-C | $R^6$-A |
| E-135 | X-A | $R^2$-Q | $R^{20}$-F | $R^3$-B | $R^{3a}$-G | $R^{3b}$-F | $R^5$-D | $R^6$-A |
| E-136 | X-A | $R^2$-Q | $R^{20}$-H | $R^3$-B | $R^{3a}$-B | $R^{3b}$-B | $R^5$-E | $R^6$-I |
| E-137 | X-A | $R^2$-Q | $R^{20}$-G | $R^3$-G | $R^{3a}$-A | $R^{3b}$-C | $R^5$-H | $R^6$-E |
| E-138 | X-A | $R^2$-Q | $R^{20}$-H | $R^3$-A | $R^{3a}$-A | $R^{3b}$-C | $R^5$-H | $R^6$-G |
| E-139 | X-A | $R^2$-Q | $R^{20}$-I | $R^3$-D | $R^{3a}$-D | $R^{3b}$-H | $R^5$-H | $R^6$-H |
| E-140 | X-A | $R^2$-Q | $R^{20}$-I | $R^3$-E | $R^{3a}$-E | $R^{3b}$-F | $R^5$-H | $R^6$-K |
| E-141 | X-A | $R^2$-Q | $R^{20}$-H | $R^3$-G | $R^{3a}$-H | $R^{3b}$-H | $R^5$-F | $R^6$-H |
| E-142 | X-A | $R^2$-Q | $R^{20}$-H | $R^3$-H | $R^{3a}$-H | $R^{3b}$-H | $R^5$-F | $R^6$-H |
| E-143 | X-A | $R^2$-Q | $R^{20}$-I | $R^3$-G | $R^{3a}$-H | $R^{3b}$-H | $R^5$-F | $R^6$-H |
| E-144 | X-A | $R^2$-Q | $R^{20}$-I | $R^3$-H | $R^{3a}$-H | $R^{3b}$-H | $R^5$-F | $R^6$-H |
| E-145 | X-A | $R^2$-Q | $R^{20}$-J | $R^3$-G | $R^{3a}$-H | $R^{3b}$-H | $R^5$-E | $R^6$-H |
| E-146 | X-A | $R^2$-Q | $R^{20}$-J | $R^3$-H | $R^{3a}$-H | $R^{3b}$-H | $R^5$-E | $R^6$-H |
| E-147 | X-A | $R^2$-Q | $R^{20}$-H | $R^3$-G | $R^{3a}$-H | $R^{3b}$-H | $R^5$-E | $R^6$-F |
| E-148 | X-A | $R^2$-Q | $R^{20}$-H | $R^3$-G | $R^{3a}$-H | $R^{3b}$-H | $R^5$-E | $R^6$-G |
| E-149 | X-A | $R^2$-Q | $R^{20}$-H | $R^3$-G | $R^{3a}$-H | $R^{3b}$-H | $R^5$-E | $R^6$-I |
| E-150 | X-A | $R^2$-Q | $R^{20}$-I | $R^3$-G | $R^{3a}$-H | $R^{3b}$-H | $R^5$-D | $R^6$-F |
| E-151 | X-A | $R^2$-Q | $R^{20}$-I | $R^3$-G | $R^{3a}$-H | $R^{3b}$-H | $R^5$-D | $R^6$-G |
| E-152 | X-A | $R^2$-Q | $R^{20}$-I | $R^3$-G | $R^{3a}$-H | $R^{3b}$-H | $R^5$-D | $R^6$-I |
| E-153 | X-A | $R^2$-Q | $R^{20}$-J | $R^3$-G | $R^{3a}$-H | $R^{3b}$-H | $R^5$-H | $R^6$-F |
| E-154 | X-A | $R^2$-Q | $R^{20}$-J | $R^3$-G | $R^{3a}$-H | $R^{3b}$-H | $R^5$-H | $R^6$-G |
| E-155 | X-A | $R^2$-Q | $R^{20}$-J | $R^3$-G | $R^{3a}$-H | $R^{3b}$-H | $R^5$-H | $R^6$-I |
| E-156 | X-B | $R^2$-Q | $R^{20}$-H | $R^3$-H | $R^{3a}$-H | $R^{3b}$-H | $R^5$-H | $R^6$-H |
| E-157 | X-B | $R^2$-Q | $R^{20}$-I | $R^3$-G | $R^{3a}$-H | $R^{3b}$-H | $R^5$-H | $R^6$-H |
| E-158 | X-B | $R^2$-Q | $R^{20}$-I | $R^3$-H | $R^{3a}$-H | $R^{3b}$-H | $R^5$-H | $R^6$-H |
| E-159 | X-B | $R^2$-Q | $R^{20}$-J | $R^3$-G | $R^{3a}$-H | $R^{3b}$-H | $R^5$-H | $R^6$-H |
| E-160 | X-C | $R^2$-Q | $R^{20}$-H | $R^3$-H | $R^{3a}$-H | $R^{3b}$-H | $R^5$-G | $R^6$-H |
| E-161 | X-C | $R^2$-Q | $R^{20}$-I | $R^3$-G | $R^{3a}$-H | $R^{3b}$-H | $R^5$-G | $R^6$-H |
| E-162 | X-C | $R^2$-Q | $R^{20}$-I | $R^3$-H | $R^{3a}$-H | $R^{3b}$-H | $R^5$-G | $R^6$-H |
| E-163 | X-C | $R^2$-Q | $R^{20}$-J | $R^3$-G | $R^{3a}$-H | $R^{3b}$-H | $R^5$-G | $R^6$-H |
| E-164 | X-B | $R^2$-Q | $R^{20}$-A | $R^3$-G | $R^{3a}$-H | $R^{3b}$-H | $R^5$-G | $R^6$-H |
| E-165 | X-B | $R^2$-Q | $R^{20}$-H | $R^3$-G | $R^{3a}$-H | $R^{3b}$-H | $R^5$-G | $R^6$-H |

Examples of most preferred compounds according to this invention are each single compound listed in the following Tables 1 and 4.

In general, all tautomeric and isomeric forms and mixtures thereof, for example, individual geometric isomers, stereoisomers, atropisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure. Compounds of the invention that contain asymmetrically substituted carbon atoms can be isolated in optically active or racemic forms.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000, herein incorporated by reference. Furthermore, there are equally well-known methods for the quantitation of enantiomeric excess or purity, for example, GC, HPLC, CE, or NMR, and assignment of absolute configuration and conformation, for example, CD, ORD, X-ray crystallography, or NMR.

The compounds according to the present invention are inhibitors of the hepatitis C virus NS5B RNA-dependent RNA polymerase and thus may be used to inhibit replication of hepatitis C viral RNA.

A compound according to the present invention may also be used as a laboratory reagent or a research reagent. For example, a compound of the present invention may be used as positive control to validate assays, including but not limited to surrogate cell-based assays and in vitro or in vivo viral replication assays.

Compounds according to the present invention may also be used as probes to study the hepatitis C virus NS5B polymerase, including but not limited to the mechanism of action of the polymerase, conformational changes undergone by the polymerase under various conditions and interactions with entities which bind to or otherwise interact with the polymerase.

Compounds of the invention used as probes may be labelled with a label which allows recognition either directly or indirectly of the compound such that it can be detected, measured and quantified. Labels contemplated for use with the compounds of the invention include, but are not limited to, fluorescent labels, chemiluminescent labels, colorimetric labels, enzymatic markers, radioactive isotopes, affinity tags and photoreactive groups.

Compounds of the invention used as probes may also be labelled with an affinity tag whose strong affinity for a receptor can be used to extract from a solution the entity to which the ligand is attached. Affinity tags include but are not limited to biotin or a derivative thereof, a histidine polypeptide, a polyarginine, an amylose sugar moiety or a defined epitope recognizable by a specific antibody.

Furthermore, compounds of the invention used as probes may be labelled with a photoreactive group which is transformed, upon activation by light, from an inert group to a reactive species, such as a free radical. Photoreactive groups include but are not limited to photoaffinity labels such as benzophenone and azide groups.

Furthermore, a compound according to the present invention may be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

Pharmaceutical Composition

Compounds of the present invention may be administered to a mammal in need of treatment for hepatitis C viral infection as a pharmaceutical composition comprising a therapeutically effective amount of a compound according to the invention or a pharmaceutically acceptable salt or ester thereof; and one or more conventional non-toxic pharmaceutically-acceptable carriers, adjuvants or vehicles. The specific formulation of the composition is determined by the solubility and chemical nature of the compound, the chosen route of administration and standard pharmaceutical practice. The pharmaceutical composition according to the present invention may be administered orally or systemically.

For oral administration, the compound, or a pharmaceutically acceptable salt or ester thereof, can be formulated in any orally acceptable dosage form including but not limited to aqueous suspensions and solutions, capsules, powders, syrups, elixirs or tablets. For systemic administration, including but not limited to administration by subcutaneous, intracutaneous, intravenous, intramuscular, intra-articular, intrasynovial, intrasternal, intrathecal, and intralesional injection or infusion techniques, it is preferred to use a solution of the compound, or a pharmaceutically acceptable salt or ester thereof, in a pharmaceutically acceptable sterile aqueous vehicle.

Pharmaceutically acceptable carriers, adjuvants, vehicles, excipients and additives as well as methods of formulating pharmaceutical compositions for various modes of administration are well-known to those of skill in the art and are described in pharmaceutical texts such as Remington: The Science and Practice of Pharmacy, 21st Edition, Lippincott Williams & Wilkins, 2005; and L. V. Allen, N. G. Popovish and N. C. Ansel, Pharmaceutical Dosage Forms and Drug Delivery Systems, 8th ed., Lippincott Williams & Wilkins, 2004, herein incorporated by reference.

The dosage administered will vary depending upon known factors, including but not limited to the activity and pharmacodynamic characteristics of the specific compound employed and its mode, time and route of administration; the age, diet, gender, body weight and general health status of the recipient; the nature and extent of the symptoms; the severity and course of the infection; the kind of concurrent treatment; the frequency of treatment; the effect desired; and the judgment of the treating physician. In general, the compound is most desirably administered at a dosage level that will generally afford antivirally effective results without causing any harmful or deleterious side effects.

A daily dosage of active ingredient can be expected to be about 0.01 to about 200 milligrams per kilogram of body weight, with the preferred dose being about 0.1 to about 50 mg/kg. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Combination Therapy

Combination therapy is contemplated wherein a compound according to the invention, or a pharmaceutically acceptable salt or ester thereof, is co-administered with at least one additional antiviral agent. The additional agents may be combined with compounds of this invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt or ester thereof, and one or more additional antiviral agent, both the compound and the additional agent should be present at dosage levels of between about 10 to 100%, and more preferably between about 10 and 80% of the dosage normally administered in a monotherapy regimen. In the case of a synergistic interaction between the compound of the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, α-, β-, δ-, ω-, and τ-interferons, while examples of class II interferons include, but are not limited to, γ-interferons. In one preferred aspect, the other anti-HCV agent is an interferon. Preferably, the interferon is selected from the group consisting of interferon alpha 2B, pegylated interferon alpha, consensus interferon, interferon alpha 2A and lymphoblastoid interferon. In one preferred aspect, the composition comprises a compound of the invention, an interferon and ribavirin.

Inhibitors of HCV NS3 protease include agents (compounds or biologicals) that are effective to inhibit the function of HCV NS3 protease in a mammal. Inhibitors of HCV NS3 protease include, for example, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700, WO 2006/007708, WO 2007/009227 (all by Boehringer Ingelheim), WO 02/060926, WO 03/053349, WO 03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune), WO 01/77113, WO 01/81325, WO 02/08187, WO 02/08198, WO 02/08244, WO 02/08256, WO 02/48172, WO 03/062228, WO 03/062265, WO 2005/021584, WO 2005/030796, WO 2005/058821, WO 2005/051980, WO 2005/085197, WO 2005/085242, WO 2005/085275, WO 2005/087721, WO 2005/087725, WO 2005/087730, WO 2005/087731, WO 2005/107745 and WO 2005/113581 (all by Schering), WO 2006/119061, WO 2007/016441, WO 2007/015855, WO 2007/015787 (all by Merck), WO 2006/043145 (Pfizer), all of which are herein incorporated by reference; and the candidates VX-950, SCH-503034, ITMN-191, TMC 435350, and MK7009.

Inhibitors of HCV polymerase include agents (compounds or biologicals) that are effective to inhibit the function of an HCV polymerase. Such inhibitors include, but are not limited to, non-nucleoside and nucleoside inhibitors of NS4A, NS5A, NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388, WO 2006/007693, WO 2007/019674, WO 2007/087717 (all by Boehringer Ingelheim), WO 01/47883 (Japan Tobacco), WO 03/000254 (Japan Tobacco), WO 2007/033032, WO 2007/033175, WO 2006/020082, US 2005/ 0119318, WO 2005/034850, WO 03/026587, WO 2007/092000, WO 2007/143521, WO 2007/136982, WO 2007/140254, WO 2007/140200, WO 2007/092888 (all by BMS), WO 2007/095269, WO 2007/054741, WO 03/062211, WO 99/64442, WO 00/06529, WO 2004/110442, WO 2005/034941, WO 2006/119975, WO 2006/046030, WO 2006/046039, WO 2005/023819, WO 02/06246, WO 2007/065883, WO 2007/129119, WO 2007/029029, WO 2006/029912, WO 2006/027628, WO 2007/028789, WO 2006/008556, WO 2004/087714 (all by IRBM), WO 2005/012288 (Genelabs), WO 2005/014543 (Japan Tobacco), WO 2005/049622 (Japan Tobacco), and WO 2005/121132 (Shionogi), WO 2005/080399 (Japan Tobacco), WO 2006/052013 (Japan Tobacco), WO 2006/119646 (Virochem Pharma), WO 2007/039146 (SmithKline Beecham), WO 2005/021568 (Biota), WO 2006/094347 (Biota), WO 2006/093801, WO 2005/019191, WO 2004/041818, US 2004/0167123, US 2005/0107364 (all by Abbott Laboratories), WO 2007/034127 (Arrow Therapeutics Limited) (all of which are herein incorporated by reference) and the candidates HCV 796 (ViroPharma/Wyeth), R-1626, R-1656 and R-7128 (Roche), NM 283 (Idenix/Novartis), VCH-759 (Virochem), GS9190 (Gilead), MK-608 (Merck) and PF868554 (Pfizer).

The term "inhibitor of another target in the HCV life cycle" as used herein means an agent (compound or biological) that is effective to inhibit the formation and/or replication of HCV in a mammal other than by inhibiting the function HCV polymerase. This includes agents that interfere with either host or HCV viral targets necessary for the HCV life cycle or agents which specifically inhibit in HCV cell culture assays through an undefined or incompletely defined mechanism. Inhibitors of another target in the HCV life cycle include, for example, agents that inhibit viral targets such as Core, E1, E2, p7, NS2/3 protease, NS3 helicase, internal ribosome entry site (IRES), HCV entry and HCV assembly or host targets such as cyclophilin B, phosphatidylinositol 4-kinase IIIα, CD81, SR-B1, Claudin 1, VAP-A, VAP-B. Specific examples of inhibitors of another target in the HCV life cycle include ISIS-14803 (ISIS Pharmaceuticals), GS9190 (Gilead), GS9132 (Gilead), A-831 (AstraZeneca), NM-811 (Novartis), and DEBIO-025 (Debio Pharma).

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

HIV inhibitors include agents (compounds or biologicals) that are effective to inhibit the formation and/or replication of HIV. This includes but is not limited to agents that interfere with either host or viral mechanisms necessary for the formation and/or replication of HIV in a mammal. HIV inhibitors include, but are not limited to:

NRTIs (nucleoside or nucleotide reverse transcriptase inhibitors) including but not limited to zidovudine (AZT), didanosine (ddI), zalcitabine (ddC), stavudine (d4T), lamivudine (3TC), emtricitabine, abacavir succinate, elvucitabine, adefovir dipivoxil, lobucavir (BMS-180194) lodenosine (FddA) and tenofovir including tenofovir disoproxil and tenofovir disoproxil fumarate salt, COMBIVIR™ (contains 3TC and AZT), TRIZIVIR™ (contains abacavir, 3TC and AZT), TRUVADA™ (contains tenofovir and emtricitabine), EPZICOM™ (contains abacavir and 3TC);

NNRTIs (non-nucleoside reverse transcriptase inhibitors) including but not limited to nevirapine, delaviradine, efavirenz, etravirine and rilpivirine;
protease inhibitors including but not limited to ritonavir, tipranavir, saquinavir, nelfinavir, indinavir, amprenavir, fosamprenavir, atazanavir, lopinavir, darunavir, lasinavir, brecanavir, VX-385 and TMC-114;
entry inhibitors including but not limited to
  CCR5 antagonists (including but not limited to maraviroc, vicriviroc, INCB9471 and TAK-652),
  CXCR4 antagonists (including but not limited to AMD-11070),
  fusion inhibitors (including but not limited to enfuvirtide (T-20), TR1-1144 and TR1-999) and
  others (including but not limited to BMS-488043);
integrase inhibitors (including but not limited to raltegravir (MK-0518), BMS-707035 and elvitegravir (GS 9137));
TAT inhibitors;
maturation inhibitors (including but not limited to berivimat (PA-457));
immunomodulating agents (including but not limited to levamisole); and
other antiviral agents including hydroxyurea, ribavirin, IL-2, IL-12 and pensafuside.

HAV inhibitors include agents (compounds or biologicals) that are effective to inhibit the formation and/or replication of HAV. This includes but is not limited to agents that interfere with either host or viral mechanisms necessary for the formation and/or replication of HAV in a mammal. HAV inhibitors include but are not limited to Hepatitis A vaccines.

HBV inhibitors include agents (compounds or biologicals) that are effective to inhibit the formation and/or replication of HBV in a mammal. This includes but is not limited to agents that interfere with either host or viral mechanisms necessary for the formation and/or replication of HBV in a mammal. HBV inhibitors include, but are not limited to, agents that inhibit the HBV viral DNA polymerase and HBV vaccines.

Therefore, according to one embodiment, the pharmaceutical composition of this invention additionally comprises a therapeutically effective amount of one or more antiviral agents.

A further embodiment provides the pharmaceutical composition of this invention wherein the one or more antiviral agent comprises at least one other anti-HCV agent.

According to a more specific embodiment of the pharmaceutical composition of this invention, the at least one other anti-HCV agent comprises at least one immunomodulatory agent.

According to another more specific embodiment of the pharmaceutical composition of this invention, the at least one other anti-HCV agent comprises at least one other inhibitor of HCV polymerase.

According to yet another more specific embodiment of the pharmaceutical composition of this invention, the at least one other anti-HCV agent comprises at least one inhibitor of HCV NS3 protease.

According to still another more specific embodiment of the pharmaceutical composition of this invention, the at least one other anti-HCV agent comprises at least one inhibitor of another target in the HCV life cycle.

EXAMPLES

Other features of the present invention will become apparent from the following non-limiting examples which illustrate, by way of example, the principles of the invention. As is well known to a person skilled in the art, reactions are performed in an inert atmosphere (including but not limited to nitrogen or argon) where necessary to protect reaction components from air or moisture. Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in Greene, "Protective Groups in Organic Chemistry", John Wiley & Sons, New York (1981), and more recent editions thereof, herein incorporated by reference. Temperatures are given in degrees Celsius (° C.). Solution percentages and ratios express a volume to volume relationship, unless stated otherwise. Flash chromatography is carried out on silica gel ($SiO_2$) according to the procedure of W. C. Still et al., J. Org. Chem., (1978), 43, 2923. Mass spectral analyses are recorded using electrospray mass spectrometry. Purification on a combiflash is performed using an Isco Combiflash (column cartridge $SiO_2$). Preparative HPLC is carried out under standard conditions using a SunFire™ Prep C18 OBD 5 µM reverse phase column, 19×50 mm and a linear gradient (20 to 98%) employing 0.1% TFA/acetonitrile and 0.1% TFA/water as solvents. Compounds are isolated as TFA salts when applicable. Analytical HPLC is carried out under standard conditions using a Combiscreen™ ODS-AQ C18 reverse phase column, YMC, 50×4.6 mm i.d., 5 µM, 120 Å at 220 nM, elution with a linear gradient as described in the following table (Solvent A is 0.06% TFA in $H_2O$; solvent B is 0.06% TFA in MeCN):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein include:
Ac: acetyl;
AcOH: acetic acid;
BINAP: (2,2'-Bis(diphenylphosphino)-1,1'-binaphthalene;
Bn: benzyl (phenylmethyl);
BOC or Boc: tert-butyloxycarbonyl;
Bu: butyl;
n-BuLi: n-butyllithium;
n-BuOAc: n-butylacetate;
m-CPBA: meta-chloroperbenzoic acid;
DBU: 1,8-diazabicyclo[5.4.0]undec-7-ene;
DCE: dichloroethane;
DCM: dichloromethane;
DEAD: diethyl azodicarboxylate;
DIAD: diisopropyl azodicarboxylate;
DIPEA: diisopropylethylamine;
DMAP: 4-dimethylaminopyridine;
DMF: N,N-dimethylformamide;
DMSO: dimethylsulfoxide;
$EC_{50}$: 50% effective concentration;
Et: ethyl;
$Et_3N$: triethylamine;
$Et_2O$: diethyl ether;
EtOAc: ethyl acetate;
EtOH: ethanol;
HATU: 2-(1H-7-Azabenzotriazol-1-yl)-1,1,3,3-tetramethyl uronium hexafluorophosphate Methanaminium;
Hex: hexane;
HPLC: high performance liquid chromatography;
$IC_{50}$: 50% inhibitory concentration;

$^i$Pr or i-Pr: 1-methylethyl (iso-propyl);
LC-MS: liquid chromatography-mass spectrometry;
LDA: lithium diisoproylamide;
Me: methyl;
MeCN: acetonitrile;
MeI: iodomethane;
MeOH: methanol;
MS: mass spectrometry (ES: electrospray);
NaHB(OAc)$_3$: sodium triacetoxyborohydride;
NaHMDS: sodium hexamethyldisilazane;
NIS: N-iodosuccinamide;
NMO: N-methylmorpholine-N-oxide;
NMP: N-methylpyrrolidone;
NMR: nuclear magnetic resonance spectroscopy;
Ph: phenyl;
Pr: n-propyl;
Psi: pounds per square inch;
Rpm: rotations per minute;
RT: room temperature (approximately 18° C. to 25° C.);
tert-butyl or t-butyl: 1,1-dimethylethyl;
tert-BuOH or t-BuOH: tert-butanol
TBABr: tetrabutylammonium bromide;
TBAF: tetrabutylammonium fluoride;
TBDPS: tert-butyldiphenylsilyloxy;
TFA: trifluoroacetic acid;
THF: tetrahydrofuran;
TLC: thin layer chromatography.

Example 1A

Preparation of Intermediate 1a10

Step 1:

1a1 (73 g, 35 mmol) is diluted in anhydrous THF (2 L) under Ar. Benzyl alcohol (80.8 mL, 800 mmol) is added and the mixture is chilled to 0° C. Sodium bis(trimethylsilyl) amide (1.0 M in THF, 800 mL, 800 mmol) is added dropwise. After stirring for about 1 h, the mixture is partitioned between saturated aqueous NH$_4$Cl and EtOAc. The organic phase is collected and dried over Na$_2$SO$_4$. The mixture is filtered and concentrated under reduced pressure. The resulting solid 1a2 is washed with cold EtOAc and dried.

Step 2:

Carboxylic acid 1a2 (112.8 g, 384 mmol) is diluted in anhydrous DMF (2 L). Potassium carbonate (108.1 g, 775 mmol) is added and the mixture is chilled to 0° C. Iodomethane (110 g, 775 mmol) is added dropwise and after about 2 h, the reaction is quenched by the addition of saturated aqueous NH$_4$Cl. The aqueous solution is extracted with EtOAc (2×). The combined organic extracts are washed with water and brine before being dried with MgSO$_4$. Removal of solvent results in methyl ester 1a3.

Step 3:

Step 3a:

The nitro intermediate 1a3 (63.8 g, 212 mmol) is diluted in THF (1 L). Aqueous HCl (1 M, 500 mL, 500 mmol) is added followed by tin powder (55 g, 46 mmol). The mixture is stirred for about 2 h at RT. The reaction mixture is diluted with EtOAc and the pH of the mixture is adjusted to approximately 7 by the addition of 1 N NaOH. The organic phase is separated, washed with water and brine, dried over Na$_2$SO$_4$ and solvent is removed to afford aniline.

Step 3b:

The aniline (97.1 g, 377 mmol) is combined with anhydrous Et$_2$O (1 L) and is then treated by the slow addition of HCl (2 M in ether, 2 L). The resulting hydrochloride salt 1a4 is collected by filtration and washed with excess ether.

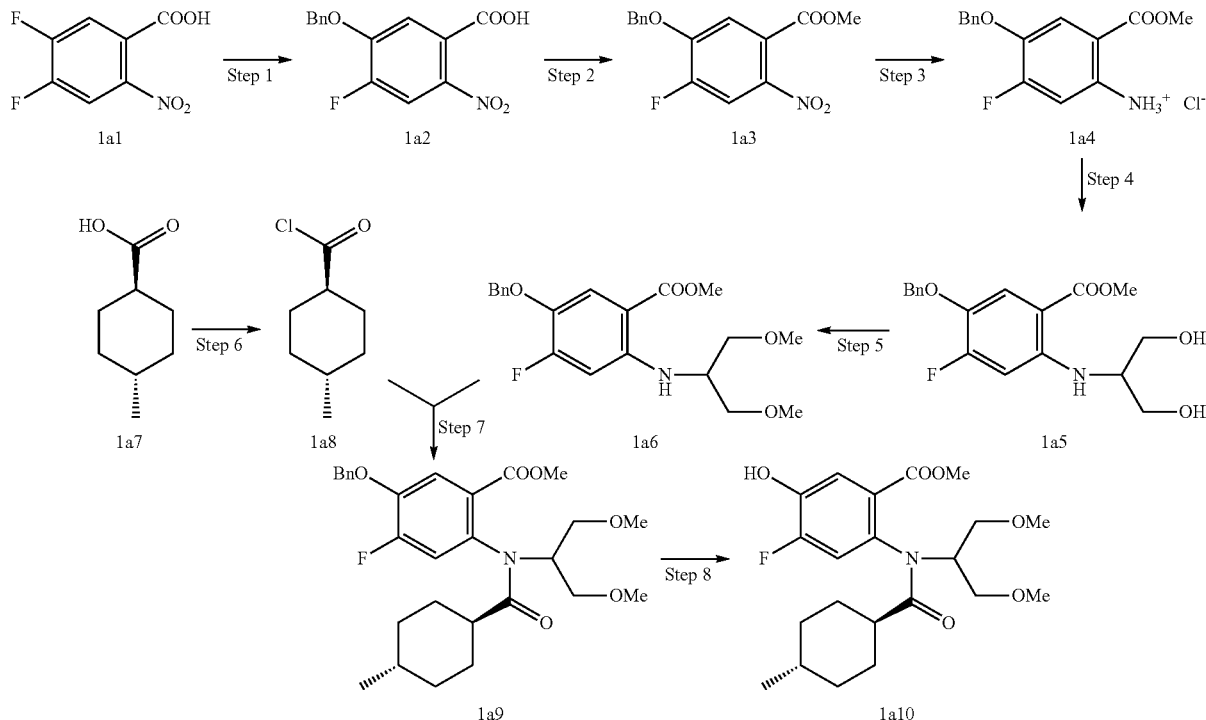

Step 4:

The aniline hydrochloride salt 1a4 (1.04 g, 3.33 mmol) and 1,3-dihydroxyacetone (1.84 g, 20.4 mmol) are combined in dry MeOH (40 mL). After stirring for about 15 min, where-upon the homogeneous solution turns vivid red, a solution of sodium cyanoborohydride (1.05 g, 16.7 mmol) pre-dissolved in MeOH (5 mL) is slowly added over about 5 min. The reaction is neutralized by slowly adding a saturated aqueous solution of NaHCO$_3$ (3 mL), then the mixture is concentrated to dryness. The remaining solid is purified by flash chromatography (2% to 5% MeOH gradient in DCM) to afford diol 1a5.

Step 5:

The diol 1a5 (1.89 g, 5.40 mmol) and methyl iodide (1.0 mL, 16.2 mmol) are dissolved in dry DMF (20 mL) and cooled to 0° C. A suspension of sodium hydride (60% w/w, 453 mg, 11.3 mmol) in DMF (5 mL) is slowly added over about 15 min and the reaction is stirred at RT. The reaction is neutralized at 0° C. by adding a saturated aqueous solution of NH$_4$Cl (10 mL). The mixture is diluted with EtOAc and the layers are separated. The organic layer is washed with water (2×) and brine (1×). The combined organic phases are dried over MgSO$_4$, filtered and concentrated under reduced pressure. Following purification by flash chromatography (10% to 25% EtOAc gradient in hexane), dimethoxy 1a6 is isolated.

Step 6:

To a mixture of compound 1a7 (43.4 g, 305 mmol) in anhydrous DCM (400 mL) under an Ar atmosphere is added oxalyl chloride (53.2 mL, 610 mmol) in DCM (305 mL) over about 1 h. The mixture is stirred for about 1 h at RT and anhydrous DMF (1 mL) is added dropwise. The mixture is stirred overnight at RT and concentrated under reduced pressure. The residue is diluted with pentane and filtered. The filtrate is concentrated under reduced pressure, diluted with pentane and filtered, then concentrated under reduced pressure to provide acid chloride 1a8.

Step 7:

The aniline 1a6 (1.25 g, 3.31 mmol) is combined with anhydrous pyridine (3 mL) and a catalytic amount of DMAP (121 mg, 0.99 mmol). A pre-mixed solution of acid chloride 1a8 (1.35 g, 8.40 mmol) in DCE (4.2 mL) is then added. The mixture is heated to 115° C. overnight, and then allowed to cool before being neutralized with a saturated aqueous solution of NaHCO$_3$. The mixture is extracted with EtOAc (3×). The combined organic phases are washed with brine, dried over MgSO$_4$ and concentrated under reduced pressure. The residue is purified by combiflash (EtOAc gradient in Hex) to yield amide 1a9.

Step 8:

Benzyl ether 1a9 (1.28 g, 2.55 mmol) is dissolved in MeOH (10 mL) and EtOAc (20 mL) and the mixture is purged with N$_2$ (2×). 10% Pd/C (20 mg) is added and the vessel is kept under an atmosphere of H$_2$ (balloon) for about 2 h. The mixture is then filtered through a pad of Celite® and rinsed with an excess MeOH. The filtrate is concentrated under reduced pressure and the residue is purified by flash chromatography (2% to 5% MeOH in DCM) to afford 1a10.

Example 1B

Preparation of Intermediate 1b8

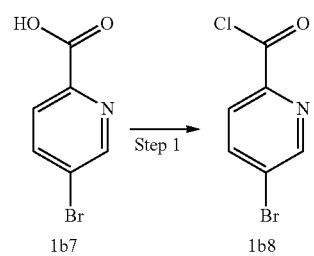 [SMILES: O=C(O)c1ccc(Br)cn1 ; O=C(Cl)c1ccc(Br)cn1]

Step 1:

Compound 1b7 is transformed to compound 1b8 using the procedure described in Example 1A, Step 6.

Example 1C

Preparation of Intermediate 1c8

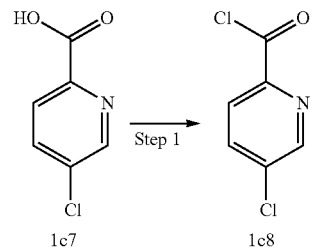 [SMILES: O=C(O)c1ccc(Cl)cn1 ; O=C(Cl)c1ccc(Cl)cn1]

Step 1:

Compound 1c7 is transformed to compound 1c8 using the procedure described in Example 1A, Step 6.

Example 1D

Preparation of Intermediate 1d8

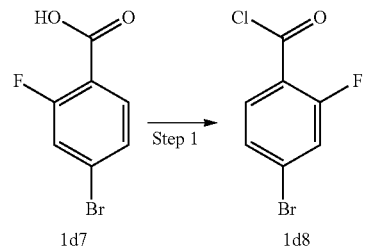 [SMILES: O=C(O)c1ccc(Br)cc1F ; O=C(Cl)c1ccc(Br)cc1F]

Step 1:

Compound 1d7 is transformed to compound 1d8 using the procedure described in Example 1A, Step 6.

Example 2A

Preparation of Intermediate 2a5

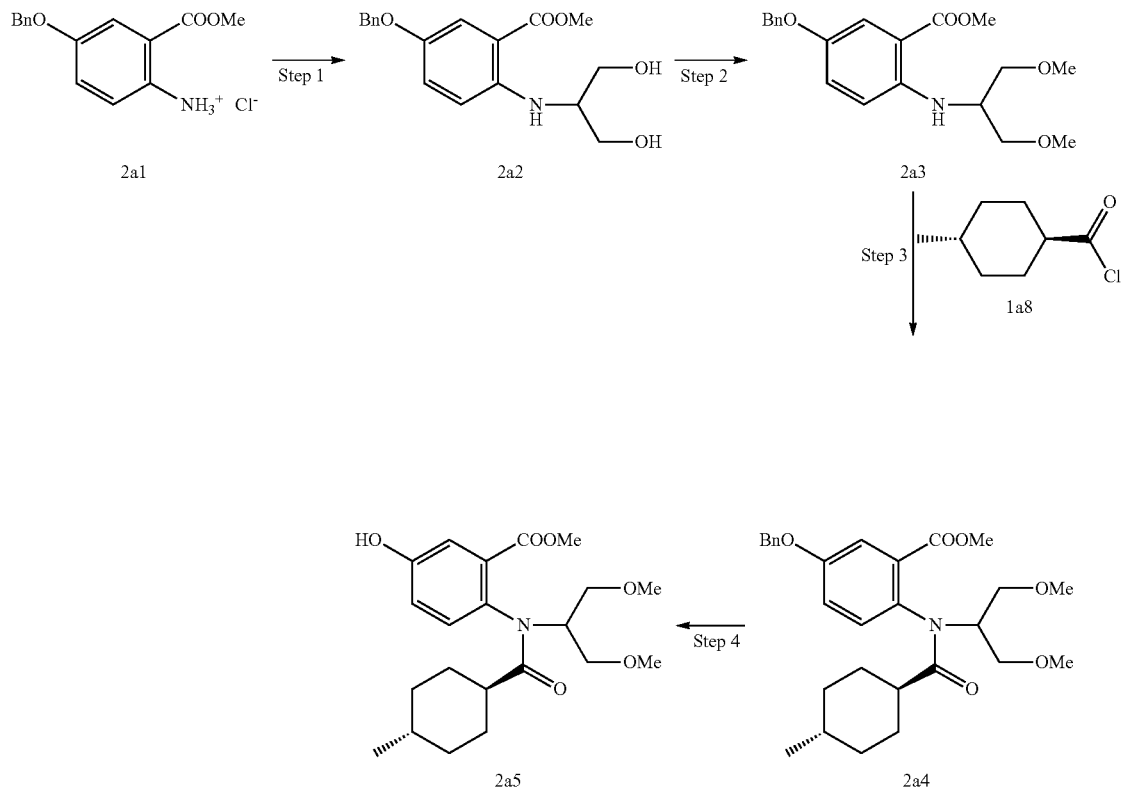

Step 1:
The aniline hydrochloride salt 2a1 (preparation described in WO2007/087717) is coupled with 1,3-dihydroxyacetone according to the conditions described in Step 4, Example 1A to provide diol 2a2.

Step 2:
Compound 2a2 is transformed to dimethoxy 2a3 using the procedure of Step 5, Example 1A.

Step 3:
Compound 2a3 is transformed to compound 2a4 using the procedure of Step 7, Example 1A.

Step 4:
Benzyl ether 2a4 is transformed to compound 2a5 using the procedure of Step 8, Example 1A.

Example 3A

Preparation of Intermediate 3a6

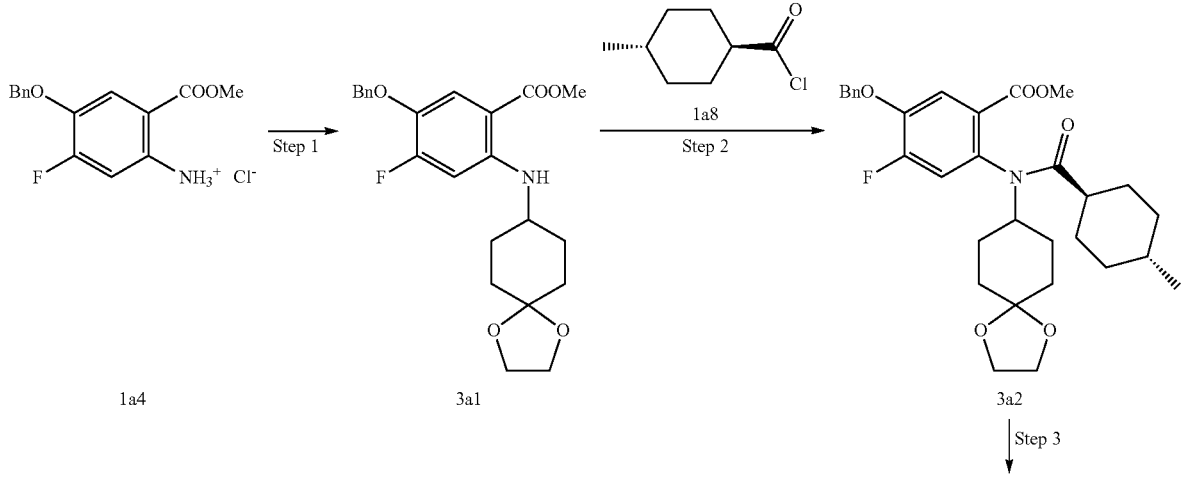

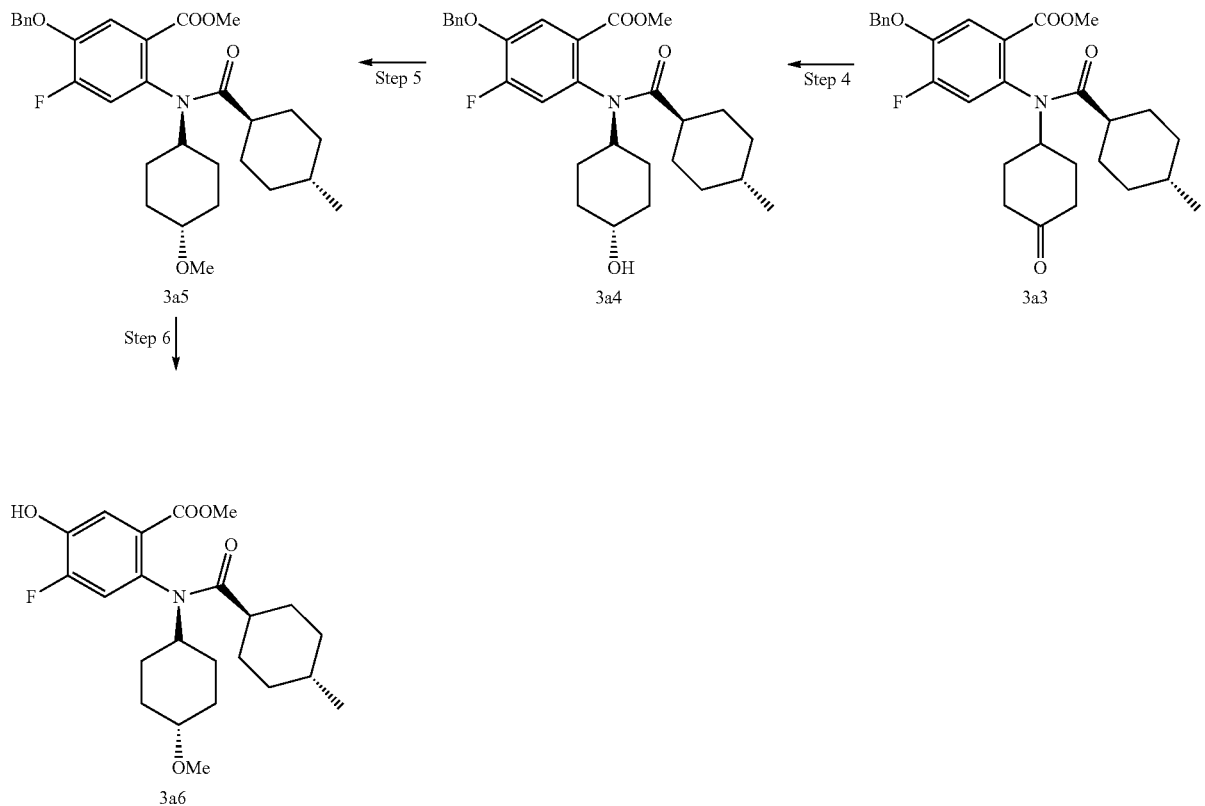

Step 1:

The hydrochloride aniline salt 1a4 (25.0 g, 90.7 mmol) is dissolved in anhydrous THF (60 mL) under Ar. 1,4-cyclohexanedione monoethylene ketal (14.3 g, 91.6 mmol) is added at RT followed by dibutyltin dichloride (1.38 g, 4.54 mmol). The mixture is stirred for about 15 min and then phenylsilane (23.0 mL, 99.8 mmol) is slowly added. The mixture is stirred at RT for about 2 days. Solvent is partially removed and the residue is dissolved in EtOAc and washed with saturated aqueous solution of $NaHCO_3$ followed by water and brine. The organic phases are dried over $Na_2SO_4$, filtered and the solvents are removed under reduced pressure to give an oily solid. This crude material is redissolved in EtOAc and an equal volume of hexanes is added followed by cooling at 0° C. As a result, a biphasic mixture with a solid is obtained. The liquid is decanted and the resulting solid is washed with hexanes. After drying, 3a1 is isolated.

Step 2:

To a solution of the ketal 3a1 (15.0 g, 36.1 mmol) in toluene (100 mL) under Ar is added the acid chloride 1a8 (9.73 g, 59.1 mmol) followed by pyridine (10 mL, 123 mmol). The mixture is heated to reflux overnight. EtOAc is added and the organic layer is washed successively with water, 10% citric acid solution, saturated solution of $NaHCO_3$ and brine. The mixture is dried over $Na_2SO_4$ and the solvent is removed under reduced pressure. Following purification by flash chromatography (10% EtOAc in hex), product 3a2 is isolated.

Step 3:

To a solution of the ketal 3a2 (13.8 g, 25.5 mmol) in toluene (50 mL) is added TFA (50 mL). After about 1 h, water (3 mL) is added and the mixture is stirred overnight. The solvents are evaporated and the crude residue is dissolved in EtOAc. The organics are successively washed with a 5% aqueous solution of $K_2CO_3$, water and brine, then dried over $Na_2SO_4$. Solvents are removed under reduced pressure to afford 3a3 which is used without further purification.

Step 4:

To a cold solution (0° C.) of the ketone 3a3 (13.5 g, 25.5 mmol) in MeOH (200 mL) is added portionwise $NaBH_4$ (0.40 g, 12.7 mmol). The reaction is stirred at 0° C. until complete conversion, then a 1 M HCl solution is slowly added. Solvent is removed under reduced pressure and the residue is dissolved in EtOAc. The organics are successively washed with a saturated aqueous solution of $NaHCO_3$, water and brine, then dried over $Na_2SO_4$. Solvents are removed under reduced pressure and the crude residue is purified by flash chromatography (EtOAc in hex) to give the trans alcohol 3a4.

Step 5:

The alcohol 3a4 (5.0 g, 10.1 mmol) is dissolved in DMF (50 mL) and cooled to 0° C. prior to adding NaH (0.81 g, 29.1 mmol) followed by MeI (42 g, 301 mmol). After being stirred at 0° C. for about 2 h, the reaction is quenched by the addition of a 1 M HCl solution. A large volume of EtOAc is added and the organics are successively washed with a saturated aqueous solution of $NaHCO_3$, water and brine, then dried over $Na_2SO_4$. Removal of the solvent under reduced pressure gives 3a5 which is used without further purification.

Step 6:

In a Parr Hydrogenator™, the ether 3a5 (5.0 g, 9.77 mmol) is dissolved in MeOH (120 mL) and 10% Pd/C (0.75 g) is added. The vessel is pressurized to 30 psi of $H_2$ and agitated overnight. The mixture is filtered through a pad of Celite®, then concentrated in vacuo to afford phenol 3a6.

Example 3B
Preparation of Intermediate 3b6
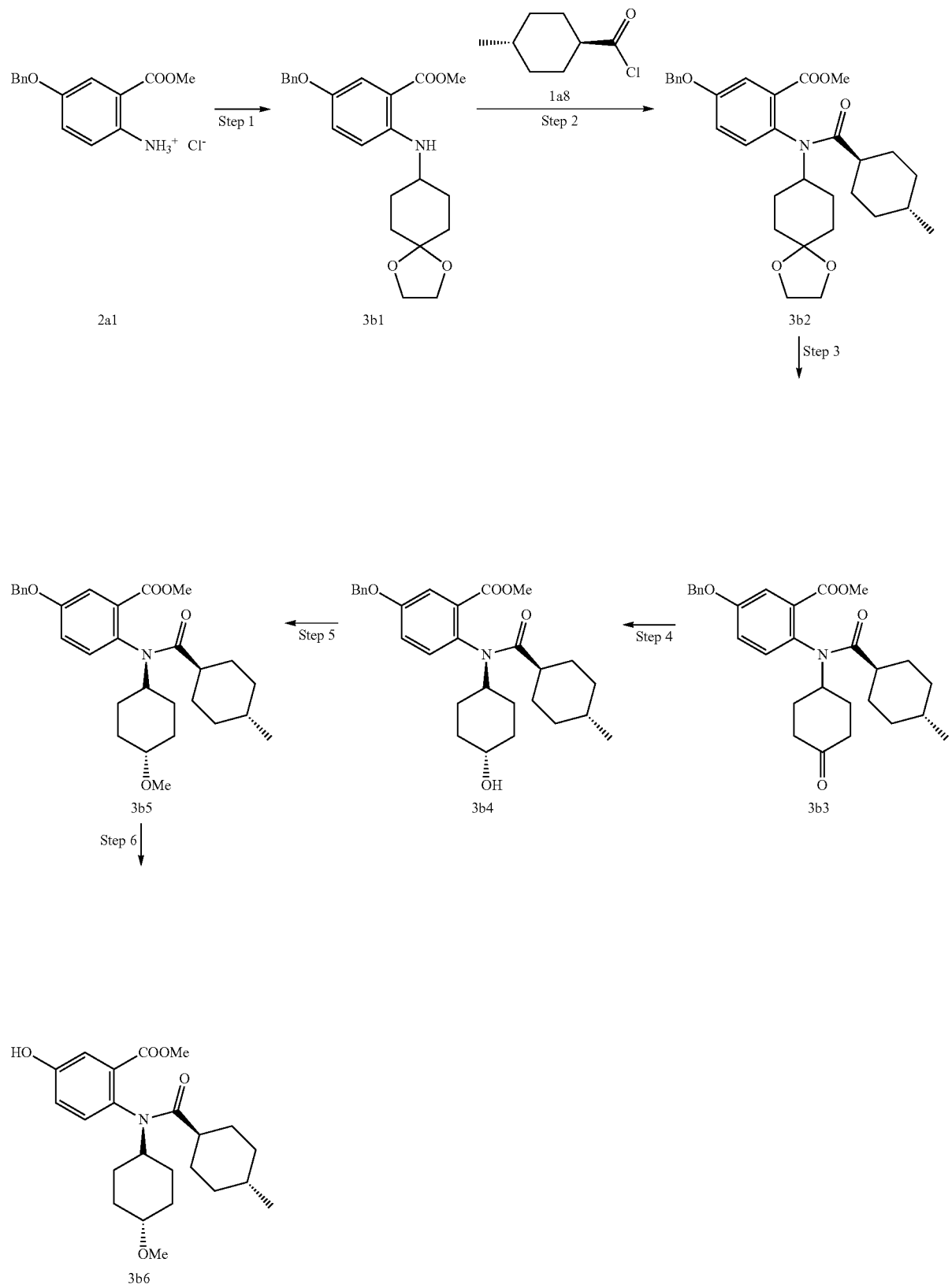

Step 1:
The aniline hydrochloride salt 2a1 (preparation described in WO2007/087717) is coupled with 1,4-cyclohexanedione monoethylene ketal according to the conditions described in Step 1, Example 3A to produce ketal 3b1.

Step 2:
Compound 3b1 is transformed to amide 3b2 using the procedure of Step 2, Example 3A.

Step 3:
Ketal 3b2 is transformed to ketone 3b3 using the procedure of Step 3, Example 3A.

Step 4:
Ketone 3b3 is transformed to alcohol 3b4 using the procedure of Step 4, Example 3A.

Step 5:
Alcohol 3b4 is transformed to compound 3b5 using the procedure of Step 5, Example 3A.

Step 6:
Ether 3b5 is transformed to phenol 3b6 using the procedure of Step 6, Example 3A.

Example 4A

Preparation of Intermediate 4a4

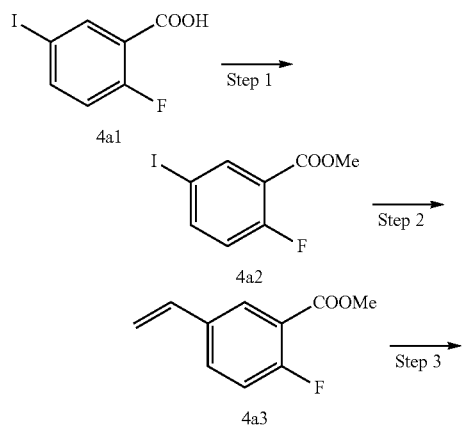

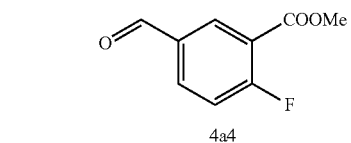

Step 1:
To a stirring mixture of 4a1 (25 g, 24 mmol) in MeCN (500 mL) and DMF (50 mL) chilled to −5° C. is added DBU (15.4 mL, 103 mmol) followed by the slow addition of MeI (8.8 mL, 141 mmol). The mixture is allowed to warm to RT and is stirred overnight. The mixture is poured into water (1 L); then extracted with EtOAc (500 mL×3). The combined organic extracts are washed with brine, dried over $Na_2SO_4$, filtered and concentrated under reduced pressure. Crude ester 4a2 is utilized without further purification.

Step 2:
To a mixture of iodoarene 4a2 (22.3 g, 79 mmol) in dioxane (200 mL) is added tributylvinyltin (20 mL, 68 mmol). The mixture is degassed with Ar before $(Ph_3P)_4Pd$ (2.4 g, 2.1 mmol) is added. The mixture is refluxed for about 1 h then stirred at RT overnight. The mixture is concentrated under reduced pressure and the resulting residue is subjected to flash chromatography to isolate alkene 4a3.

Step 3:
To a mixture of alkene 4a3 (9.6 g, 89 mmol) in THF (360 mL) and water (270 mL) is added $OsO_4$ (2.5% solution in t-BuOH, 5.4 mL) followed by the portionwise addition of $NaIO_4$ (34 g, 160 mmol). The mixture is stirred for about 2 h at RT before being partially concentrated and diluted in EtOAc. The organic phase is washed with brine, dried over $Na_2SO_4$, filtered and concentrated. The residue is subjected to flash chromatography to isolate aldehyde 4a4.

Example 5A

Preparation of intermediates 5a6 and 5a7

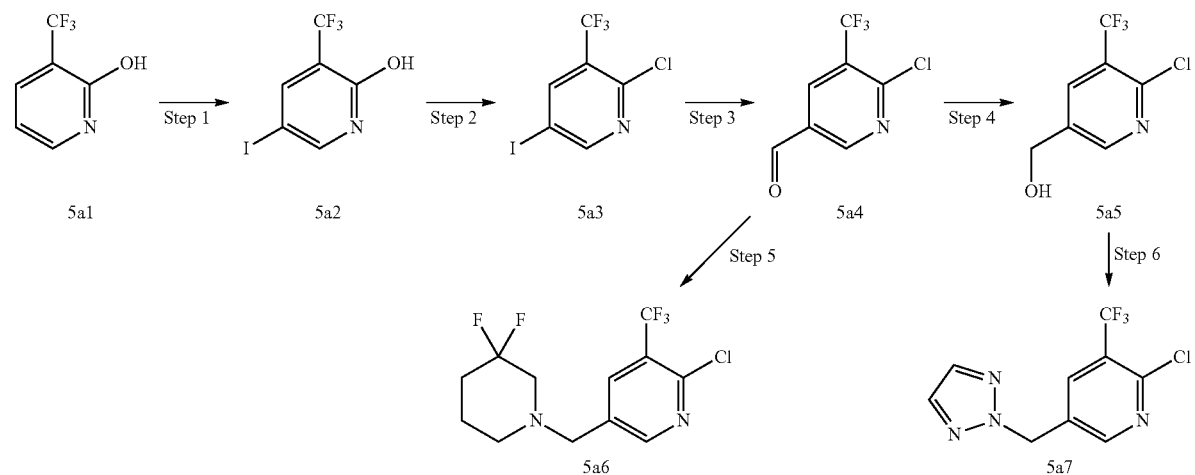

Step 1:
2-Hydroxy-3-trifluoromethylpyridine (500 g, 3.06 mol) is placed in a 22 L round bottom flask under Ar. Anhydrous DMF (8 L) is added followed by potassium carbonate (430 g, 1 eq) and N-iodosuccinimide (700 g, 1 eq). The mixture is stirred under Ar and heated to an internal temperature of 55° C. for about 2 h. The heating is removed and the suspension stirred overnight. The mixture is filtered and the solvent removed. The residue is dissolved in DCM (8 L) and water (4 L) is added. The mixture is stirred and acidified to approximately pH 3-4 with HCl. The organic phases are separated and the aqueous phase extracted with additional DCM. The organics are combined, washed with brine and dried over $MgSO_4$. Cooling of the DCM and concentration affords the product 5a2 as a precipitate.

Step 2:
The phenol 5a2 (125 g, 424 mmol) is placed in a 3-neck 2 L flask. Phenylphosphonic dichloride (500 mL) is added and the mixture heated to 136° C. under Ar with stirring. After consumption of starting material (about 4-5 h), the reaction is cooled to RT and carefully quenched by the slow addition of the reaction mixture to crushed ice (caution: very exothermic!). A white solid forms which is filtered. The solid is dissolved in EtOAc (2 L) and aqueous NaOH is added with stirring. A NaOH solution is added until the aqueous layer is neutral. The EtOAc layer is separated, washed with water and brine and dried over anhydrous $Na_2SO_4$. Removal of solvent gives a white solid which is washed with cold hexane to afford chloride 5a3.

Step 3:
Iodide 5a3 (10 g, 32.5 mmol) is combined with a 1:3 mixture of anhydrous THF and anhydrous toluene (100 mL) under an Ar atmosphere. The mixture is cooled to −78° C. then n-BuLi (1.6 M in hexanes, 24 mL, 38.4 mmol) is added slowly by syringe over about 40 min. Stirring is continued for about 1 h before ethylformate (3.2 mL, 39.7 mmol) in THF (10 mL) is added over a period of about 40 min. The mixture is stirred for about 1 h before being quenched by the addition of 2 M HCl. The mixture is partitioned between EtOAc and saturated aqueous $NaHCO_3$. The organic phase is collected, washed with brine and dried over $Na_2SO_4$. The mixture is filtered and concentrated under reduced pressure. Purification is performed by flash chromatography where the silica gel is pre-treated with 3% $Et_3N$ in hexanes then eluted with 1:1 EtOAc/Hex to isolate aldehyde 5a4.

Step 4:
A mixture of aldehyde 5a4 (19 g, 81 mmol) in MeOH (225 mL) is chilled to 0° C. Sodium borohydride (4.1 g, 109 mmol) is added portionwise and the mixture is stirred at 0° C. for about 1.5 h. Another portion of $NaBH_4$ (1 g) is added and the mixture is stirred for about another 30 min. The reaction is quenched by the addition of $NaHSO_4$ (5% aqueous) then diluted in EtOAc (500 mL). The organic phase is separated then washed with water (500 mL) and brine. The organic phase is dried over $Na_2SO_4$, filtered then concentrated under reduced pressure. The residue is subjected to flash chromatography (1:1 EtOAc/Hex) to isolate alcohol 5a5.

Step 5:
To the crude aldehyde 5a4 (2 g, 9.5 mmol) in 45 mL of DCE is added difluoropiperidine-HCl salt (1.6 g, 10.5 mmol) and triacetoxy sodium borohydride (2.8 g, 13.4 mmol). This reaction is stirred overnight at RT. The mixture is diluted with EtOAc (300 mL) and washed with water (100 mL) and brine (100 mL). The organic phase is then dried over $MgSO_4$, filtered and concentrated. The residue is purified by flash chromatography (Combiflash, 15-40% EtOAc/Hex.) to afford 5a6 as an orange oil.

Step 6:
Alcohol 5a5 (10.5 g, 48 mmol) is combined with triazole (3.42 g, 48 mmol) and triphenylphosphine (14.3 g, 54 mmol) in anhydrous THF (500 mL). The mixture is chilled to 0° C. and DIAD (10.6 mL, 54 mmol) is added dropwise. Stirring continues at 0° C. for about 1 h before the mixture is allowed to warm to RT and is then stirred overnight. The mixture is diluted in EtOAc and washed with water (500 mL) and brine (500 mL) before being dried over $Na_2SO_4$. The solvents are removed under reduced pressure and the residue is subjected to flash chromatography (1:3 EtOAc/Hex) to afford benzylic triazole 5a7.

Example 5B

Preparation of intermediates 5b4 and 5b5

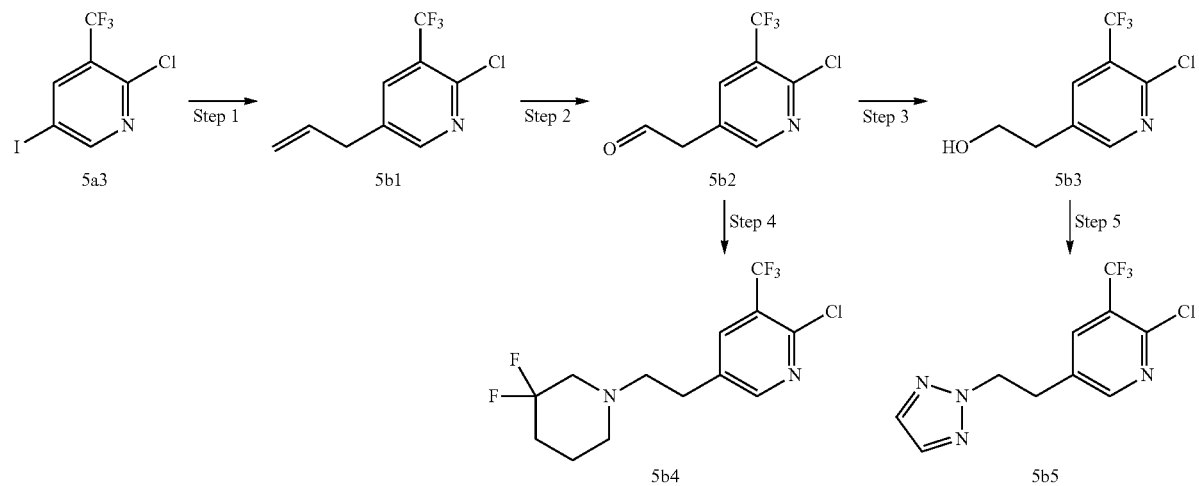

Step 1:
To a solution of iodide 5a3 (300 mg, 0.98 mmol) in THF (3 mL) is added i-PrMgCl (0.54 mL 2.0 M soln in THF) at −40° C. The reaction mixture is stirred for about 30 min and allyl bromide (0.13 mL, 1.5 mmol) is then added. This mixture is stirred at −40° C. for about 15 min and then stirring is continued at RT for about 30 min. The mixture is quenched with water and extracted with EtOAc (3×). The organic layers are combined, washed with brine, dried over anhydrous $Na_2SO_4$, filtered under vacuum and concentrated. A light brown oil 5b1 is obtained which is employed without further purification in the subsequent step.

Step 2:

Alkene 5b1 is transformed to aldehyde 5b2 using the procedure described in Step 3, Example 4A.

Step 2:

Aldehyde 5b2 is transformed to alcohol 5b3 using the procedure described in Step 4, Example 5A.

Step 4:

Aldehyde 5b2 is transformed to compound 5b4 using the procedure of Step 5, Example 5A.

Step 5:

Alcohol 5b3 is transformed to triazole 5b5 using the procedure of Step 6, Example 5A.

Example 6A

Preparation of Compounds 1001 and 1002

Step 1:

To an 8-mL vial are successively added $K_2CO_3$ (46 mg, 0.33 mmol), aldehyde 4a4 (50 mg, 0.275 mmol in 0.5 mL DMSO) and 2-methoxyethylamine (103.9 mg, 1.4 mmol). The mixture is agitated on a J-Kem® orbital shaker (270 rpm) at 70° C. overnight. Water (1 mL) and concentrated HCl (0.7 mL) are added to the mixture. The mixture is heated at 70° C. for about 3 h, extracted with EtOAc (2 mL) and washed with $H_2O$ (3×). After concentration, the crude aniline 6a1 is obtained and used as such in the following step.

Step 2:

To the crude aldehyde 6a1 dissolved in MeOH (1.5 mL in an 8-mL vial) at 2° C. are successively added hydrogen peroxide (43 μL of a 30% aqueous solution) and concentrated $H_2SO_4$ (20 μL). The mixture is agitated on a J-Kem® orbital shaker (290 rpm) at 2° C. for about 15 min and then a saturated aqueous solution of NaCl is added (2 mL). The mixture is extracted with EtOAc (2 mL) and the combined organic extracts are successively washed with water (1 mL) and brine (1 mL). The organic phase is dried with $MgSO_4$, filtered and concentrated to afford the crude phenol 6a2 which is used as such in the following step.

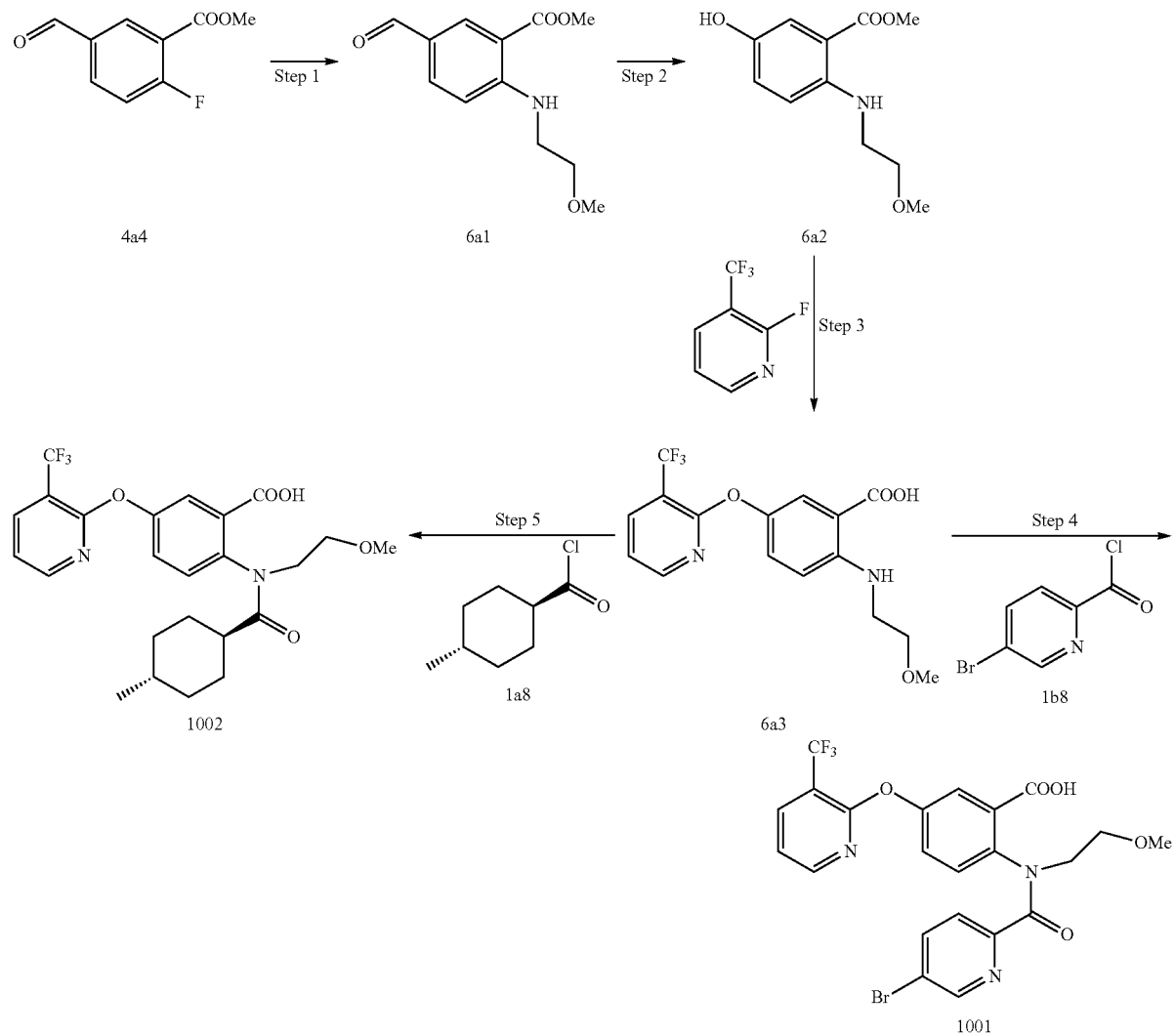

Step 3:

To the crude phenol 6a2 obtained above in dry DMSO (0.5 mL) are successively added K$_2$CO$_3$ (133 mg, 0.96 mmol) and 2-fluoro-3-trifluoromethylpyridine (40 μL, 0.33 mmol). The suspension is agitated overnight on a J-Kem® orbital shaker (290 rpm) at 85° C. Aqueous NaOH solution (5 N, 250 μL) is added at RT and the reaction mixture is agitated at 50° C. for about 3 h. After acidification using a 1 N aqueous KHSO$_4$ Step 5:

Amine 6a3 is transformed to compound 1002 using the procedure in Step 2, Example 3a.

Example 7A

Preparation of Compound 1007

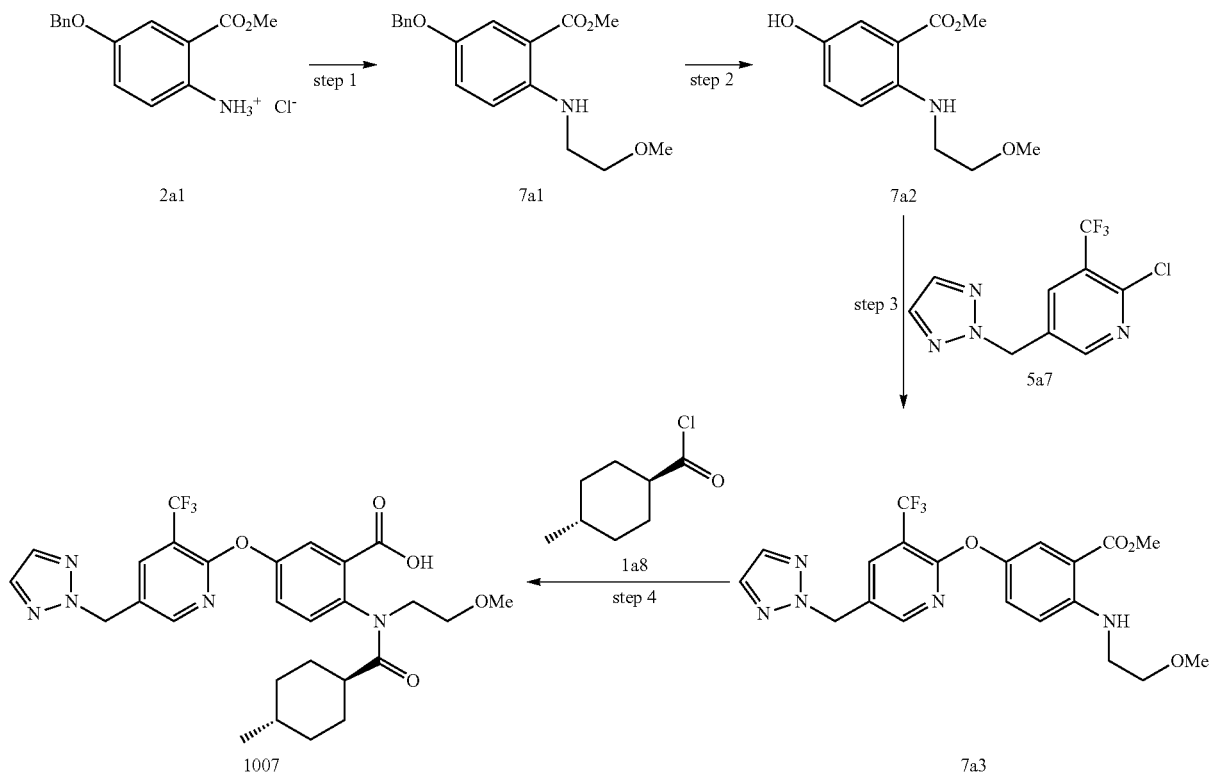

solution, the mixture is extracted with EtOAc (3×). The combined organic extracts are successively washed with water and brine, dried over MgSO$_4$ and filtered. After concentration, the residue is dissolved in a mixture of DMSO and AcOH (1.5 mL) and purified by reverse phase preparative LC-MS. Conditions; column: Agilent SB-C18, 5 uM, 21.2 mm×50 mm; gradient: 5% to 100% H$_2$O 0.06% TFA/MeCN 0.06% TFA; flow: 30 mL/min for 13.5 min; makeup: 25% H$_2$O 0.05% Ammonium formate/75% MeCN; 1 mL/min. After lyophilization the desired ether 6a3 is isolated.

Step 4:

To a mixture of aniline 6a3 (10.0 mg, 0.028 mmol) in DCE (0.3 mL) is added acid chloride 1b8 (6.31 mg, 0.039 mmol) and pyridine (9.8 μL, 0.121 mmol). The mixture is heated at 150° C. for 15 min in a microwave. After concentration, the residue is dissolved in DMSO and AcOH, and purified by reverse phase preparative LC-MS. Conditions; column: Agilent SB-C18, 5 uM, 21.2 mm×50 mm; gradient: 5% to 100% H$_2$O 0.06% TFA/MeCN 0.06% TFA; flow: 30 mL/min for 13.5 min; makeup: 25% H$_2$O 0.05% Ammonium formate/ 75% MeCN; 1 mL/min. After lyophilization compound 1001 is isolated.

Step 1

2-Bromoethyl methyl ether (2.22 g, 15.9 mmol) is added to aniline 2a1 (712.0 mg, 2.42 mmol) dissolved in dry DMF (8.0 mL) in a pressure tube. KI (2.0 g, 12.0 mmol) is added, followed by DIPEA (2.72 mL, 16.0 mmol) and the mixture is heated at 120° C. for about 16 h. The mixture is cooled to RT, diluted with aqueous saturated NaHCO$_3$ (100 mL) and extracted with EtOAc (2×50 mL). The combined organic phases are washed with aqueous saturated sodium bicarbonate (2×100 mL), brine (100 mL), dried over Na$_2$SO$_4$, filtered and concentrated under reduced pressure. The residue is purified by column chromatography (20% EtOAc in hexanes) to afford 7a1.

Step 2

Benzyl ether 7a1 is transformed to phenol 7a2 using the procedure described in Step 8, Example 1A.

Step 3

Potassium carbonate (19 mg, 1.4 mmol) is added to a DMSO solution (3.0 mL) of phenol 7a2 (100 mg, 0.44 mmol) and chloropyridine 5a7 (6.6 mg, 0.44 mmol). The mixture is heated at 70° C. for about 20 h. The solution is cooled to RT, diluted with aqueous saturated sodium bicarbonate (100 mL) and extracted with EtOAc (2×50 mL). The combined organic phases are washed with aqueous saturated sodium bicarbonate (2×50 mL), brine (50 mL), dried over Na$_2$SO$_4$, filtered and concentrated under reduced pressure. The crude residue is purified by column chromatography (40% EtOAc in hexanes) to afford triazole 7a3 (158.0 mg, 79% yield).

Step 4

Pyridine (27 μL, 0.33 mmol) is added to a DCE solution (0.5 mL) of aniline 7a3 (50 mg, 0.11 mmol) and acid chloride 1a8 (21.4 mg, 0.113 mmol). The mixture is heated at 150° C. in a microwave for 15 min. The solution is cooled to RT and concentrated under reduced pressure. The residue is dissolved in DMSO (1 mL) and then 2.5 N NaOH (0.4 mL) is added. The solution is stirred at 50° C. for about 1 h; then acidified with AcOH and purified by preparative HPLC to afford 1007.

Step 1

Aniline 1a4 is transformed to compound 8a1 using the procedure described in Step 1, Example 7A.

Step 2

Benzyl ether 8a1 is transformed to compound 8a2 using the procedure described in Step 8, Example 1A.

Step 3

Phenol 8a2 is transformed to triazole 8a3 using the procedure described in Step 3, Example 7A.

Step 4

Amine 8a3 is transformed to compound 1008 using the procedure described in Step 4, Example 7A.

Example 8A

Preparation of Compound 1008

Example 9A

Preparation of Compounds 1009 and 1010

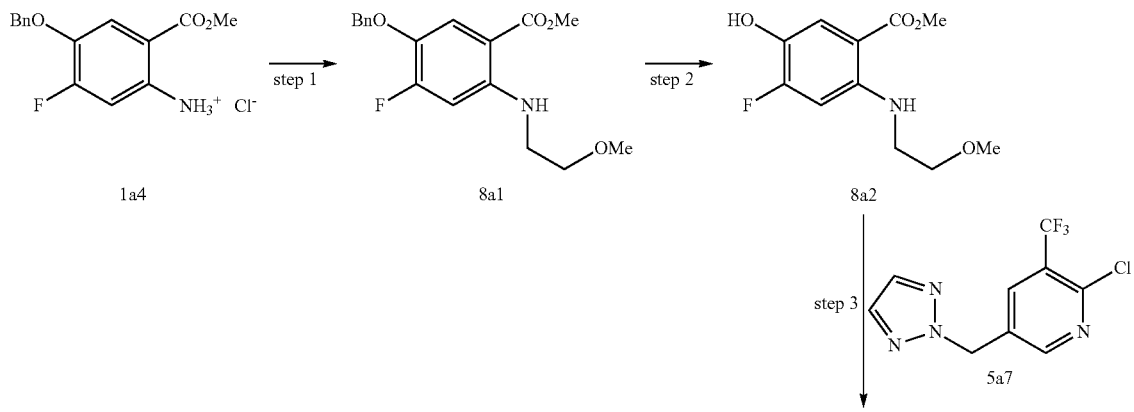

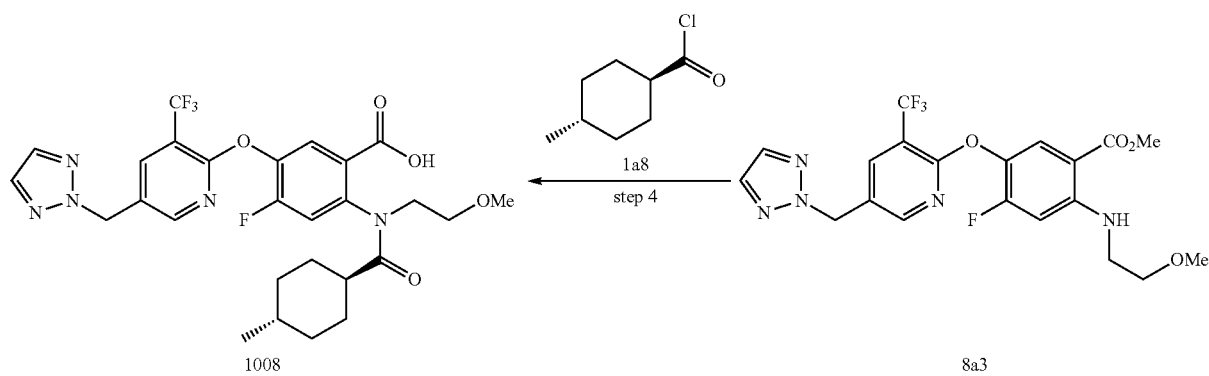

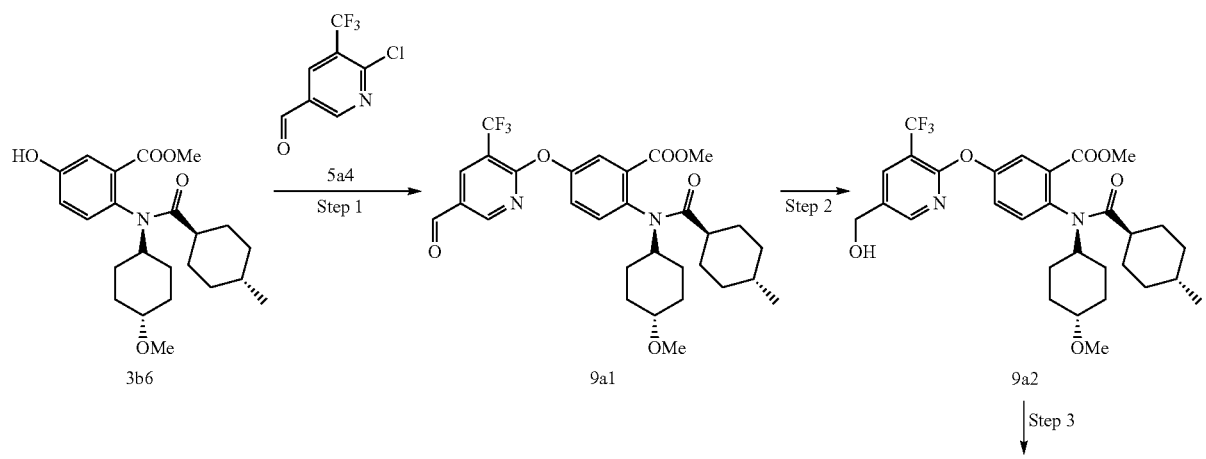

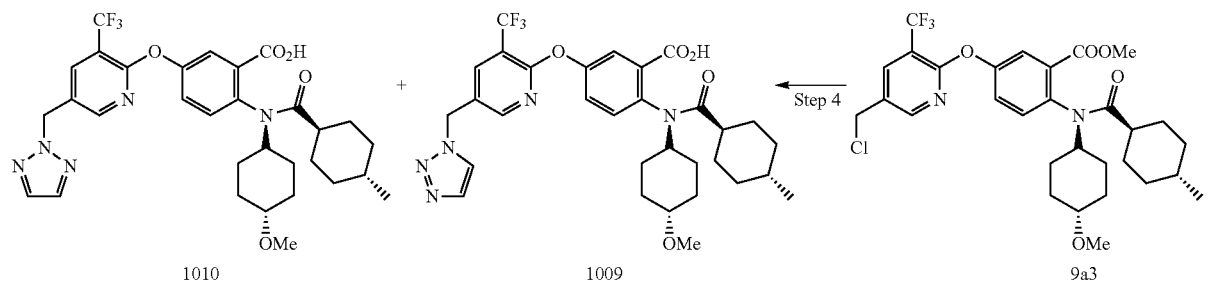

Step 1:

To a solution of phenol 3b6 (1.15 g, 2.85 mmol) and K$_2$CO$_3$ (0.59 g, 4.2 mmol) in anhydrous DMSO (20 mL) is added pyridine 5a4 (500 mg, 2.92 mmol). The resulting mixture is stirred at 100° C. for about 30 min, then diluted with EtOAc and successively washed with water, brine and concentrated under reduced pressure. Following purification by silica gel column chromatography on a Combiflash (50% EtOAc in hex), 9a1 is isolated.

Step 2:

NaBH$_4$ (0.11 g, 2.8 mmol) is added portionwise to a cold solution (0° C.) of aldehyde 9a1 (1.10 g, 1.91 mmol) in MeOH. After being stirred for about 1 h, the reaction mixture is evaporated to dryness and redissolved in EtOAc. This mixture is successively washed with 10% aqueous solution of NaHSO$_4$, saturated aqueous solution of NaHCO$_3$ and brine. The organics are dried over Na$_2$SO$_4$, filtered and concentrated under reduced pressure. The crude compound is purified by silica gel column chromatography on a Combiflash (50% EtOAc in Hex) to afford alcohol 9a2.

Step 3:

To a solution of alcohol 9a2 (1.0 g, 1.7 mmol) in anhydrous DCM (25 mL) is added thionyl chloride (0.25 mL, 3.4 mmol) followed by a catalytic amount of DMF (2 drops). The resulting solution is stirred for about 30 min at RT, diluted with DCM and washed with a saturated solution of NaHCO$_3$ and brine. The organics are dried over Na$_2$SO$_4$, filtered and concentrated to give chloride 9a3 which is directly used in the next step.

Step 4:

The chloride 9a3 (120 mg, 0.22 mmol) along with 1,2,3-triazole (17 mg, 0.25 mmol), Cs$_2$CO$_3$ (124 mg, 0.38 mmol) and KI (16 mg, 0.099 mmol) are mixed in DMF (2 mL). The mixture is warmed to 70° C. for about 2 h, then cooled down to RT. A solution of NaOH (2.5 N, 0.8 mL, 2 mmol) and DMSO (0.5 mL) is then added. The mixture is warmed to 50° C. for about 1 h, neutralized at RT with AcOH and injected onto the preparative HPLC to isolate 1009 and 1010.

Example 10A

Preparation of Compounds 1040, 1041 and 1014

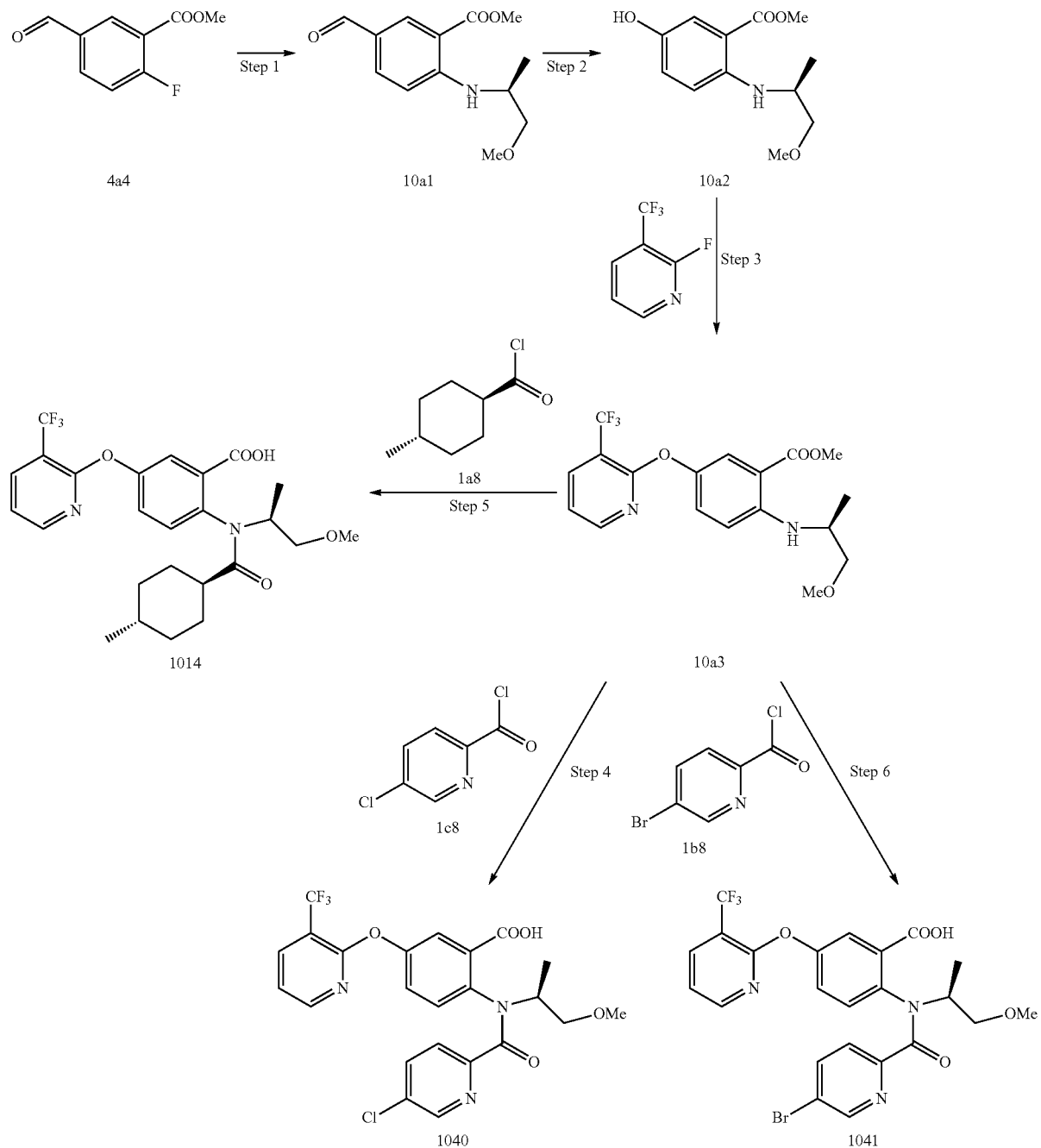

Step 1:

Potassium carbonate (400 mg, 2.89 mmol) is added to a DMSO (4.0 mL) solution of fluoride 4a4 (438 mg, 2.4 mmol) and (S)-(+)-1-methoxy-2-propylamine (858 mg, 9.63 mmol). The mixture is heated at 70° C. for about 20 h, cooled to RT and diluted with water. Concentrated HCl is then added. The solution is stirred at RT for about 1 h, basified with aqueous 2.5 N NaOH and extracted with EtOAc. The organic phase is washed with brine, dried over $Na_2SO_4$, filtered and concentrated under reduced pressure. The crude product 10a1 is used directly in the next step.

Step 2:

Hydrogen peroxide (374 µL, 3.3 mmol) is added to a 0° C. MeOH (3.0 mL) solution of the aldehyde 10a1 and sulfuric acid (180 µL, 2.9 mmol). The solution is stirred at 0° C. for about 2 h, basified with aqueous 2.5 N NaOH and extracted with EtOAc. The organic phase is washed with brine, dried over $Na_2SO_4$, filtered and concentrated under reduced pressure. The crude residue is purified by column chromatography to afford phenol 10a2 as a yellow solid.

Step 3:

Potassium carbonate (829 mg, 6.0 mmol) is added to a DMSO (8.0 mL) solution of the phenol 10a2 (337 mg, 1.41 mmol) and 2-fluoro-3-(trifluoromethyl)pyridine (247 mg, 1.5 mmol). The mixture is stirred at 85° C. for about 6 h then cooled to RT and diluted with EtOAc. The organic phase is washed with aqueous saturated sodium bicarbonate, brine, dried over $Na_2SO_4$, filtered and concentrated under reduced pressure. The crude residue is purified by column chromatography to afford ether 10a3 as a white solid.

Step 4:

Pyridine (100 µL) is added to a DCE (1 mL) solution of the aniline 10a3 (50 mg, 0.13 mmol) and the acid chloride 1c8 (105 mg, 0.60 mmol). The mixture is stirred at 150° C. for 15 min in a microwave, cooled to RT and concentrated under reduced pressure. The residue is dissolved in DMSO (2.0 mL) and aqueous 2.5 N NaOH (200 µL) is added. The reaction mixture is stirred at RT for about 2 h, acidified with AcOH and purified by preparative HPLC to afford 1040.

Step 5:

Pyridine (500 µL) is added to a DCE (1 mL) solution of the aniline 10a3 (490 mg, 1.27 mmol) and the acid chloride 1a8 (422 mg, 2.62 mmol). The mixture is stirred at 150° C. for about 15 min in a microwave, cooled to RT and concentrated under reduced pressure. The residue is dissolved in DMSO (2.0 mL) and aqueous 2.5 N NaOH (200 µL) is added. The reaction mixture is stirred at RT for about 2 h, acidified with AcOH and purified by preparative HPLC to give 1014.

Step 6:

Pyridine (40 µL) is added to a DCE (1 mL) solution of the aniline 10a3 (41 mg, 0.11 mmol) and the acid chloride 1b8 (48.8 mg, 0.22 mmol). The mixture is stirred at 150° C. for 15 min in a microwave, cooled to RT and concentrated under reduced pressure. The residue is dissolved in DMSO (2.0 mL) and aqueous 2.5 N NaOH (200 µL) is added. The reaction mixture is stirred at RT for about 2 h, acidified with AcOH and purified by preparative HPLC to give 1041.

Example 11A

Preparation of Compound 1042

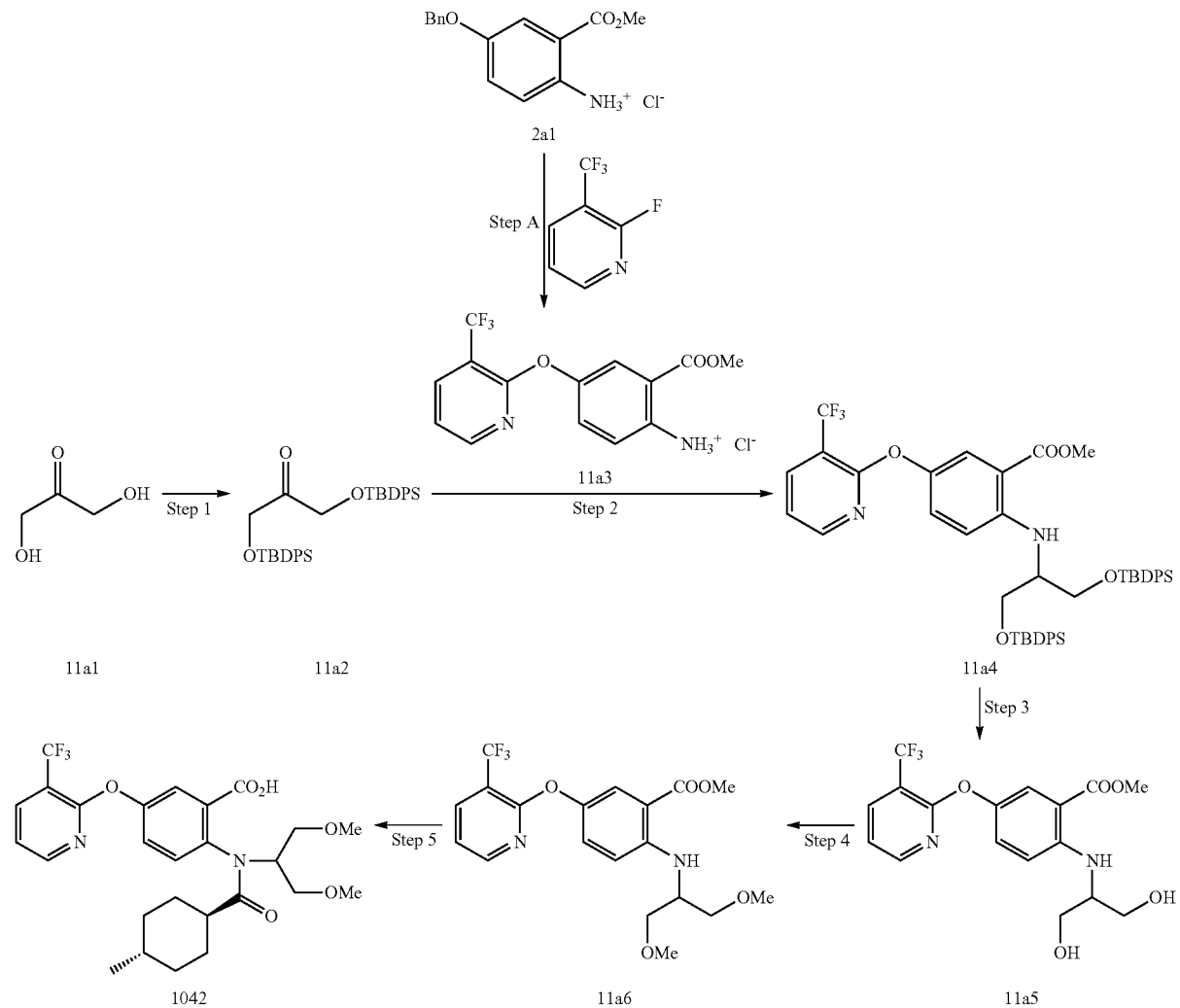

Step A:

Compound 2a1 is transformed to compound 11a3, using the procedure in Steps 2 and 3, Example 8A.

Step 1:

1,3-dihydroxyacetone 11a1 (964 mg, 10.7 mmol) is dissolved in DCM (25 mL) and imidazole (2.19 g, 32.1 mmol) followed by tert-butyldiphenylchlorosilane (5.8 mL, 22.5 mmol) are added. The mixture is stirred at RT until the reaction is complete, then water is added. The layers are separated; the organics are dried over MgSO$_4$, filtered and concentrated under reduced pressure to afford 11a2 which is used without further purification.
Step 2:

The hydrochloride aniline salt 11a3 (200 mg, 0.57 mmol) is dissolved in DCM (10 mL) along with ketone 11a2 (651 mg, 1.15 mmol). After being stirred for about 10 min, NaBH(OAc)$_3$ (243 mg, 1.15 mmol) is added and the mixture is refluxed. The mixture is neutralized by adding a saturated aqueous solution of NaHCO$_3$; then extracted with DCM (3×). The organics are washed with brine, dried over MgSO$_4$, filtered and concentrated under reduced pressure. The crude mixture is purified by flash chromatography (2% EtOAc in hex) to give aniline 11a4.
Step 3:

To a solution of compound 11a4 (674 mg, 0.78 mmol) in THF (10 mL) is added a solution of TBAF (1.0 M in THF, 1.6 mL, 1.6 mmol). The solution is stirred at RT until the reaction is complete, diluted with a saturated aqueous solution of NH$_4$Cl and extracted with DCM (3×). The combined organics are washed with brine, dried over MgSO$_4$, filtered and concentrated under reduced pressure. Following purification by flash chromatography (2% to 8% MeOH in DCM), diol 11a5 is isolated.
Step 4:

Diol 11a5 is transformed to dimethoxy 11a6 using the procedure of Step 5, Example 1A.
Step 5:

In a microwave tube, dimethoxy 11a6 (37 mg, 0.089 mmol) along with pyridine (36 µL, 0.45 mmol) and DMAP (1.1 mg, 9 µmol) are mixed in DCE (1 mL). The acid chloride 1a8 (91 mg, 0.57 mmol) is added and the tube is sealed and placed in a microwave at 175° C. for 15 min. The mixture is diluted in EtOAc and washed with a saturated aqueous solution of NaHCO$_3$ (3×). The organics are dried over MgSO$_4$ and concentrated. The crude residue is re-dissolved in a THF (1 mL)/MeOH (0.5 mL)/H$_2$O (0.5 mL) mixture and an aqueous NaOH solution (10 N, 45 µL, 0.45 mmol) is added. The mixture is stirred overnight before being acidified with AcOH, filtered then injected onto a preparative HPLC to isolate compound 1042.

Example 12A

Preparation of Compound 1043

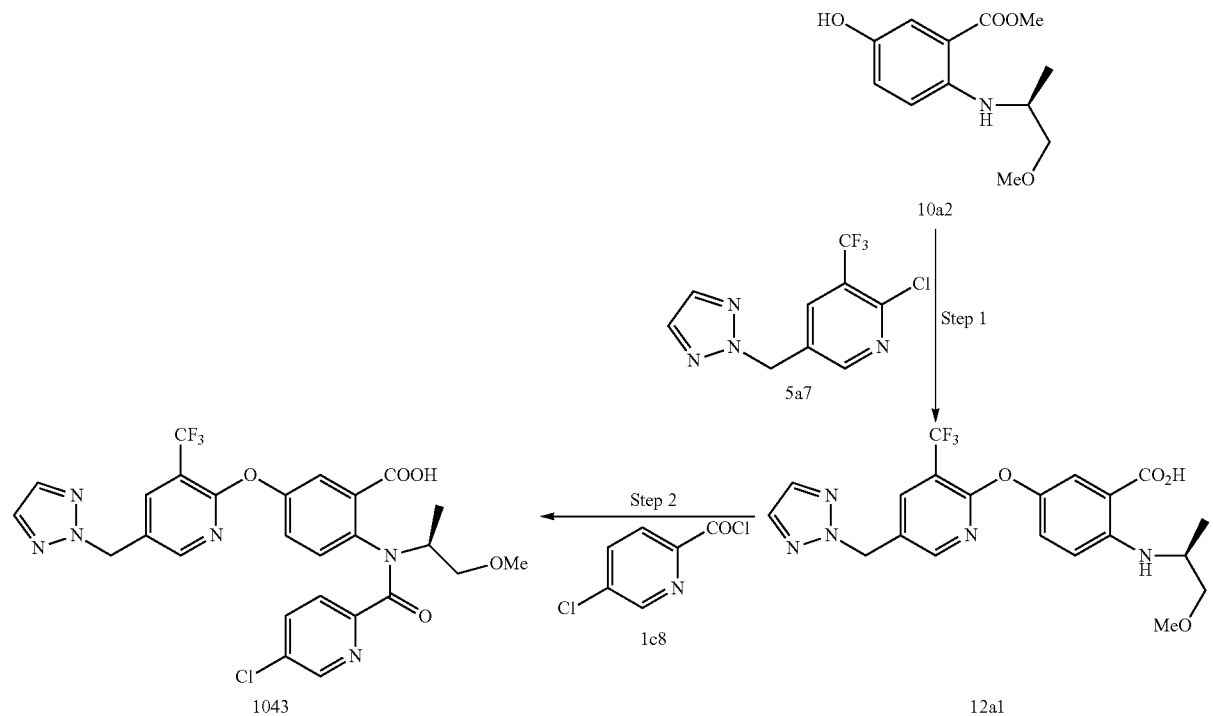

Step 1:

Potassium carbonate (193 mg, 1.40 mmol) is added to a DMSO (6.0 mL) solution of phenol 10a2 (136.6 mg, 0.571 mmol) and chloropyridine 5a7 (150 mg, 0.571 mmol). The mixture is stirred at 80° C. for about 12 h, cooled to RT and aqueous 2.5 N NaOH (0.90 mg, 2.25 mmol) is added. The solution is stirred at RT for about 1 h, diluted with water and acidified with AcOH. The solid is filtered and dried to afford the acid 12a1 as a beige solid.
Step 2:

Pyridine (49 µL) is added to a DCE (1 mL) solution of aniline 12a1 (60 mg, 0.133 mmol) and the acid chloride 1c8 (47.5 mg, 0.270 mmol). The mixture is stirred at 150° C. for 15 min in a microwave, cooled to RT, acidified with AcOH and purified by preparative HPLC to afford 1043.

Example 13A

Preparation of Compound 1044

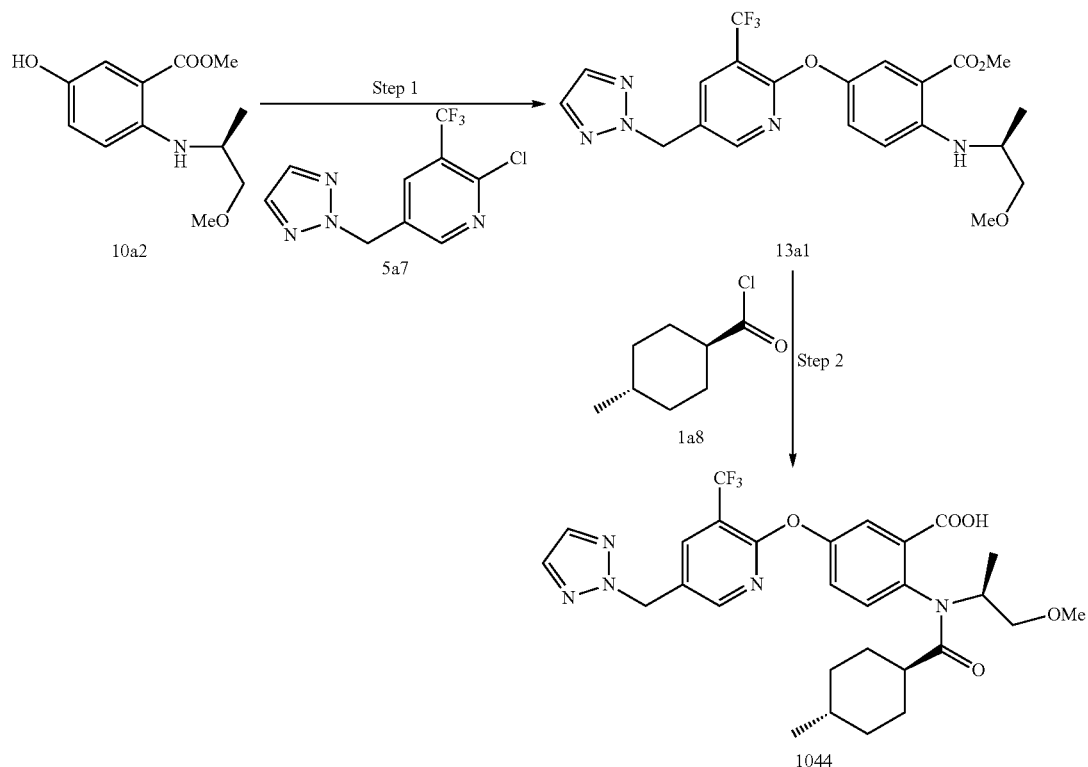

Step 1:

Potassium carbonate (650 mg, 4.703 mmol) is added to a DMSO (15.0 mL) solution of phenol 10a2 (456.0 mg, 1.906 mmol) and chloropyridine 5a7 (500 mg, 1.904 mmol). The mixture is stirred at 80° C. for about 12 h, cooled to RT and diluted with EtOAc. The organic phase is washed with aqueous saturated sodium bicarbonate, brine, dried over $Na_2SO_4$, filtered and concentrated under reduced pressure. The crude residue is purified by column chromatography (30% EtOAc in hexanes) to afford triazole 13a1.

Step 2:

Pyridine (404 μL, 5.0 mmol) is added to a DCE (1 mL) solution of aniline 13a1 (433 mg, 0.930 mmol) and acid chloride 1a8 (450 mg, 2.801 mmol). The mixture is stirred at 140° C. for 60 min in a microwave, cooled to RT and concentrated under reduced pressure. The residue is dissolved in MeOH/THF (1:2) and aqueous 1 N NaOH (660 μL) is added. The mixture is stirred at RT for about 2 days, acidified with aqueous HCl and purified by preparative HPLC to afford 1044.

Example 14A

Preparation of Compound 1046

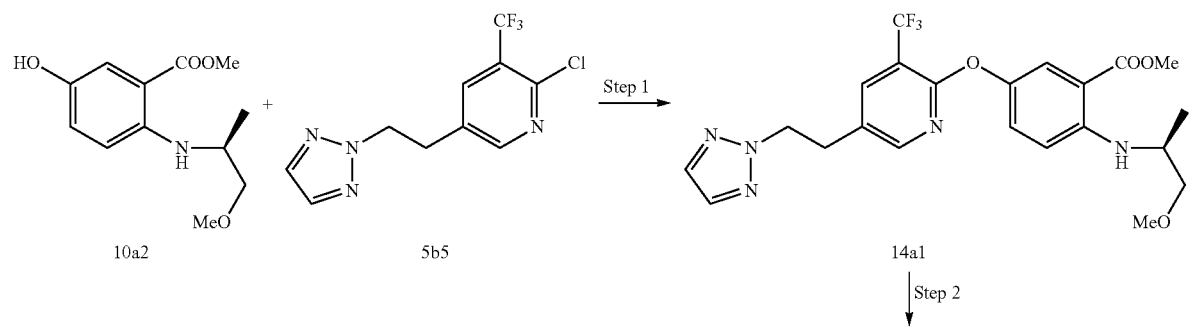

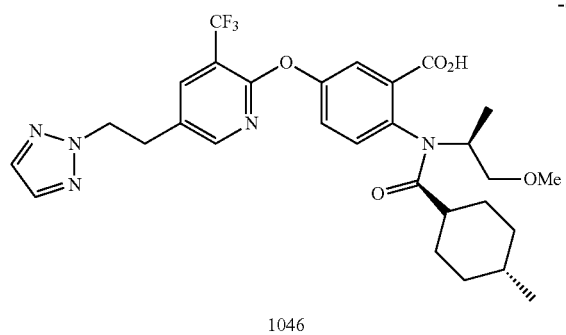

1046

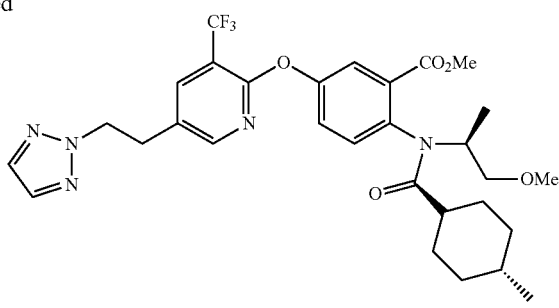

14a2

Step 1:

Compound 14a1 is generated via a reaction between compounds 10a2 and 5b5 using the procedure of Step 1, Example 13A.

Step 2:

Compound 14a1 is transformed to compound 14a2 using the procedure of Step 5, Example 11A.

Step 3:

To a solution of 14a2 (190 mg, 0.32 mmol) in MeCN/deionized water is added aqueous NaOH (0.32 mL, 1 M). This is stirred at RT for about 96 h. An additional amount of aqueous NaOH (0.64 mL, 1 M) is added and the resulting solution is allowed to stir for about 18 h. A 1 M HCl solution in water is added at 0° C. until acidic pH. The solution is extracted with EtOAc (4×). The organic layers are combined, washed with brine, dried over anhydrous $Na_2SO_4$, filtered under vacuum and concentrated. A light yellow oil (194 mg) is obtained which is dissolved in MeCN/deionized water (100 mL, 1:1) and 1 equivalent of 1 M aqueous NaOH is added. The solvent is then removed by lyophilization (~2 days) to yield 1046.

Example 15A

Preparation of Compound 1047 and 1048

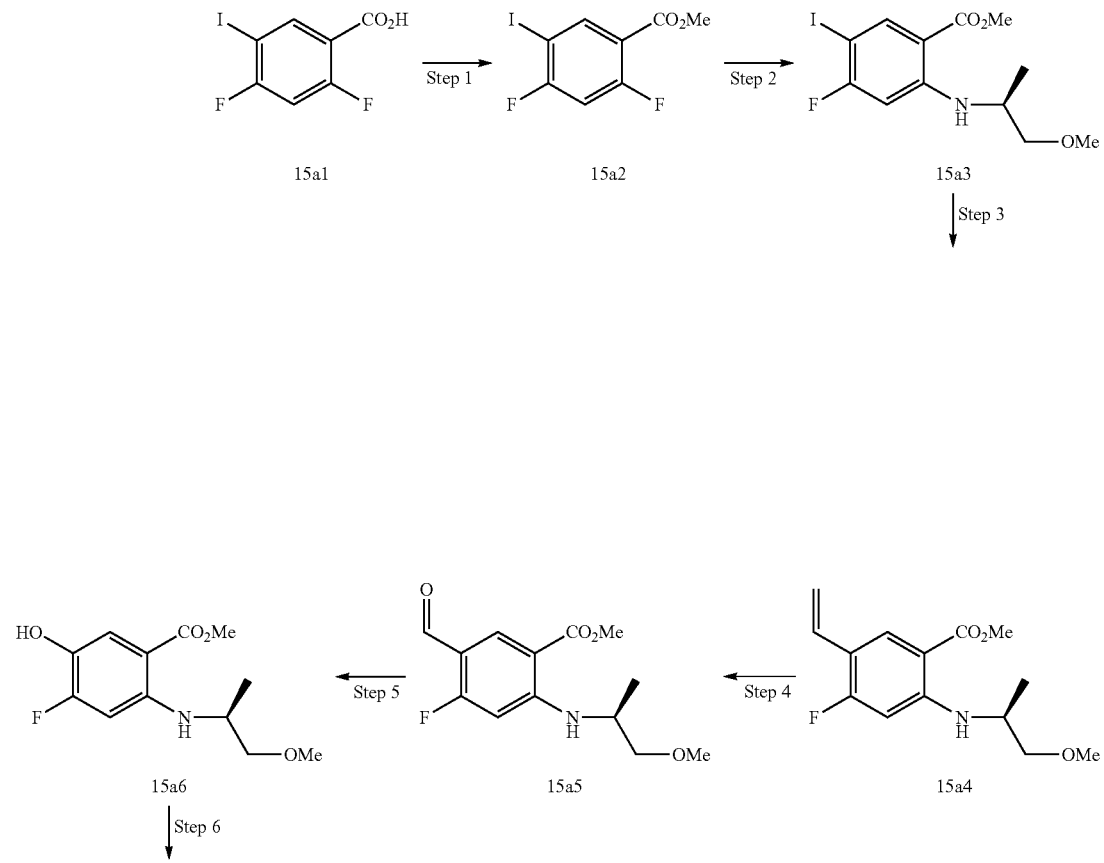

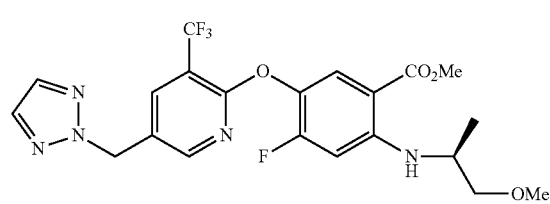

15a7

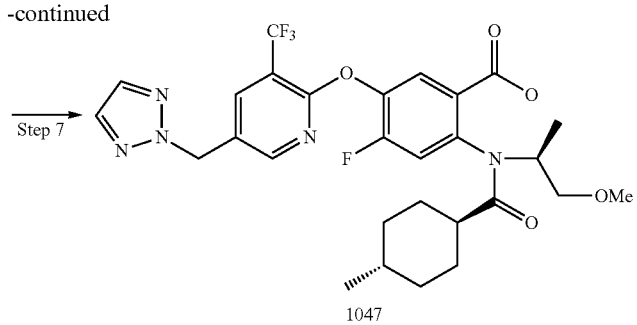

1047

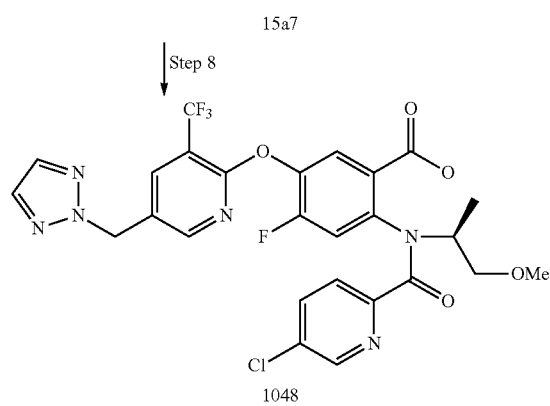

1048

Step 1:

Sulfuric acid (1 mL) is added to a solution of acid 15a1 (5.00 g, 17.6 mmol) in MeOH (100 mL). The solution is stirred overnight at 80° C. The mixture is cooled to RT, concentrated under reduced pressure, diluted with EtOAc (300 mL), washed with saturated aqueous NaHCO$_3$ (3×100 mL), brine (100 mL), dried over Na$_2$SO$_4$, filtered and concentrated under reduced pressure. The crude mixture is purified by flash chromatography (100% hexanes then 5% to 10% EtOAc in hexanes) to afford methyl ester 15a2 as an oil that solidifies upon standing under high vacuum.

Step 2 (S)-(+)-1-methoxy-2-propylamine (1.47 g, 16.7 mmol) is added to a DMF (30 mL) solution of fluoride 15a2 (3.30 g, 11.1 mmol) and potassium carbonate (2.28 g, 16.7 mmol). The mixture is stirred at 90° C. overnight, cooled to RT, diluted with saturated aqueous NaHCO$_3$ (200 mL) and extracted with EtOAc (2×200 mL). The combined organic phases are washed with saturated aqueous NaHCO$_3$ (2×100 mL), brine (100 mL) dried over Na$_2$SO$_4$, filtered and concentrated under reduced pressure. The crude mixture is purified by flash chromatography (100% hexanes then 5% to 20% EtOAc in hexanes) to afford amine 15a3 as an oil.

Step 3:

Pd(PPh$_3$)$_4$ (774 mg, 0.67 mmol) is added to a mixture of iodide 15a3 (2.46 g, 0.670 mmol) and tributylvinyltin (2.2 mL, 0.73 mmol) in DMF (30 mL). The mixture is degassed by simultaneously bubbling Ar and sonicating the solution for about 15 min. The mixture is stirred at 110° C. for about 2.5 h, cooled to RT, diluted with saturated aqueous NaHCO$_3$ (200 mL) and extracted with EtOAc (2×200 mL). The combined organic phases are washed with saturated aqueous NaHCO$_3$ (2×100 mL), brine (100 mL), dried over Na$_2$SO$_4$, filtered and concentrated under reduced pressure. The crude residue is purified by flash chromatography (100% hexanes then 5% to 10% EtOAc in hexanes) to afford vinyl compound 15a4 as an oil.

Step 4:

Vinyl compound 15a4 (1.00 g, 3.75 mmol) is dissolved in a mixture of acetone/tert-butanol/water (20 mL:8 mL:4 mL). The solution is cooled to 0° C., NMO (572 mg, 5.62 mmol) is added, followed by OsO$_4$ (2.5% in tert-butanol, 1.96 mL, 0.18 mmol). The solution is stirred at 0° C. for about 2 h, diluted with aqueous 10% sodium thiosulphate (100 mL) and extracted with EtOAc (2×100 mL). The combined organic phases are washed with aqueous 10% thiosulphate (100 mL), brine (2×100 mL), dried over Na$_2$SO$_4$, filtered and concentrated under reduced pressure to afford the crude diol which is dissolved in THF (30 mL) and water (15 mL). This solution is cooled to 0° C. and NaIO$_4$ is added (1.2 g, 5.6 mmol). The solution is stirred at 0° C. for about 4 h. The reaction mixture is diluted with saturated aqueous NaHCO$_3$ (100 mL) and extracted with EtOAc (2×100 mL). The combined organic phases are washed with aqueous saturated sodium bicarbonate (100 mL), brine (100 mL), dried over Na$_2$SO$_4$, filtered, and concentrated under reduced pressure. The crude material is purified by flash chromatography (100% hexanes then 5% to 20% EtOAc in hexanes) to afford aldehyde 15a5 as an oil.

Step 5:

Sulfuric acid (0.162 mL, 2.6 mmol) is added to a 0° C. MeOH (10 mL) solution of aldehyde 15a5 (500 mg, 1.86 mmol), followed by aqueous 30% hydrogen peroxide (0.295 mL, 2.6 mmol). The solution is stirred at 0° C. for about 1 h then diluted with aqueous 10% KH$_2$PO$_4$ (50 mL) and extracted with ether (2×100 mL). The combined organic phases are washed with aqueous 10% KH$_2$PO$_4$ (2×100 mL), brine (2×100 mL), dried over Na$_2$SO$_4$, filtered and concentrated under reduced pressure. The crude phenol 15a6 is used directly in the next step without further purification.

Step 6:

Phenol 15a6 is transformed to triazole 15a7 using the procedure described in Step 1, Example 13A.

Step 7:

Amine 15a7 is transformed to compound 1047 using the procedure described in Step 2, Example 13A.

Step 8:
Amine 15a7 is transformed to compound 1048 using the procedure described in Step 4, Example 10A

Example 16A

Preparation of Compounds 1051 and 1052

Step 2:
The coupling of phenol 3a6 with pyridine 5b5 is performed as described previously in Step 1, Example 16A. The saponification of the crude methyl ester (0.18 mmol) is performed in MeOH (1 mL) with NaOH (1 M, 0.9 mL, 0.9 mmol). Following complete conversion, the mixture is acidified with AcOH, filtered, then injected onto a preparative HPLC to afford 1052.

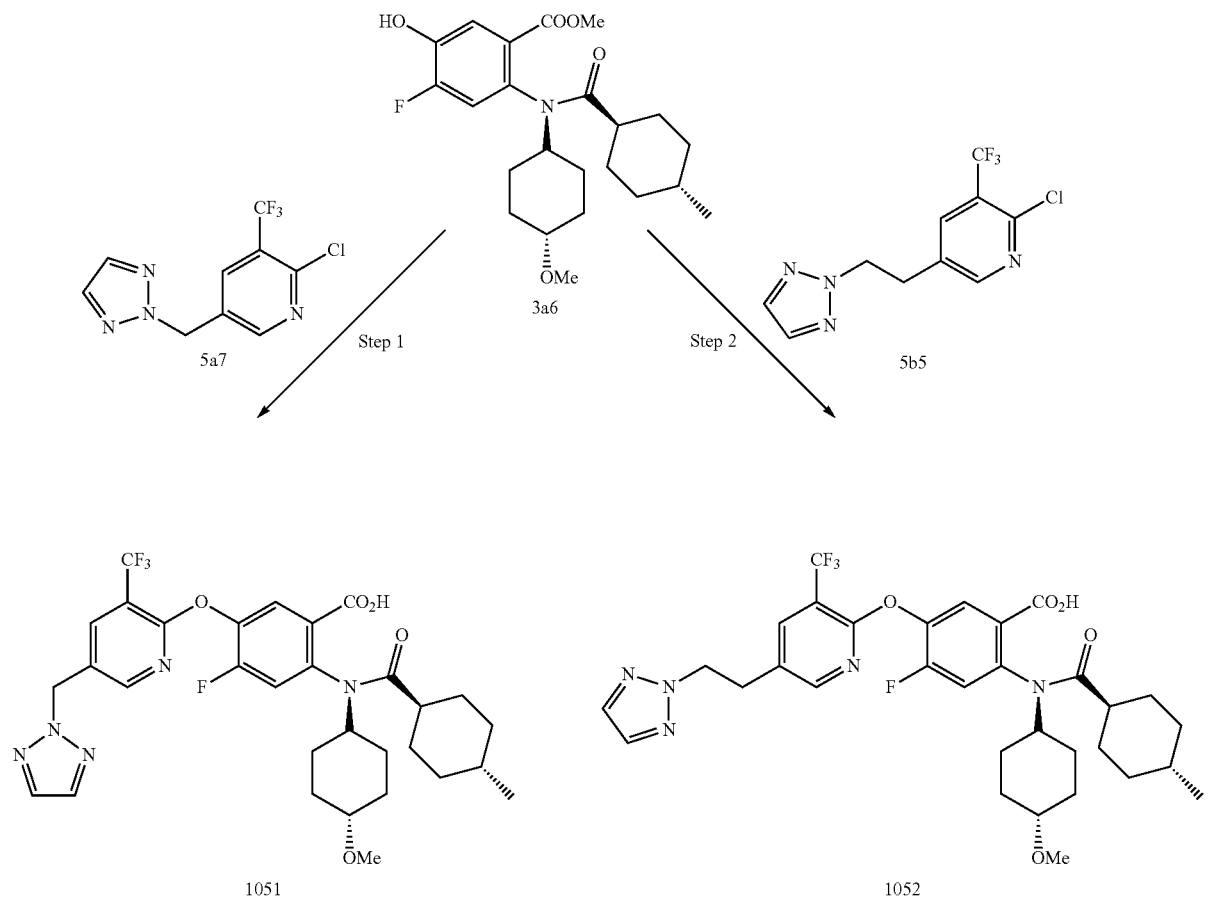

Step 1:
To a solution of phenol 3a6 (701 mg, 1.66 mmol) and $Cs_2CO_3$ (737 mg, 2.27 mmol) in anhydrous DMSO (8 mL) is added chloropyridine 5a7 (397 mg, 1.51 mmol). The resulting mixture is stirred at 80° C. for about 2 h, then diluted with EtOAc and successively washed with water, brine and concentrated under reduced pressure. Following purification by combiflash (15% EtOAc in hex), the intermediate methyl ester is isolated. This ester is redissolved in a THF (20 mL)/MeOH (10 mL) mixture and an aqueous NaOH solution (10 N, 0.8 mL, 8.0 mmol) is added. The mixture is stirred overnight before being acidified with AcOH, filtered, and injected onto a preparative HPLC. The combined fractions are lyophilized and the solid is dissolved in EtOAc. This organic solution is washed with 1 M NaOH (3x). The combined aqueous fractions are acidified with 1 M HCl until ~pH 6 and extracted with EtOAc (3x). The organics are dried over $MgSO_4$ and concentrated. The product is re-dissolved in MeCN and water and lyophilized to afford 1051.

Example 17A

Preparation of Compound 1054

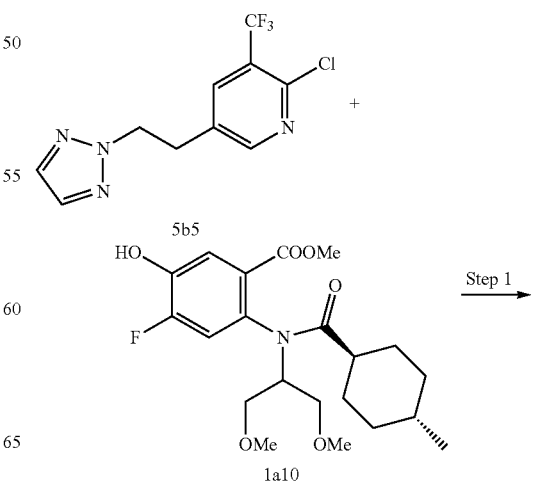

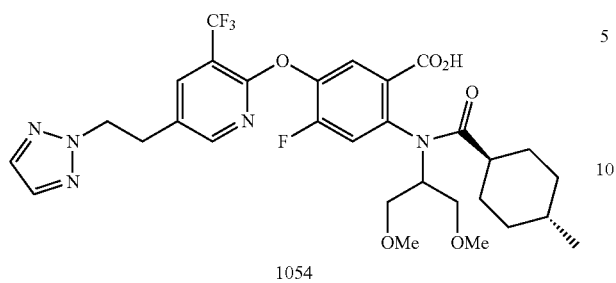

1054

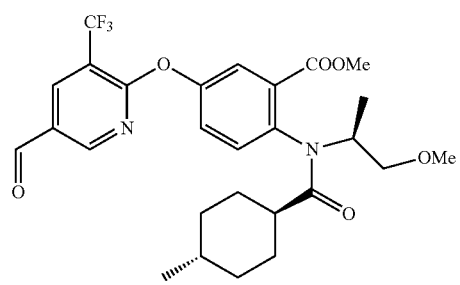

18a2

Step 2

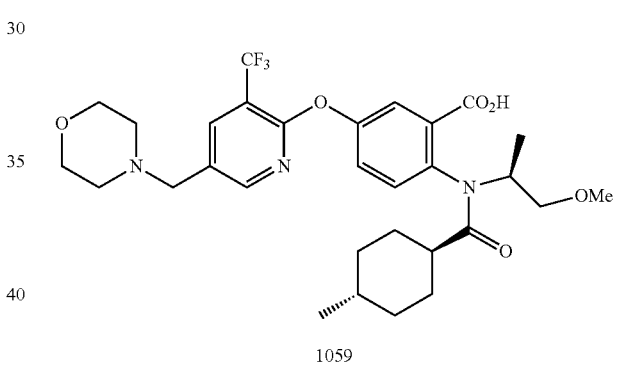

1059

Step 1:

To a solution of phenol 1a10 (1.96 g, 4.77 mmol) and $Cs_2CO_3$ (1.83 g, 5.64 mmol) in anhydrous DMSO (30 mL) is added pyridine 5b5 (1.20 g, 4.34 mmol). The resulting mixture is stirred at 95° C. overnight, then poured in water and extracted with $Et_2O$ (3×). The combined organic fractions are concentrated under reduced pressure. Following purification by combiflash (10% to 50% EtOAc in hex), the intermediate methyl ester is isolated. This ester is redissolved in MeOH (2 mL) and an aqueous NaOH solution (1 N, 2.34 mL, 2.34 mmol) is added. The mixture is stirred overnight before being washed with $Et_2O$, then acidified at 0° C. with 1 M HCl and extracted with EtOAc (4×). The combined fractions are dried and concentrated. The product is triturated (3×) with a pentane/$Et_2O$ (3:1) mixture, dissolved in MeCN and water and lyophilized to afford 1054 as the sodium salt.

Example 18A

Preparation of Compound 1059

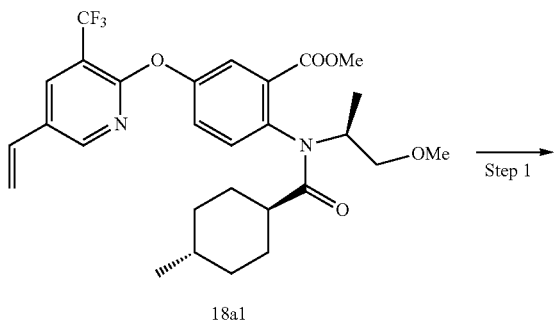

18a1

Step 1:

Vinyl compound 18a1 (prepared according to the same procedure described in Step 2, Example 25A) is transformed to aldehyde 18a2 using the procedure in Step 4, Example 15A.

Step 2:

To a solution of aldehyde 18a2 (60 mg, 0.11 mmol) in DCM (1 mL) is sequentially added morpholine (34 μL, 0.56 mmol), a solution of HCl (4 M in dioxane, 28 μL, 0.11 mmol) and $NaBH(OAc)_3$ (47 mg, 0.22 mmol). The reaction is stirred at RT, then concentrated to dryness. The mixture is re-dissolved in MeOH (1 mL) and NaOH (10 N, 0.1 mL, 1 mmol) is added. When complete, the reaction is neutralized with AcOH and injected onto the preparative HPLC to isolate 1059.

Example 19A

Preparation of Compound 1060

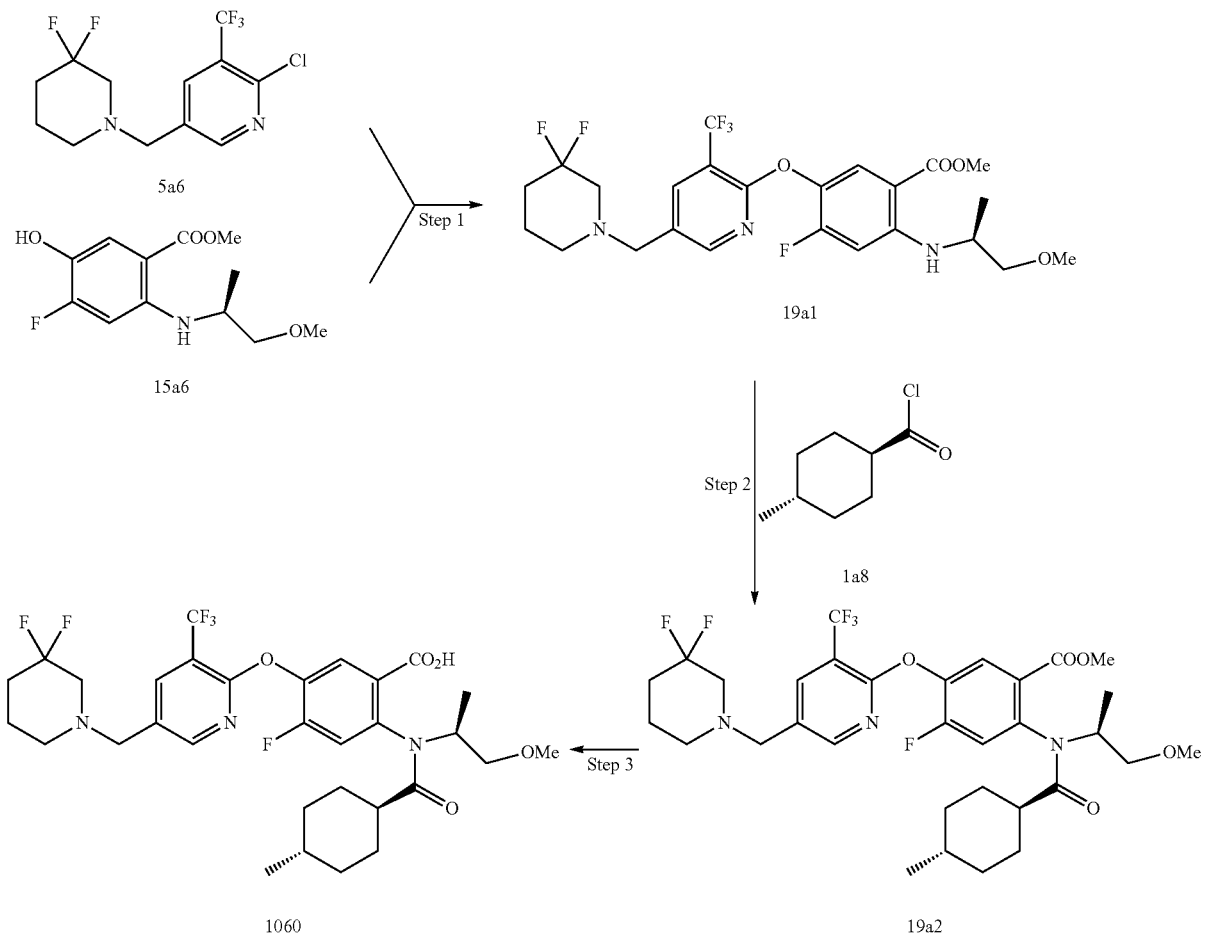

Step 1:

Compound 19a1 is generated via a reaction between compounds 5a6 and 15a6 using the procedure of Step 1, Example 16A.

Step 2:

In a microwave tube, the intermediate 19a1 (75 mg, 0.14 mmol) is dissolved in pyridine (1 mL) and a solution of acid chloride 1a8 (2 M in DCE, 0.5 mL, 0.90 mmol) is then added followed by a catalytic amount of DMAP (7 mg, 56 µmol). The tube is sealed and put in microwave at 150° C. for 20 min. The mixture is diluted in EtOAc and washed with water (2×) and brine (1×). The combined organics are dried over MgSO$_4$, filtered and concentrated. The crude residue is purified by flash chromatography (5% to 70% EtOAc in hex) to afford 19a2.

Step 3:

Methyl ester 19a2 (16 mg, 24 µmol) is dissolved in a 2:1 THF/MeOH mixture (0.5 mL) and an aqueous NaOH solution (1.0 M, 25 µL, 25 µmol) is then added. The reaction is stirred at RT, diluted in water and the aqueous layer is washed with Et$_2$O (2×) to remove organic impurities. The aqueous fraction is lyophilized and the compound 1060 is isolated as its sodium salt.

Example 20A

Preparation of Compound 1061

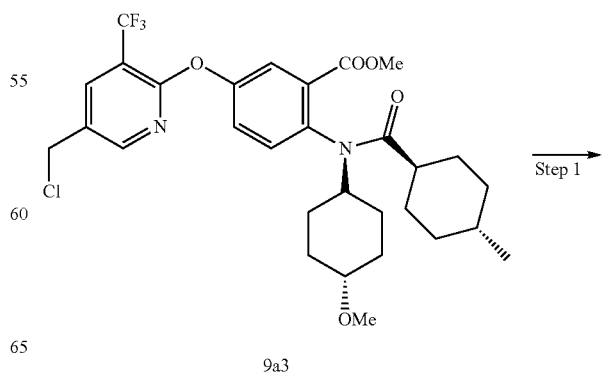

9a3

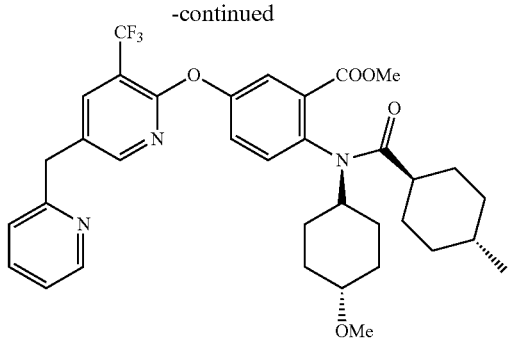

20a1

Step 2

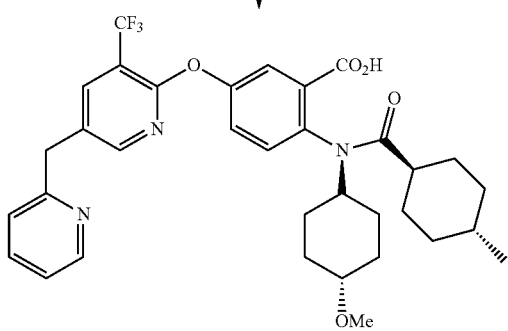

1061

Step 1:

In a microwave tube, the chloride 9a3 (60 mg, 0.10 mmol) is dissolved in degassed DMF (2 mL, degassed by bubbling Ar while sonicating for about 10 min). 2-(tributylstannyl) pyridine (92 mg, 0.25 mmol) and Pd(PPh$_3$)$_4$ catalyst (12 mg, 10 µmol) are then added. The mixture is further degassed and the tube is sealed and put in microwave at 120° C. for 20 min. The mixture is diluted in EtOAc and washed with water (2×) and brine (2×). The combined organics are dried over MgSO$_4$, filtered and concentrated. The crude residue is purified by flash chromatography (25% to 75% EtOAc in hex) to afford 20a1.

Step 2:

The intermediate 20a1 (35 mg, 0.055 mmol) is dissolved in a THF (3 mL)/MeOH (0.5 mL)/H$_2$O (0.5 mL) mixture and an aqueous NaOH solution (10 N, 27 µL, 0.27 mmol) is added. When complete, the reaction is neutralized with AcOH and injected onto the preparative HPLC to isolate 1061.

Example 21A

Preparation of Compound 1072

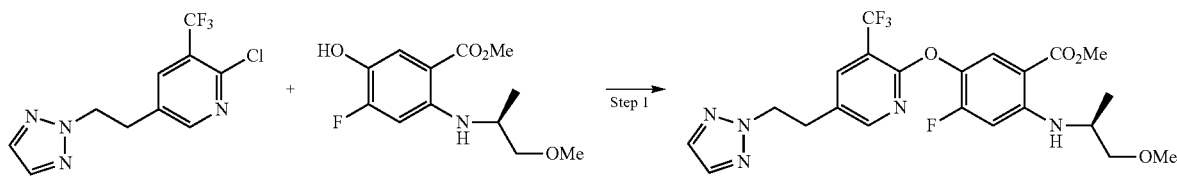

Step 2

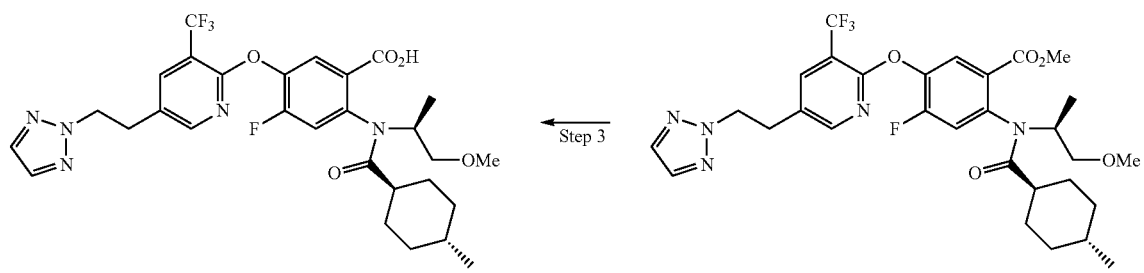

Step 1:
Compound 21a1 is generated via a reaction between compounds 5b5 and 15a6 using the procedure of Step 1, Example 13A.
Step 2:
Compound 21a1 is transformed to compound 21a2 using the procedure of Step 5, Example 11A.
Step 3:
Compound 21a2 is transformed to compound 1072 using the procedure of Step 3, Example 14A.

Example 22A

Preparation of Compound 1082

Step 2:
In a 25 mL flask is added 22a1 (60 mg, 0.14 mmol), pyridine (0.25 mL, 3.1 mmol), acylchloride 1d8 (99 mg, 0.42 mmol) and DMAP (5.1 mg, 0.04 mmol). This mixture is heated to 150° C. for about 4 h and then cooled and stirred at RT for about 65 h. This is quenched with $NaHCO_3$ (saturated), extracted with DCM (3×), passed through a phase separator and concentrated under reduced pressure to obtain crude product 22a2 which is employed in the subsequent step without further purification.

Step 3:
Compound 22a2 is dissolved in THF/MeOH/$H_2O$ (2:1:1 mL), NaOH (10 M, 0.07 mL) is added and the reaction is

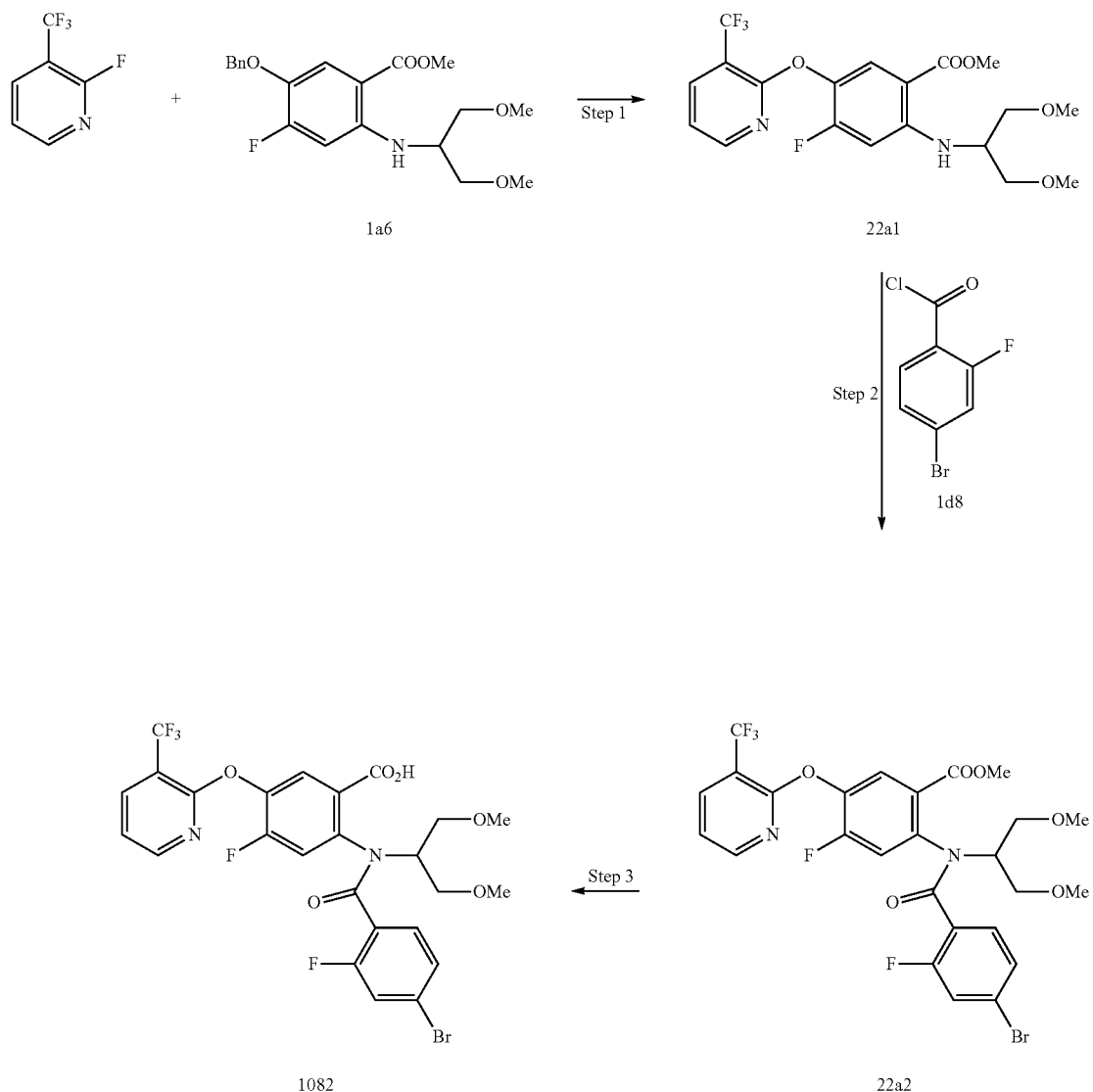

Step 1:
Compound 22a1 is generated via the reaction of compound 1a6 and 2-fluoro-3-trifluoromethylpyridine using the procedures of Steps 2 and 3, Example 8A.

stirred for about 36 h at RT. A minimum amount of aqueous AcOH is added to neutralize the solution and the solvent is evaporated. Purification by preparative HPLC affords compound 1082 as a white lyophilized solid.

Example 23A
Preparation of Compounds 1092 and 1093
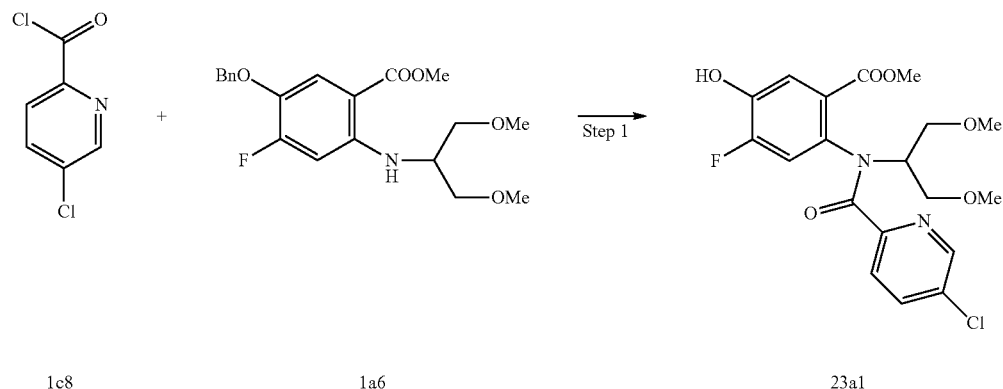
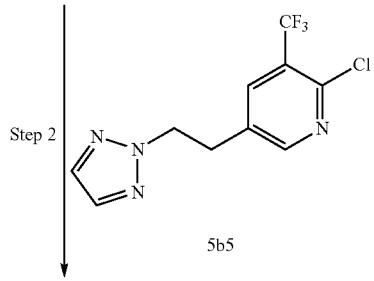
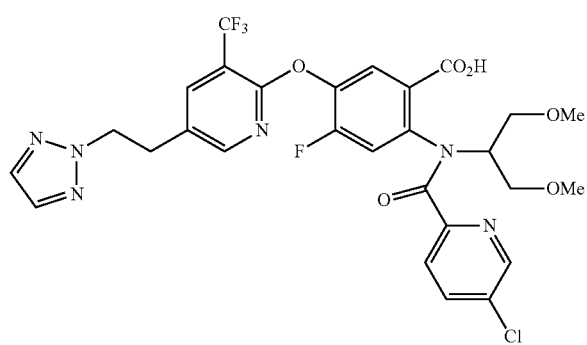
1093
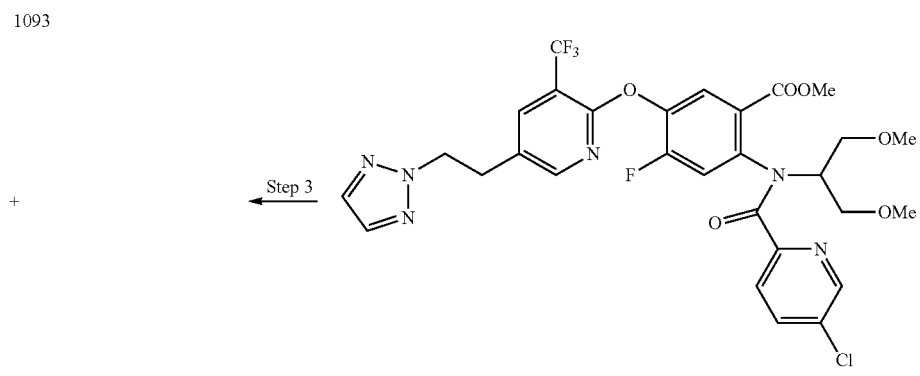
23a2

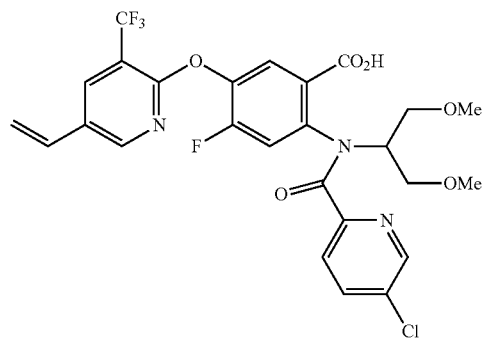

1092

Step 1:
Compounds 1c8 and 1a6 are reacted using the procedure in Step 2, Example 19A. The deprotection of the benzyl ether is performed employing the same procedure as that in Step 2, Example 8A to produce compound 23a1.

Steps 2 and 3:
To a solution of phenol (50 mg, 0.12 mmol) in DMSO (1 mL) is added $CsCO_3$ (57 mg, 0.18 mmol) followed by chloropyridine 5b5 (90 mg, 0.33 mmol). This is stirred at 105° C. for about 18 h, then cooled to RT. MeOH (1 mL), NaOH (1 eq, 1 M in water) and LiOH (1 eq) are added and this is stirred for about 4 h at RT. The mixture is then concentrated, diluted in AcOH (4 mL) and purified by preparative HPLC. The fractions are combined and solvent is removed by lyophilization to yield two products, 1093 and 1092.

Example 24A

Preparation of Compound 1094

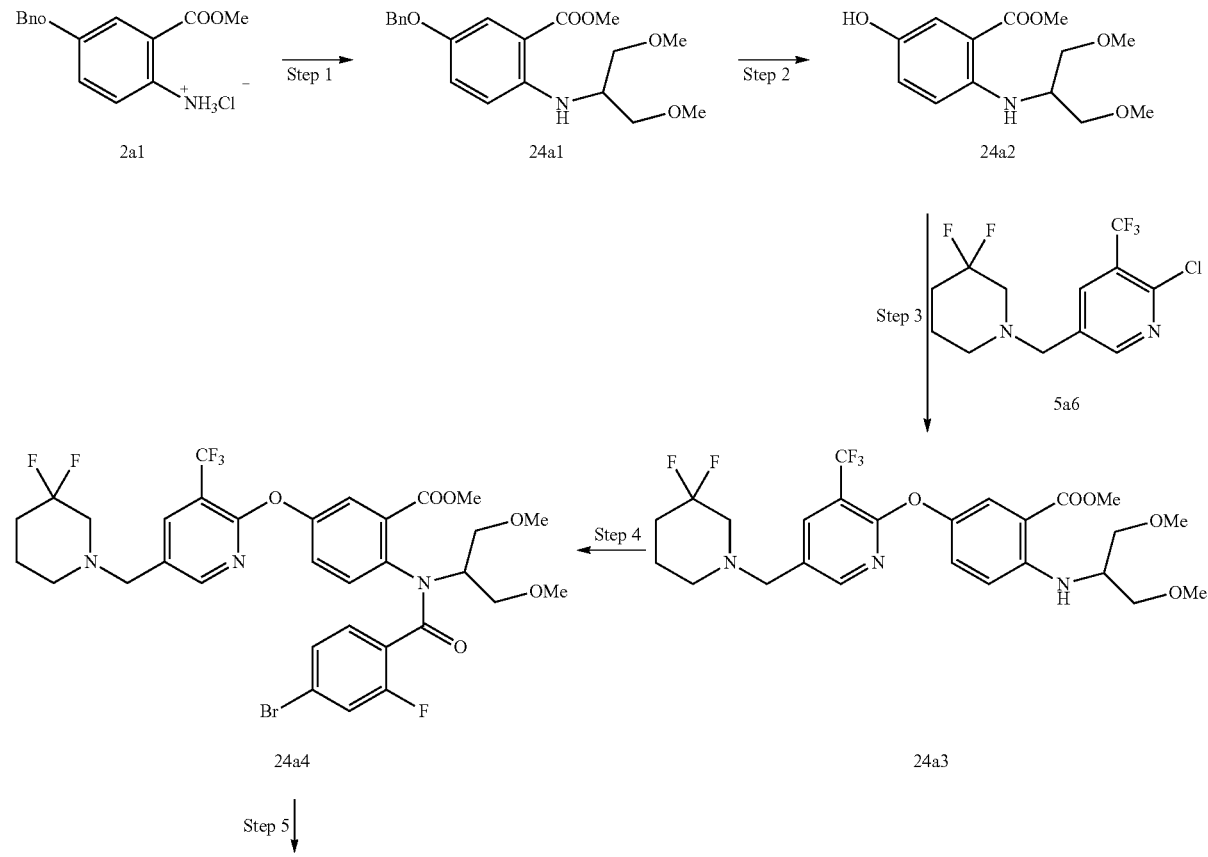

-continued

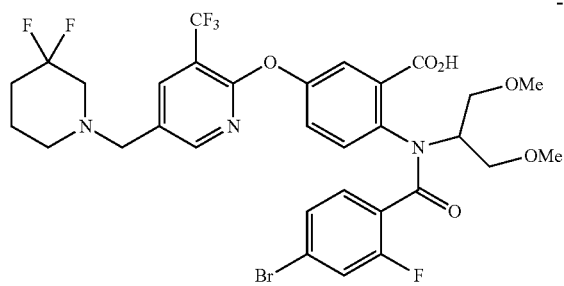

1094

Step 1:
Compound 2a1 is transformed to compound 24a1 using the procedure in Steps 4 and 5, Example 1A.

Step 2:
Compound 24a1 is transformed to compound 24a2 using the procedure in Step 8, Example 1A.

Step 3:
Compounds 24a2 and 5a6 are combined to form compound 24a3 using the procedure in Step 3, Example 8A.

Steps 4 and 5:
Compound 24a3 is transformed to 24a4 and thereafter to compound 1094 using the procedure in Steps 2 and 3, Example 22A, respectively.

Example 25A

Preparation of Compound 1099

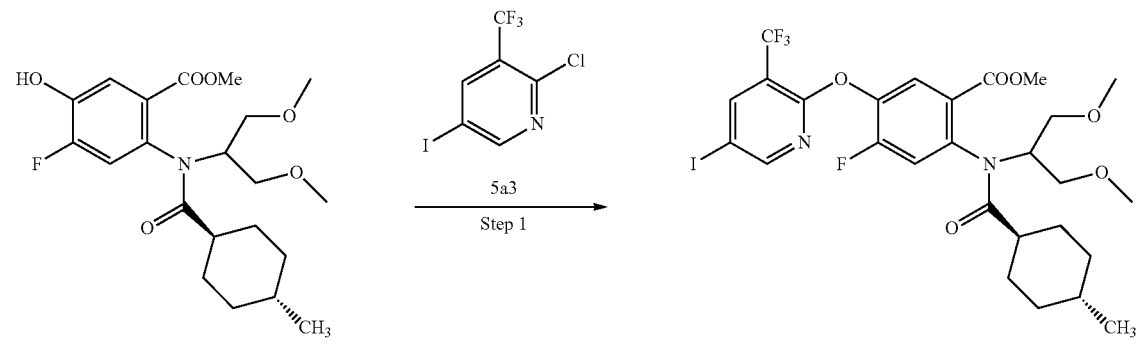

1a10          25a1

Step 2

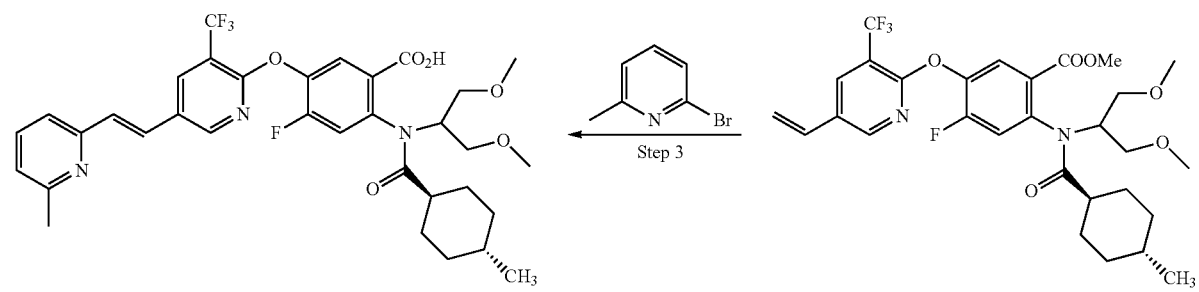

1099          25a2

Step 1:

To a solution of phenol 1a10 (400 mg, 0.97 mmol) in DMSO (5 mL) is added CsCO$_3$ (474 mg, 1.4 mmol) and chloropyridine 5a3 (430 mg, 1.40 mmol). The solution is stirred at 75° C. for about 4 h and then washed with water and brine. The solution is then dried over anhydrous Na$_2$SO$_4$, filtered under vacuum and concentrated under reduced pressure. Purification by flash chromatography using (20:80 to 60:40) EtOAc/Hex yields 25a1.

Step 2:

To a solution of iodide 25a1 (370 mg, 0.54 mmol) in dioxane (4 mL) is added tributyl(vinyl)tin (0.2 mL, 0.69 mmol) at RT. Argon is bubbled through the solution followed by the addition of dichloro-bis(triphenylphosphine)palladium (42 mg, 0.06 mmol). The reaction mixture is heated at reflux for about 1 h; then concentrated and purified by flash chromatography using (10:90 to 70:30) EtOAc/Hex to obtain 25a2.

Step 3:

To a solution of olefin 25a2 (40 mg, 0.07 mmol) in DMF (1 mL) is added bromopyridine (18 mg, 0.10 mmol), TBABr (35 mg, 0.21 mmol), Et$_3$N (0.014 mL, 0.10 mmol) and palladium acetate (1.5 mg, 0.007 mmol) at RT. This is stirred at 120° C. in the microwave for 10 min followed by heating at 140° C. (oil bath) for about 16 h. The reaction mixture is quenched with water and extracted with EtOAc (3×). The organic layers are combined, washed with brine, dried over anhydrous Na$_2$SO$_4$, filtered under vacuum and concentrated. THF (2 mL), MeOH (1 mL) and NaOH (1 M in water, 5 eq) are added and then this is stirred for about 14 h at RT. The reaction mixture is diluted with AcOH (1 mL) and purified by preparative HPLC. The fractions are combined and solvent is removed by lyophilization to yield 1099.

Example 26A

Preparation of Compound 1102

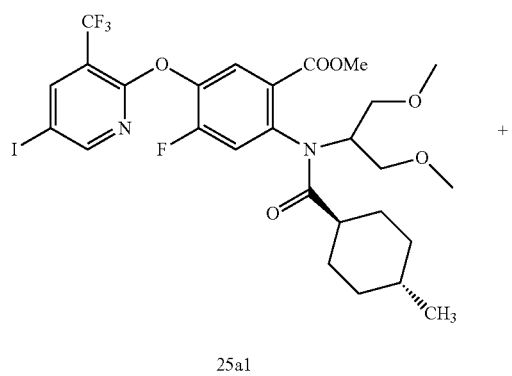

25a1

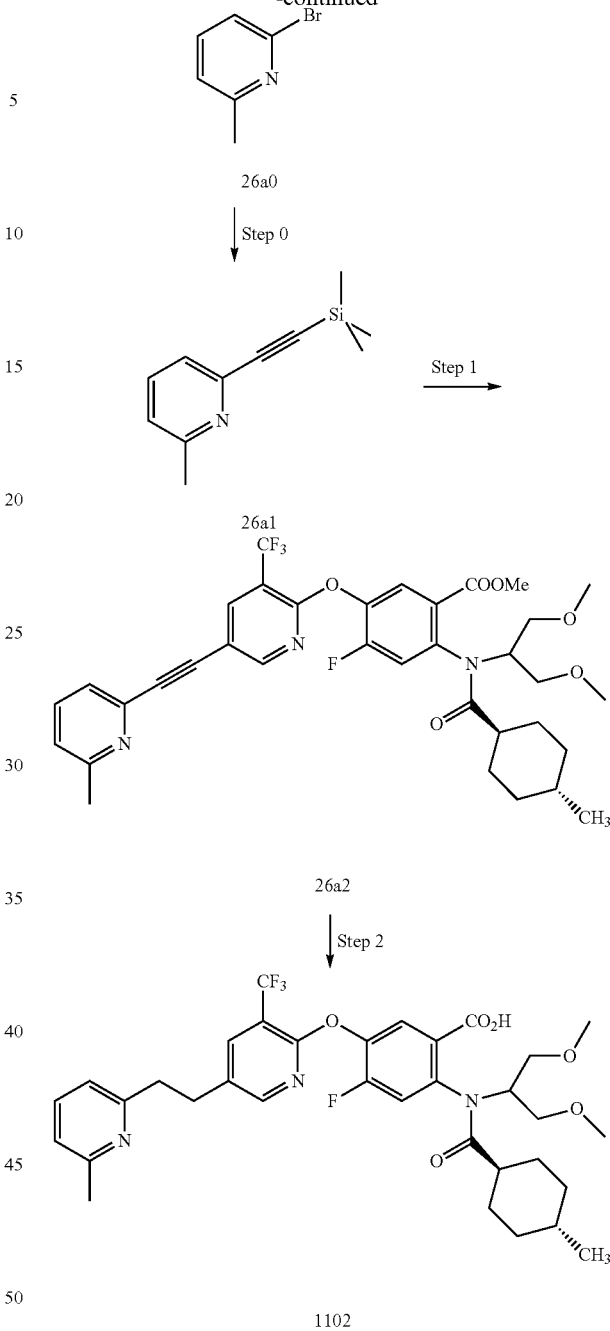

Step 0:

In a microwave tube containing DMF (2 mL) is added 2-bromo-6-methylpyridine (300 mg, 1.74 mmol), trimethylsilylacetylene (257 mg, 2.62 mmol), CuI (33 mg, 0.17 mmol), Pd(PPh$_3$)$_4$ (201 mg, 0.17 mmol) and Et$_3$N (1.2 mL). The tube is sealed and placed in microwave for 10 min at 120° C. The mixture is then diluted with EtOAc, washed with water and brine, dried over Na$_2$SO$_4$, filtered and concentrated. The crude residue is purified by flash chromatography (Hex/EtOAc, 20% to 80%) to afford pyridine 26a1.

Step 1:

To a solution of alkyne 26a1 (33 mg, 0.18 mmol) in DMF (1 mL) is added TBAF (0.18 mL, 1 M solution in THF) at RT. This is stirred for about 10 min, then iodide 25a1 (40 mg, 0.06 mmol), CuI (1.1 mg, 0.006 mmol), Et₃N (0.04 mL, 0.3 mmol) and Pd(PPh₃)₄ (6.8 mg, 0.006 mmol) are added at RT. This mixture is stirred at 120° C. in the microwave for 12 min. The reaction mixture is quenched with water and extracted with EtOAc (3×). The organic layers are combined, washed with brine, dried over anhydrous Na₂SO₄, filtered under vacuum and concentrated. Purification by flash chromatography using (40:60 to 90:10) EtOAc/Hex affords 26a2.

Step 2:

Compound 26a2 is dissolved in MeOH, Pd/C (10% w/w, 33 mg) is added and the mixture is purged with H₂ (3×). The mixture is stirred under a H₂ atmosphere (balloon) for about 1 h, filtered and concentrated under reduced pressure. The residue is dissolved in MeOH and NaOH (1 M in water, 1 mL) is added followed by LiOH (3 eq). This mixture is stirred at RT for 2 h, concentrated, dissolved in AcOH (2 mL) and purified by preparative HPLC. The fractions are combined and solvent is removed by lyophilization to yield compound 1102.

Example 27A

Preparation of Compound 1104

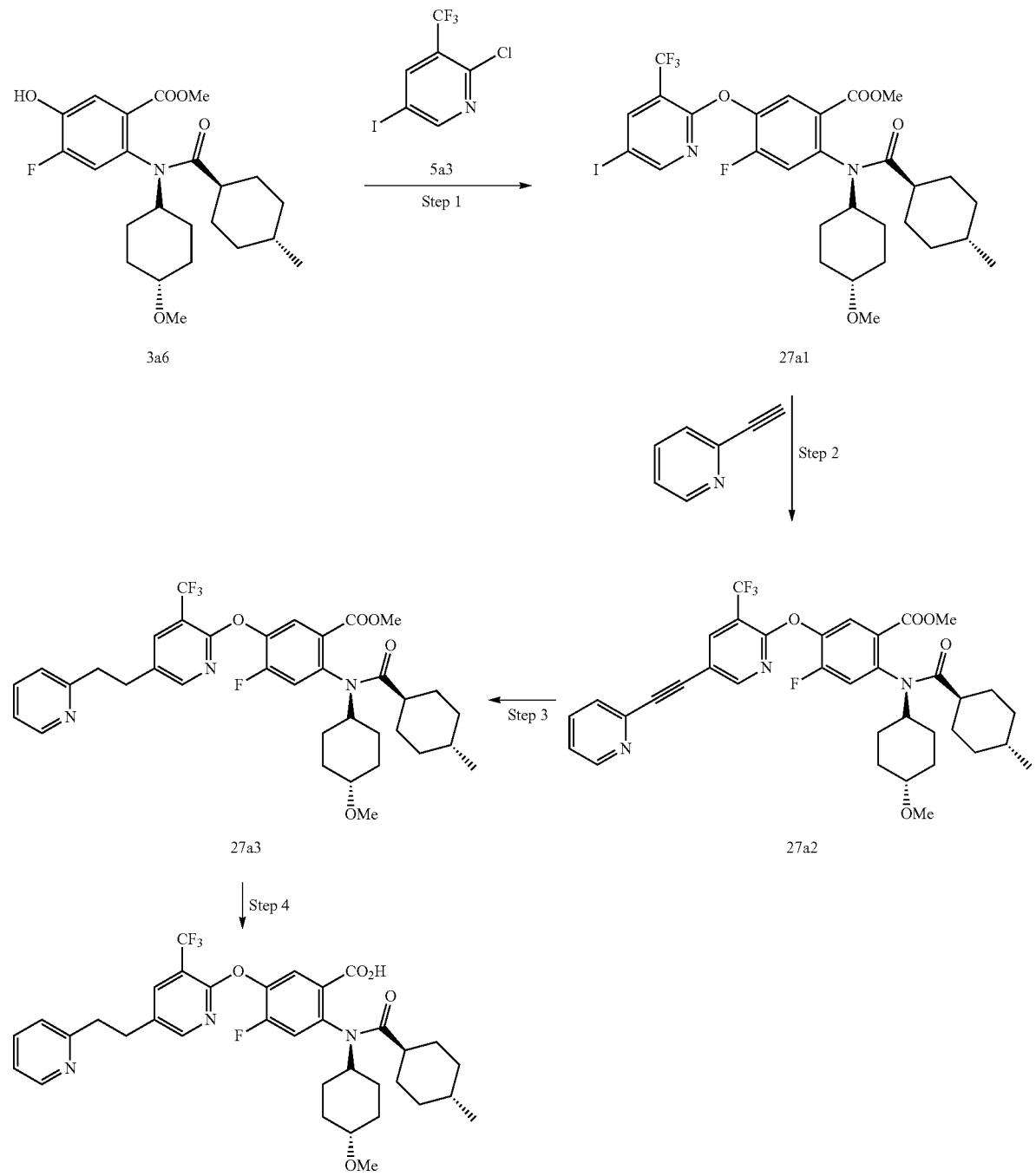

Step 1:
Compound 3a6 is transformed to compound 27a1 using the procedure in Step 1, Example 13A.
Step 2:
A mixture of iodide 27a1 (90 mg, 0.13 mmol), ethylnylpyridine (27 mg, 0.26 mmol), CuI (2.5 mg, 0.013 mmol), Pd(PPh$_3$)$_4$ (15 mg, 0.013 mmol) and Et$_3$N (0.09 mL, 0.7 mmol) in degassed DMF is heated in a microwave at 120° C. for 20 min. This mixture is dissolved in EtOAc (50 mL), washed with water and brine, dried (MgSO$_4$) and concentrated. Purification by flash chromatography (1/2 then 1/1 EtOAc/Hex) yields 27a2 as pale yellow foam.
Step 3:
To the alkyne 27a2 (70 mg, 0.10 mmol) in MeOH (2 mL) is added Pd/C catalyst (10% w/w, 70 mg) which is then hydrogenated with ~15 psi of H$_2$ at RT for about 2.5 h. The catalyst is filtered and the residue is concentrated to dryness. The crude product 27a3 is isolated and employed in the subsequent reaction without further purification.
Step 4:
To the solution of the ester 27a3 (68 mg, 0.10 mmol) dissolved in DMSO (2 mL), MeOH (1 mL) and water (0.3 mL) is added at RT an aqueous solution of NaOH (10 N, 0.06 mL). This is stirred at RT for about 5 h and then maintained at 0° C. overnight. The reaction is quenched with aqueous TFA and purified by preparative HPLC. The fractions are combined and lyophilized to yield 1104.

Example 28A

Preparation of Compound 1105

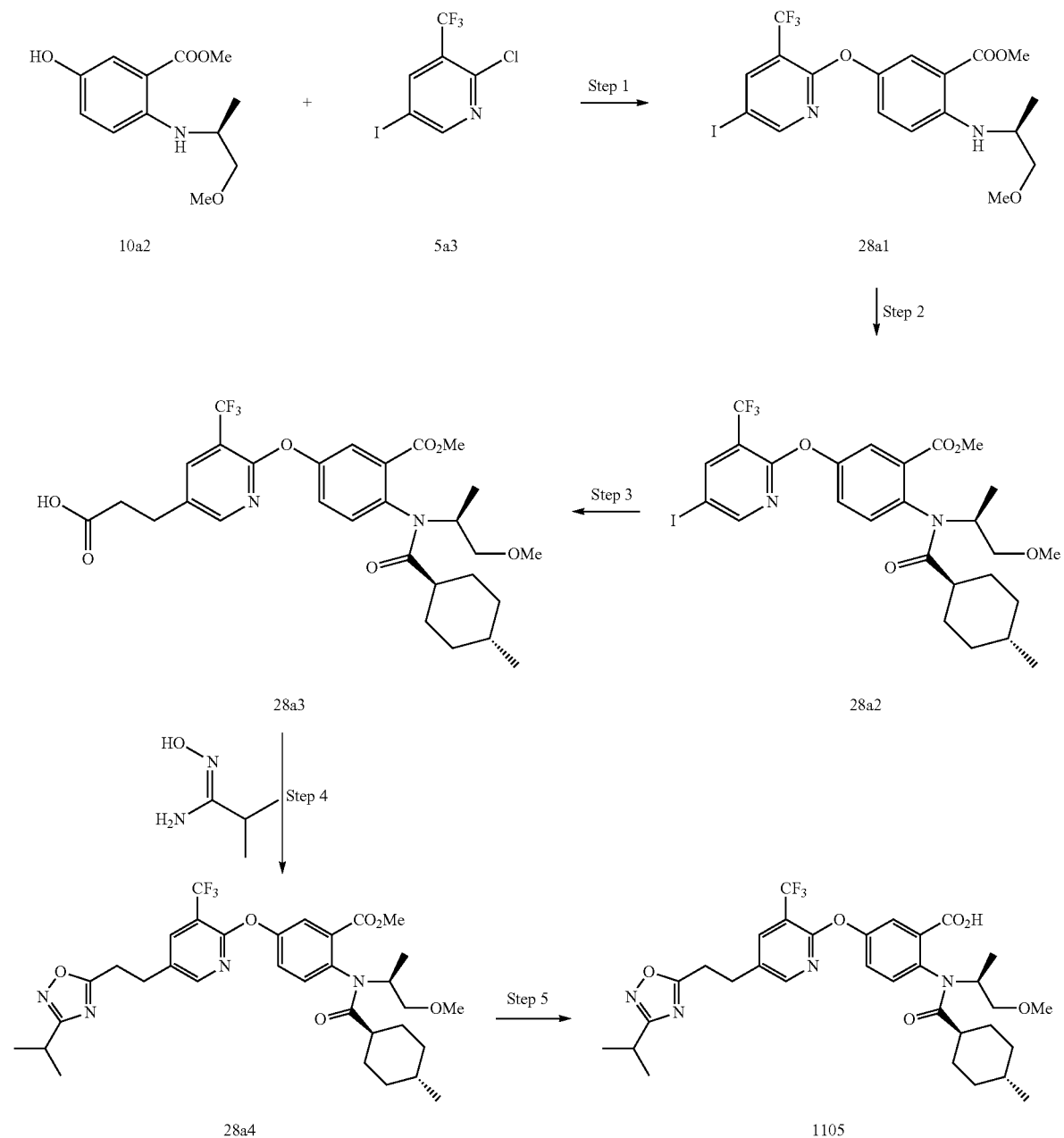

Step 1:
    Compound 28a1 is generated through the reaction of compound 10a2 with compound 5a3 using the procedure of Step 1, Example 13A.
Step 2:
    Compound 28a1 is transformed to compound 28a2 using the procedure of Step 5, Example 11A.
Step 3:
    A mixture of iodide 28a2 (500 mg, 0.79 mmol), benzyl acrylate (1.3 g, 7.9 mmol), Pd(OAc)₂ (50 mg, 0.23 mmol), Et₃N (5.0 mL) and MeCN (20 mL) is stirred at 60° C. in a sealed tube for about 4 h. The reaction mixture is cooled to RT, filtered and concentrated. Purification by flash chromatography (7:3 to 1:1 Hex:EtOAc) affords an oil which is taken up in EtOH (20 mL). Pd/C (10%, 50 mg) is added and then stirred under H₂ for about 30 min. The reaction mixture is filtered on Celite® and concentrated to give 28a3 as a white foam.
Steps 4 and 5:
    To the acid 28a3 (50 mg, 0.09 mmol) in DMF (2.0 mL) is added Et₃N (0.06 mL, 0.4 mmol), and HATU (40 mg, 0.11 mmol). The reaction is stirred for about 10 min; then amidooxime (8.8 mg, 0.09 mmol) is added and stirring is continued for about 2 h. The reaction mixture is poured into Et₂O, washed with H₂O (3×), saturated NH₄Cl (1×), dried over MgSO₄, filtered and concentrated in vacuo. The residue is redissolved THF (3 mL); TBAF (0.1 mL, 1.0 M solution in THF) is then added and this is stirred for about 1 h at 45° C. The mixture is concentrated in vacuo and the residue is then taken up in DMSO (2 mL). Aqueous NaOH (1 M, 1 mL) is added and the solution is stirred at RT for about 1 h. AcOH is added and purification by preparative HPLC, followed by lyophilization affords compound 1105.

Example 29A

Preparation of Compound 1109

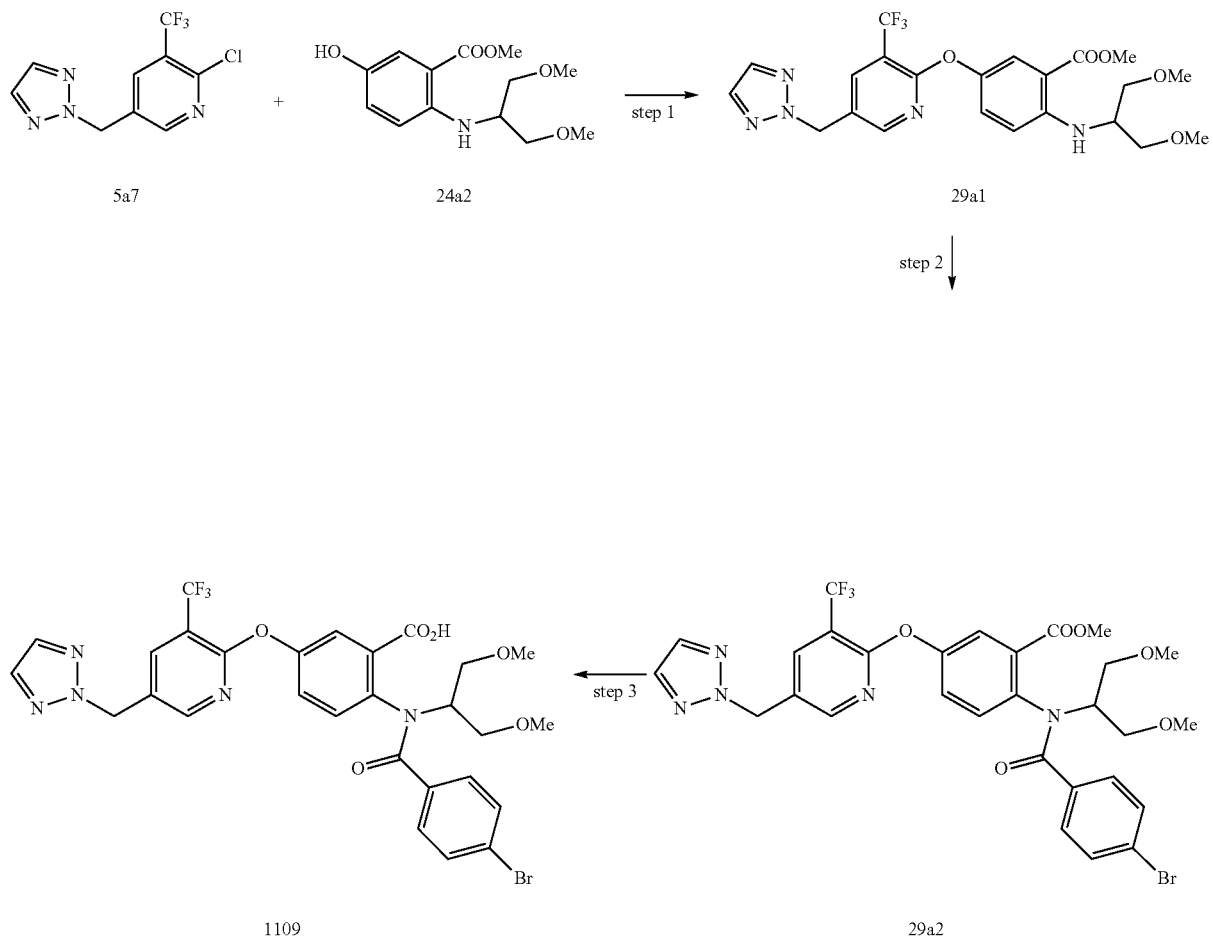

Step 1:
    Compound 29a1 is generated through the reaction of compounds 5a7 and 24a2 using the procedure of Step 3, Example 8A.
Step 2:
    Compound 29a1 is transformed to compound 29a2 using the procedure of Step 2, Example 22A.
Step 3:
    Compound 29a2 is transformed to compound 1109 using the procedure of Step 3, Example 22A.

Example 30A
Preparation of Compound 1110
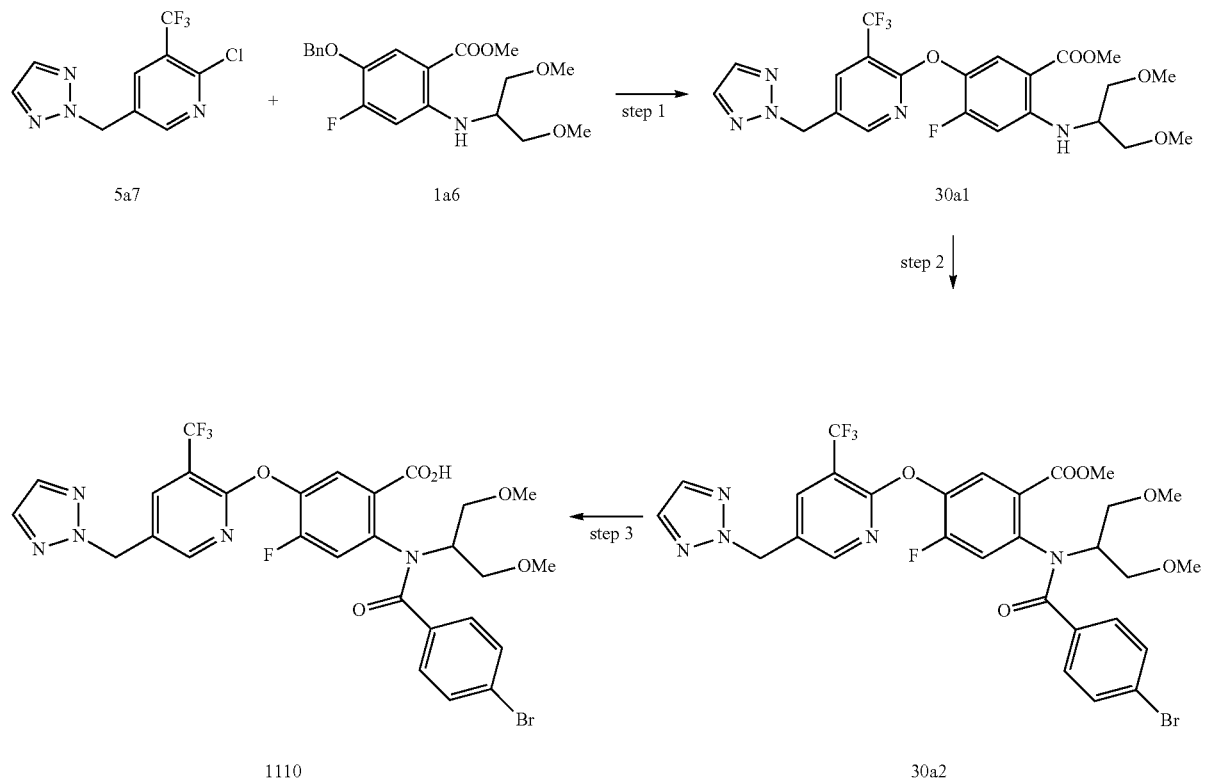
Steps 1 and 2:
Compounds 5a7 and 1a6 are transformed to compound 30a1 is generated using the procedure of Steps 2 and 3, Example 8A and thereafter to compound 30a2 using the procedure of Step 2, Example 22A.
Step 3:
Compound 30a2 is transformed to compound 1110 using the procedure of Step 3, Example 22A.
Example 31A
Preparation of Compound 1113
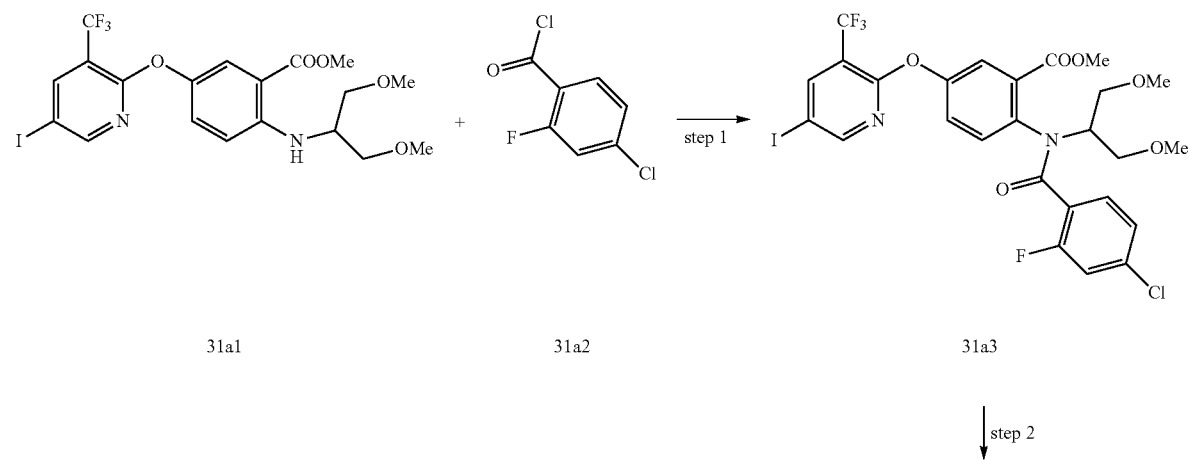

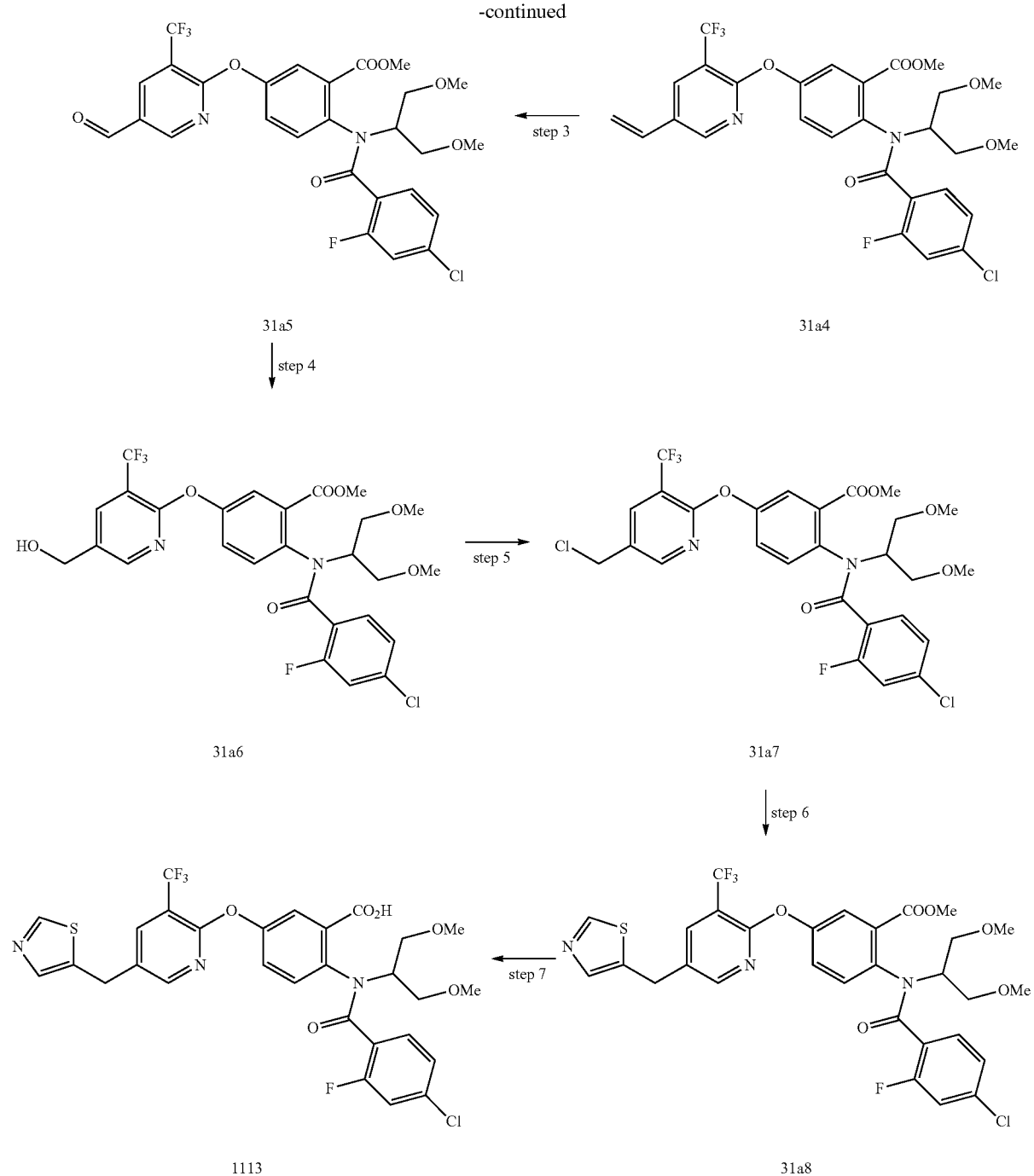

Step 1:
Using the procedure of Step 2, Example 22A, compound 31a1 (generated according to the condensation of 5a3 and 24a2 using the procedure described in Step 3, Example 24) is acylated with 31a2 (synthesized according to the procedure described in Step 6, Example 1A) to afford compound 31a3.

Step 2:
Compound 31a3 is transformed to compound 31a4 using the procedure of Step 2, Example 25A.

Steps 3 and 4:
Compounds 31a4 is transformed to 31a5 and thereafter to compound 31a6 using the procedure of Steps 2 and 3, Example 5B, respectively.

Step 5:
Compound 31a6 is transformed to compound 31a7 using the procedure of Step 3 Example 9A, respectively.

Steps 6 and 7:
To a solution of the chloride 31a7 (56 mg, 0.09 mmol) in DMF (1 mL) is added Pd(PPh$_3$)$_4$ (9.9 mg, 0.009 mmol) and 5-(tri-butylstannyl)thiazole (64 mg, 0.17 mmol) at RT. This solution is stirred at 120° C. for about 12 min. MeOH (1 mL) and aqueous NaOH (1 M, 1 mL) are added and stirring continues for about 3 h at RT. The reaction mixture is concentrated, diluted in AcOH (4 mL) and purified by preparative HPLC. The fractions are combined and solvent is removed by lyophilization to yield compound 1113.

Example 32A

Preparation of Compounds 1114 and 1118

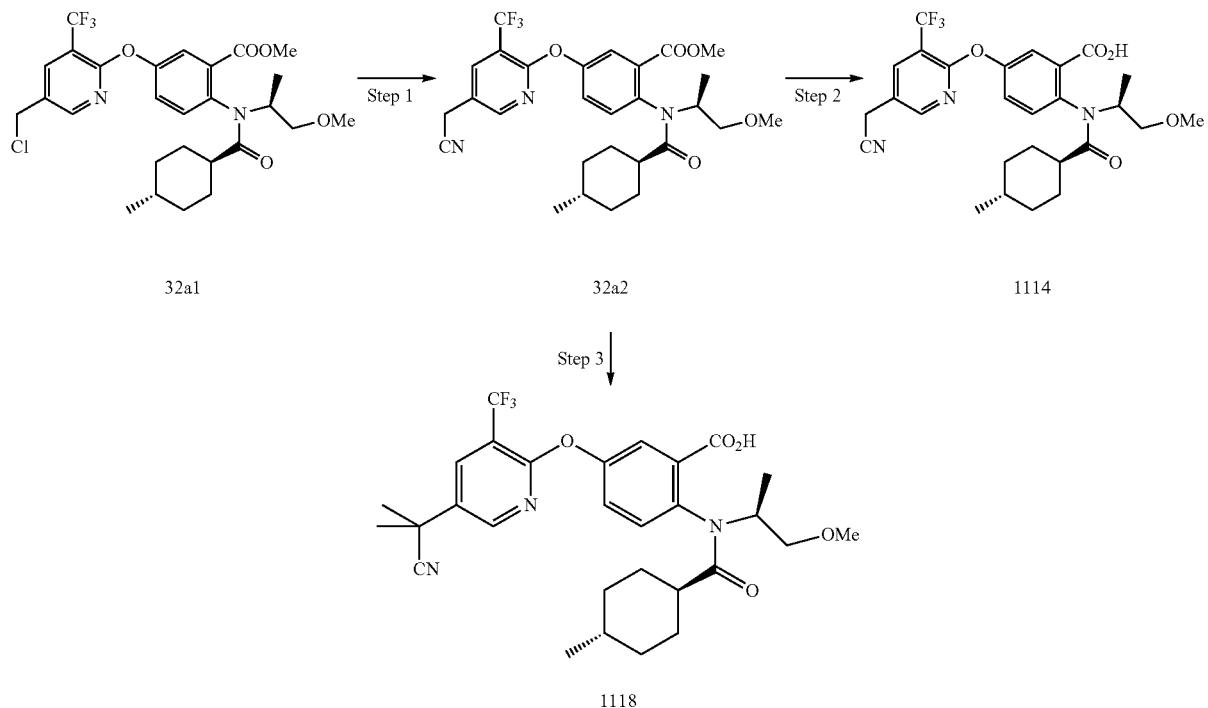

Step 1:

The chloride 32a1 (356 mg, 0.639 mmol), which is prepared from phenol 10a2 using the procedure described in Steps 1 to 3, Example 9A, is dissolved in DMSO (1 mL) and NaCN (63 mg, 1.28 mmol) is added. The reaction is stirred at RT for about 1 h, then water is added. The mixture is extracted with DCM (3×), the organics are dried and concentrated. Purification by flash chromatography (1% to 5% MeOH in DCM) affords nitrile 32a2.

Step 2:

The nitrile 32a2 (42 mg, 0.08 mmol) is dissolved in a THF (1 mL)/MeOH (0.5 mL)/$H_2O$ (0.5 mL) mixture and an aqueous NaOH solution (10 N, 77 µL, 0.77 mmol) is added. When the reaction is complete, the reaction is neutralized with AcOH and injected onto the preparative HPLC to isolate compound 1114.

Step 3:

The nitrile 32a2 (49 mg, 0.09 mmol) and iodomethane (22 mL, 0.36 mmol) are dissolved in DMF (1 mL) at 0° C. and a suspension of NaH (95% w/w, 4.5 mg, 0.18 mmol) in DMF (0.5 mL) is slowly added. After about 2 h, the reaction is neutralized with water, extracted with DCM (3×) and the organics are concentrated. The crude residue is re-dissolved in a THF (1 mL)/MeOH (0.5 mL)/$H_2O$ (0.5 mL) mixture and an aqueous NaOH solution (10 N, 90 µL, 0.90 mmol) is added. When the reaction is complete, the reaction is neutralized with AcOH and injected onto the preparative HPLC to isolate compound 1118.

Example 33A

Preparation of Compound 1115

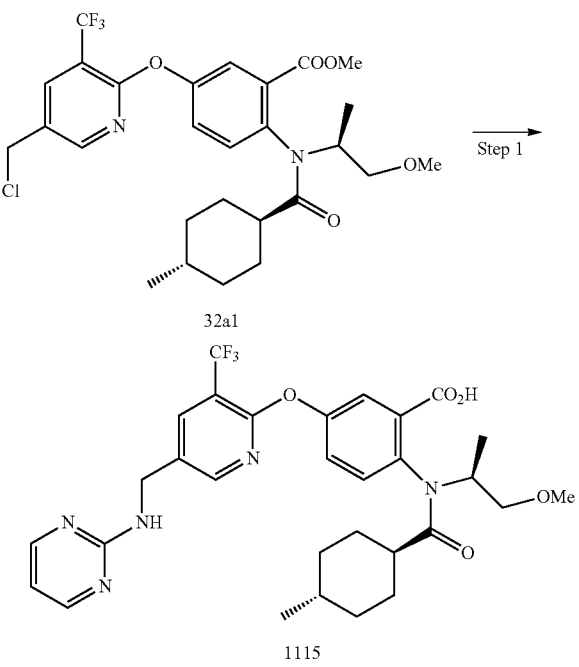

Step 1:

To a solution of chloride 32a1 (75 mg, 0.14 mmol) in DMF (1.5 mL) is added 2-amino pyrimidine (43 mg, 0.46 mmol) and a catalytic amount of KI (11 mg, 0.07 mmol). The mixture is warmed at 80° C. for about 2 h, then cooled to RT. Acetonitrile (1 mL) and an aqueous solution of NaOH (2.5 N, 240 μL, 0.6 mmol) are added, the mixture is warmed at 50° C. for about 2 h, then neutralized at RT with AcOH and injected onto the preparative HPLC to isolate compound 1115.

Example 34A

Preparation of Compound 1116

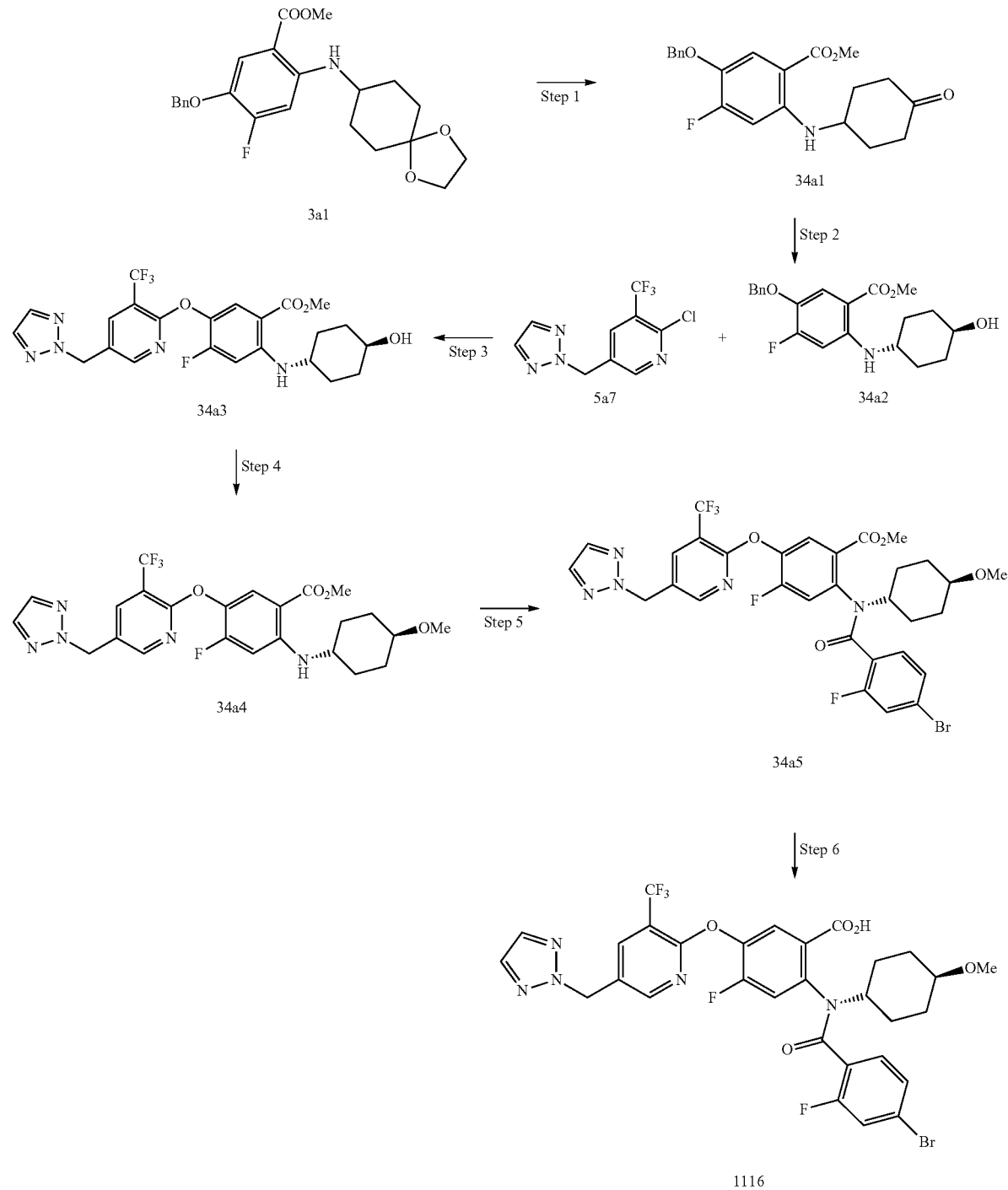

Step 1:

To a solution of the ketal 3a1 (1.5 g, 3.6 mmol) in toluene (7 mL) is added TFA (7 mL). This mixture is stirred for about 1 h, then water (0.4 mL) is added. The stirring is continued overnight and the mixture is concentrated. The resulting residue is diluted with EtOAc, washed with Na$_2$CO$_3$ (1 M), water and brine, dried with Na₂SO₄, filtered, evaporated and concentrated to obtain 34a1.

Step 2:

The ketone 34a1 (1.7 g, 4.6 mmol) is suspended in MeOH (40 mL), and the solution is cooled to 0° C. NaBH₄ (87 mg, 2.3 mmol) is added and the mixture is stirred for about 1 h. The reaction is quenched with 1 M HCl, and the MeOH is evaporated under reduced pressure. The residue is diluted with EtOAc, and washed with aqueous, saturated NaHCO₃, water and brine. Then the residue is dried with Na₂SO₄, filtered, evaporated and employed in the subsequent reaction without further purification.

Step 3:

The benzyl ether 34a2 (410 mg, 1.1 mmol) is dissolved in MeOH (3 mL) and EtOAc (6 mL). 10% Pd/C (4 mg) is added and the flask is placed under an atmosphere of hydrogen. After about 2 h, the mixture is filtered on Celite®, and DMSO (9 mL) is added to the organic phase. The MeOH is removed under reduced pressure. Chloropyridine 5a7 (258 mg, 0.98 mmol) and cesium carbonate (448 mg, 1.4 mmol) are added, and the mixture is stirred at 70° C. for about 4 h. The reaction mixture is then diluted with EtOAc, washed with aqueous, saturated NaHCO₃ and brine, dried with MgSO₄, filtered and evaporated. Purification by flash chromatography (10:90 to 50:50 EtOAc:Hex) yields 34a3.

Step 4:

The alcohol 34a3 (400 mg, 1.1 mmol) is dissolved in DMF (10 mL) and iodomethane (1.7 mL, 27 mmol) is added. This solution is cooled to 0° C., then sodium hydride (133 mg, 3.3 mmol, 60% in oil) is added and the mixture is stirred for about 4 h. Saturated NH₄Cl (10 mL) is added, followed by EtOAc (100 mL) and water (40 mL) are added and the mixture is shaken in a separatory funnel. The layers are separated and the organic layer is washed with brine, dried with MgSO₄, filtered, evaporated, concentrated and purified by flash chromatography (100% Hex to 60% Hex/EtOAc) to yield 34a4.

Step 5:

Compound 34a4 is transformed to compound 34a5 using the procedure of Step 2, Example 22A.

Step 6:

Compound 34a5 is transformed to compound 1116 using the procedure of Step 3, Example 22A.

Example 35A

Preparation of Compound 2001

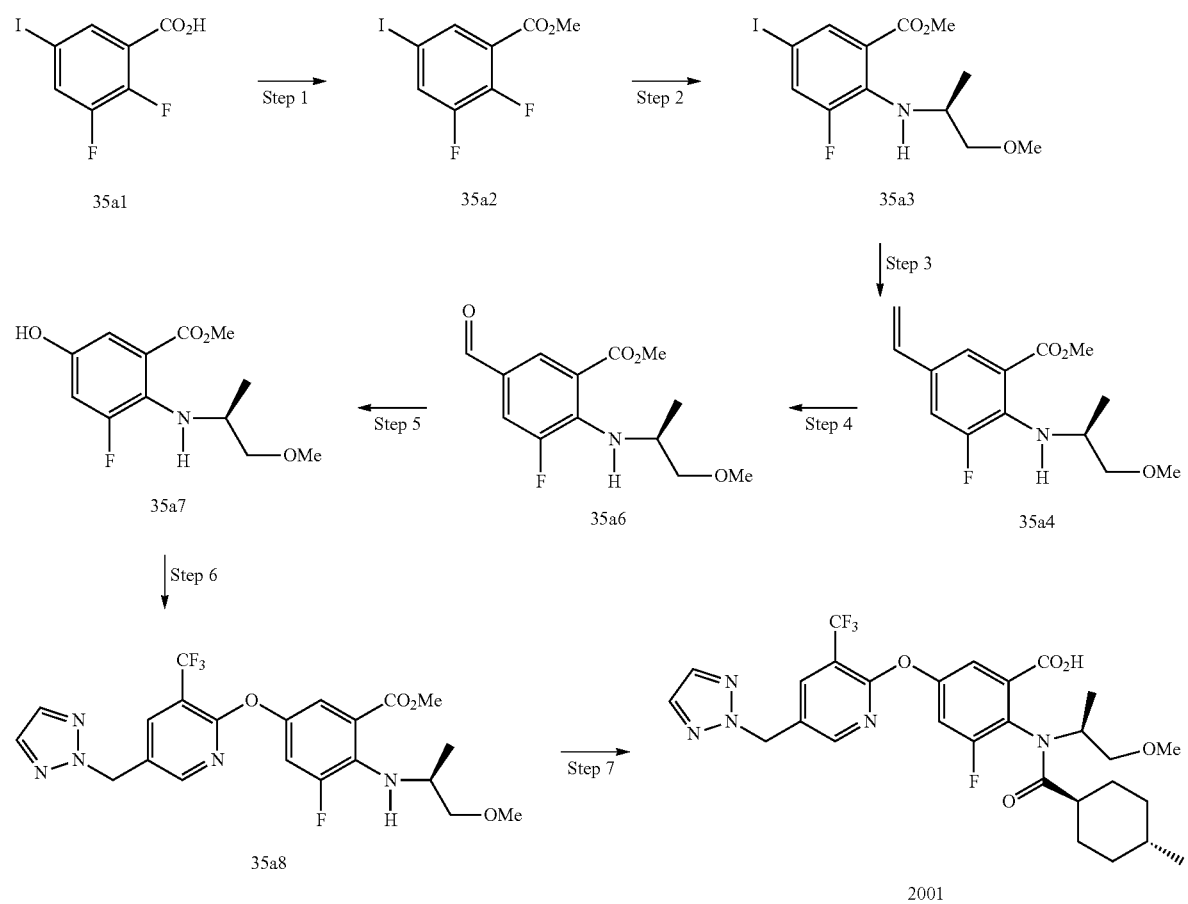

Step 1:

Sulfuric acid (3 mL) is added to a solution of 35a1 (16.3 g, 57.4 mmol) in MeOH (200 mL). The solution is stirred overnight at 80° C. The mixture is cooled to RT, concentrated under reduced pressure, diluted with EtOAc (300 mL), washed with aqueous saturated sodium bicarbonate (3×100 mL), brine (100 mL), dried over Na₂SO₄, filtered and concentrated under reduced pressure. The crude mixture is purified by flash chromatography (10% EtOAc in Hex) to afford methyl ester 35a2 as an oil which solidifies upon standing under high vacuum.

Step 2

(S)-(+)-1-methoxy-2-propylamine (1.90 g, 21.3 mmol) is added to a DMF (30 mL) solution of 35a2 (4.53 g, 15.2 mmol) and potassium carbonate (3.15 g, 22.8 mmol). The mixture is stirred at 75° C. overnight, cooled to RT, diluted with saturated aqueous sodium bicarbonate (200 mL) and extracted with EtOAc (2×200 mL). The combined organic phases are washed with saturated aqueous sodium bicarbonate (2×100 mL), brine (100 mL) dried over $Na_2SO_4$, filtered and concentrated under reduced pressure. The crude mixture is purified by flash chromatography (100% Hex then 5% to 20% EtOAc in Hex) to afford 35a3 as an oil.

Step 3:

$Pd(PPh_3)_4$ (297 mg, 0.26 mmol) is added to a mixture of iodide 35a3 (2.36 g, 6.43 mmol) and tributylvinyl tin (2.06 mL, 7.07 mmol) in DMF (25 mL). The mixture is degassed by simultaneously bubbling Ar and sonicating the solution for about 15 min. The mixture is stirred at 90° C. for about 30 min, cooled to RT, diluted with saturated aqueous sodium bicarbonate (200 mL) and extracted with EtOAc (2×200 mL). The combined organic phases are washed with saturated aqueous sodium bicarbonate (2×100 mL), brine (100 mL), dried over $Na_2SO_4$, filtered and concentrated under reduced pressure. The crude residue is purified by flash chromatography (100% Hex then 5% to 10% EtOAc in Hex) to afford 35a4 as an oil.

Step 4:

Vinyl compound 35a4 (1.45 g, 5.42 mmol) is dissolved in a mixture of acetone/tert-butanol/water (40 mL:10 mL:9.6 mL). The solution is cooled to 0° C., NMO (956 mg, 8.14 mmol) is added, followed by $OsO_4$ (2.5% in tert-butanol, 276 µL, 0.027 mmol). The solution is stirred at 0° C. overnight, diluted with aqueous 10% sodium thiosulphate (100 mL) and extracted with EtOAc (2×100 mL). The combined organic phases are washed with aqueous 10% thiosulphate (100 mL), brine (2×100 mL), dried over $Na_2SO_4$, filtered and concentrated under reduced pressure to afford the crude diol which is dissolved in THF (10 mL) and water (10 mL). This solution is cooled to 0° C., $NaIO_4$ is added (1.60 g, 7.47 mmol) and then stirred at 0° C. for about 4 h. The reaction mixture is diluted with saturated aqueous sodium bicarbonate (100 mL) and extracted with EtOAc (2×100 mL). The combined organic phases are washed with saturated aqueous sodium bicarbonate (100 mL), brine (100 mL), dried over $Na_2SO_4$, filtered, and concentrated under reduced pressure. The crude material is purified by flash chromatography (100% Hex then 5% to 20% EtOAc in Hex) to afford 35a6 as an oil.

Step 5:

Sulfuric acid (223 µL, 3.56 mmol) is added to a 0° C. MeOH (20 mL) solution of 35a6 (640 mg, 2.38 mmol), followed by aqueous 30% hydrogen peroxide (404 µL, 3.57 mmol). The solution is stirred at 0° C. for about 1 h then diluted with aqueous 10% $KH_2PO_4$ (50 mL) and extracted with ether (2×100 mL). The combined organic phases are washed with aqueous 10% $KH_2PO_4$ (2×100 mL), brine (2×100 mL), dried over $Na_2SO_4$, filtered and concentrated under reduced pressure. The crude phenol 35a7 is used directly in the next step without further purification.

Step 6:

Compound 35a7 is transformed to compound 35a8 using the procedure of Step 1, Example 13A.

Step 7:

Compound 35a8 is transformed to compound 2001 using the procedure of Step 2, Example 13A.

Example 36A

Preparation of Compound 2002

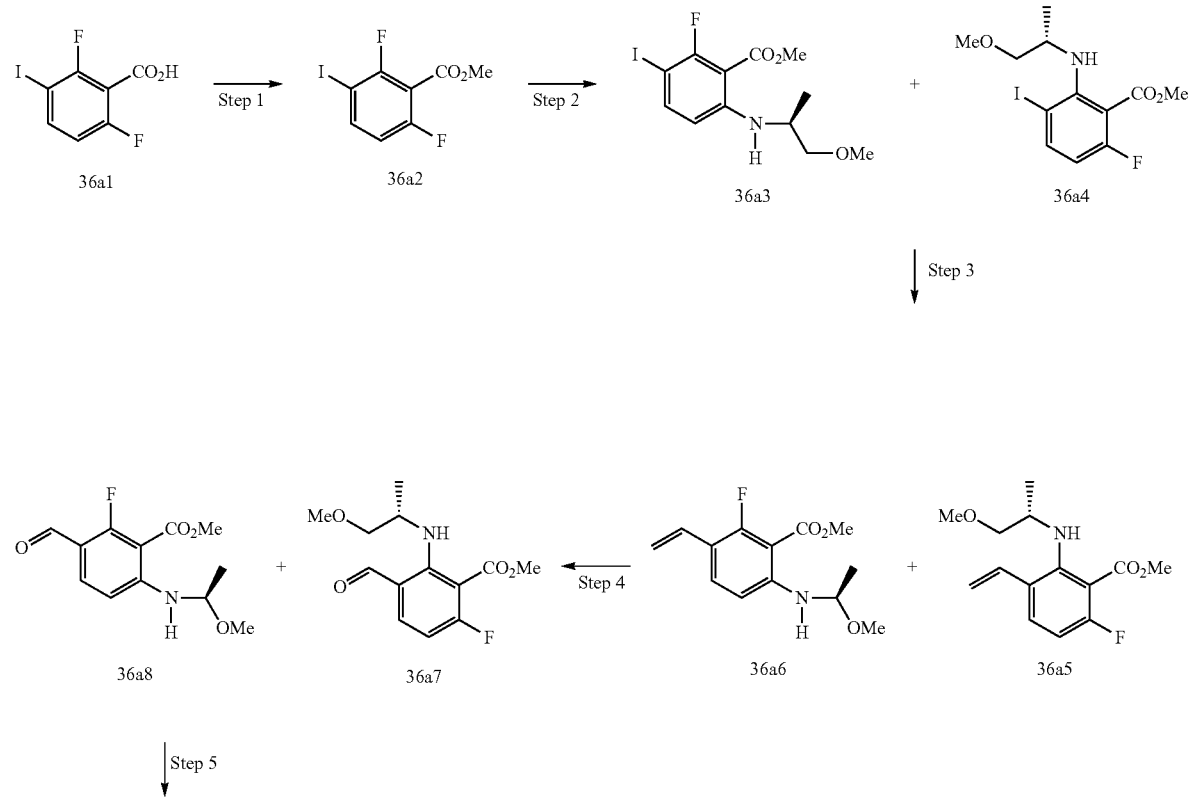

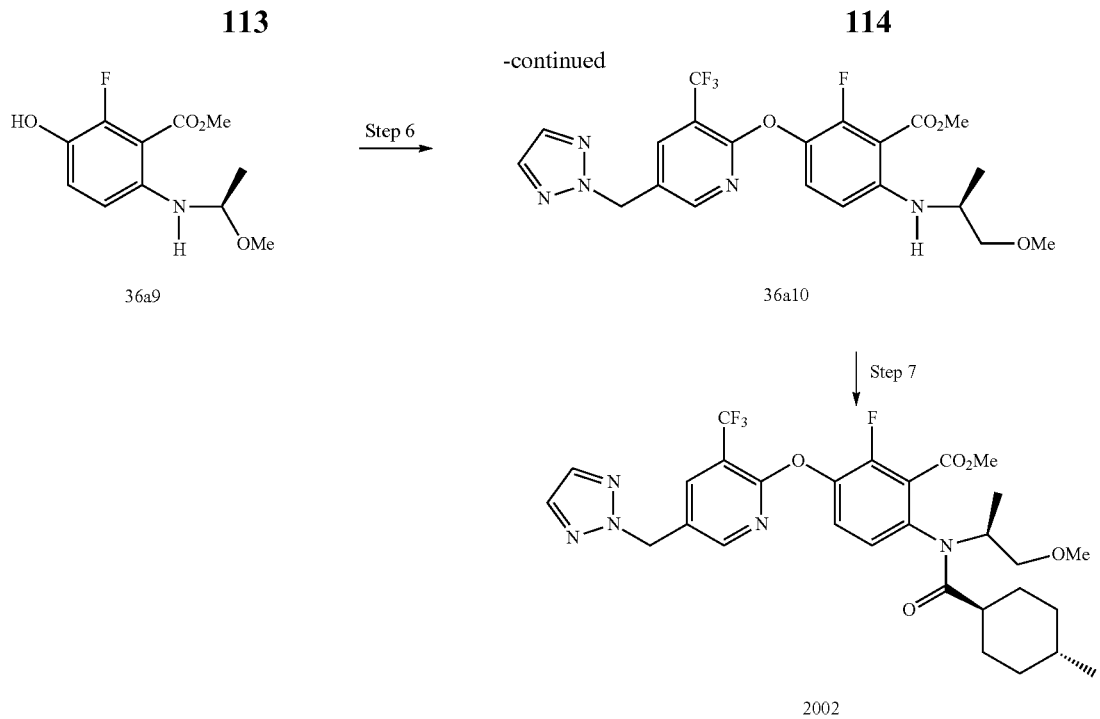

Step 1:
Sulfuric acid (3 mL) is added to a solution of 36a1 (15.0 g, 36.9 mmol) in MeOH (200 mL) and the resulting solution is stirred overnight at 80° C. The mixture is cooled to RT, concentrated under reduced pressure, diluted with EtOAc (300 mL), washed with aqueous saturated sodium bicarbonate (3×100 mL), brine (100 mL), dried over $Na_2SO_4$, filtered and concentrated under reduced pressure to afford methyl ester 36a2.

Step 2
(S)-(+)-1-methoxy-2-propylamine (1.49 g, 16.8 mmol) is added to a DMF (30 mL) solution of 36a2 (3.84 g, 12.9 mmol) and potassium carbonate (2.67 g, 19.3 mmol). The mixture is stirred at 75° C. overnight, cooled to RT, diluted with saturated aqueous sodium bicarbonate (200 mL) and extracted with EtOAc (2×200 mL). The combined organic phases are washed with aqueous saturated sodium bicarbonate (2×100 mL), brine (100 mL) dried over $Na_2SO_4$, filtered and concentrated under reduced pressure. The crude mixture is purified by flash chromatography (100% Hex then 5% to 20% EtOAc in Hex) to afford a mixture of isomers 36a3 and 36a4.

Step 3:
$Pd(PPh_3)_4$ (315 mg, 0.272 mmol) is added to a mixture of iodide 36a3 and 36a4 (2.00 g, 5.45 mmol) and tributylvinyltin (1.91 mL, 6.54 mmol) in DMF (40 mL). The mixture is degassed by simultaneously bubbling Ar and by sonicating the solution for about 15 min. The mixture is stirred at 100° C. for about 2.5 h, cooled to RT, diluted with aqueous saturated sodium bicarbonate (200 mL) and extracted with EtOAc (2×200 mL). The combined organic phases are washed with aqueous saturated sodium bicarbonate (2×100 mL), brine (100 mL), dried over $Na_2SO_4$, filtered and concentrated under reduced pressure. The crude residue is purified by flash chromatography (100% Hexa then 5% to 10% EtOAc in Hex) to afford a mixture of compounds 36a5 and 36a6.

Step 4:
Vinyl compounds 36a5 and 36a6 (1.19 g, 4.45 mmol) are dissolved in a mixture of acetone/tert-butanol/water (40 mL:10 mL:9.6 mL). The solution is cooled to 0° C., NMO (732 mg, 6.23 mmol) is added, followed by $OsO_4$ (2.5% in tert-butanol, 226 µL, 0.022 mmol). The solution is stirred at 0° C. overnight, diluted with aqueous 10% sodium thiosulphate (100 mL) and extracted with EtOAc (2×100 mL). The combined organic phases are washed with aqueous 10% thiosulphate (100 mL), brine (2×100 mL), dried over $Na_2SO_4$, filtered and concentrated under reduced pressure to afford the crude diols which are dissolved in THF (10 mL) and water (10 mL). This solution is cooled to 0° C. and sodium metaperiodate is added (1.38 g, 6.45 mmol). The solution is stirred at 0° C. for about 2 h. The reaction mixture is diluted with aqueous saturated sodium bicarbonate (100 mL) and extracted with EtOAc (2×100 mL). The combined organic phases are washed with aqueous saturated sodium bicarbonate (100 mL), brine (100 mL), dried over $Na_2SO_4$, filtered, and concentrated under reduced pressure. The crude material is purified by flash chromatography (100% Hex then 5% to 10% EtOAc in Hex\) to afford compounds 36a7 (elutes first) and 36a8 as an oil.

Step 5:
Sulfuric acid (147 µL, 2.35 mmol) is added to a 0° C. MeOH (10 mL) solution of 36a8 (400 mg, 1.49 mmol), followed by aqueous 30% hydrogen peroxide (252 µL, 2.23 mmol). The solution is stirred at 0° C. for about 1 h then diluted with aqueous 10% $KH_2PO_4$ (50 mL) and extracted with ether (2×100 mL). The combined organic phases are washed with aqueous 10% $KH_2PO_4$ (2×100 mL), brine (2×100 mL), dried over $Na_2SO_4$, filtered and concentrated under reduced pressure. The crude phenol 36a9 is used directly in the next step without further purification.

Step 6:
Compound 36a9 is transformed to compound 36a10 using the procedure described in Step 1, Example 13A.

Step 7:
Compound 36a10 is transformed to compound 2002 using the procedure described in Step 2, Example 13A.

Example 37A

Preparation of Compound 3001

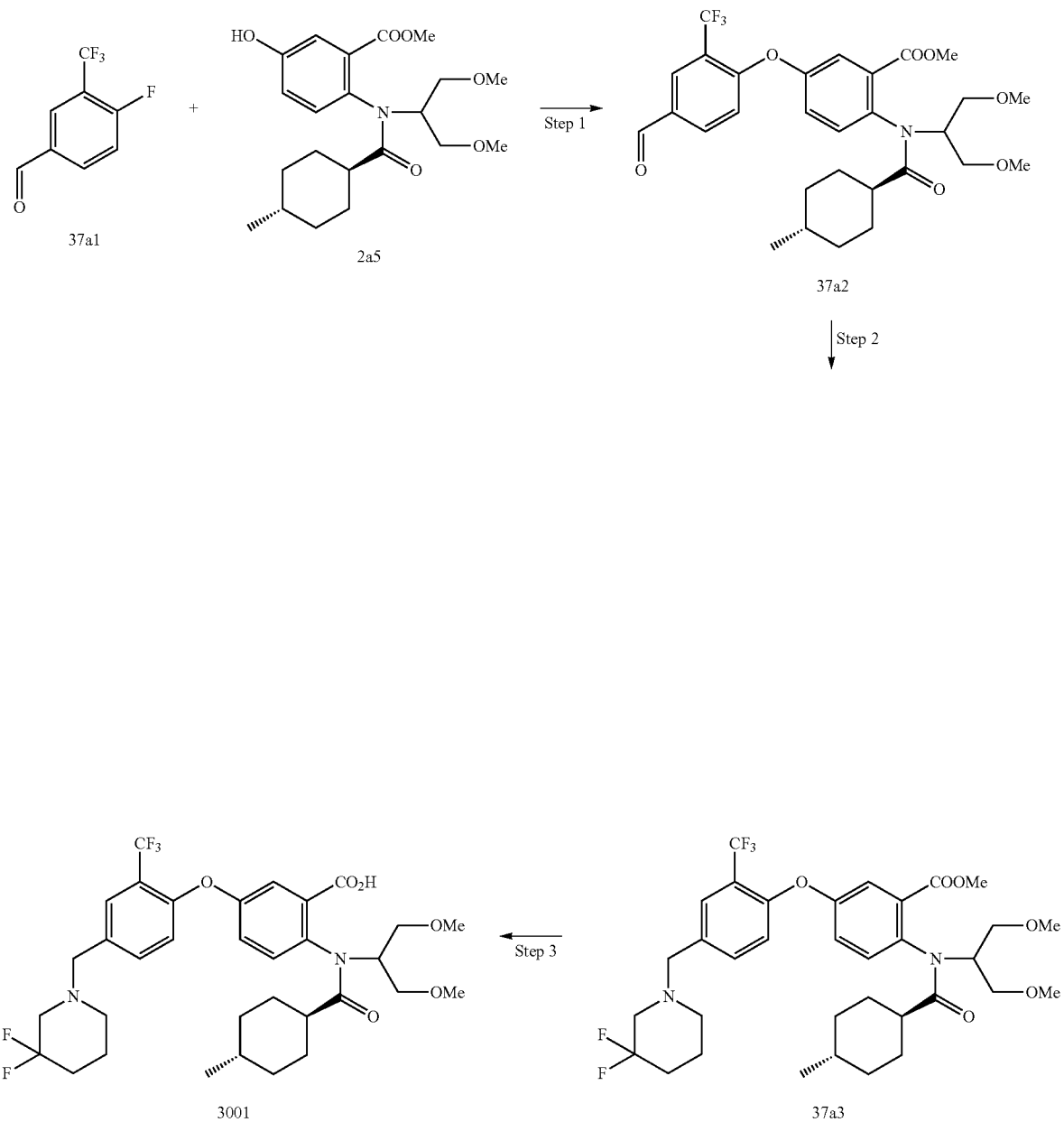

Step 1:

Phenol 2a5 (1.0 g, 2.54 mmol) is combined with $K_2CO_3$ (878 mg, 6.35 mmol) and 37a1 (586 mg, 3.05 mmol) in DMSO (15 mL). The mixture is heated under Ar at 60° C. until complete conversion, then cooled to RT. A saturated aqueous solution of $NaHCO_3$ is then added. The mixture is extracted with EtOAc (3×), the combined organics are dried over $MgSO_4$, filtered and concentrated under reduced pressure to afford crude 37a2 which is used without further purification.

Step 2:

To a solution of 37a2 (100 mg, 0.18 mmol) and 3,3-difluoropiperidine hydrochloride (31 mg, 0.20 mmol) in DCE (1.5 mL) is added $NaBH(OAc)_3$ (52 mg, 0.25 mmol). The mixture is stirred at RT overnight, then water is added. The mixture is extracted with DCM (3×), the organics are dried and concentrated under reduced pressure. Purification by combiflash (15% EtOAc in hex) gives 37a3.

Step 3:

Compound 37a3 is transformed to compound 3001 using the procedure of Step 2, Example 32A.

Example 38A

Preparation of Compound 3002

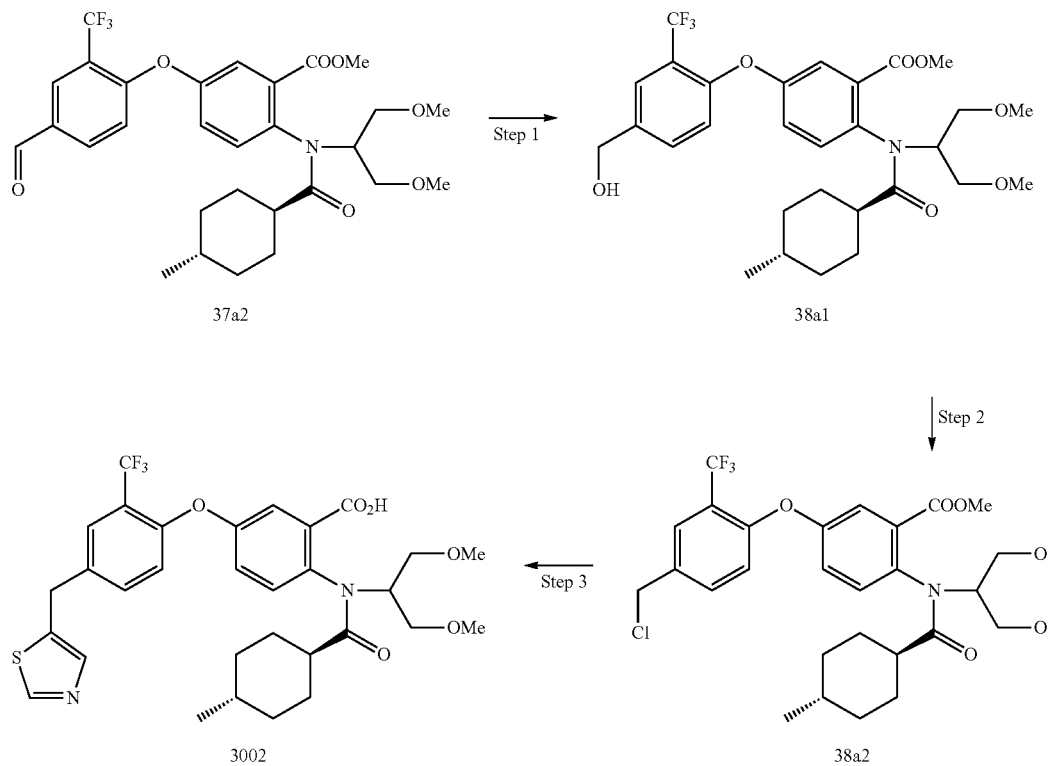

Step 1:
The aldehyde 37a2 (1.30 g, 2.30 mmol) is dissolved in MeOH (25 mL) at 0° C. and NaBH$_4$ (104 mg, 2.76 mmol) is added. After being stirred for about 1 h, the reaction is quenched with a saturated aqueous solution of citric acid and extracted with EtOAc (3×). The organics are dried over MgSO$_4$, filtered and concentrated. Purification by combiflash gives alcohol 38a1.

Step 2:
The alcohol 38a1 (700 mg, 1.23 mmol) is dissolved in DCM (15 mL) and thionyl chloride (0.19 mL, 2.59 mmol) and a catalytic amount of DMF (10 μL) is added. The reaction is stirred at RT; then successively washed with a saturated aqueous solution of citric acid, NaHCO$_3$ and brine. The organics are dried over Na$_2$SO$_4$, filtered and concentrated under reduced pressure. The crude chloride 38a2 is used as such without further purification.

Step 3:
In a microwave tube, the chloride 38a2 (75 mg, 0.13 mmol) is put in degassed DMF (1 mL, degassed by bubbling a volume of Ar while sonicating for about 10 min) along with 5-(tributylstannyl)thiazole (96 mg, 0.26 mmol). Pd(PPh$_3$)$_4$ catalyst (15 mg, 13 μmol) is added and the tube is sealed and put in microwave at 125° C. for 20 min. The mixture is diluted in EtOAc and washed with water (2×) and brine (2×). The combined organics are dried over MgSO$_4$, filtered and concentrated. The crude residue is passed on a short silica gel column (20% to 70% EtOAc in hex) to remove most impurities and the combined fractions are concentrated. The resulting yellow oil is re-dissolved in THF (1 mL)/MeOH (0.5 mL)/H$_2$O (0.5 mL) and NaOH (10 N, 0.13 mL, 1.3 mmol) is added. When complete, the reaction is neutralized with AcOH and injected onto a preparative HPLC to isolate 3002.

Example 39A

Preparation of Compound 3005 and 3006

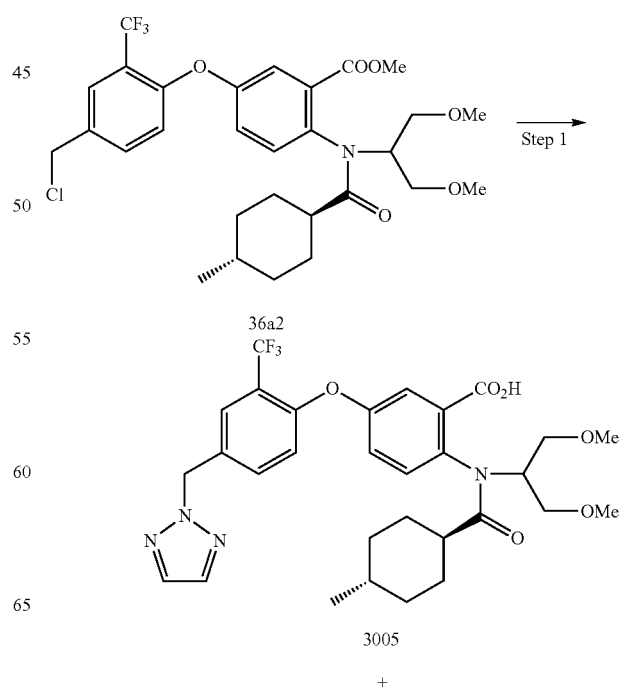

+

-continued

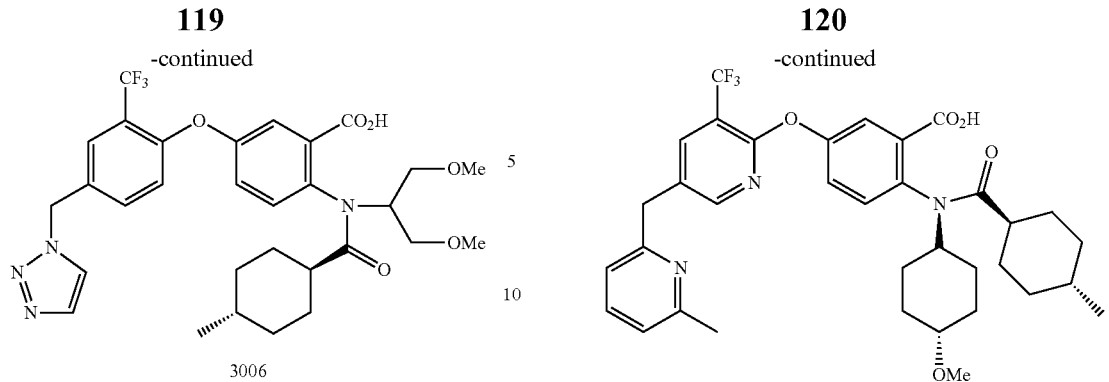

3006

Step 1:

1,2,3-Triazole (15 µL, 0.13 mmol) is added to a suspension of NaH (60% w/w, 10 mg, 0.26 mmol) in THF (0.5 mL) and stirred for about 15 min at RT. This mixture is transferred to a solution of chloride 38a2 (75 mg, 0.13 mmol) in dry DMF (1 mL) and is stirred overnight. The mixture is partially concentrated under reduced pressure and pre-adsorbed on silica gel for purification by combiflash (50% to 100% EtOAc in hex). Two products are recovered corresponding to each isomeric triazole intermediate. After being combined and concentrated, each intermediate is separately re-dissolved in THF (2 mL)/MeOH (1 mL) and NaOH (10 N, 0.13 mL, 1.3 mmol) is added. When complete, each reaction is neutralized with AcOH and injected onto the preparative HPLC to isolate 3005 and 3006.

Example 40A

Preparation of Compounds 1121

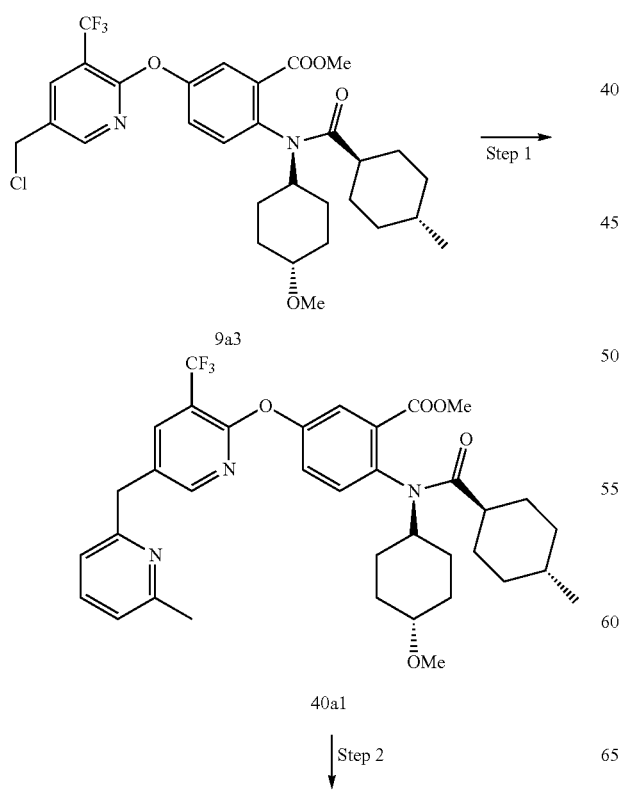

Step 1:
Compound 9a3 is transformed to compound 40a1 using the procedure of Step 1, Example 20A.

Step 2:
To the methyl ester 40a1 (27 mg, 41 µmol) in MeOH and THF (1:1 mixture, 1 mL) is added an aqueous NaOH solution (1.0 M, 41 µL, 41 µmol). The mixture is stirred for about 2 days at RT, and then water is added. The aqueous layer is washed with Et₂O (2×) and lyophilized. The compound 1121 is quantatively obtained in its sodium salt form.

Example 41A

Preparation of Compounds 1133

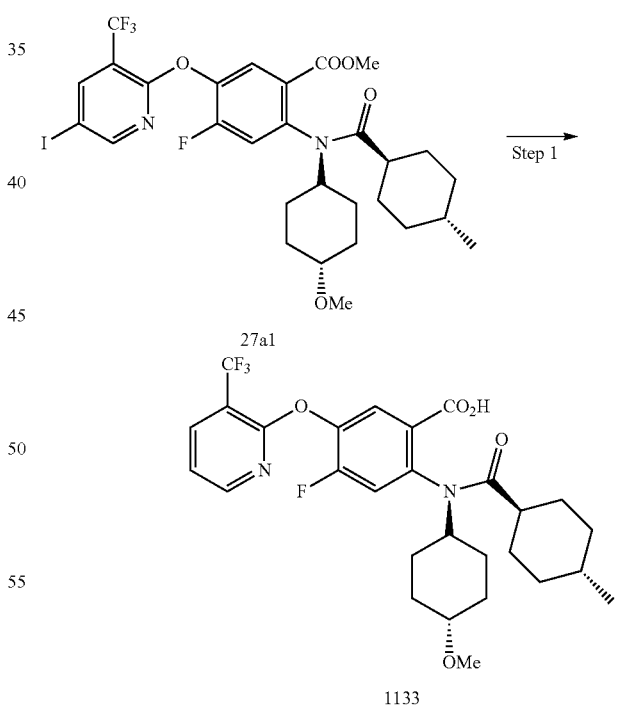

Step 1:
The iodide 27a1 (72 mg, 0.104 mmol) is dissolved in MeOH (5 mL) and 10% Pd/C (50 mg) is added. The mixture is stirred for about 1 h under a balloon atmosphere of hydrogen. The mixture is filtered through Celite® and concentrated under reduced pressure. The crude residue is re-dissolved in DMSO (3 mL) and water (0.5 mL), then aqueous NaOH (10 N, 50 µL, 0.50 mmol) is added. When complete, the reaction is neutralized with AcOH and injected onto the preparative HPLC to isolate 1133.

Example 42A

Preparation of Compounds 1139

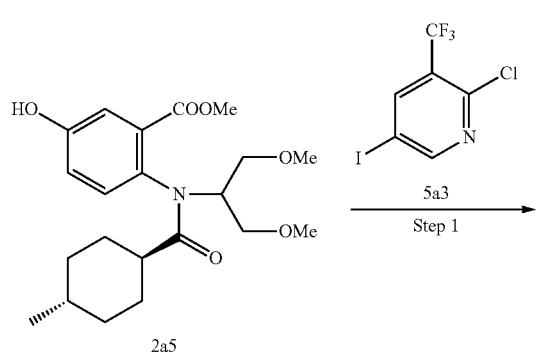

2a5

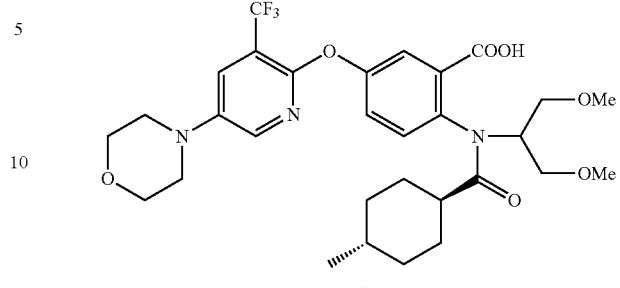

1139

Step 1:
Compound 42a1 is generated via the reaction of 2a5 (715 mg, 2.33 mmol) and pyridine 5a3 (879 mg, 2.23 mmol) using the procedure of Step 1, Example 16A.

Step 2:
A mixture of iodide 42a1 (56.7 mg, 85 µmol), morpholine (42.5 mg, 0.49 mmol) and cesium carbonate (184 mg, 0.57 mmol) is prepared in anhydrous toluene (3 mL). This mixture is sonicated and purged for about 10 min with a balloon atmosphere of Ar. To this mixture is added palladium acetate (1.9 mg, 9 µmol) and BINAP (8.0 mg, 13 µmol) and the heterogeneous mixture is further sonicated/purged for about 10 min upon which time it solubilizes. The reaction is placed at reflux for about 16 h, cooled to RT, then EtOAc is added and the mixture is washed with a saturated aqueous solution of NaHCO$_3$ (2×). The organics are dried over MgSO$_4$ and concentrated. The crude residue is re-dissolved in THF (1 mL)/MeOH (0.5 mL)/water (0.5 mL) and NaOH (10 N, 85 µL, 0.85 mmol) is added. When complete, the reaction is neutralized with AcOH and injected onto the preparative HPLC to isolate 1139.

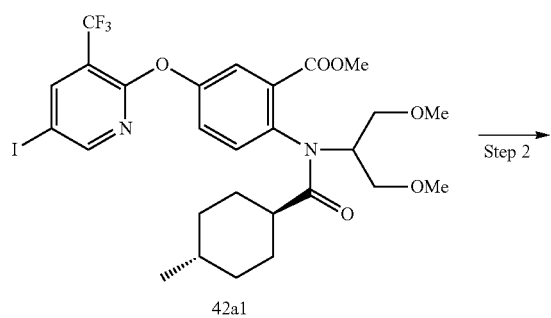

42a1

Example 43A

Preparation of Compounds 1160 and 1161

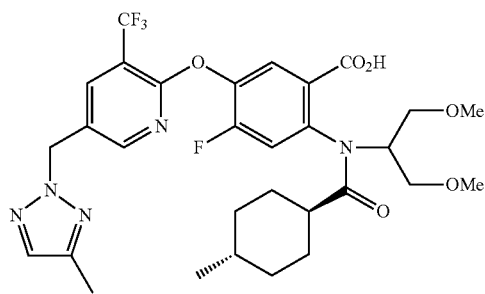

1170

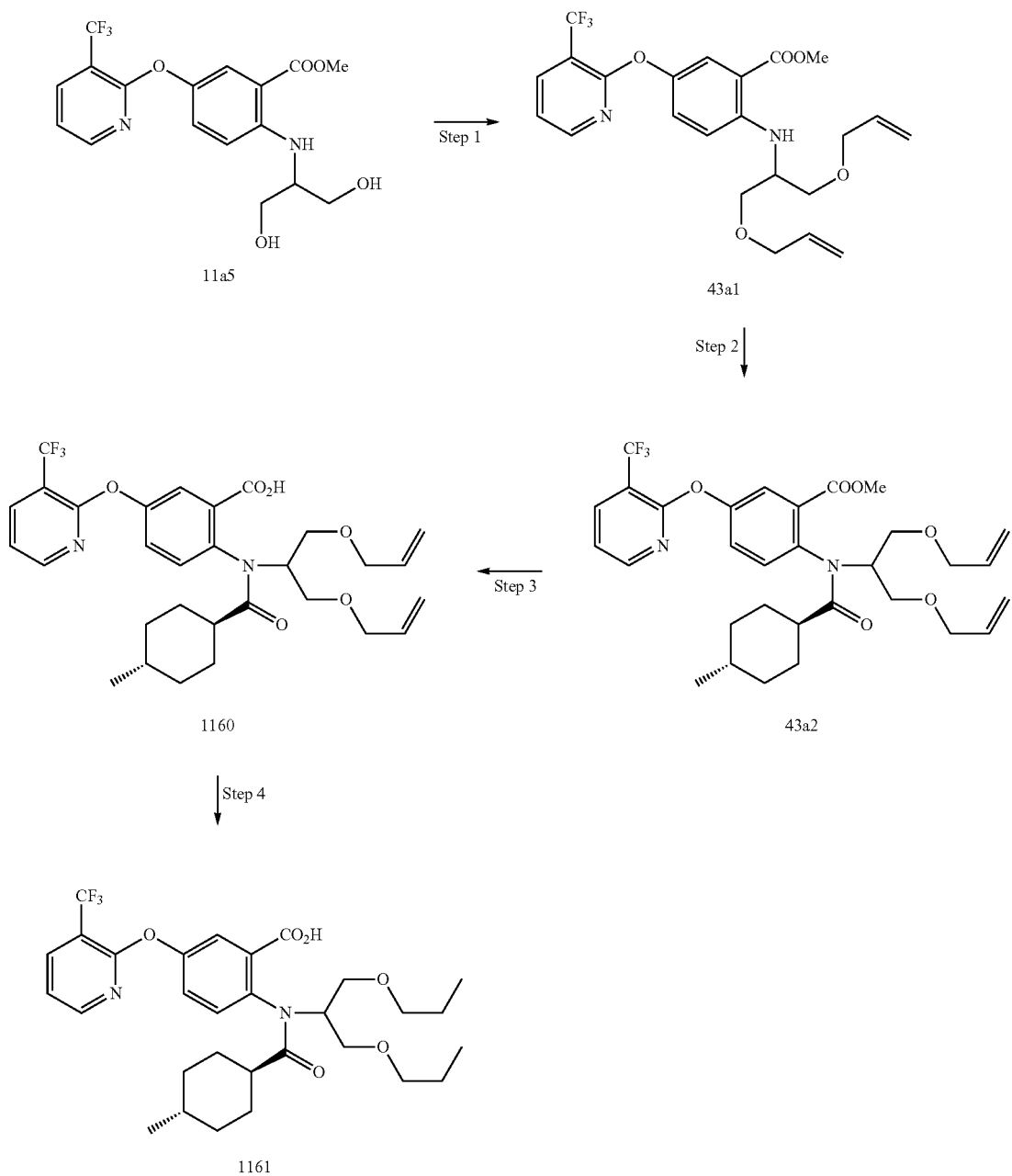 [SMILES: COC(=O)c1cc(Oc2ncccc2C(F)(F)F)ccc1NC(CO)CO ; C=CCOCC(COCC=C)Nc1ccc(Oc2ncccc2C(F)(F)F)cc1C(=O)OC ; C=CCOCC(COCC=C)N(c1ccc(Oc2ncccc2C(F)(F)F)cc1C(=O)O)C(=O)[C@H]1CC[C@H](C)CC1 ; C=CCOCC(COCC=C)N(c1ccc(Oc2ncccc2C(F)(F)F)cc1C(=O)OC)C(=O)[C@H]1CC[C@H](C)CC1 ; CCCOCC(COCCC)N(c1ccc(Oc2ncccc2C(F)(F)F)cc1C(=O)O)C(=O)[C@H]1CC[C@H](C)CC1]

Step 1:

The diol 11a5 (221 mg, 0.57 mmol) is dissolved in DMF (3 mL) and cooled to 0° C. Allyl iodide (0.11 mL, 1.20 mmol) and sodium hydride (95%, 30.3 mg, 1.20 mmol) are successively added and the mixture is stirred at RT for about 1 h. Water is added and the mixture is extracted with DCM (3×). The organic phases are dried and concentrated. The crude residue is purified by combiflash (hex/EtOAc, 15% to 25%) to afford aniline 43a1.

Step 2:

Compound 43a1 is transformed to compound 43a2 using the procedure of Step 4, Example 7A.

Step 3:

Compound 43a2 is transformed to compound 1160 using the procedure of Step 2, Example 32A.

Step 4:

Compound 1160 (18 mg, 31 μmol) is dissolved in MeOH (3 mL) and activated Raney Nickel (50% slurry in water, 20 mg) is added. The reaction flask is purged and filled with a hydrogen atmosphere. After being stirred for about 1 h, the mixture is filtered through Celite® and rinsed thoroughly with MeOH. The filtrate is concentrated; the residue is redissolved in water/MeCN, filtered through a microdisc, then lyophilized to afford 1161.

Example 44A

Preparation of Intermediate 44a4

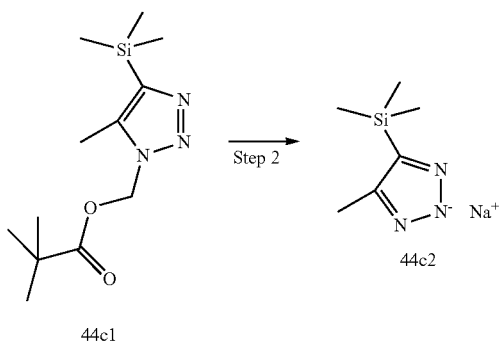

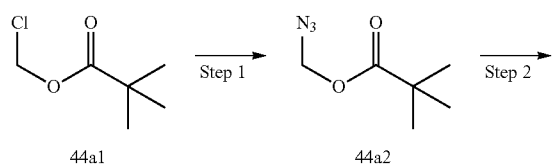

Reference: Loren, J. C.; Krasinski, A.; Fokin, V. V.; Sharpless, K. B. *Synlett* 2005, 18, 2847.

Step 1:
To a suspension of chloromethyl pivalate 44a1 (20 mL, 186 mmol) in water (37 mL) is added sodium azide (18.1 g, 279 mmol) and the mixture is warmed at 90° C. for about 12 h. Additional water is then added and the phases are separated. The organic layer is passed through a filter funnel containing MgSO₄ to afford the azide 44a2.

Step 2:
The azide 44a2 (100 mg, 0.64 mmol) and cyclopropylacetylene (54.7 mg, 0.83 mmol) are dissolved in tert-butanol (0.5 mL) and water (0.5 mL). An aqueous solution of copper sulfate (0.3 M, 0.43 mL, 0.13 mmol) is added followed by an aqueous solution of ascorbic acid sodium salt (1.0 M, 0.51 mL, 0.51 mmol). After stirring for about 16 h at RT, the mixture is diluted in EtOAc and water and the phases are separated. The organics are washed with a 5% aqueous NH₄OH/brine solution (2×), then dried over MgSO₄, and the solvent removed in vacuo. The oil corresponding to 44a3 is used as such for the next step.

Step 3:
To the ester 44a3 (102 mg, 0.46 mmol) in MeOH (1 mL) is added aqueous NaOH (1 N, 1 mL, 1 mmol). The reaction is stirred for about 30 min at RT, then neutralized with aqueous HCl (1 M, 1 mL, 1 mmol) and diluted in water. The mixture is extracted with EtOAc (3×), washed with brine, dried and the solvent is removed under reduced pressure. The crude oil corresponding to 44a4 is used as such.

Example 44B

Preparation of Compound 1167

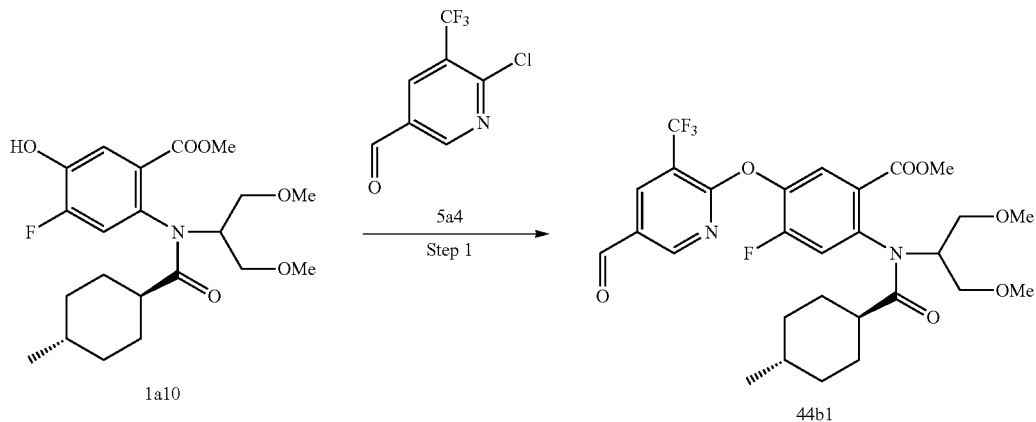

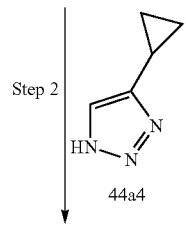

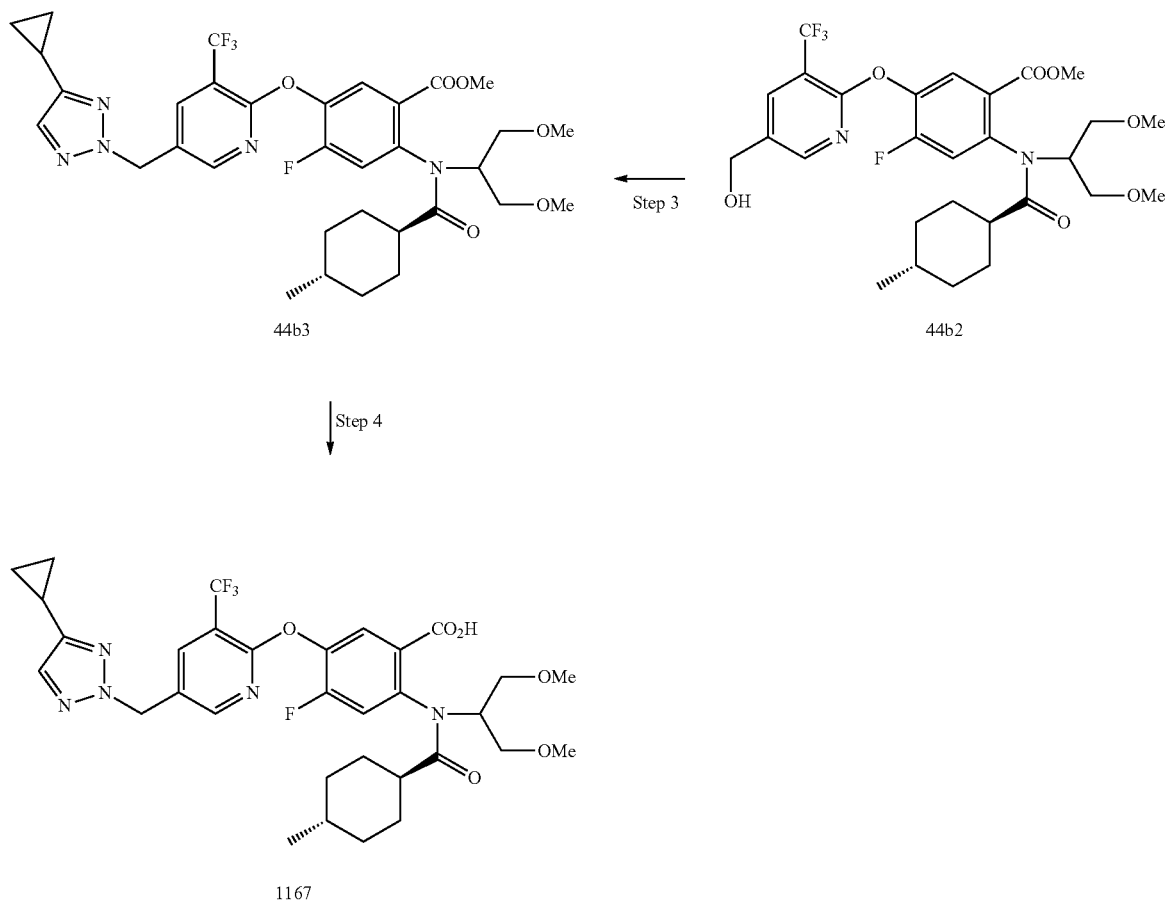

Step 1:

Compound 44b1 is generated via the reaction of 1a10 and chloropyridine 5a4 using the procedure of Step 1, Example 9A.

Step 2:

To the aldehyde 44b1 (1.25 g, 2.14 mmol) in MeOH (20 mL) chilled at 0° C. is added NaBH$_4$ (98 mg, 2.6 mmol). When the reaction is complete, a saturated aqueous solution of citric acid is added. The mixture is extracted with EtOAc (3×), dried over MgSO$_4$, and concentrated. Purification by combiflash (hex/EtOAc, 15% to 50%) affords 44b2.

Step 3:

To a chilled (0° C.) THF solution (2 mL) containing the alcohol 44b2 (100 mg, 0.17 mmol), PPh$_3$ (54 mg, 0.21 mmol) and triazole 44a4 (28 mg, 0.21 mmol) is slowly added DEAD (38 μL, 0.21 mmol). The reaction is allowed to slowly warmed to RT over about 16 h. When the reaction is complete, the solvent is removed in vacuo and the crude residue is directly purified by combiflash (hex/EtOAc, 15% to 50%) to afford 44b3.

Step 4:

The saponification using 1 eq of NaOH is performed using the procedure described in Step 2, Example 32A to give 1167 as the sodium salt.

Example 44C

Preparation of Intermediate 44c2

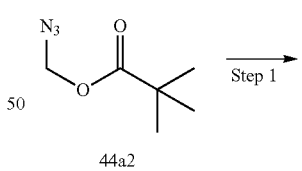

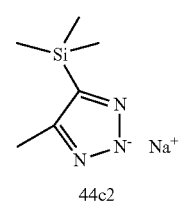

Step 1:

In a sealed tube, azide 44a2 (1.50 g, 9.54 mmol) is mixed with 1-(trimethylsilyl)-1-propyne (1.61 g, 14.32 mmol) in DCE (6 mL). The mixture is warmed at 80° C. for about 16 h,

Example 45A

Preparation of Compound 1170

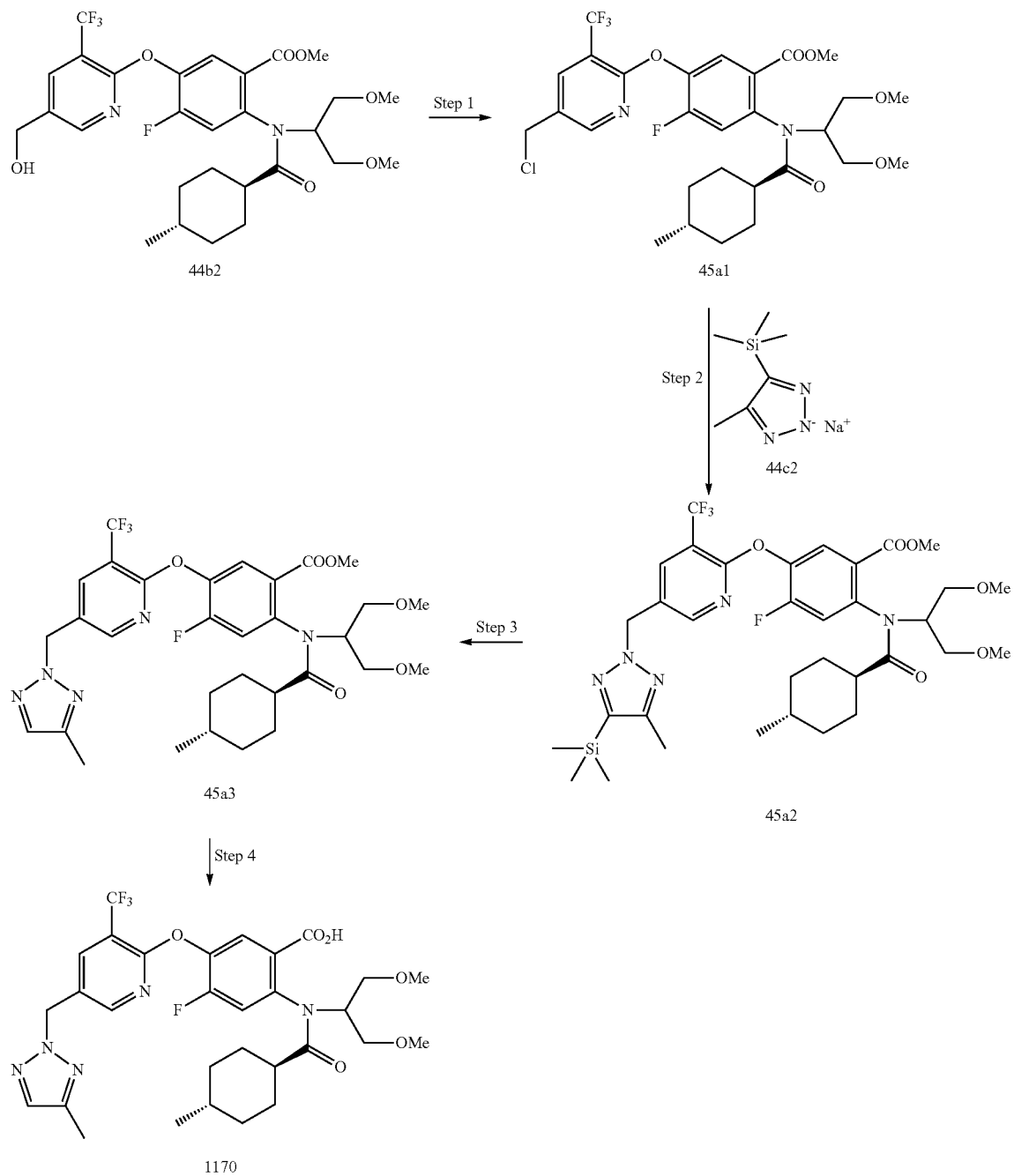

then the solvent is concentrated in vacuo to afford triazole 44c1 which is directly used in the next step.

Step 2:

Triazole 44c1 (1.9 g, 7.05 mmol) is dissolved in MeOH (14 mL) and NaOH solution (10N, 1.55 mL, 15.5 mmol) is added. The reaction is stirred at RT for about 16 h. The solvent is concentrated under reduced pressure to afford the crude triazole 44c2 as the sodium salt.

Step 1:

To the alcohol 44b2 (105 mg, 0.18 mmol) in DCM (2 mL) is added thionyl chloride (28 µL, 0.38 mmol). To this solution is slowly added DMF (50 µL) and the reaction proceeds at RT for about 1 h. A saturated aqueous solution of citric acid is then added and the layers are separated. The organics are successively washed with a saturated solution of $NaHCO_3$ and brine, dried over $MgSO_4$, filtered and concentrated to afford chloride 45a1 which is used as such for the next step.
Step 2:
The chloride 45a1 (150 mg, 0.25 mmol) and 44c2 (53 mg, 0.30 mmol) are mixed in DMF (2 mL) and stirred at RT overnight. The mixture is diluted in EtOAc and washed with water (2×) and brine (1×), dried over MgSO₄, filtered and concentrated. Following purification by flash chromatography (hex/EtOAc, 15% to 40%), all isomeric triazole intermediates are isolated in the same fraction. These isomers are further separated on a preparative HPLC. The less polar fraction corresponds to 45a2.
Step 3:
To the compound 45a2 (17 mg, 23 μmol) in THF (1 mL) is added TBAF (1.0 M in THF, 70 μL, 70 μmol). When the reaction is complete, the solvent is removed in vacuo and the crude residue containing 45a3 is used directly in the following step.
Step 4:
Compound 45a3 is transformed to compound 1170 using the procedure of Step 2, Example 32A.

Example 46A

Preparation of Compound 4001

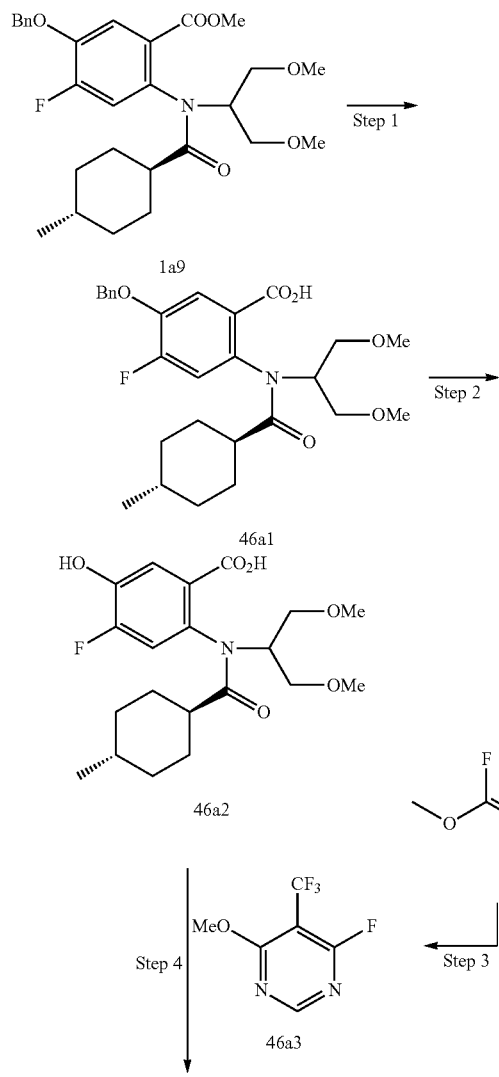

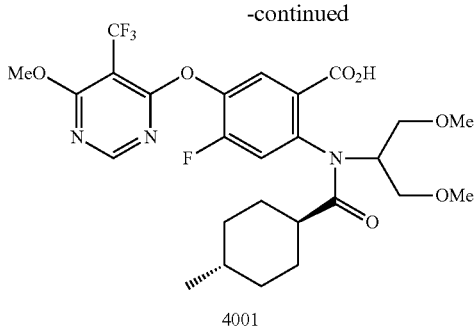

Step 1:
To compound 1a9 (101 mg, 0.20 mmol) in THF (2 mL)/MeOH (1 mL)/water (1 mL) is added aqueous NaOH (10 N, 0.2 mL, 2.0 mmol) and the mixture is stirred at RT. When the reaction is complete, AcOH is added to neutralize the reaction and solvents are removed under reduced pressure to afford crude 46a1 which is used directly in the next step.
Step 2:
The crude 46a1 (98 mg, 0.2 mmol) is dissolved in MeOH (3 mL)/EtOAc (5 mL) and activated Pd/C (10% w/w, 10 mg) is then added. The mixture is purged and filled with an atmosphere of hydrogen. When the reaction is complete, the mixture is filtered through a pad of Celite®, rinsed thoroughly with MeOH and the filtrate is concentrated. Acetonitrile and water are added and the mixture is lyophilized to afford 46a2.
Step 3:
Formamidine acetate (15.3 g, 147 mmol) and 1,3,3,3-tetrafluoro-1-methoxy-2-(trifluoromethyl)prop-1-ene (20.8 g, 98 mmol) are mixed in DCM (100 mL) and water (100 mL) at 0° C. To this vigorously stirred mixture is slowly added aqueous NaOH (6 N, 71 mL, 424 mmol) over about a 30 min period. Stirring is then continued for about 35 min. The layers are separated and the organic layer is concentrated. The crude residue is purified by bulb-to-bulb distillation (80° C., 3 mmHg) and purified further by Vigreux distillation under reduced pressure to afford 46a3.
Step 4:
Pyrimidine 46a3 (55 mg, 0.28 mmol) and phenol 46a2 (112 mg, 0.28 mmol) are mixed in DMSO (2 mL) along with K₂CO₃ (132 mg, 0.96 mmol). The mixture is stirred at RT for about 15 h, and then stirring is continued for about 1 h at 60° C. The mixture is filtered to remove the solid residue. The filtrate is acidified with AcOH and injected onto the preparative HPLC to isolate 4001.

Example 47A

Preparation of Compound 4008

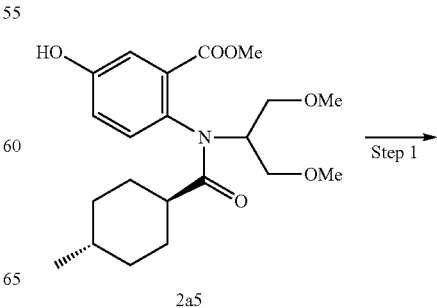

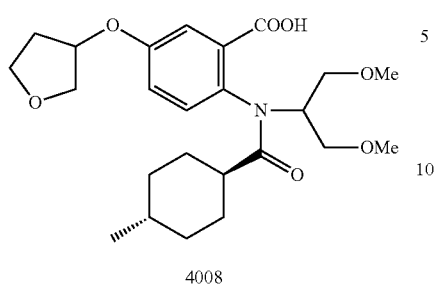

4008

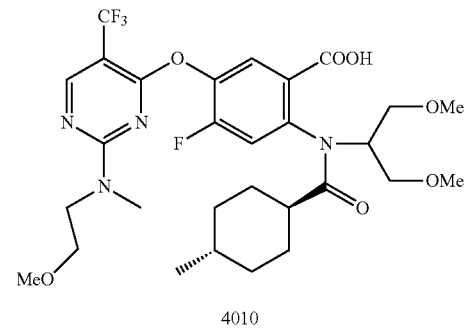

4010

Step 1:

A mixture of phenol 2a5 (100 mg, 0.25 mmol), 3-hydroxytetrahydrofuran (31 mg, 0.36 mmol) and PPh₃ (100 mg, 0.38 mmol) are mixed in THF (2 mL) and cooled at 0° C. DIAD (70 µL, 0.38 mmol) is slowly added over about 10 min, and the reaction is stirred at RT. More reagent is added to complete conversion if necessary. Silica gel is then directly added and solvent is removed under reduced pressure. The crude product is quickly passed on a silica gel column eluting with a mixture of hex/EtOAc (20% to 70%) to remove most of the triphenylphosphine oxide. The combined fractions are combined and concentrated under reduced pressure. The residue is re-dissolved in THF (2 mL)/MeOH (1 mL) and NaOH (1 N, 1 mL, 1 mmol) is then added. When complete, the reaction is neutralized with AcOH and injected onto the preparative HPLC to isolate 4008.

Example 48A

Preparation of Compound 4010

Step 1:

A suspension of 2,4-dichloro-5-(trifluoromethyl)pyrimidine (50 mg, 0.22 mmol), N-(2-methoxyethyl)methylamine (20 mg, 0.22 mmol) and K₂CO₃ (90 mg, 0.65 mmol) is prepared in DMSO (2 mL) and stirred at RT. When the reaction is complete, phenol 46a2 (81 mg, 0.21 mmol) is added and the mixture is warmed at 65° C. until the reaction is complete. When complete, the reaction is cooled and filtered through a microdisc to remove unsoluble material, then the homogeneous solution is neutralized with AcOH and injected onto the preparative HPLC to isolate 4010.

Example 48B

Preparation of Compound 4021

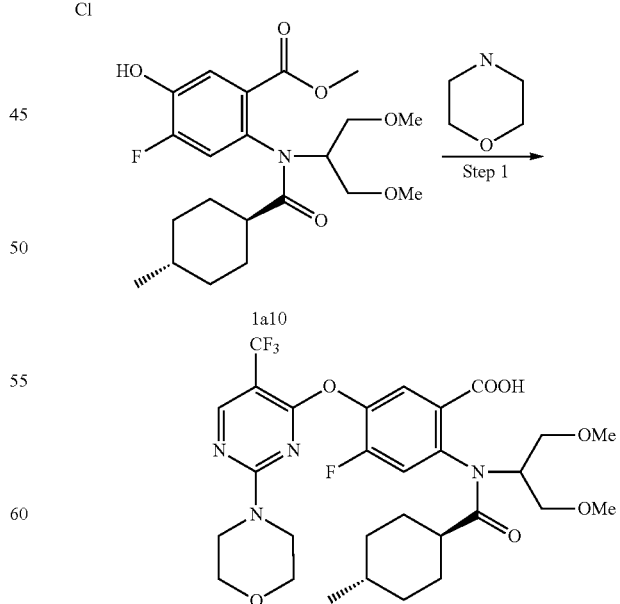

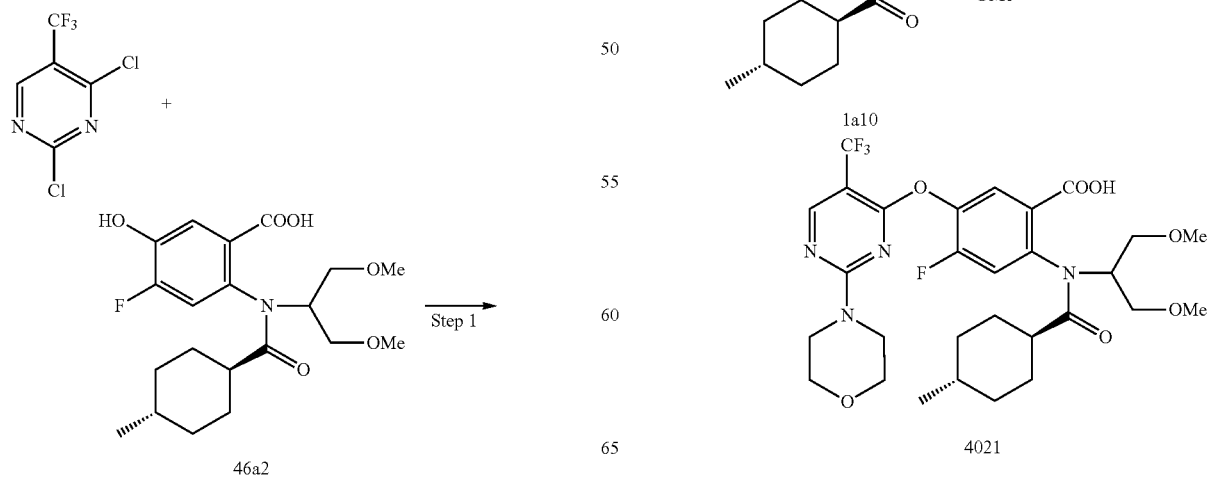

Step 1:

A suspension of 2,6-dichloro-3-(trifluoromethyl)pyridine (75 mg, 0.35 mmol), morpholine (33 mg, 0.38 mmol) and K₂CO₃ (144 mg, 1.04 mmol) is prepared in DMSO (2 mL) and stirred at 60° C. for about 6 h. When the reaction is complete, phenol 1a10 (30 mg, 0.073 mmol) is added and the mixture is warmed at 100° C. for about 20 h. When complete, the reaction is diluted in water and the mixture is extracted with DCM (3×) and concentrated. The residue is then dissolved in THF (2 mL)/MeOH (1 mL)/water (1 mL) and NaOH solution (10N, 75 µL, 0.75 mmol) is added. When complete, the mixture is filtered and the homogeneous solution is neutralized with AcOH and injected onto the preparative HPLC to isolate 4021.

Example 49A

Preparation of Compound 1124 phases are washed successively with aqueous saturated sodium bicarbonate (2×50 mL), brine (2×50 mL), dried over Na₂SO₄, filtered and concentrated under reduced pressure. The crude residue is dissolved in EtOH (10 mL) to receive Pd/C (10% w/w, 80 mg). The reaction flask is evacuated and filled back with hydrogen at atmospheric pressure. The mixture is stirred at RT for about 4 h, filtered through Celite®, washed with EtOH and heated to 80° C. for about 1 h. The reaction mixture is concentrated under reduced pressure to afford crude 49a1 which is used directly in the next step.

Step 2:

49a1 (214 mg, 0.35 mmol) is dissolved in DCM (8 mL), followed by the addition of oxalyl chloride (0.3 mL, 0.2 M in DCM, 0.60 mmol) and DMF (0.01 mL). This mixture is stirred for about 1 h at 40° C., then concentrated in vacuo. The residue is redissolved in DCM (10 mL) and then CH₂N₂ (6.0 mL, 0.12 M in Et₂O, 0.72 mmol) is added dropwise. The solution is stirred for about 30 min and then concentrated in vacuo. The yellow oil is redissolved in THF (20 mL), cooled to 0° C. and HBr (0.1 mL, 48%, 0.93 mmol) is added slowly. This is stirred for about 20 min. Saturated NaHCO₃ is slowly

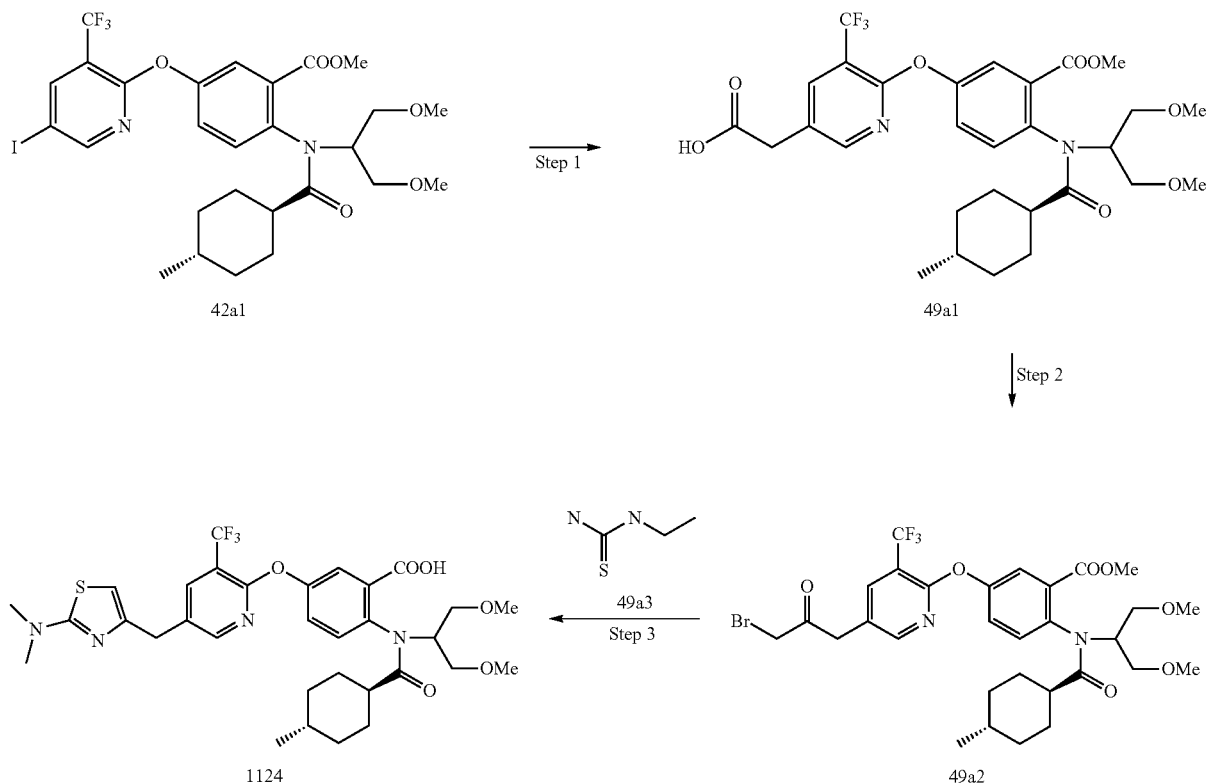

Step 1:

Copper (I) iodide (28 mg, 0.147 mmol) is added to a dioxane (2 mL) solution of iodide 42a1 (195 mg, 0.286 mmol), dibenzyl malonate (207 µL, 0.829 mmol), picolinic acid (35 mg, 0.286 mmol) and cesium carbonate (382 mg, 1.172 mmol). Argon is bubbled into the reaction mixture for about 2 min and the reaction vessel is sealed and heated at 70° C. for about 20 h. The reaction mixture is cooled to RT to receive more copper (I) iodide (28 mg, 0.147 mmol) and then resubmitted to 70° C. for about 20 h. The mixture is cooled to RT, diluted with aqueous saturated ammonium chloride (50 mL) and extracted with EtOAc (2×50 mL). The combined organic added and then the reaction is diluted with EtOAc, washed with H₂O (1×), NaHCO₃ (1×), brine (1×), dried over MgSO₄, filtered, concentrated in vacuo to yield yellow oil 49a2.

Step 3:

The bromide 49a2 (80 mg, 0.12 mmol) is dissolved in PrOH (3 mL) and the thiourea 49a3 (19 mg, 0.18 mmol) is added. The mixture heated at 70° C. for about 4 h. The mixture is cooled to RT, then NaOH (0.2 mL, 0.25 M) is added and stirred for about 2 h. The mixture is diluted with AcOH and purified by preparative HPLC to yield the desired compound 1124.

Example 50A
Preparation of Compound 1127
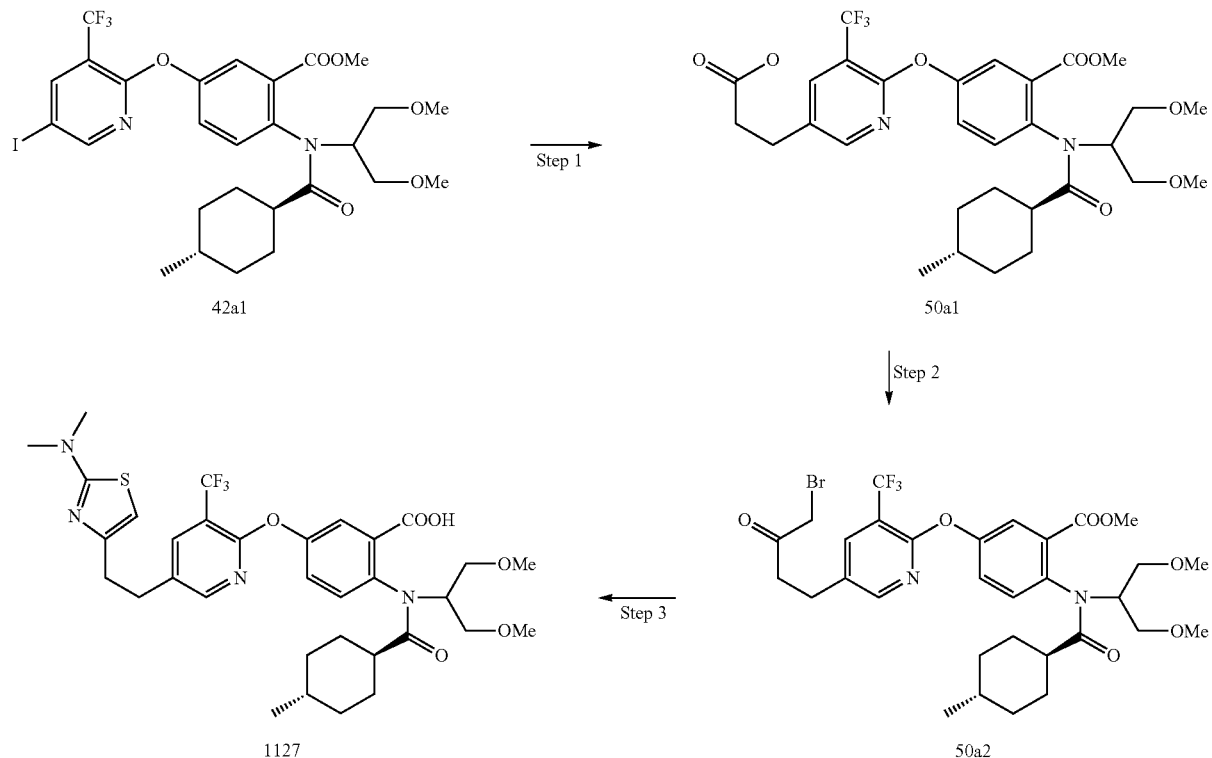
Step 1: Compound 42a1 is transformed to compound 50a1 using the procedure of Step 3, Example 28A.
Step 2: Compound 50a1 is transformed to compound 50a2 using the procedure of Step 2, Example 49A.
Step 3: Compound 50a2 is transformed to compound 1127 using the procedure of Step 3, Example 49A.
Example 51A
Preparation of Intermediates 51a3 and 51a4
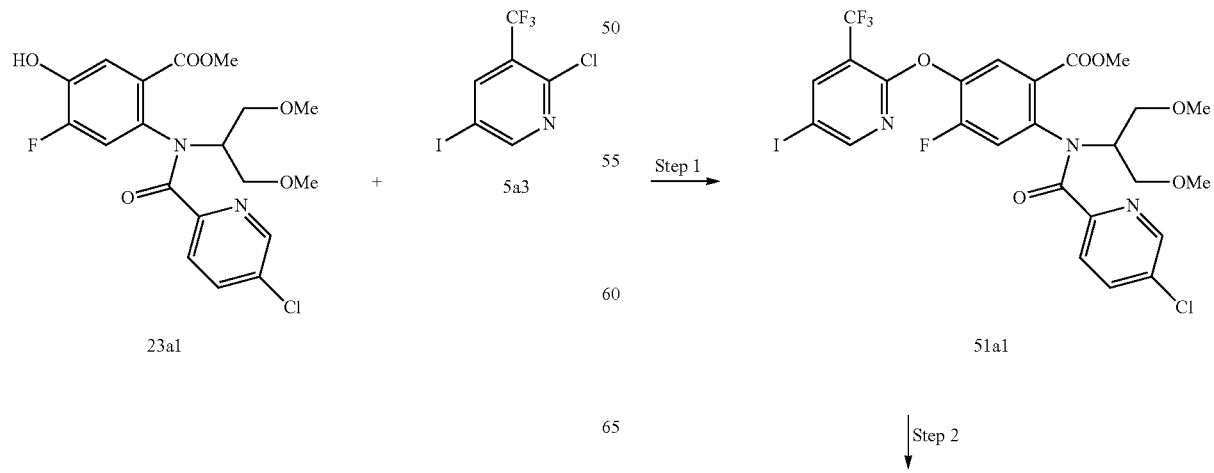

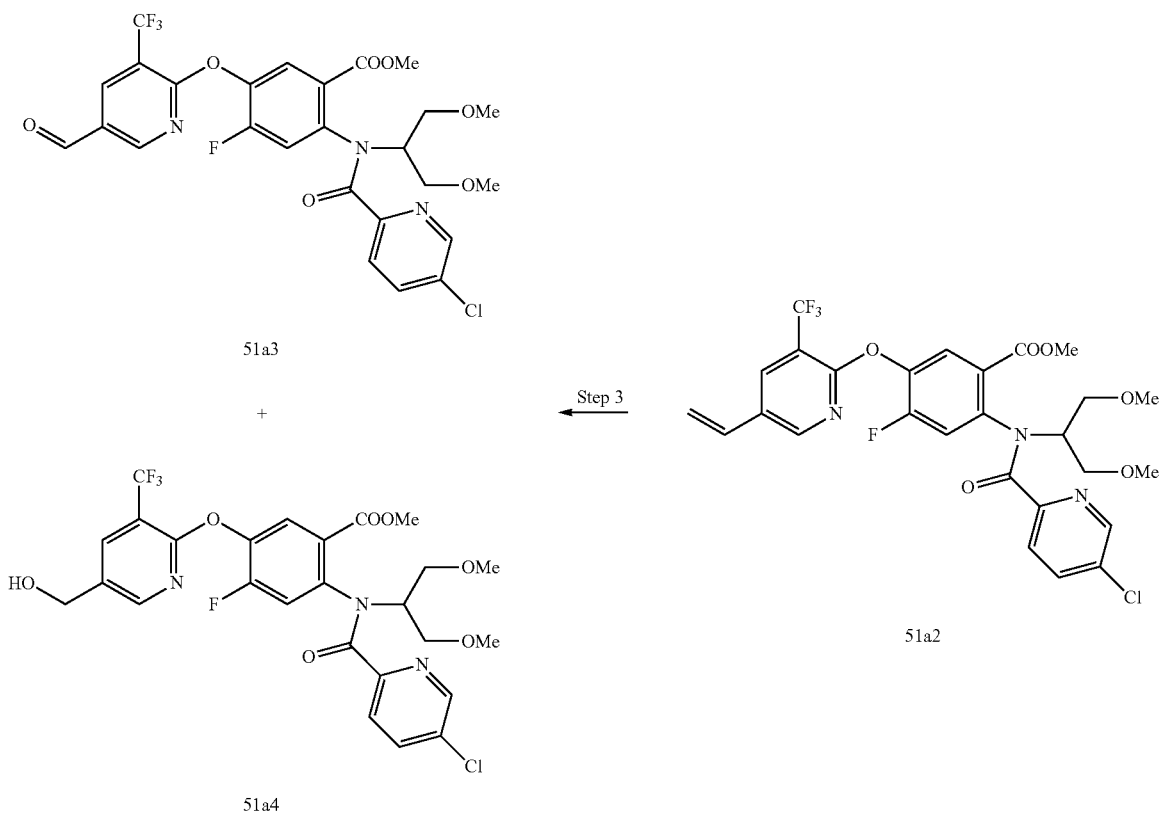

Step 1:
To a solution of iodide 5a3 (191 mg, 0.62 mmol) in DMSO (3 mL) is added CsCO₃ (216 mg, 0.66 mmol) and 23a1 (189 mg, 0.44 mmol). This is stirred at 75° C. for about 4 h and then cooled to RT. The mixture is washed with water and brine, dried over anhydrous Na₂SO₄, filtered under vacuum and concentrated. Purification by flash chromatography using (20:80 to 60:40) EtOAc/Hex affords an off-white solid 51a1.

Step 2:
To a solution of 51a1 (256 mg, 0.37 mmol) in dioxane (3 mL) is added tributyl(vinyl)tin (0.14 mL, 0.48 mmol) at RT. The solution is degassed by bubbling a balloon of Ar into it. Dichloro-bis(triphenylphosphine)palladium (26 mg, 0.04 mmol) is added and the reaction mixture is heated at reflux for about 1.5 h. The mixture is concentrated and purified by flash chromatography using (10:90 to 70:30) EtOAc/Hex to obtain 51a2.

Step 3:
To a solution of 51a2 (181 mg, 0.30 mmol) in water (0.5 mL), acetone (2 mL) and MeOH (0.4 mL) is added OsO₄ (0.04 mL, 2.5% solution in t-BuOH) and NMO (40 mg, 0.34 mmol) at RT. This is stirred at RT for about 1.5 h. Sodium periodate (71 mg, 0.33 mmol) is then added and reaction mixture is stirred at RT for about 16 h. The reaction mixture is poured into a saturated solution of aqueous Na₂S₂O₃ and then extracted with EtOAc (4×). The organic layers are combined, washed with brine, dried over anhydrous Na₂SO₄, filtered under vacuum and concentrated. The residue is dissolved in MeOH (2 mL) and NaBH₄ (58 mg, 1.5 mmol) is slowly added and stirred for about 1 h at RT. The reaction mixture is poured into a saturated solution of aqueous NH₄Cl and then extracted with EtOAc (3×). The organic layers are combined, washed with brine, dried over anhydrous Na₂SO₄, filtered under vacuum and concentrated. Purification by flash chromatography using (30:70 to 80:20) EtOAc/Hex yields a mixture of aldehyde 51a3 and alcohol 51a4.

Example 51B

Preparation of Compound 1132

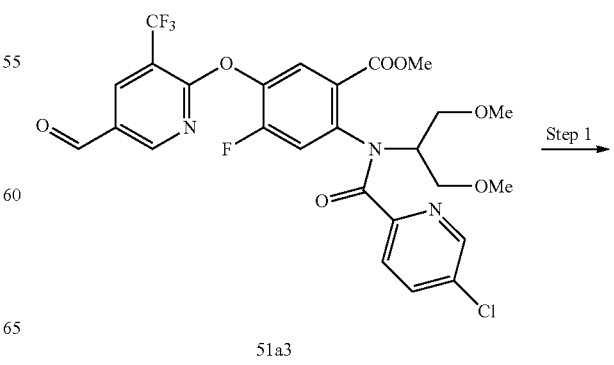

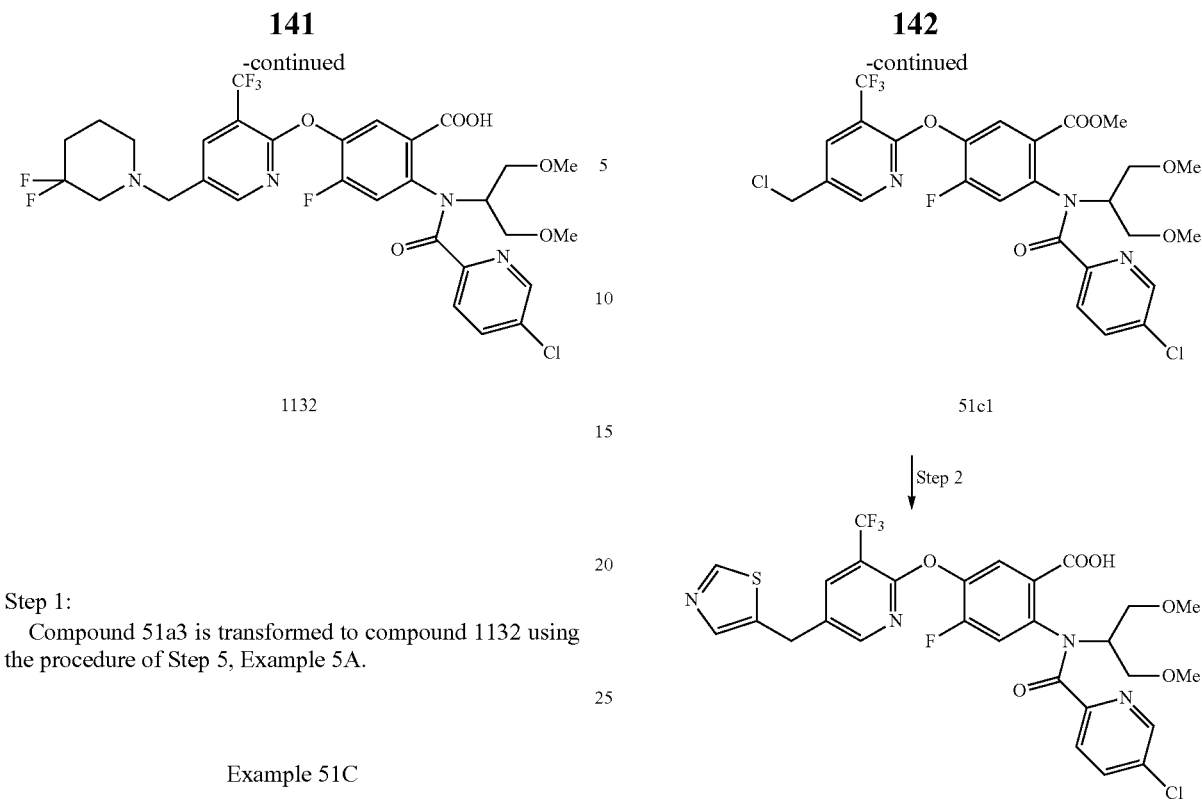
Step 1:
Compound 51a3 is transformed to compound 1132 using the procedure of Step 5, Example 5A.
Example 51C
Preparation of Compounds 1135
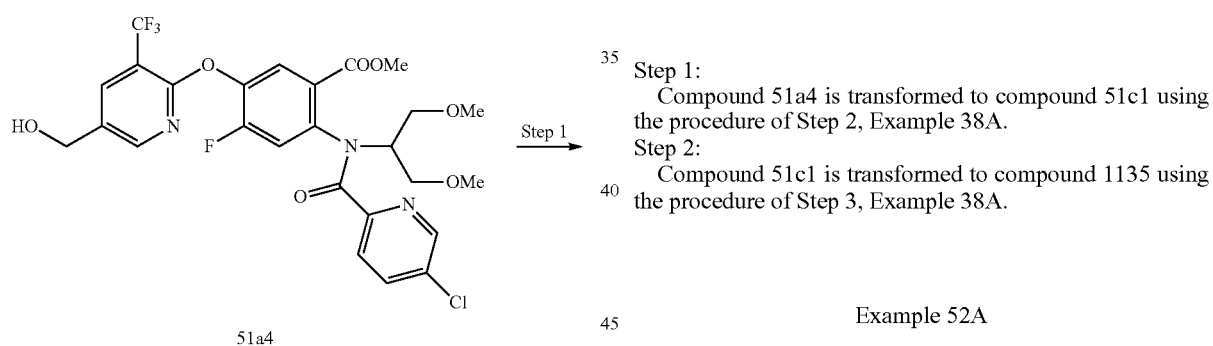
Step 1:
Compound 51a4 is transformed to compound 51c1 using the procedure of Step 2, Example 38A.
Step 2:
Compound 51c1 is transformed to compound 1135 using the procedure of Step 3, Example 38A.
Example 52A
Preparation of Compounds 1147
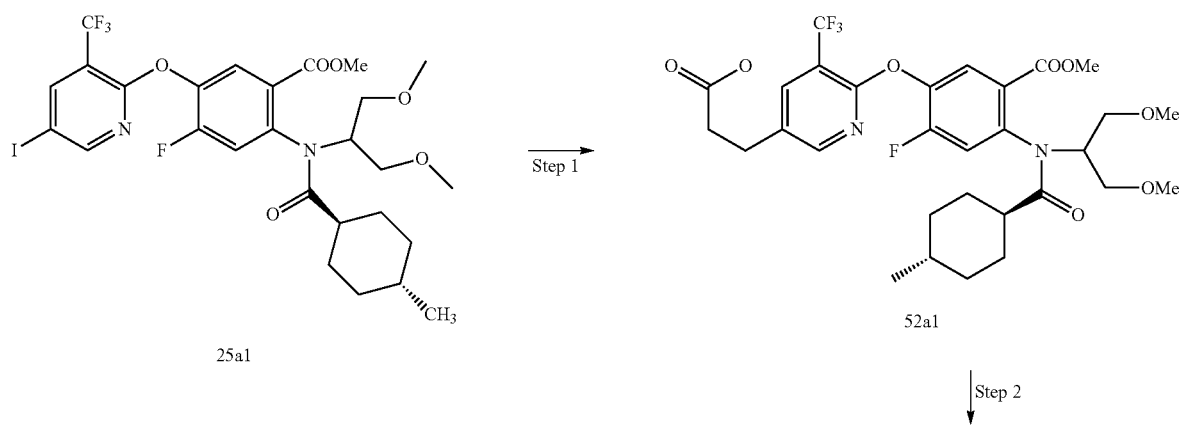

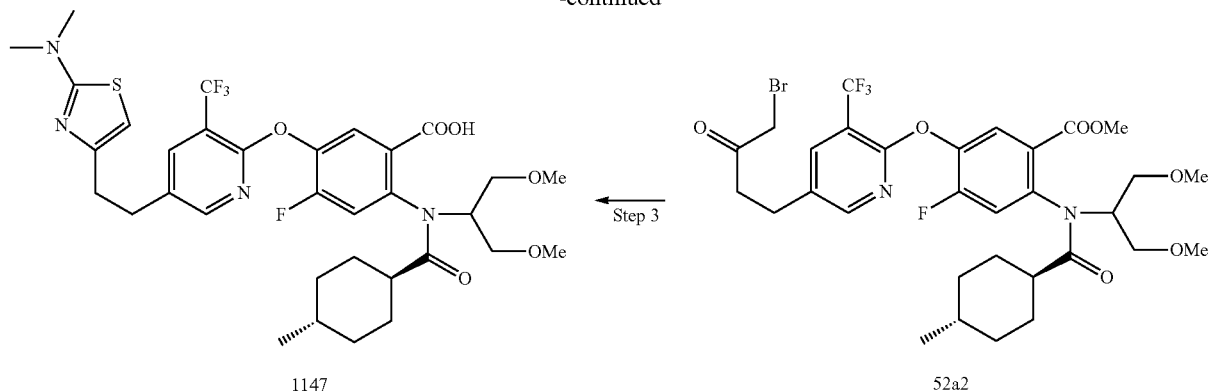

Step 1:
Compound 25a1 is transformed to compound 52a1 using the procedure of Step 3, Example 28A.
Step 2: Compound 52a1 is transformed to compound 52a2 using the procedure of Step 2, Example 49A.
Step 3: Compound 52a2 is transformed to compound 1147 using the procedure of Step 3, Example 49A.

Example 53A

Preparation of Compound 1152

Step 1:
Compound 25a1 is transformed to compound 53a1 using the procedure of Step 1, Example 49A.
Step 2:
Compound 53a1 is transformed to compound 53a2 using the procedure of Step 2, Example 49A.
Step 3:
Compound 53a2 is transformed to compound 1152 using the procedure of Step 3, Example 49A.

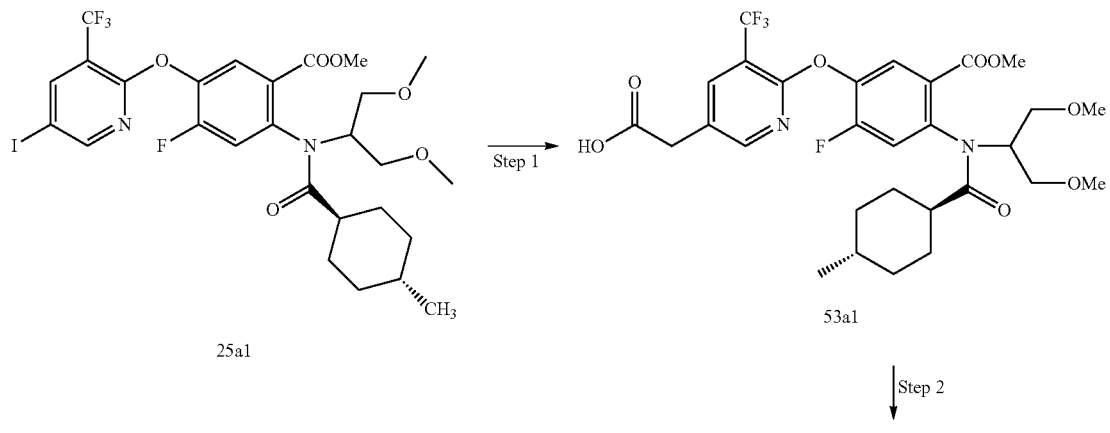

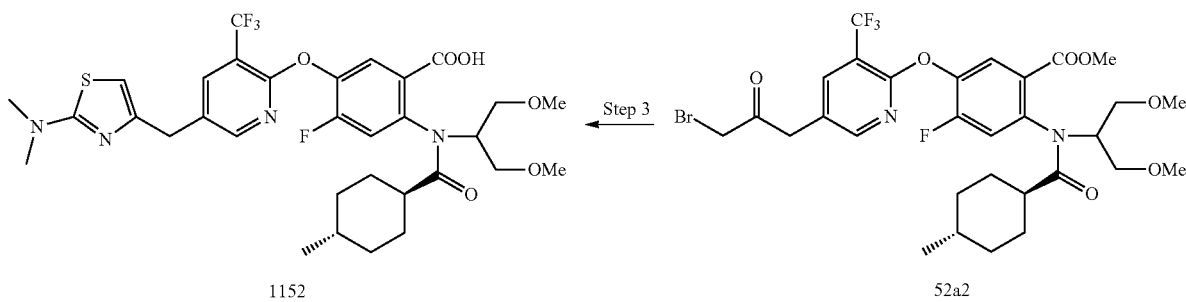

Example 54A

Preparation of Compounds 1165

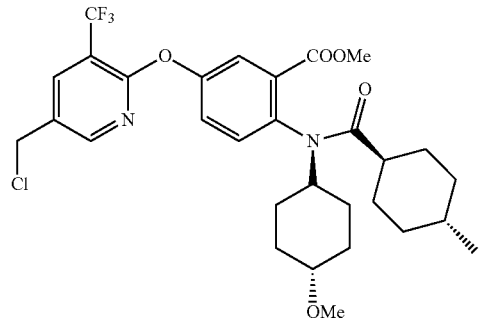

9a3

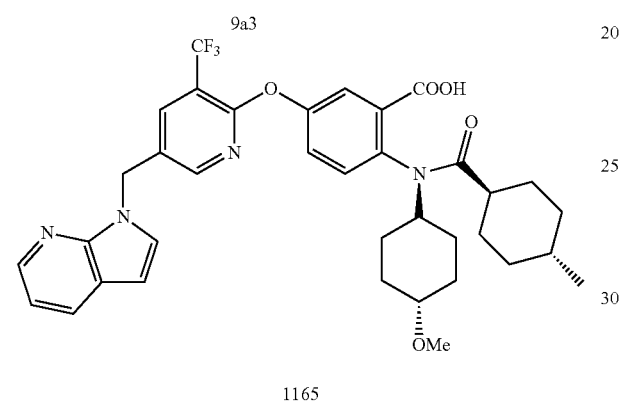

1165

Step 1:

To the solution of 7-azaindole (15 mg, 0.13 mmol) dissolved in anhydrous DMF (1 mL), at RT is added cesium carbonate (55 mg, 0.17 mmol) followed by the addition of the benzylic chloride 9a3 (dissolved in anhydrous DMF 0.5 mL) is added, followed by KI (3.5 mg, 0.02 mmol). This is heated at 110° C. for about 14 h, then cooled to RT. THF (1 mL), MeOH (1 mL) and NaOH (1 M, 1 mL) is added and then this is stirred for about 24 h at RT. The mixture is then concentrated, diluted with AcOH and purified by preparative HPLC to yield the desired product 1165.

Example 55A

Preparation of Compound 1166

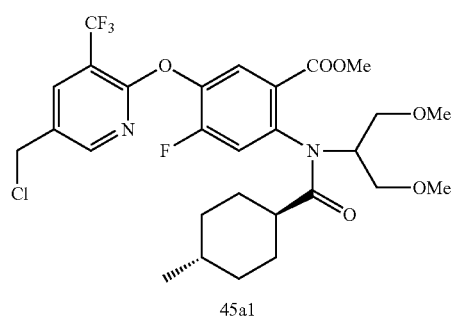

45a1

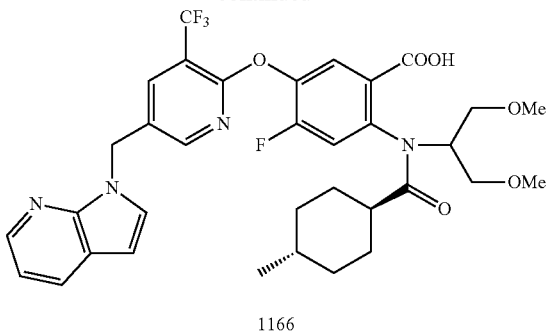

1166

Step 1:

Compound 45a1 is transformed to compound 1166 using the procedure described in Step 1, Example 54A.

Example 56A

Preparation of Compounds 1168

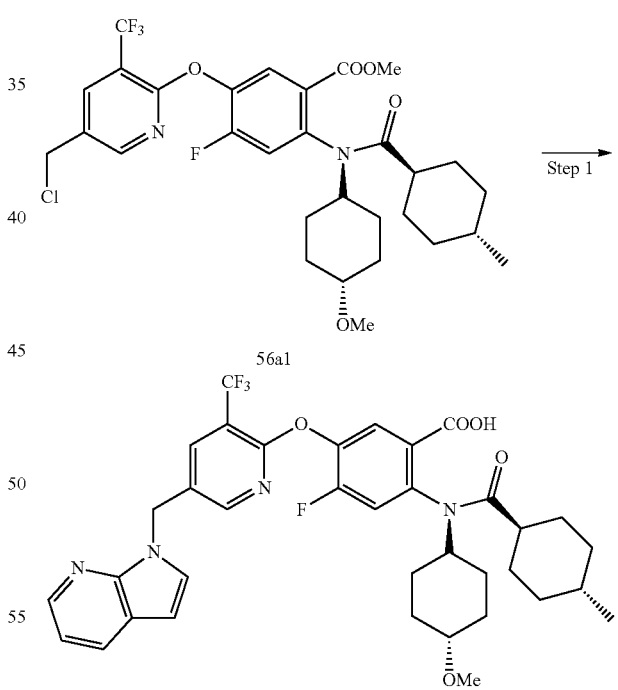

Step 1:

Compound 56a1 is transformed to compound 1168 using the procedure of Step 1, Example 55A.

147
Example 57A
Preparation of Intermediate 57a1
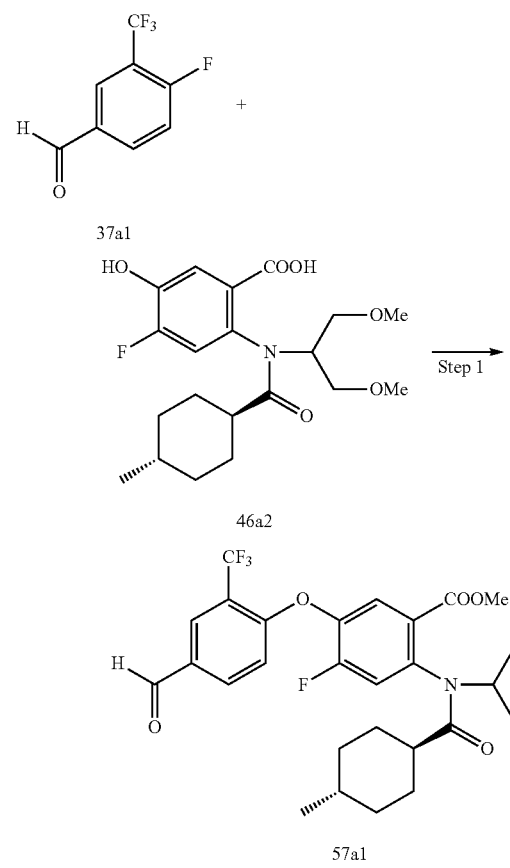
Step 1:
Compound 57a1 is generated via the reaction of compounds 37a1 and 46a2 using the procedure of Step 1, Example 37A.
Example 57B
Preparation of Compound 3008
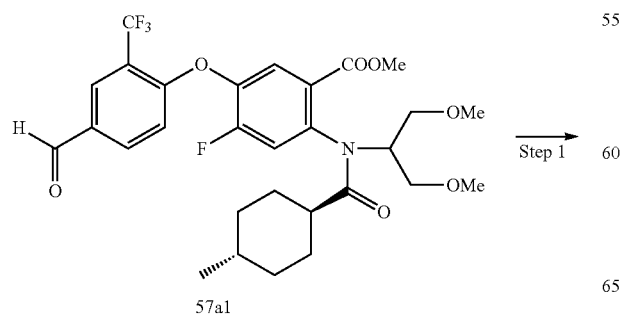
148
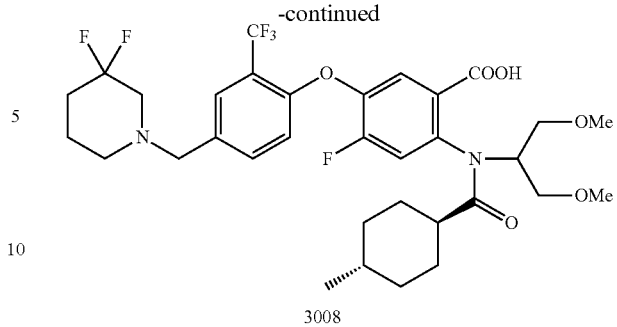
Step 1:
Compound 57a1 is transformed to compound 3008 using the procedure of Step 5, Example 5A.
Example 57C
Preparation of Intermediate 57c2
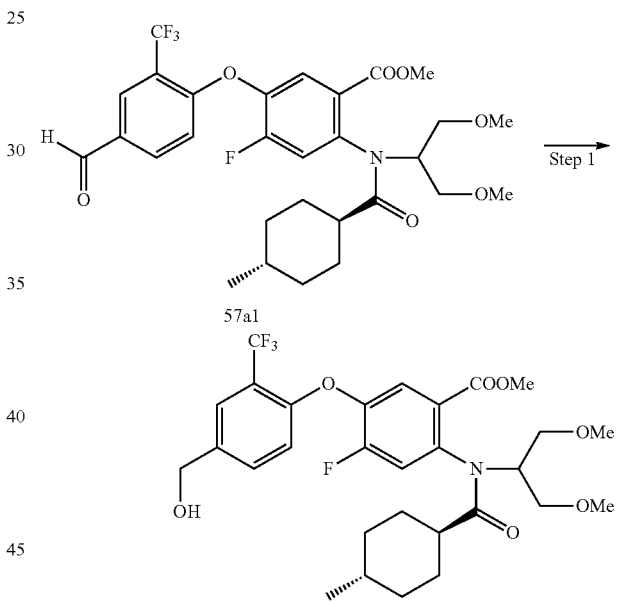
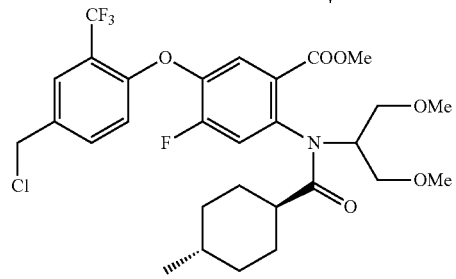

Step 1:
Compound 57a1 is transformed to compound 57c1 using the procedure of Step 2, Example 9A.

Step 2:
Compound 57c1 is transformed to compound 57c2 using the procedure of Step 3, Example 9A.

Example 57D

Preparation of Compounds 3009 AND 3010

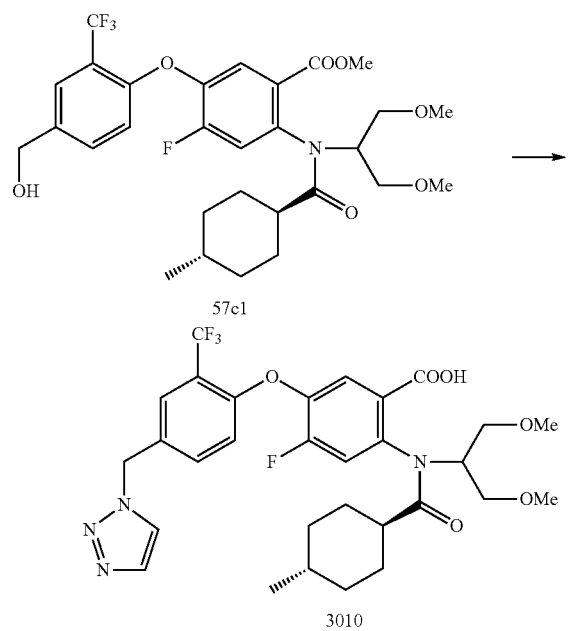

Step 1:
To a solution of 57c1 (49 mg, 0.08 mmol) in THF (1 mL) is added PPh$_3$ (24 mg, 0.09 mmol) and triazole (0.005 mL, 0.08 mmol). The solution is cooled to 0° C. and DEAD (0.017 mL, 0.09 mmol) is added. This is stirred at 0° C. for about 45 min, warmed to RT and stirring is continued for about another 72 h. MeOH (1 mL) and NaOH (1 mL, 1 M solution in water) are added and this mixture is stirred for about 24 h at RT. The reaction mixture is then concentrated, dissolved in AcOH/MeOH (4 mL, 1:1) and purified by preparative HPLC. The fractions are combined and solvent removed by lyophilization to yield 3010 and 3009.

Example 58A

Preparation of Compound 3011

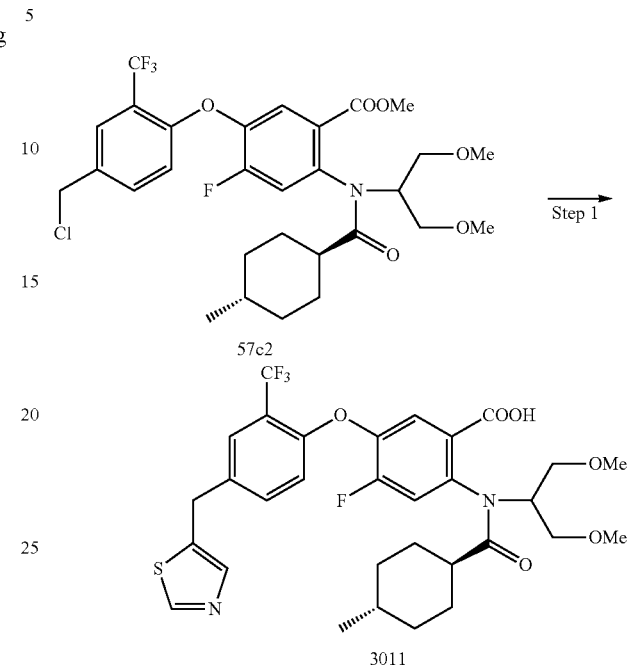

Step 1:
Compound 57c2 is transformed to compound 3011 using the procedure of Step 3, Example 38A.

Example 59A

Preparation of Compound 3015

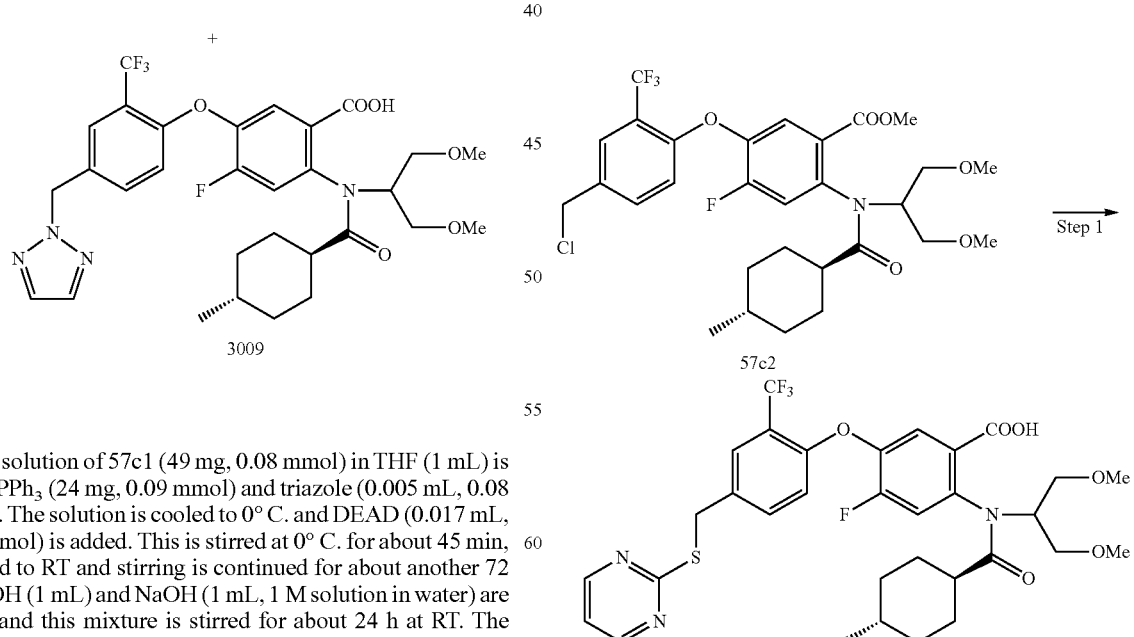

Step 1:

Compound 57c2 is transformed to compound 3015 using 2-mercaptopyrimidine in the procedure of Step 1, Example 33A.

Example 60A

Preparation of Compound 4004

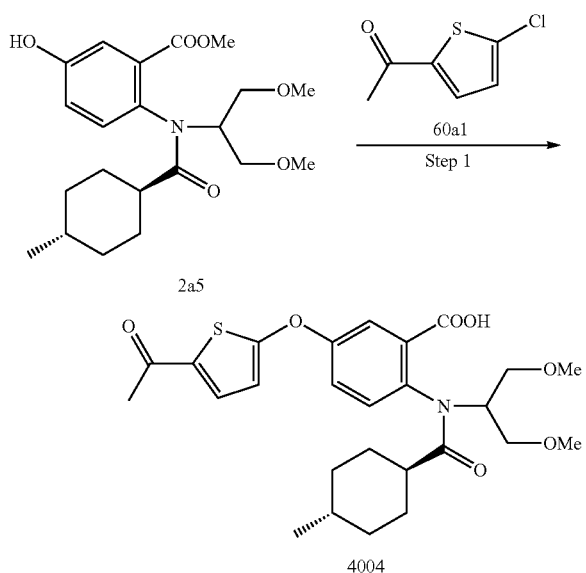

Step 1:

Alcohol 2a5 is transformed to compound 4004 using the thiophene 60a1 in the procedure of Step 1, Example 25A.

Example 61A

Preparation of Intermediate 61a5

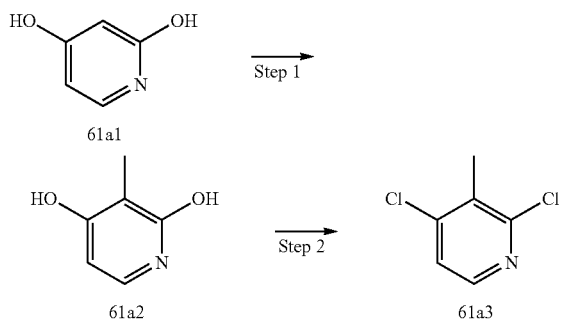

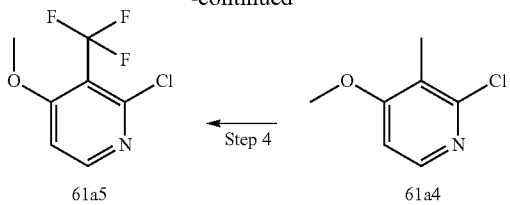

Step 1:

A mixture of dihydroxypyridine 61a1 (24 g, 216 mmol), $K_2CO_3$ (29.9 g, 216 mmol) and water (240 mL) is heated to 100° C. until it becomes homogeneous. Solid $I_2$ (54.8 g, 216 mmol) is added portionwise (caution: evolution of gas!). When the iodine is consumed, the reaction is quenched with potassium hydrogen sulfate (216 mL, 216 mmol) which generates a precipitate. The precipitate is collected by filtration and dried under a stream of $N_2$ to yield 61a2.

Step 2:

A mixture of the diol 61a2 (49.3 g, 208 mmol), DMF (0.161 mL, 2.08 mmol) and phosphorous oxychloride (252 mL, 2704 mmol) is heated to 90° C. overnight. The reaction mixture is concentrated, quenched with saturated aqueous $NaHCO_3$, extracted with DCM, dried and concentrated to yield 61a3.

Step 3:

The di-chloride 61a3 (49 g, 179 mmol) and NaOMe (43.2 mL, 233 mmol) in MeOH (550 mL) is stirred at RT overnight. The reaction mixture is extracted with EtOAc and water and concentrated. Upon standing, crystals are formed. The crystals are collected and washed with a small amount of isopropyl ether. The crystals are transferred with heptane onto a glass filter and dried under a stream of air to yield 61a4.

Step 4:

A solution/suspension of iodide 61a4 (1 g, 3.71 mmol), KF (0.216 g, 3.71 mmol) and CuI (0.707 g, 3.71 mmol) in NMP (10 mL) in a microwave tube is degassed with Ar. Methyl 2-chloro-2,2-difluoroacetate (3.64 mL, 34.5 mmol) is added and the vessel is closed under Ar and heated to 120° C. for 30 min. in a microwave (caution: pressure buildup observed, take appropriate caution). The mixture is cooled to RT and the excess pressure is slowly released. A brine solution is added; then the reaction mixture is extracted with $Et_2O$. The combined organic layers are washed with brine, dried and concentrated followed by multiple purifications by flash column chromatography to yield 61a5.

Example 61B

Preparation of Compound 4013

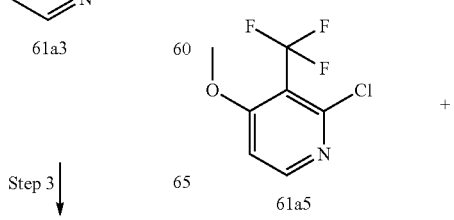

+

153
-continued
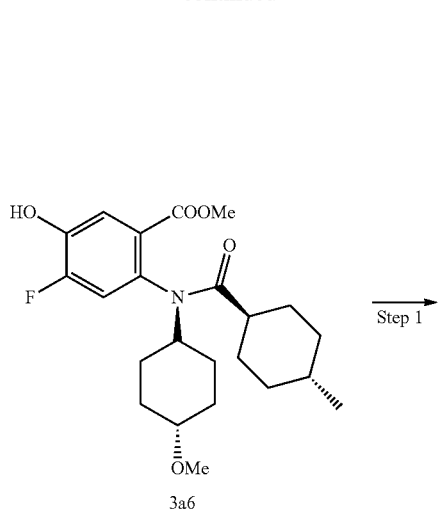
3a6
→ Step 1
154
-continued
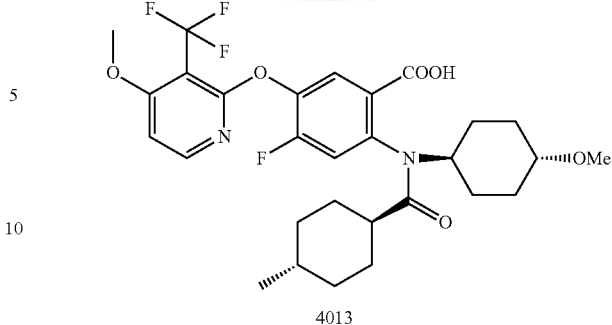
4013
Step 1:
Compound 4013 is generated via the reaction of compounds 61a5 and 3a6 using the procedure of Step 1, Example 16A.
Example 62A
Preparation of Compound 1122
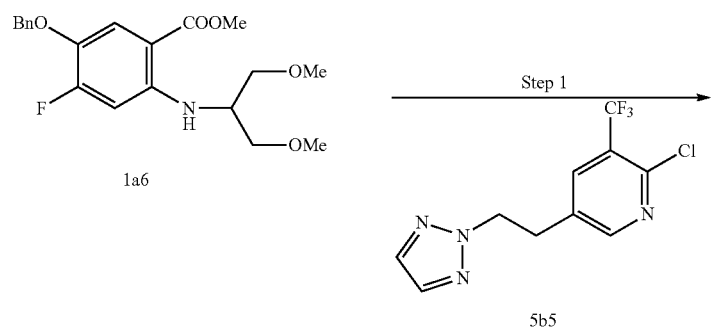
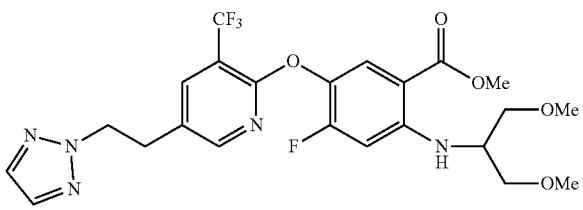
62a1
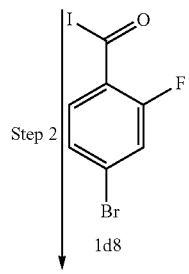
1d8

-continued

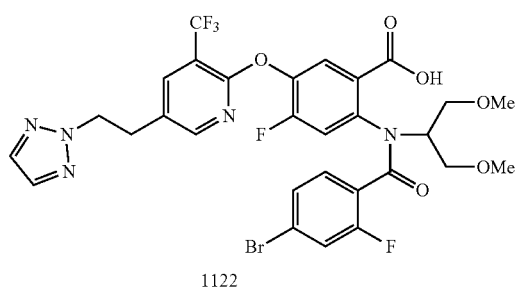

1122

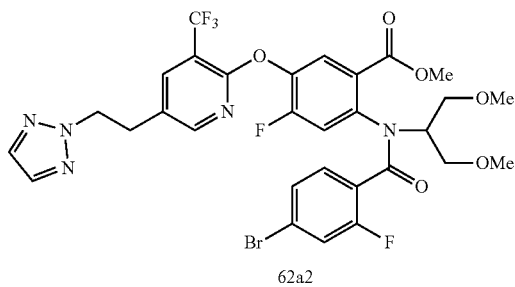

62a2

Step 1:

Pd/C (10%, 50 mg) is added to an EtOAc/MeOH (2:1, 9 mL) solution of compound 1a6 (640 mg, 1.69 mmol). The flask is closed with a septum, placed under vacuum, filled with hydrogen at atmospheric pressure and stirred at RT for about 2 h. The reaction vessel is placed under vacuum, filled with Ar and the solution is filtered over Celite®. DMSO (6 mL) is added to the solution, which is then concentrated under reduced pressure to a minimal volume. Cesium carbonate (661 mg, 2.03 mmole) is added, followed by chloropyridine 5b5 (422 mg, 1.53 mmol). The resulting mixture is heated at 75° C. for about 12 h, cooled to RT, diluted with aqueous saturated sodium bicarbonate (100 mL) and extracted with EtOAc (2×100 mL). The combined organic phases are washed with aqueous saturated sodium bicarbonate (2×50 mL), brine (2×50 mL), dried over $Na_2SO_4$, filtered and concentrated under reduced pressure. The residue is purified by column chromatography (10% to 40% EtOAc/hexanes) to afford compound 62a1.

Step 2:

DMAP (7.7 mg, 0.063 mmol) and pyridine (0.152 mL, 1.88 mmol) are added to a DCE (4 mL) solution of aniline 62a1 (166 mg, 0.315 mmol) and acid chloride 1d8 (299 mg, 1.259 mmol). The reaction mixture is heated at 150° C. under microwave conditions, for 1 h, cooled to RT, diluted with EtOAc (100 mL) and washed successively with aqueous saturated sodium bicarbonate (2×50 mL) and brine (2×50 mL). The organic phase is dried over $Na_2SO_4$, filtered and concentrated under reduced pressure. The crude residue is purified by column chromatography (80% EtOAc/hex) to afford compound 62a2.

Step 3:

Aqueous 5 M NaOH (0.115 mL, 0.577 mmol) is added dropwise to a 0° C. MeOH/THF solution (1:1, 2 mL) of ester 62a2 (63 mg, 0.086 mmol). The solution is stirred for about 2 h at RT, acidified with AcOH (1 mL) and purified by preparative HPLC to afford compound 1122.

Example 63A

Preparation of Compound 1136

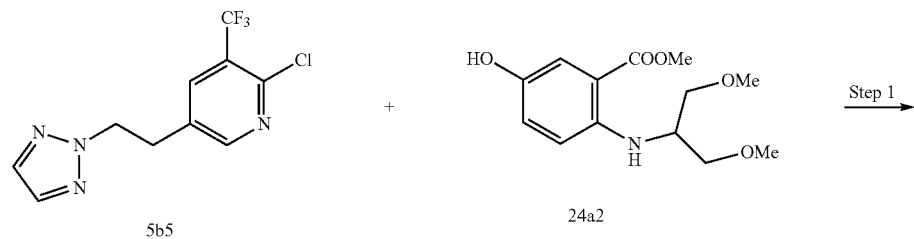

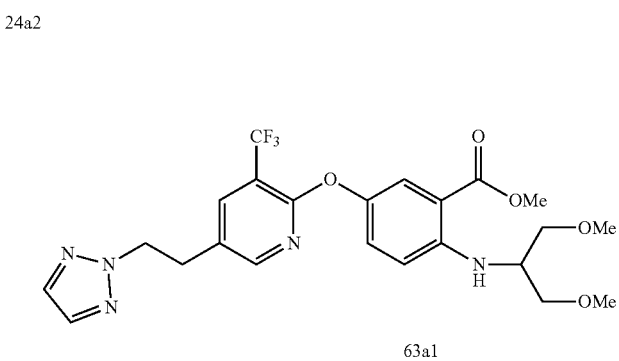

63a1

Step 2

157 -continued 158

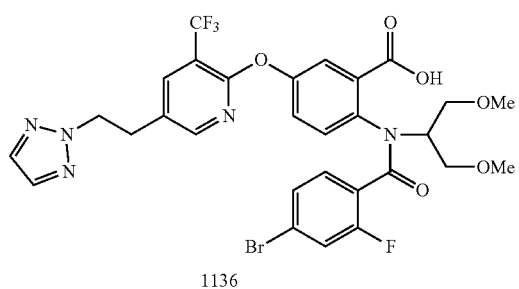

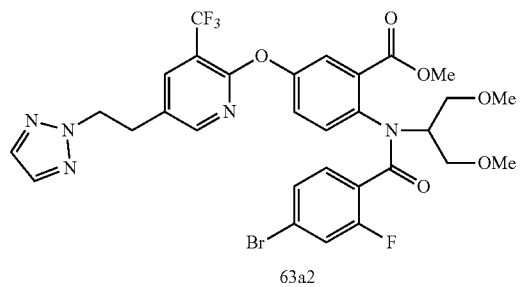

Step 1:

Potassium carbonate (414 mg, 3.00 mmol) is added to a RT DMSO (10 mL) solution of the chloropyridine 5b5 (380 mg, 1.37 mmol) and the phenol 24a2 (412 mg, 1.53 mmol). The reaction mixture is heated at 80° C. overnight. The solution is cooled to RT, diluted with aqueous saturated sodium bicarbonate and extracted with EtOAc (2×50 mL). The combined organic phases are washed with aqueous saturated sodium bicarbonate (2×50 mL), brine (2×50 mL), dried over $Na_2SO_4$, filtered and concentrated under reduced pressure. The crude residue is purified by column chromatography (30% to 75% EtOAc/hexanes) to afford 63a1.

Step 2:

DMAP (1.2 mg, 0.010 mmol) and pyridine (0.024 mL, 0.31 mmol) are added to a DCE (2 mL) solution of aniline 63a1 (52.1 mg, 0.102 mmol) and acid chloride 1d8 (60.6 mg, 0.255 mmol). The reaction mixture is heated at 150° C. in a microwave for 1 h, cooled to RT, diluted with EtOAc (100 mL) and washed successively with aqueous saturated sodium bicarbonate (2×50 mL) and brine (2×50 mL). The organic phase is dried over $Na_2SO_4$, filtered and concentrated under reduced pressure. The crude residue is purified by column chromatography (80% to 100% EtOAc/hex) to afford compound 63a2.

Step 3:

Aqueous 5 M NaOH (0.140 mL, 0.700 mmol) is added dropwise to a 0° C. MeOH/THF solution (1:1, 2 mL) of ester 63a2 (50 mg, 0.070 mmol). The solution is stirred for about 2 h at RT, acidified with AcOH (1 mL) and purified by preparative HPLC to afford compound 1136.

Example 64A

Preparation of Compound 1143

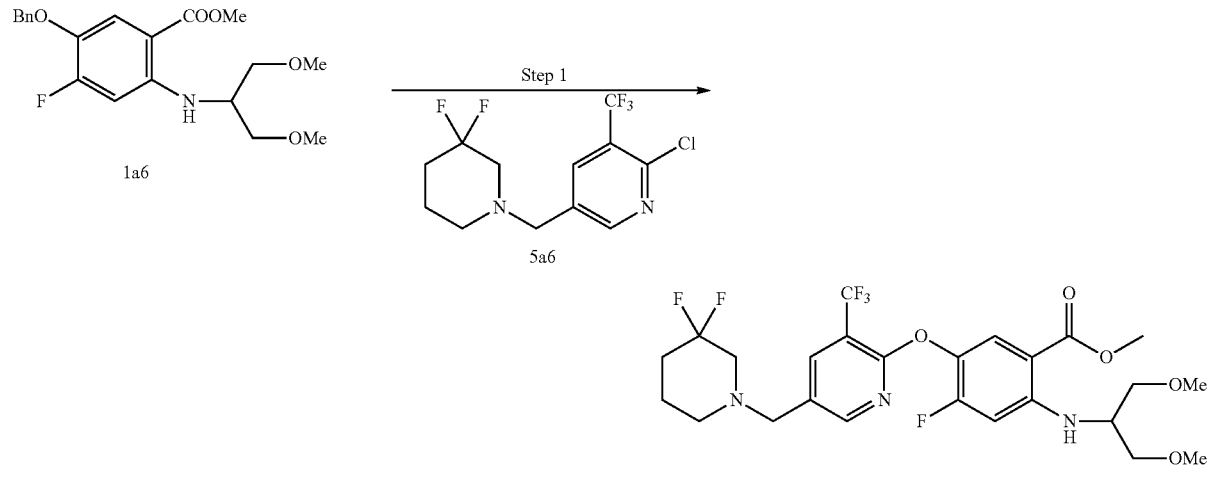

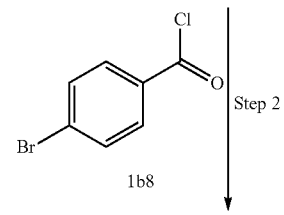

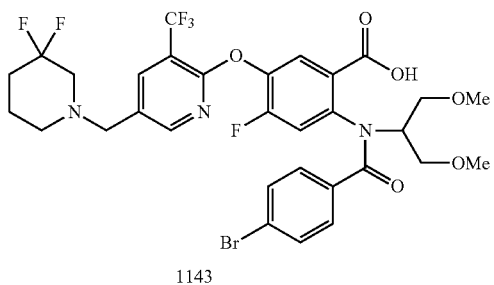

1143

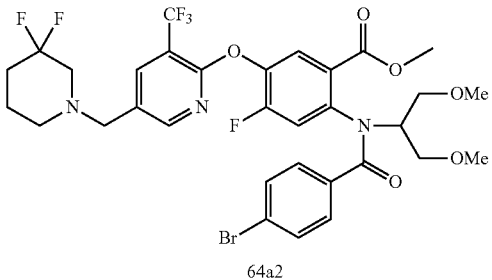

64a2

Step 1:

Pd/C (10%, 24 mg) is added to an EtOAc/MeOH (2:1, 9 mL) solution of compound 1a6 (715 mg, 1.89 mmol). The flask is closed with a septum, placed under vacuum, filled with hydrogen at atmospheric pressure and stirred at RT for about 2 h. The reaction vessel is placed under vacuum, filled with Ar and the solution is filtered over Celite®. DMSO (6 mL) is added to the solution, which is then concentrated under reduced pressure to a minimal volume. Cesium carbonate (739 mg, 2.27 mmole) is added, followed by chloropyridine 5a6 (357 mg, 1.14 mmol). The resulting mixture is heated at 75° C. for about 12 h, cooled to RT, diluted with aqueous saturated sodium bicarbonate (100 mL) and extracted with EtOAc (2×100 mL). The combined organic phases are washed with aqueous saturated sodium bicarbonate (2×50 mL), brine (2×50 mL), dried over $Na_2SO_4$, filtered and concentrated under reduced pressure. The residue is purified by column chromatography (20% to 60% EtOAc/hexanes) to afford compound 64a1.

Step 2:

DMAP (7.7 mg, 0.063 mmol) and pyridine (0.078 mL, 0.973 mmol) are added to a DCE (4 mL) solution of aniline 64a1 (100 mg, 0.177 mmol) and acid chloride 1b8 (116 mg, 0.530 mmol). The reaction mixture is heated at 150° C. under microwave conditions, for 1 h, cooled to RT, diluted with EtOAc (100 mL) and washed successively with aqueous saturated sodium bicarbonate (2×50 mL) and brine (2×50 mL). The organic phase is dried over $Na_2SO_4$, filtered and concentrated under reduced pressure. The crude 64a2 is used directly in the next step.

Step 3:

Aqueous 5 M NaOH (0.695 mL, 3.475 mmol) is added dropwise to a 0° C. THF/DMSO solution (2:1, 3 mL) of the crude ester 64a2. The solution is stirred for about 2 h at RT, acidified with AcOH (1 mL) and purified by preparative HPLC to afford compound 1143.

Example 65A

Preparation of Compound 1162

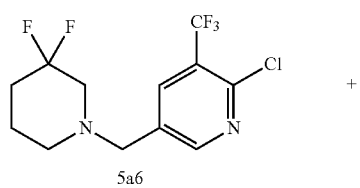

5a6

+

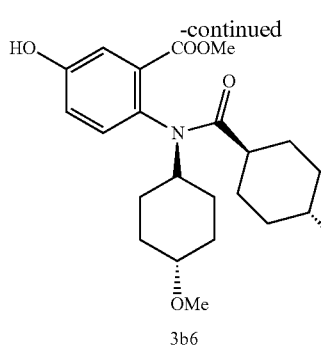

3b6

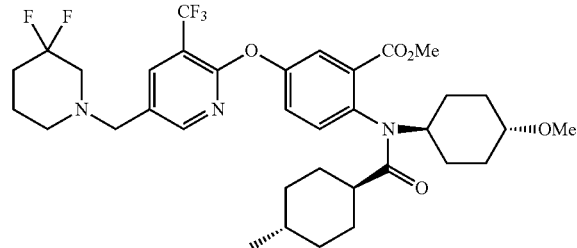

65a1

Step 2

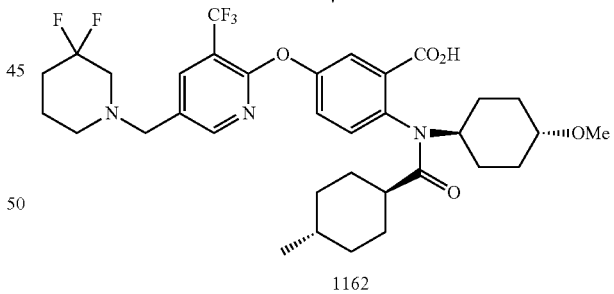

1162

Step 1:

Potassium carbonate (103 mg, 0.744 mmol) is added to a DMSO (4 mL) solution of the chloropyridine 5a6 (175 mg, 0.558 mmol) and phenol 3b6 (150 mg, 0.372 mmol). The reaction mixture is stirred at 80° C. overnight, cooled to RT, diluted with aqueous saturated sodium bicarbonate (100 mL) and extracted with EtOAc (2×50 mL). The combined organic phases are washed successively with aqueous saturated sodium bicarbonate (2×50 mL), brine (2×50 mL), dried over $Na_2SO_4$, filtered and concentrated under reduced pressure. The crude residue is purified by column chromatography (30% EtOAc/hexanes to 100% EtOAc) to afford 65a1.

Step 2:

Aqueous 5 M NaOH (0.486 mL, 2.43 mmol) is added dropwise to a 0° C. THF/MeOH solution (2:1, 3 mL) of the ester 65a1 (166 mg, 0.243 mmol). The solution is stirred at RT for about 5 days, acidified with AcOH (1 mL) and purified by preparative HPLC to afford compound 1162.

Example 66A

Preparation of Compound 1163 is applied onto a silica gel column and eluted with 20% EtOAc/hexanes to afford vinyl ether 66a1.

Step 2:

Pd/C (10%, 14 mg) is added to a MeOH solution (10 mL) of the benzyl ether 66a1 (135 mg, 0.267 mmol). The reaction vessel is closed with a septum, placed under vacuum and filled back with hydrogen at atmospheric pressure. The reaction mixture is stirred overnight under hydrogen. The reaction vessel is placed under vacuum and filled back with Ar. The reaction mixture is filtered over Celite® and washed with

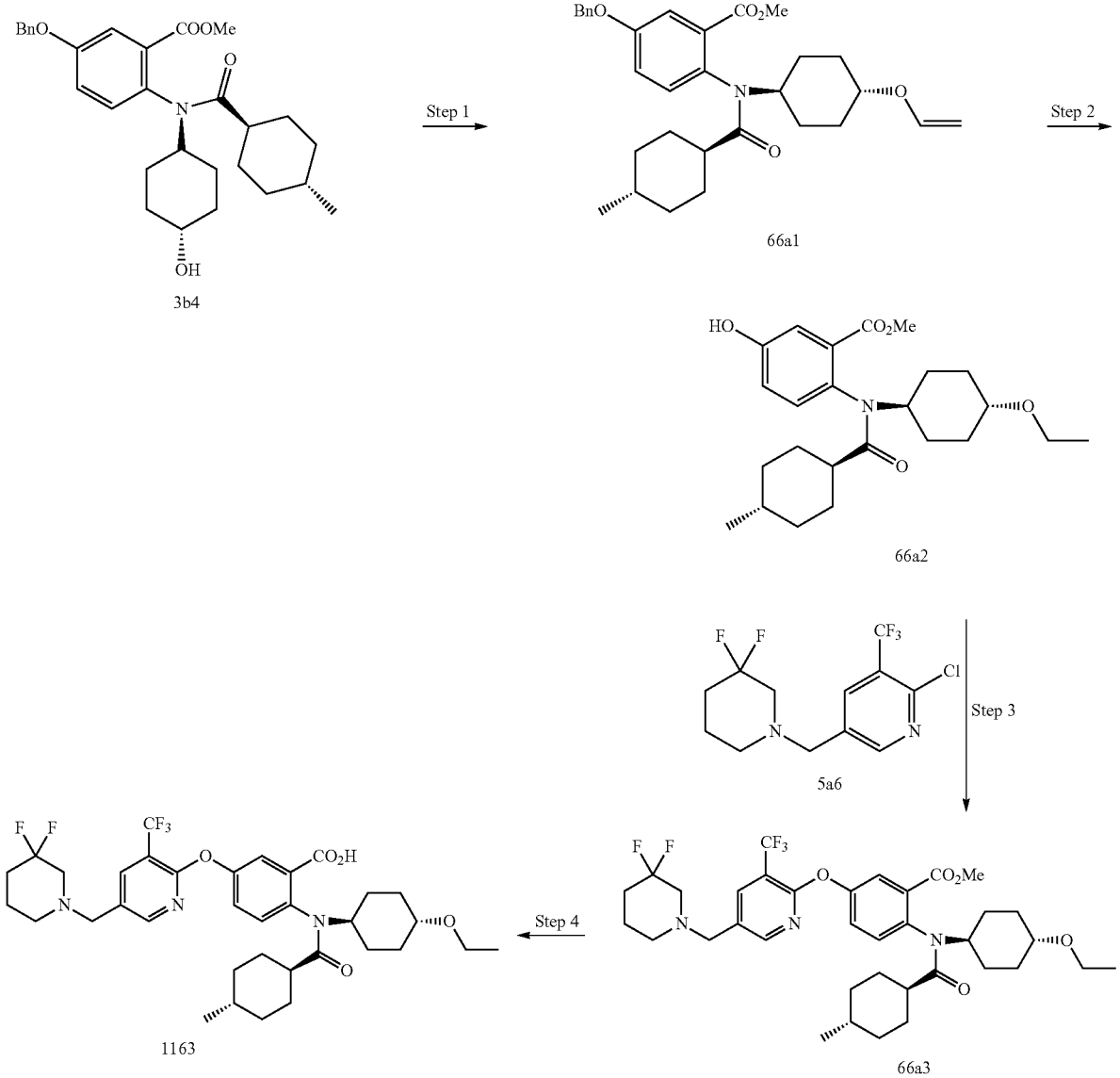

Step 1:

Palladium acetate (14 mg, 0.021 mmol) is added to a solution of 1,10-phenanthroline (3.6 mg, 0.020 mmol) in ethyl vinyl ether (5 mL). The mixture is stirred at RT for about 15 min to receive a solution of alcohol 3b4 (500 mg, 1.04 mmol) in ethyl vinyl ether (5 mL). The reaction mixture is heated at 60° C. for about 46 h and cooled to RT. Silica gel is added and the mixture is concentrated under reduced pressure. The solid EtOAc (100 mL). The organic phase is concentrated under reduced pressure and the residue 66a2 is utilized crude in the following step.

Step 3:

Potassium carbonate (71 mg, 0.512 mmol) is added to a DMSO (2 mL) solution of chloropyridine 5a6 (89 mg, 0.282 mmol) and phenol 66a2 (107 mg, 0.256 mmol). The reaction mixture is stirred at 80° C. overnight, cooled to RT, diluted with aqueous saturated sodium bicarbonate (100 mL) and extracted with EtOAc (2×50 mL). The combined organic phases are washed successively with aqueous saturated sodium bicarbonate (2×50 mL), brine (2×50 mL), dried over Na₂SO₄, filtered and concentrated under reduced pressure. The crude residue is purified by column chromatography (30% to 80% EtOAc/hexanes) to afford 66a3.

Step 4:

Aqueous 5 M NaOH (0.122 mL, 0.610 mmol) is added dropwise to a 0° C. THF/MeOH solution (2:1, 3 mL) of the ester 66a3 (85 mg, 0.122 mmol). The solution is stirred at RT for about 5 days, acidified with AcOH (1 mL) and purified by preparative HPLC to afford compound 1163.

Example 67A

Preparation of Compound 1164

Celite®, washed with EtOAc (50 mL) and concentrated under reduced pressure. The residue is purified by column chromatography (10% to 40% EtOAc in hexanes) to afford compound 67a1.

Step 2:

Pd/C (10%, 10 mg) is added to a MeOH solution (10 mL) of the benzyl ether 67a1 (132 mg, 0.254 mmol). The reaction vessel is closed with a septum, placed under vacuum and filled back with hydrogen at atmospheric pressure. The reaction mixture is stirred overnight under hydrogen. The reaction vessel is placed under vacuum and filled back with Ar. The reaction mixture is filtered over Celite® and washed with EtOAc (100 mL). The organic phase is concentrated under reduced pressure to afford crude 67a2 which is utilized crude in the following step.

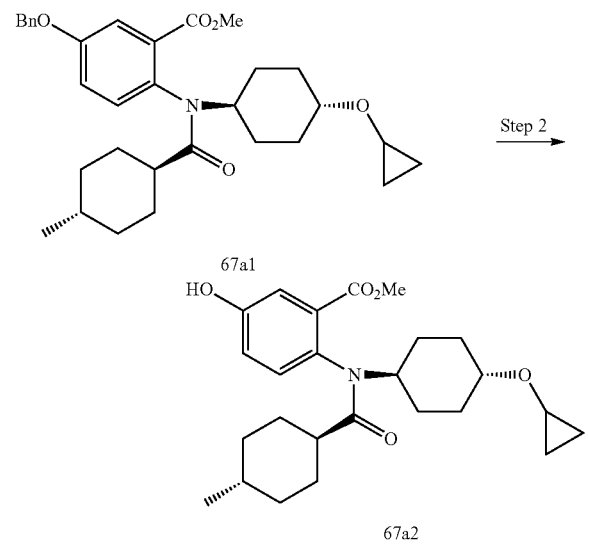

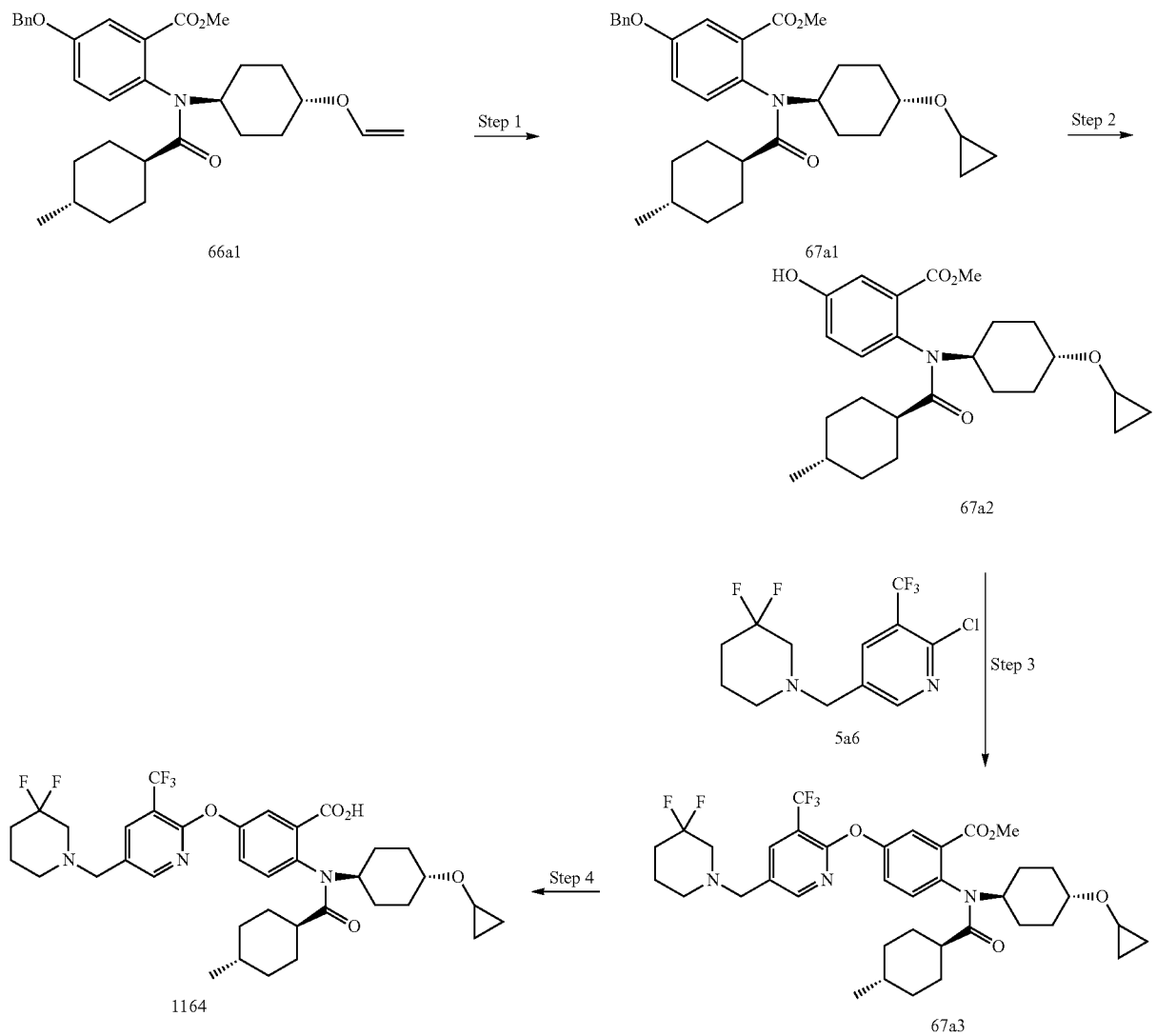

Step 1:

Diazomethane (5 mL, 0.6 M in ether) is added to an ice cold ether solution (10 mL) of vinyl ether 66a1 (170 mg, 0.336 mmol) and palladium acetate (10 mg, 0.045 mmol). The reaction mixture is stirred overnight at RT, filtered over Step 3:

Potassium carbonate (212 mg, 1.53 mmol) is added to a DMSO (10 mL) solution of chloropyridine 5a6 (241 mg, 0.768 mmol) and crude phenol 67a2. The reaction mixture is stirred at 80° C. overnight, cooled to RT, diluted with saturated aqueous sodium bicarbonate (100 mL) and extracted with EtOAc (2×50 mL). The combined organic phases are washed successively with aqueous saturated sodium bicarbonate (2×50 mL), brine (2×50 mL), dried over $Na_2SO_4$, filtered and concentrated under reduced pressure. The crude residue is purified by column chromatography (30% to 80% EtOAc/hex) to afford 67a3.

Step 4:

Aqueous 5 M NaOH (0.354 mL, 1.77 mmol) is added dropwise to a 0° C. THF/MeOH solution (2:1, 3 mL) of the ester 67a3 (125 mg, 0.177 mmol). The solution is stirred at RT for about 5 days, acidified with AcOH (1 mL) and purified by preparative HPLC to afford compound 1164.

Example 68A

Preparation of Intermediate 68a1

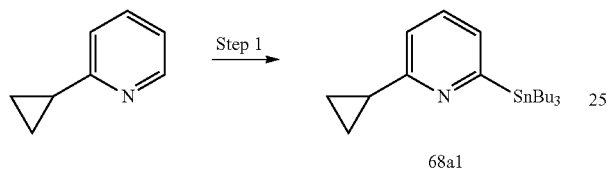

68a1

Step 1:

n-Butyllithium (2.1 M in hexanes, 8.82 mL, 18.5 mmol) is added dropwise to an ice cold hexanes (10 mL) solution of N,N-dimethylethanolamine (0.900 mL, 9.063 mmol). The reaction mixture is stirred at 0° C. for about 30 min at which time a hexanes solution (10 mL) of 2-cyclopropylpyridine (360 mg, 3.02 mmole) is added. The reaction mixture is stirred for about 45 min at 0° C. and then cooled to −78° C. to receive a hexanes solution (10 mL) of tributylstannyl chloride (3.44 g, 10.5 mmol). The mixture is stirred at −78° C. for about 30 min, warmed to RT over about a 30 min period, diluted with water (100 mL) and extracted with ether (2×50 mL). The combined organic phases are washed with brine (2×50 mL), dried over $Na_2SO_4$, filtered and concentrated under reduced pressure to obtain crude 68a1.

Example 68B

Preparation of Compound 1169

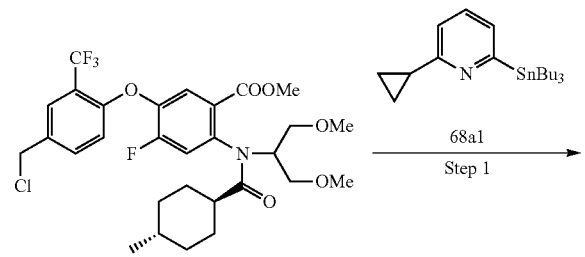

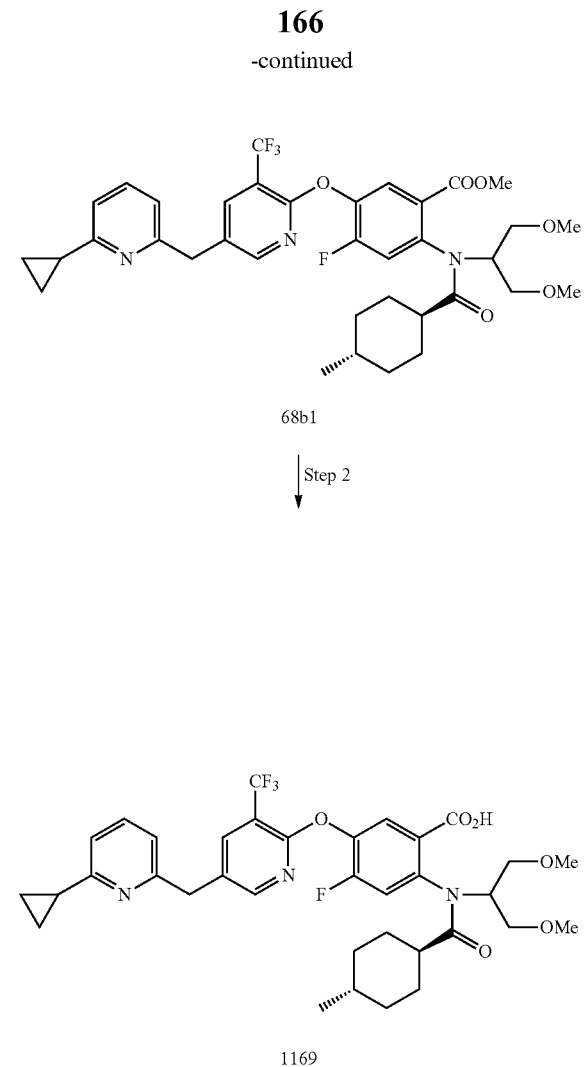

Step 1:

In a microwave tube, chloride 57c2 (102 mg, 0.169 mmol) is put in degassed DMF (2 mL, degassed by bubbling a volume of Ar while sonicating for about 10 min) along with stannyl 68a1 (241 mg, 0.177 mmol). $Pd(PPh_3)_4$ (49 mg, 0.017 mmol) is added, the tube is sealed and put in the microwave at 125° C. for 20 min. The mixture is diluted in EtOAc and washed with water (2×) and brine (2×). The combined organics are dried over $MgSO_4$, filtered and concentrated. The crude residue is passed on a short silica gel column (20% to 70% EtOAc in hex) to afford compound 68b1.

Step 2:

Aqueous 5 M NaOH (0.301 mL, 1.505 mmol) is added dropwise to a 0° C. THF/DMSO solution (2:1, 3 mL) of ester 68b1 (85 mg, 0.124 mmol). The solution is stirred at RT for about 5 days, acidified with AcOH (1 mL) and purified by preparative HPLC to afford compound 1169.

Example 69A

Preparation of Compounds 1172, 1173 and 1174

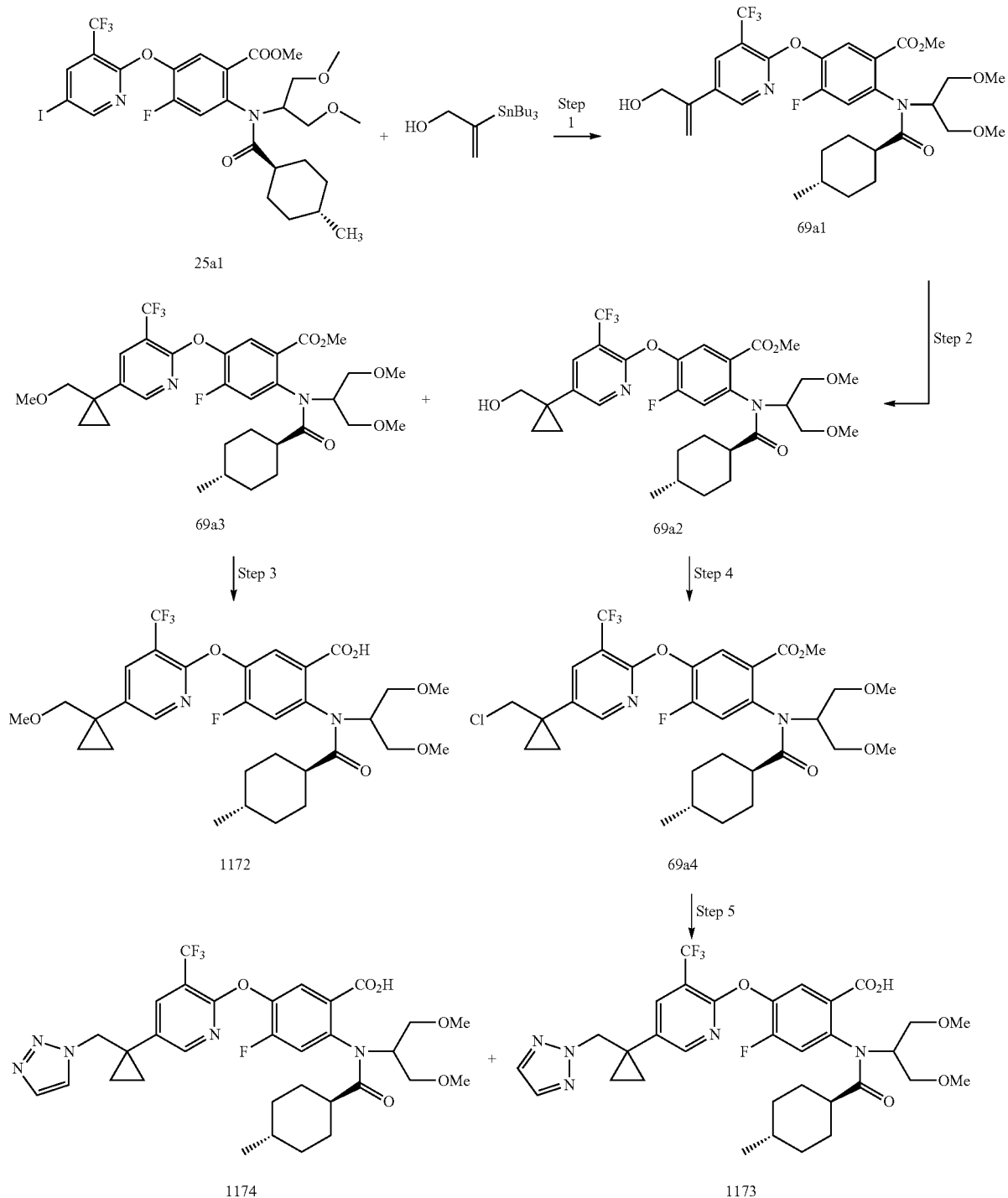

Step 1:

Bis(tri-tert-butylphosphine)palladium (38 mg, 0.075 mmol) is added to a DMF solution (4 mL) of compound 25a1 (510 mg, 0.747 mmol) and stannane (285 mg, 0.822 mmol). The reaction mixture is degassed by bubbling Ar in the solution for about 15 min, stirred at 100° C. for about 2 h, cooled to RT, diluted with aqueous saturated sodium bicarbonate and extracted with EtOAc (2×50 mL). The combined organic phases are washed successively with aqueous saturated sodium bicarbonate (2×50 mL), brine (2×50 mL), dried over $Na_2SO_4$, filtered and concentrated under reduced pressure. The crude residue is purified by column chromatography (40% to 60% EtOAc in hexanes) to afford compound 69a1.

Step 2:

Diazomethane (5 mL, 0.6 M) is added to an ice cold ether solution (10 mL) of compound 69a1 (100 mg, 0.163 mmol) and palladium acetate (10 mg, 0.045 mmol). The reaction mixture is stirred overnight at RT, filtered over Celite®, washed with EtOAc (50 mL) and concentrated under reduced pressure. The residue is purified by column chromatography (50% to 90% EtOAc in hexanes) to afford methyl ether 69a3 and alcohol 69a2.

Step 3:

Aqueous 5 M NaOH (0.112 mL, 0.560 mmol) is added dropwise to a 0° C. THF/MeOH solution (2:1, 3 mL) of ester 69a3 (36 mg, 0.056 mmol). The solution is stirred at RT for about 24 h, acidified with AcOH (1 mL) and purified by preparative HPLC to afford compound 1172.

Step 4:

Thionyl chloride (12 µL, 0.163 mmol) is added to a 0° C. DMF solution (2 mL) of alcohol 69a2 (40 mg, 0.065 mmol), followed by one drop of DMF. The reaction mixture is stirred at RT for about 3 h, diluted with saturated aqueous sodium bicarbonate (50 mL) and extracted with EtOAc (2×50 mL). The combined organic phases are washed successively with saturated aqueous sodium bicarbonate (2×50 mL), brine (50 mL), dried over $Na_2SO_4$, filtered and concentrated under reduced pressure. The crude compound 69a4 is used directly in the following step.

Step 5:

Sodium hydride (60% in mineral oil, 5.2 mg, 0.130 mmol) is added to an ice cold solution of 1,2,3-triazole (8.9 mg, 0.130 mmol). The solution is transferred over an ice cold DMF solution of chloride 69a4 (41.8 mg, 0.065 mmol) and stirred at RT overnight. The reaction mixture is diluted with saturated aqueous sodium bicarbonate (50 mL) and extracted with EtOAc (2×50 mL). The combined organic phases are washed successively with aqueous saturated sodium bicarbonate (2×50 mL), brine (50 mL), dried over $Na_2SO_4$, filtered and concentrated under reduced pressure. The crude residue is dissolved in THF/MeOH (2:1, 3 mL) and cooled to 0° C. Aqueous 5 N sodium hydroxide (64 µL, 0.320 mmol) is added. The solution is stirred at RT for about 5 days, acidified with AcOH (1 mL) and purified by preparative HPLC to afford 1174 and 1173.

Example 70A

Preparation of Intermediate

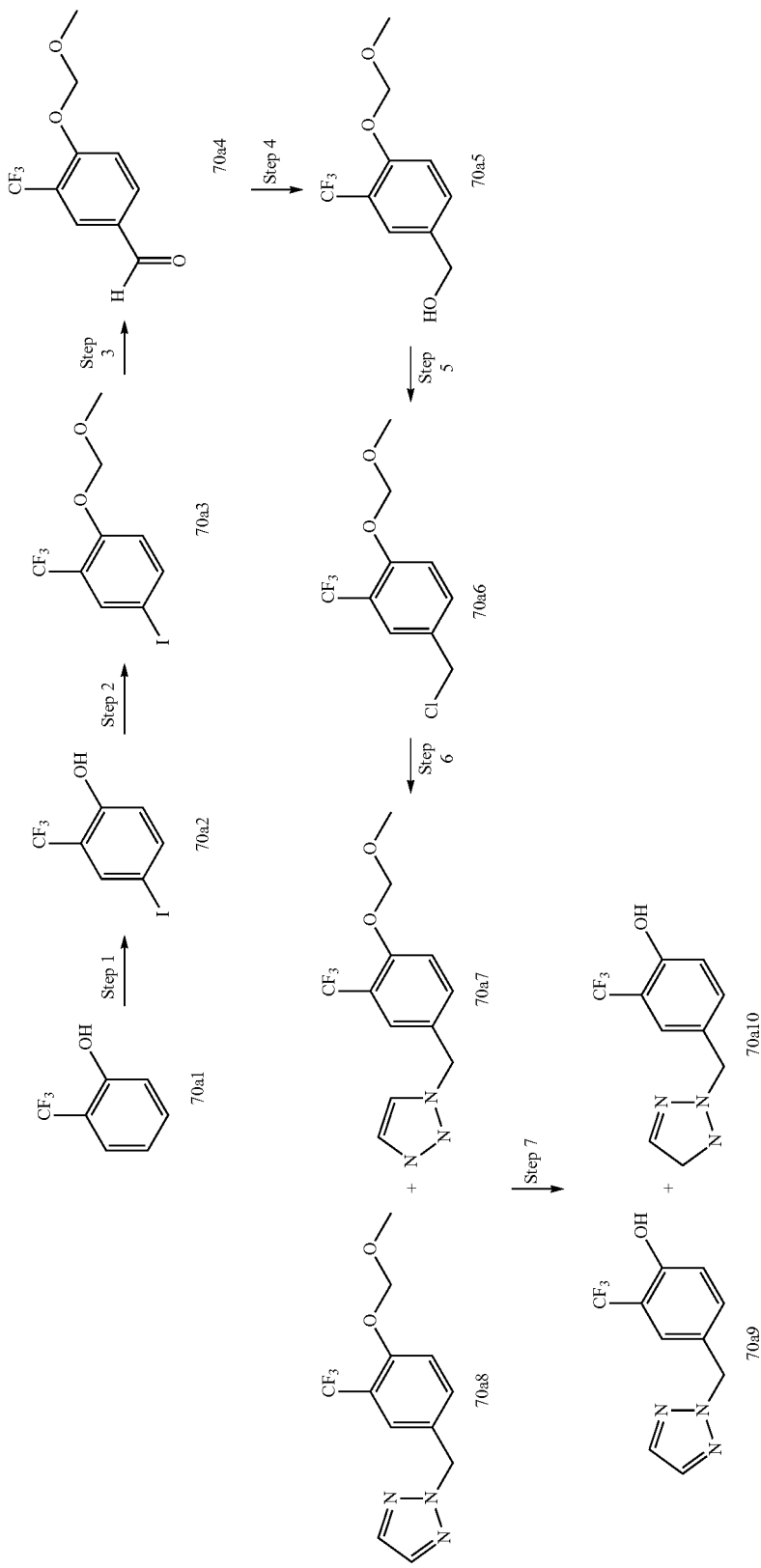

Step 1:
Iodine monochloride (5.00 g, 30.8 mmol) is slowly added to a RT glacial acetic acid solution (40 mL) of 2-hydroxybenzotrifluoride 70a1 (5.00 g, 30.8 mmol). The reaction mixture is stirred overnight at RT then poured over water (200 mL). The mixture is extracted with EtOAc (3×100 mL) and the combined organic phases are washed with water (100 mL), brine (100 mL), dried over $Na_2SO_4$, filtered and concentrated under reduced pressure. The crude residue is purified by column chromatography (100% hexanes then 2% to 20% EtOAc/hexanes) to afford compound 70a2.

Step 2:
Sodium hydride (60% in mineral oil, 312 mg, 7.82 mmol) is added to a 0° C. DMF solution of phenol 70a2 (1.50 g, 5.21 mmol). The solution is stirred at 0° C. for about 5 min and chloromethylmethylether (514 µL, 6.77 mmole) is added. The reaction mixture is stirred at RT overnight, diluted with saturated aqueous sodium bicarbonate (100 mL) and extracted with EtOAc (2×100 mL). The combined organic phases are washed with water (2×50 mL), brine (100 mL), dried over $Na_2SO_4$, filtered and concentrated under reduced pressure. The crude residue is purified by column chromatography (100% hexanes then 2% to 20% EtOAc/hexanes) to afford compound 70a3.

Step 3:
n-Butyllithium (2.5 M in hexanes, 1.66 mL, 4.14 mmol) is slowly added to a −78° C. ether solution (35 mL) of iodophenol 70a3 (1.18 g, 3.54 mmol). The reaction mixture is stirred for about 15 min at −78° C. and DMF is added (418 µL, 5.40 mmol). The reaction mixture is stirred at RT for about 1 h, diluted with saturated aqueous sodium bicarbonate (100 mL) and extracted with EtOAc (2×100 mL). The combined organic phases are washed with water (2×50 mL), brine (100 mL), dried over $Na_2SO_4$, filtered and concentrated under reduced pressure. The crude residue is purified by column chromatography (100% hexanes then 2% to 20% EtOAc/hexanes) to afford compound 70a4.

Step 4:
Sodium borohydride (143 mg, 3.79 mmol) is added to a 0° C. MeOH (30 mL) solution of aldehyde 70a4 (740 mg, 3.16 mmol). The reaction is stirred at 0° C. for about 2 h, diluted with saturated aqueous sodium bicarbonate (50 mL), concentrated under reduced pressure and extracted with EtOAc (3×50 mL). The combined organic phases are washed with brine (100 mL), dried over $Na_2SO_4$, filtered and concentrated under reduced pressure. The crude residue is purified by column chromatography (100% hexanes then 2% to 20% EtOAc/hexanes) to afford compound 70a5.

Step 5:
Thionyl chloride (377 µL, 5.17 mmol) is added to a 0° C. DCM (20 mL) solution of alcohol 70a5 (610 mg, 2.58 mmol). The reaction mixture is stirred at RT for about 1 h, diluted with saturated aqueous sodium bicarbonate (50 mL) and extracted with EtOAc (3×50 mL). The combined organic phases are washed with brine (100 mL), dried over $Na_2SO_4$, filtered and concentrated under reduced pressure. The crude residue 70a6 is used directly in the next step.

Step 6:
Sodium hydride (60% in mineral oil, 196 mg, 4.90 mmol) is added to a 0° C. DMF solution (3 mL) of 1,2,3-triazole (336 mg, 4.87 mmol). The reaction mixture is stirred at 0° C. for about 30 min and transferred over a 0° C. DMF solution (20 mL) of benzyl chloride 70a6 (620 mg, 2.44 mmol). The reaction mixture is stirred for about 2 h at RT, diluted with saturated aqueous sodium bicarbonate (50 mL) and extracted with EtOAc (3×50 mL). The combined organic phases are washed with brine (100 mL), dried over $Na_2SO_4$, filtered and concentrated under reduced pressure. The crude residue is purified by column chromatography (100% hexanes then 20% to 80% EtOAc/hexanes) to afford a mixture of compounds 70a7 and 70a8.

Step 7:
Aqueous 1 N HCl (2.0 mL) is added to a 0° C. THF solution (10 mL) of compounds 70a7 and 70a8 (699 mg, 2.44 mmol). The reaction mixture is warmed up to RT and then heated at 65° C. for about 3 h. The reaction mixture is cooled to RT, diluted with saturated aqueous sodium bicarbonate (50 mL) and extracted with EtOAc (3×50 mL). The combined organic phases are washed with brine (100 mL), dried over $Na_2SO_4$, filtered and concentrated under reduced pressure. The crude residue is purified by column chromatography (30% EtOAc/hexanes to 100% EtOAc) to afford a mixture of compounds 70a9 (elutes first) and 70a10.

Example 70B

Preparation of Compound 2003

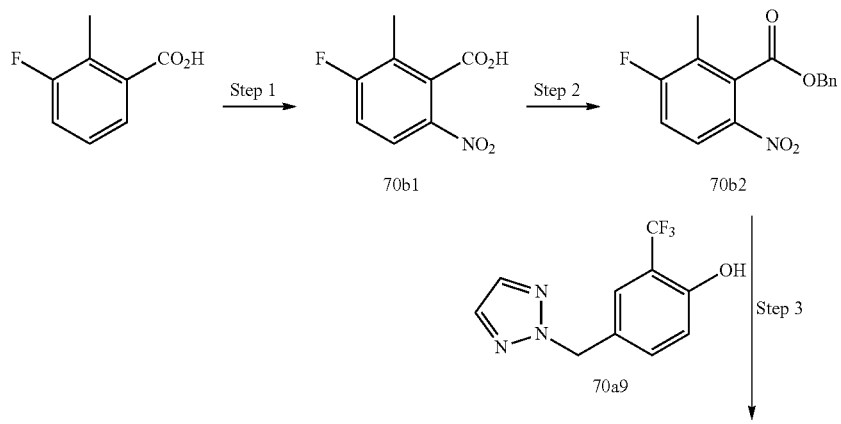

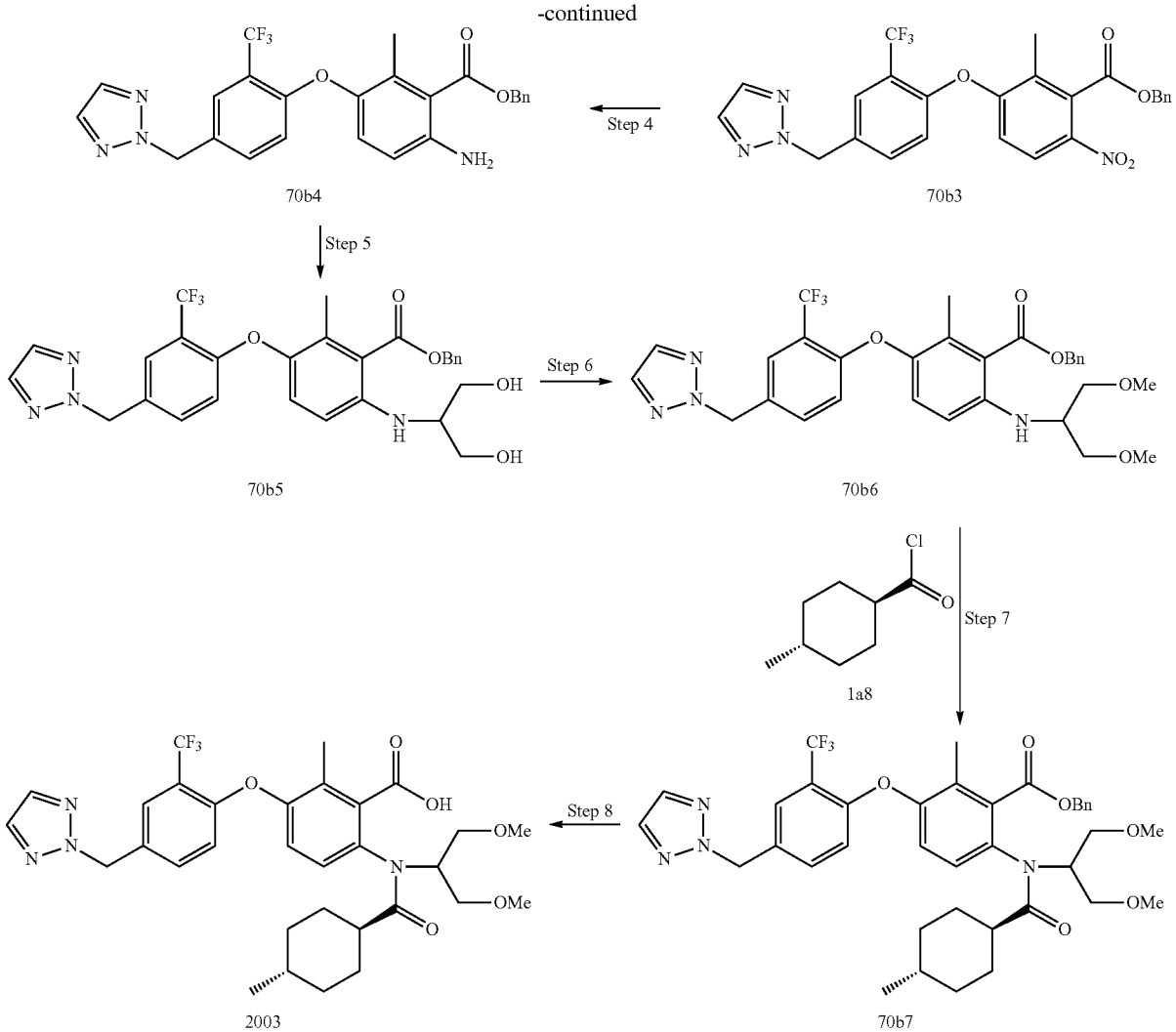

Step 1:

3-fluoro-2-methylbenzoic acid (5.0 g, 32.4 mmol) is dissolved in sulfuric acid (35 mL) and the resulting mixture is cooled to 0° C. Nitric acid (4.0 mL) is added dropwise over about a 10 min period. The reaction mixture is stirred at 0° C. for about 2 h, poured over ice and extracted with EtOAc (2×50 mL). The combined organic phases are dried over $Na_2SO_4$, filtered and concentrated under reduced pressure to afford crude 70b1.

Step 2:

Potassium carbonate (2.05 g, 14.8 mmol) is added to a RT DMF (60 mL) solution of acid 70b1 (1.48 g, 7.32 mmol), followed by benzyl bromide (1.06 mL, 8.91 mmol).

The reaction mixture is stirred at 80° C. overnight, cooled to RT, poured over water and extracted with EtOAc (2×100 mL). The combined organic phases are washed with brine (2×100 mL), dried over $MgSO_4$, filtered and concentrated under reduced pressure. The crude residue is purified by column chromatography (20% EtOAc in hexanes) to afford ester 70b2.

Step 3:

Cesium carbonate (1.41 g, 4.36 mmol) is added to a DMSO solution of ester 70b2 (1.050 g, 3.63 mmol) and phenol 70a9 (883 mg, 3.63 mmol). The reaction mixture is stirred for about 2 h at 75° C. After cooling to RT, the solution is diluted with aqueous saturated sodium bicarbonate (100 mL) and extracted with EtOAc (2×50 mL). The combined organic phases are washed with aqueous saturated sodium bicarbonate (2×50 mL), brine (50 mL), dried over $MgSO_4$, filtered and concentrated under reduced pressure. The crude residue is purified by column chromatography (20% to 50% EtOAc/hexanes) to afford 70b3.

Step 4:

Saturated aqueous ammonium chloride (20 mL) is added to a RT 2-propanol (20 mL) solution of nitro 70b3 (855 mg, 1.67 mmol). Iron powder (652 mg, 11.5 mmol) is added and the resulting reaction mixture is stirred at 60° C. for about 3 h. The mixture is cooled to RT, filtered through Celite® and washed with EtOAc. The organic phase is collected, washed with brine (2×50 mL), dried over $Na_2SO_4$, filtered and concentrated under reduced pressure. As approximately half of the material is saponified to the acid, the crude reside is redissolved in DMF (50 mL) and potassium carbonate (461 mg, 3.37 mmol) and benzyl bromide (0.245 mL, 2.02 mmol) are added. The reaction mixture is stirred at 80° C. overnight, cooled to RT, poured over water and extracted with EtOAc (2×100 mL). The combined organic phases are washed with brine (2×100 mL), dried over MgSO₄, filtered and concentrated under reduced pressure. The crude aniline 70b4 is used directly in the next step.

Step 5:

The crude aniline 70b4 (550 mg, 1.14 mmol) is dissolved in MeOH (1 mL) and 2 M HCl in ether (1 mL) is added. The mixture is stirred at RT for about 1 h and concentrated under reduced pressure. The resulting residue is dissolved in MeOH (10 mL) and a MeOH (3 mL) solution of dihydroxyacetone (649 mg, 7.21 mmol) is added. The reaction mixture is stirred at RT for about 1 h and a MeOH solution (3 mL) of sodium cyanoborohydride (266 mg, 4.24 mmol) is added. The reaction mixture is stirred at RT for about 1 h, diluted with aqueous saturated sodium bicarbonate (50 mL), concentrated under reduced pressure to a minimal volume and extracted with EtOAc (2×50 mL). The combined organic phases are washed with aqueous saturated sodium bicarbonate (2×50 mL), brine (50 mL), dried over Na₂SO₄, filtered and concentrated under reduced pressure. The crude reside is purified by column chromatography (50% EtOAc/hex to 100% EtOAc) to afford 70b5.

Step 6:

A DMF suspension (2 mL) of sodium hydride (95%, 44 mg, 1.74 mmol) is added to a 0° C. DMF solution of compound 70b5 (440 mg, 0.791 mmol) and iodomethane (247 µL, 3.95 mmol). The reaction mixture is stirred at 0° C. for about 1 h and more sodium hydride is then added (95%, 44 mg, 1.74 mmol in 2 mL of DMF). The reaction mixture is stirred at 0° C. for about 1 h, diluted with aqueous saturated ammonium chloride (50 mL) and extracted with EtOAc (2×50 mL). The combined organic phases are washed with aqueous saturated sodium bicarbonate (2×50 mL), brine (50 mL), dried over Na₂SO₄, filtered and concentrated under reduced pressure. The crude 70b6 is used directly in the next step without further purification.

Step 7:

DMAP (1.6 mg, 0.014 mmol) is added to a DCE (1 mL) solution of aniline 70b6 (40 mg, 0.068 mmol), acid chloride 1a8 (44 mg, 0.27 mmol) and pyridine (32 µL, 0.41 mmol). The reaction mixture is heated at 150° C. for about 45 min in a microwave. The reaction mixture is cooled to RT and then pyridine (32 µL, 0.41 mmol) and acid chloride 1a8 (44 mg, 0.27 mmol) are added. The reaction mixture is resubmitted to microwave conditions (45 min at 150° C.), cooled to RT, diluted with aqueous 1 N HCl (10 mL) and extracted with EtOAc (2×50 mL). The combined organic phases are washed with aqueous 1 N HCl (50 mL), saturated aqueous sodium bicarbonate (2×50 mL), brine (50 mL), dried over Na₂SO₄, filtered and concentrated under reduced pressure. The crude reside is purified by column chromatography (20% EtOAc/hex to 100% EtOAc) to afford 70b7.

Step 8:

Palladium 10% on charcoal (15 mg) is added to an EtOAc/MeOH (2:1, 6 mL) solution of the benzyl ester 70b7 (12 mg, 0.017 mmol). The reaction mixture is evacuated and filled back with hydrogen at atmospheric pressure. The reaction mixture is stirred at RT for about 15 min, filtered over Celite®, washed with EtOAc and concentrated under reduced pressure. The crude residue is purified by preparative HPLC to afford 2003.

Example 71A

Preparation of Compound 4002

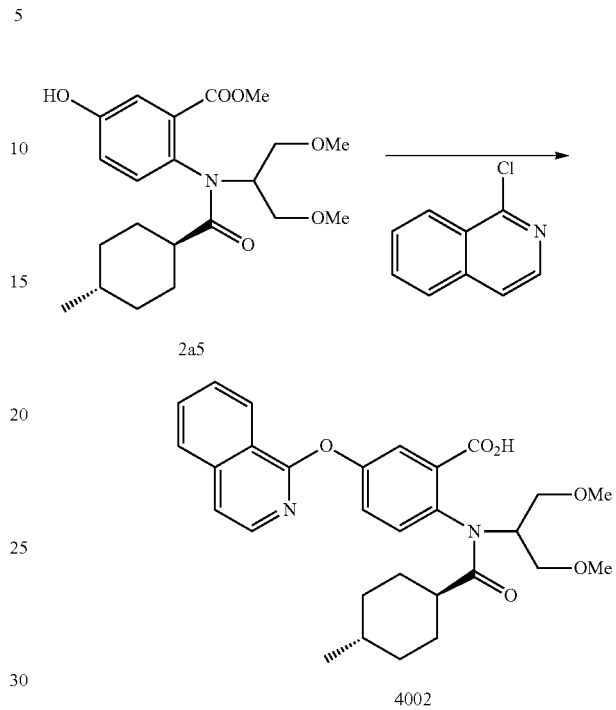

Potassium carbonate (277 mg, 0.854 mmol) is added to a DMSO solution (5 mL) of phenol 2a5 (160 mg, 0.407 mmol) and chloroisoquinoline (73 mg, 0.477 mmol). The reaction mixture is stirred at 150° C. for about 10 min, cooled to RT and filtered. To the resulting solution is added aqueous 2.5 N NaOH (0.3 mL, 0.750 mmol). The reaction mixture is stirred at RT for about 3 h, acidified with glacial AcOH (2 mL) and purified by preparative HPLC to afford compound 4002.

Example 72A

Preparation of Compound 4003

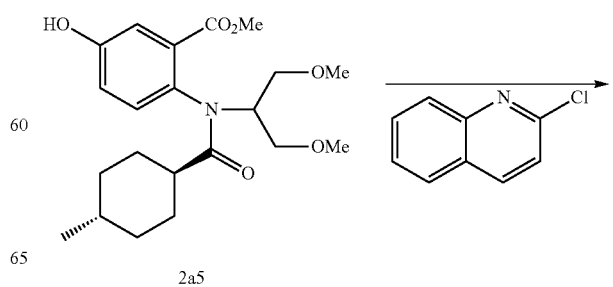

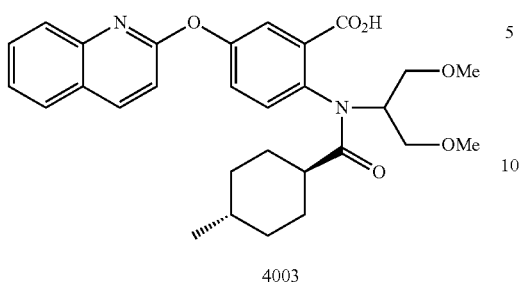

4003

Cesium carbonate (208 mg, 0.640 mmol) is added to a DMSO solution (5 mL) of phenol 2a5 (120 mg, 0.305 mmol) and chloroquinoline (50 mg, 0.305 mmol). The reaction mixture is stirred at 150° C. for about 10 min, cooled to RT and filtered. To the resulting solution is added aqueous 2.5 N NaOH (0.3 mL, 0.750 mmol). The reaction mixture is stirred at RT for about 3 h, acidified with glacial AcOH (2 mL) and purified by preparative HPLC to afford compound 4003.

Example 73A

Preparation of Compound 4006

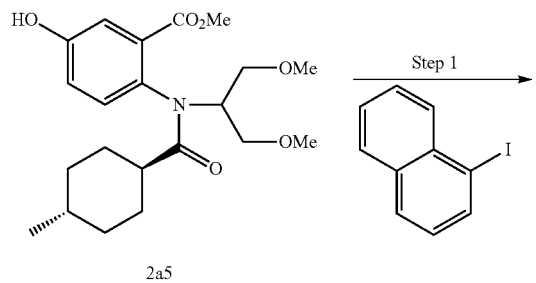

2a5

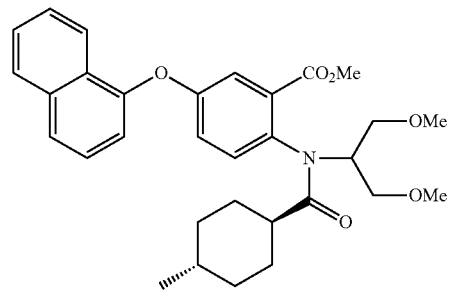

73a1

| Step 2

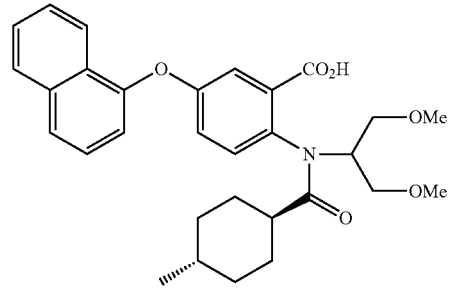

4006

Step 1:

Copper (I) chloride (13 mg, 0.13 mmol) is added to a NMP solution (3 mL) of phenol 2a5 (100 mg, 0.254 mmol), iodide (77 mg, 0.35 mmol), cesium carbonate (166 mg, 0.508 mmol) and 2,2,6,6-tetramethylheptane-3,5-dione (5 μL, 0.025 mmol). The reaction mixture is evacuated and filled with nitrogen. The cycle is repeated 5 times then the reaction mixture is stirred at 120° C. for about 2 h, cooled to RT, diluted with saturated aqueous sodium bicarbonate and extracted with EtOAc (50 mL). The organic phase is washed with aqueous saturated sodium bicarbonate (2×50 mL), brine (50 mL), dried over $Na_2SO_4$, filtered and concentrated under reduced pressure. The crude reside is purified by column chromatography (20% EtOAc/hex to 60% EtOAc) to afford 73a1.

Step 2:

Aqueous 5 M NaOH (0.265 mL, 1.32 mmol) is added dropwise to a 0° C. THF/DMSO solution (1:1, 2 mL) of ester 73a1 (46 mg, 0.089 mmol). The solution is stirred at 40° C. for about 2 h, acidified with AcOH (1 mL) and purified by preparative HPLC to afford compound 4006.

Example 74A

Preparation of Compound 1175

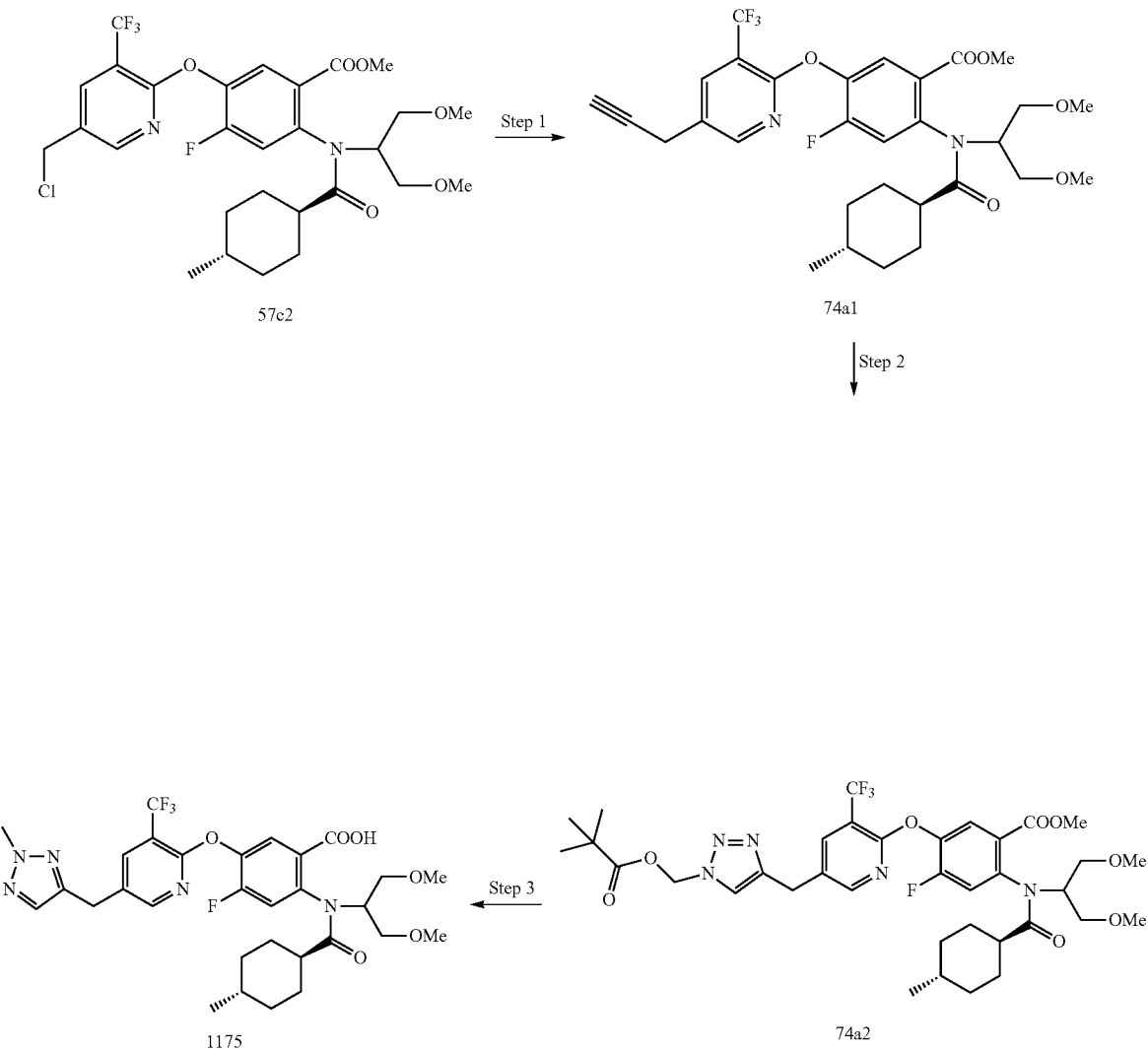

Step 1:

To a solution of chloride 57c2 (200 mg, 0.33 mmol) in DMF (2 mL) are added trimethylsilylacetylene (162 mg, 1.65 mmol), CuI (6.3 mg, 0.033 mmol), Et$_3$N (0.230 mL, 1.65 mmol) and Pd(PPh$_3$)$_4$ (38 mg, 0.033 mmol) at RT. This mixture is stirred at 120° C. in the microwave for 10 min. TBAF (1.65 mL, 1 M solution in THF) is added at RT and the reaction mixture is stirred for about 30 min. A saturated aqueous solution of NH$_4$Cl is added and the mixture is extracted with Et$_2$O (3×). The organic layers are combined, washed with brine, dried over anhydrous Na$_2$SO$_4$, filtered and concentrated. The crude residue is then purified by flash chromatography using (20:80 to 60:40) EtOAc/Hex to afford compound 74a1.

Step 2:

To a solution of alkyne 74a1 (123 mg, 0.21 mmol) in water (1 mL) is added azide 44a2 (97 mg, 0.62 mmol) at RT. This mixture is stirred at 120° C. for about 3 h, then at 85° C. for about 16 h. The reaction mixture is extracted with Et$_2$O (3×). The organic layers are combined, washed with brine, dried over anhydrous Na$_2$SO$_4$, filtered under vacuum and concentrated. The crude residue is purified by flash chromatography using (20:80 to 70:30) EtOAc/Hex to afford compound 74a2.

Step 3:

To a solution of ester 74a2 in MeOH (1 mL) is added an aqueous NaOH solution (5 N, 0.024 mL, 0.12 mmol) at RT. The mixture is stirred for about 5 h before being acidified with 1 M HCl and extracted with EtOAc (4×). The combined fractions are dried and concentrated. The residue is re-dissolved in MeOH (2 mL) and (trimethylsilyl)diazomethane (0.120 mL, 2 M solution in Et$_2$O) is added at 0° C. The reaction mixture is stirred for about 1 h at 0° C., then concentrated. The residue is re-dissolved in a THF (1 mL)/MeOH (1 mL) mixture and an aqueous NaOH solution (5 N, 0.024 mL, 0.12 mmol) is added at RT. The mixture is stirred for about 3 h, then concentrated. The residue is re-dissolved in a MeOH (1 mL)/AcOH (1 mL) mixture and purified by preparative HPLC. The fractions are combined and solvent removed by lyophilization to afford pure compound 1175.

Example 75A

Preparation of Compound 4016

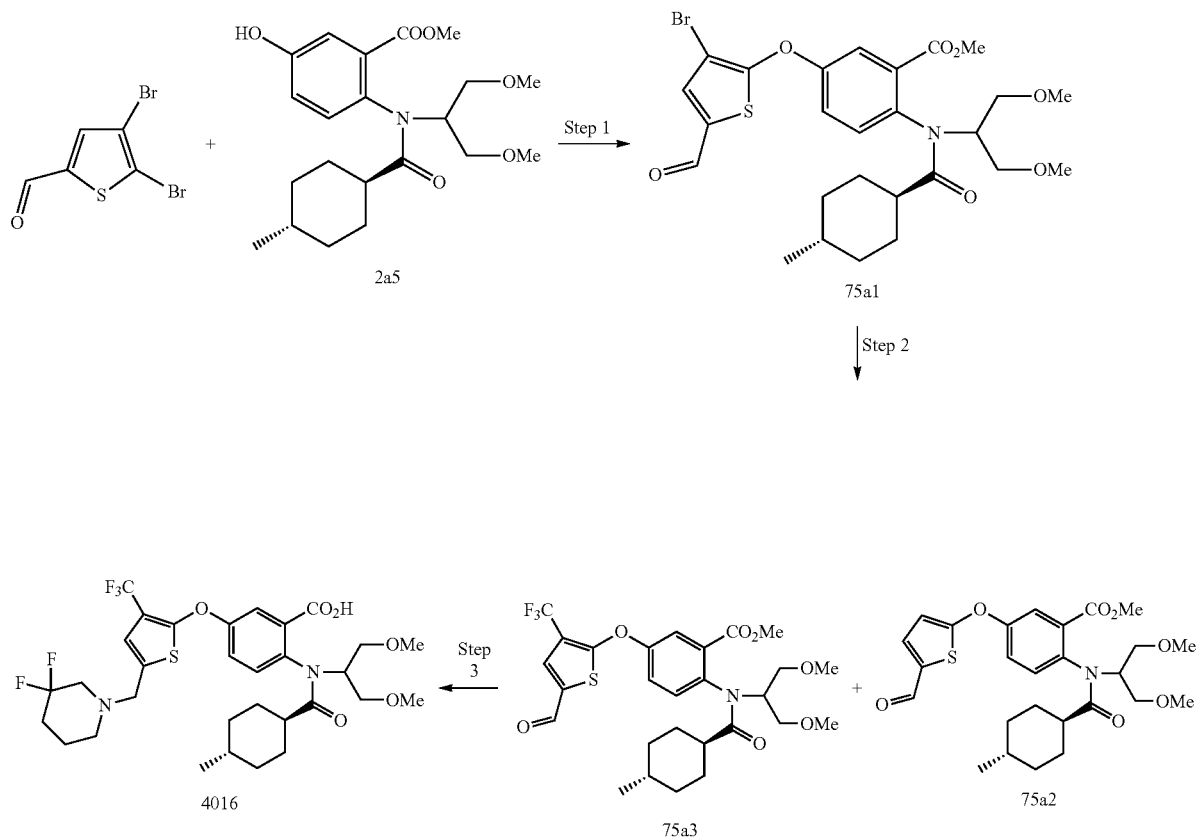

Step 1:

Cesium carbonate (2.48 g, 7.62 mmol) is added to a DMSO solution (10 mL) of the phenol 2a5 (1.78 g, 6.61 mmol) and 4,5-dibromo-thiophene-2-carbaldehyde (35 mL, 5.08 mmol). The reaction mixture is stirred at 80° C. for about 16 h, cooled to RT, poured over water and extracted with $Et_2O$ (3×50 mL). The combined organic phases are concentrated under reduced pressure. The crude residue is purified by column chromatography (30% to 70% EtOAc in hexanes) to afford compound 75a1.

Step 2:

Sodium trifluoroacetate (383 mg, 2.82 mmol) is added to a NMP solution (2 mL) of the bromide 75a1 (410 mg, 0.704 mmol) and copper iodide (268 mg, 1.41 mmol). The reaction mixture is stirred at 160° C. in the microwave for 10 min, then at 180° C. for another 10 min and cooled to RT. The reaction mixture was poured over water and extracted with EtOAc (3×50 mL). The combined organic phases are washed with brine (2×50 mL), dried over $Na_2SO_4$, filtered and concentrated under reduced pressure. The crude residue is purified by column chromatography (40% to 70% EtOAc in hexanes) to afford compound 75a2 and compound 75a3.

Step 3:

Compound 75a3 is transformed to compound 4016 using the procedure in Steps 2 and 3, Example 37A.

Example 76A

Preparation of Compound 4017

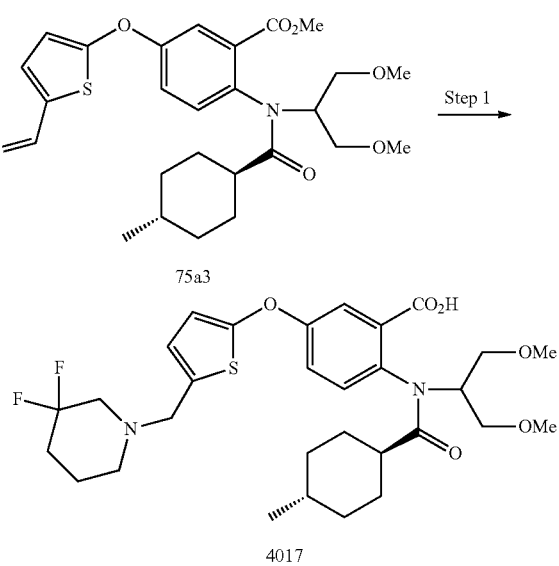

Step 1:
Compound 75a3 is transformed to compound 4017 using the procedure described in Step 3, Example 75A.
Example 77A
Preparation of Compound 4018
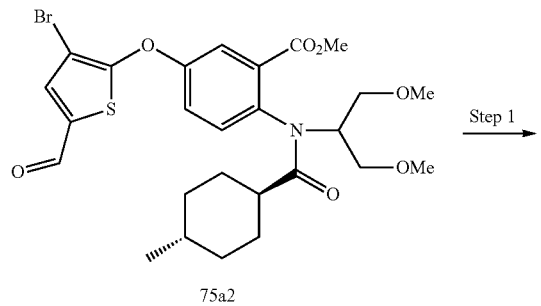
75a2
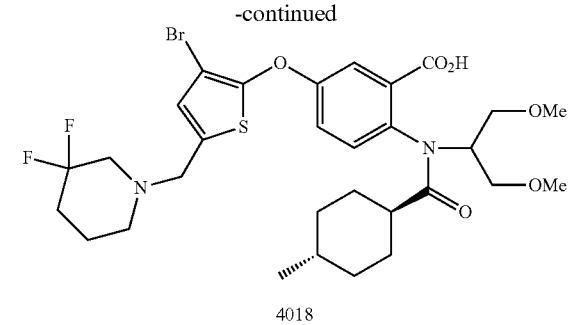
4018
Step 1:
Compound 75a2 is transformed to compound 4018 using the procedure described in Step 3, Example 75A.
Example 78A
Preparation of Compounds 4019 and 4020
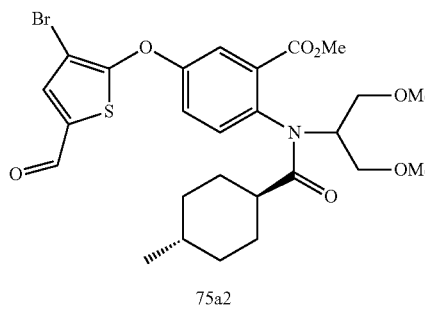
75a2
Step 1a →
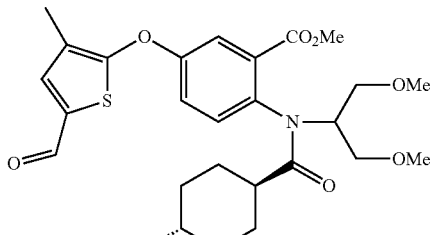
78a1
Step 1b ↓
Step 2a ↓
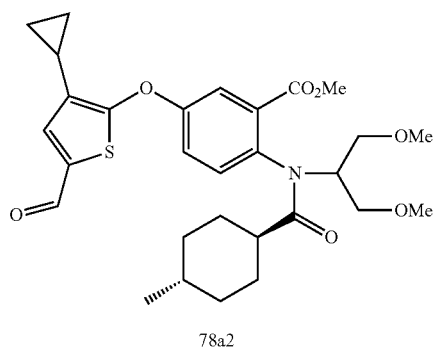
78a2
Step 2b ↓
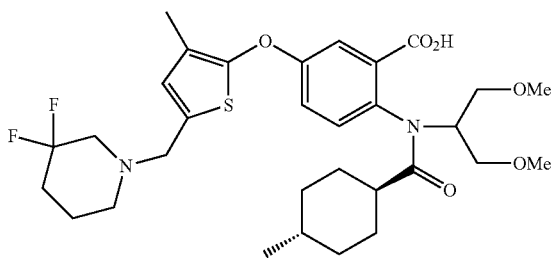
4019

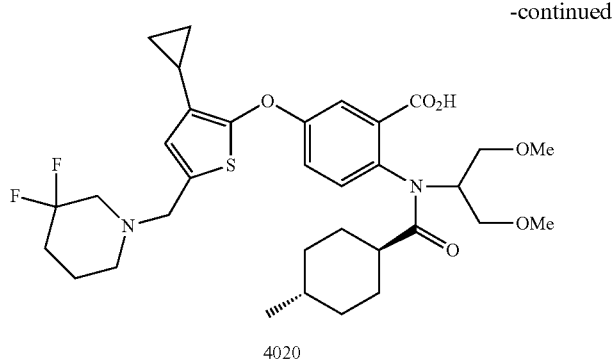

4020

Step 1a:

Pd(PPh$_3$)$_4$ (1.35 mg, 0.005 mmol) and sodium carbonate (2 M solution in water, 0.375 mL, 0.750 mmol) are added to a DMF solution (1 mL) of the bromide 75a2 (150 mg, 0.258 mmol) and trimethylboroxine (97 mg, 0.773 mmol). The reaction mixture is stirred at 120° C. in the microwave for 20 min, cooled to RT, poured over water and extracted with Et$_2$O (3×50 mL). The combined organic phases are washed with brine (2×50 mL), dried over Na$_2$SO$_4$, filtered and concentrated under reduced pressure. The crude residue is purified by column chromatography (40% to 80% EtOAc in hexanes) to afford compound 78a1.

Step 2a:

Compound 78a1 is transformed to compound 4019 using the procedure described in Steps 2 and 3, Example 37A.

DMF solution (1 mL) of the bromide 75a2 (150 mg, 0.258 mmol) and cyclopropylboronic acid (66 mg, 0.773 mmol). The reaction mixture is stirred at 120° C. in the microwave for 20 min, cooled to RT, poured over water and extracted with Et$_2$O (3×50 mL). The combined organic phases are washed with brine (2×50 mL), dried over Na$_2$SO$_4$, filtered and concentrated under reduced pressure. The crude residue is purified by column chromatography (40% to 80% EtOAc in hexanes) to afford compound 78a2.

Step 2b:

Compound 78a2 is transformed to compound 4020 using the procedure described in Steps 2 and 3, Example 37A.

Example 79A

Preparation of Compound 4014 and 4015

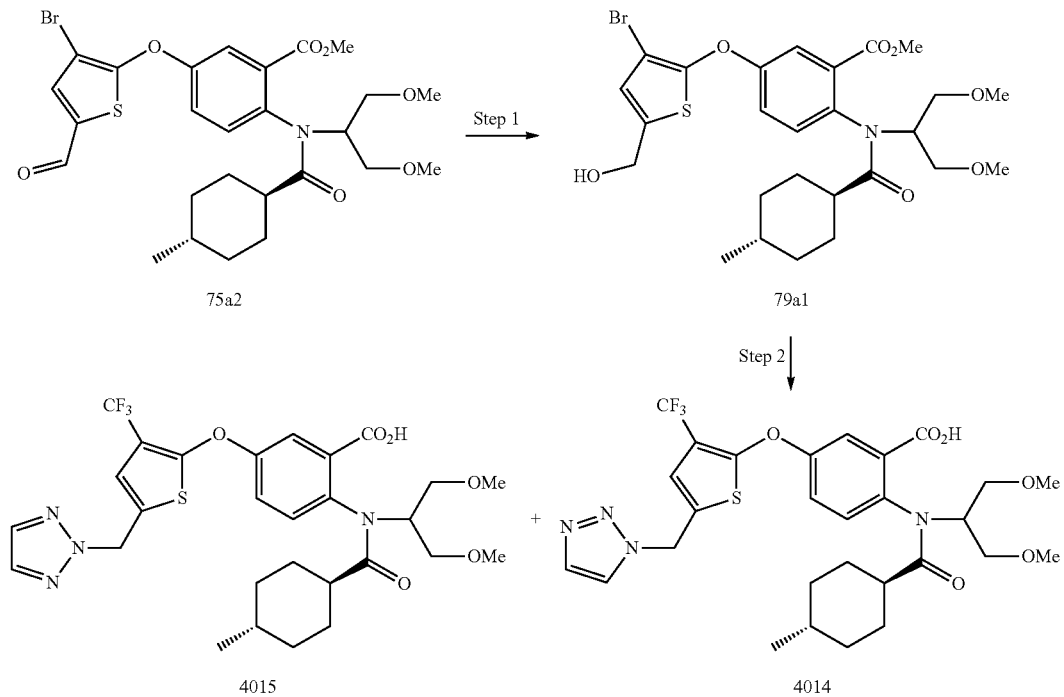

Step 1b:

Pd(PPh$_3$)$_4$ (1.35 mg, 0.005 mmol) and sodium carbonate (2 M solution in water, 0.386 mL, 0.773 mmol) are added to a Step 1:

Compound 75a2 is transformed to compound 79a1 using the procedure described in Step 1, Example 57C.

Step 2:

Compound 79a1 is transformed to compounds 4014 and 4015 using the procedure described in Step 1, Example 57D.

Example 80A

Preparation of Compound 1053

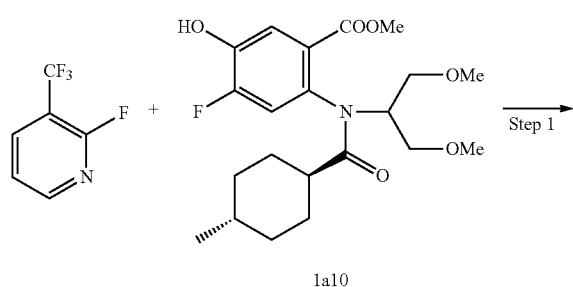

1a10

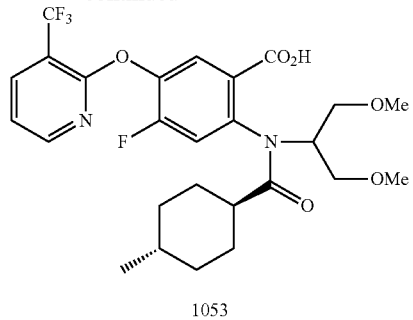

1053

Step 1:

Phenol 1a10 (16.8 mg, 0.041 mmol) is combined with $K_2CO_3$ (16.9 mg, 0.122 mmol) and 2-fluoro-3-trifluoromethylpyridine (39.0 mg, 0.24 mmol) in DMSO (1 mL). The mixture is heated under Ar at 75° C. until complete conversion, then cooled to RT. Water and DCM are added, the mixture is extracted with DCM (3×) and the combined organic fractions are concentrated under reduced pressure. The crude residue is dissolved in a THF (1 mL)/MeOH (0.5 mL)/$H_2O$ (0.5 mL) mixture and an aqueous NaOH solution (10 N, 41 µL, 0.41 mmol) is added. The mixture is stirred overnight before being acidified with AcOH, filtered, and injected onto a preparative HPLC to isolate compound 1053.

Example 81A

Preparation of Compound 1171

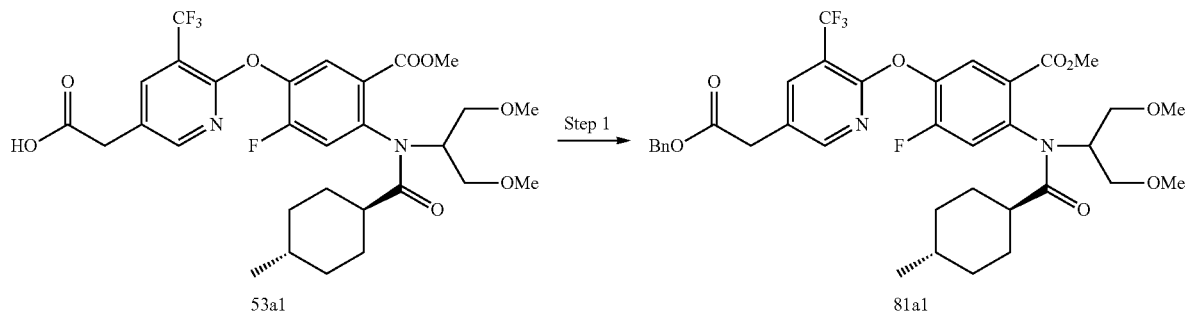

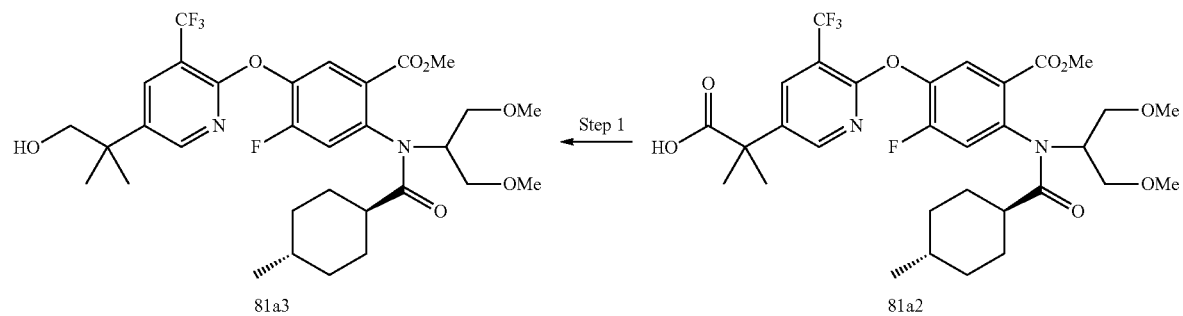

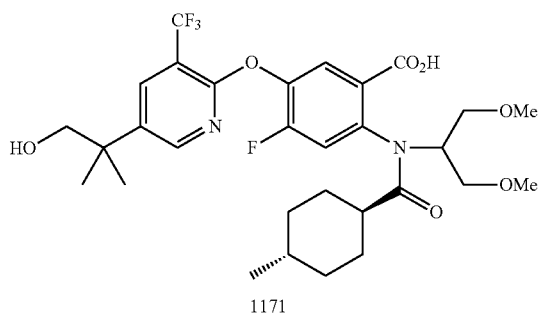

1171

Step 1:

Potassium carbonate (67 mg, 0.488 mmol) is added to a DMF solution (2 mL) of the acid 53a1 (150 mg) and benzyl bromide (35 μL, 0.293 mmol). The reaction mixture is stirred at 80° C. overnight, cooled to RT, poured over water and extracted with EtOAc (3×50 mL). The combined organic phases are washed successively with saturated aqueous sodium bicarbonate (2×50 mL), brine (2×50 mL), dried over $Na_2SO_4$, filtered and concentrated under reduced pressure. The crude residue is purified by column chromatography (20% EtOAc in hexanes) to afford compound 81a1.

Step 2:

Sodium hydride (13 mg, 0.511 mmol) is added to a 0° C. DMF (12 mL) solution of ester 81a1 (120 mg, 0.170 mmol) followed by iodomethane (42 μL, 0.681 mmol). The reaction mixture is stirred at RT for about 2 h, diluted with saturated aqueous sodium bicarbonate (50 mL) and extracted with EtOAc (2×50 mL). The combined organic phases are washed successively with saturated aqueous sodium bicarbonate (2×50 mL), brine (2×50 mL), dried over $Na_2SO_4$, filtered and concentrated under reduced pressure. The crude residue is dissolved in 80% EtOAc in hexanes and passed through a silica plug. The resulting organic phase is concentrated under reduced pressure to obtain a residue which is redissolved in EtOH (25 mL). The reaction flask is evacuated and filled back with hydrogen at atmospheric pressure. The mixture is stirred at RT for about 4 h, filtered through Celite®, washed with EtOH and concentrated under reduced pressure to afford crude 81a2 which is used directly in the next step.

Step 3:

Isobutyl chloroformate (30 μL, 0.23 mmol) is added to a 0° C. THF (2 mL) solution of acid 81a2 (100 mg, 0.156 mmol) and triethylamine (39 μL, 0.28 mmol). The reaction mixture is stirred at 0° C. for about 30 min and filtered directly over a water (0.2 mL) suspension of sodium borohydride (18 mg, 0.467 mmol). The reaction mixture is stirred at 0° C. for about 20 min, diluted with saturated aqueous sodium bicarbonate (50 mL) and extracted with EtOAc (2×50 mL). The combined organic phases are washed successively with saturated aqueous sodium bicarbonate (2×50 mL), brine (2×50 mL), dried over $Na_2SO_4$, filtered and concentrated under reduced pressure to afford crude 81a3.

Step 4:

Aqueous 5 M NaOH (1.0 mL, 5.0 mmol) is added dropwise to a 0° C. DMSO solution (2 mL) of ester 81a3 (20 mg, 0.032 mmol). The solution is stirred at RT for about 2 h, acidified with AcOH (1 mL) and purified by preparative HPLC to afford compound 1171.

Example 82

Inhibition of NS5B RNA Dependent RNA Polymerase Activity

Representative compounds of the invention are tested for inhibitory activity against the hepatitis C virus RNA dependent polymerase (NS5B), according to the assay described in WO 2007/087717, herein incorporated by reference.

Example 83

Specificity of NS5B RNA Dependent RNA Polymerase Inhibition

Representative compounds of the invention are tested for inhibitory activity against polio virus RNA dependent RNA polymerase and calf thymus DNA dependent RNA polymerase II as described in McKercher et al., (2004) Nucleic Acids Res. 32: 422-431, herein incorporated by reference.

Example 84

Cell-Based Luciferase Reporter HCV RNA Replication Assay

Representative compounds of the invention are tested for activity as inhibitors of hepatitis C virus RNA replication in cells expressing a stable subgenomic HCV replicon, using the assay described in WO 2005/028501, herein incorporated by reference.

Tables of Compounds

The following tables list compounds representative of the invention. Representative compounds listed in Tables 1 and 4 below are tested in the assay of Example 82 and are found to have $IC_{50}$ value below 30 μM. Representative compounds listed in Tables 1 and 4 below are tested in the assay of Example 84 and are found to have a $EC_{50}$ values below 30 μM.

Retention times ($t_R$) for each compound are measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions. The synthetic method used to generate each compound in Tables 1 to 4 is identified in the table. A person skilled in the art will recognize that obvious modifications to the synthetic methods may be required to generate each of the specific compounds listed in Tables 1 to 4.

TABLE 1

| Cpd | R20 | R3 | R5 | R6 | $t_R$ (min) | MS $(M + H)^+$ | Method |
|---|---|---|---|---|---|---|---|
| 1001 | H | H | (2-methoxyethyl) | (5-bromopyridin-2-yl) | 5.8 | 540 | 6A |
| 1002 | H | H | (2-methoxyethyl) | (trans-4-methylcyclohexyl) | 6.7 | 481.2 | 6A |
| 1003 | H | H | ((benzyloxy)cyclopentyl) | (trans-4-methylcyclohexyl) | 7.8 | 597.2 | 6A |
| 1004 | H | H | ((benzyloxy)cyclopentyl) | (trans-4-methylcyclohexyl) | 7.8 | 597.2 | 6A |
| 1005 | H | H | ((benzyloxy)cyclopentyl) | (5-bromopyridin-2-yl) | 7.5 | 656 | 6A |

TABLE 1-continued
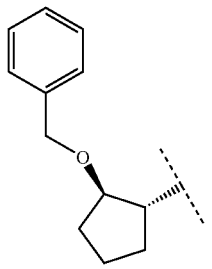
| Cpd | R20 | R3 | R5 | R6 | $t_R$ (min) | MS $(M+H)^+$ | Method |
|---|---|---|---|---|---|---|---|
| 1006 | H | H | 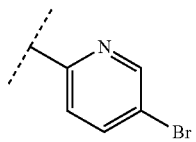 | 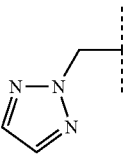 | 7.5 | 656.1 | 6A |
| 1007 | 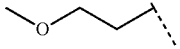 | H | 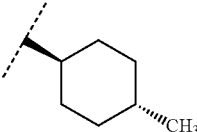 | 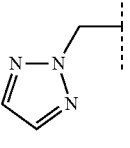 | 6.3 | 562.4 | 7A |
| 1008 | 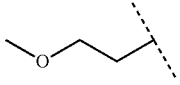 | F | 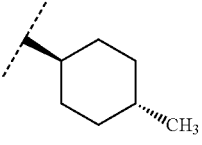 | 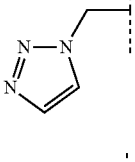 | 6.5 | 580.4 | 8A |
| 1009 | 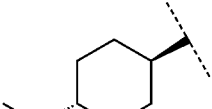 | H | 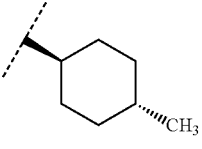 | 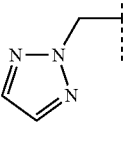 | 6.3 | 616.3 | 9A |
| 1010 | 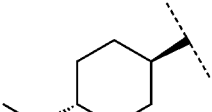 | H | 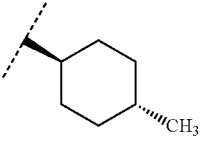 | 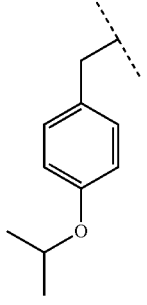 | 6.8 | 616.3 | 9A |
| 1011 | H | H | 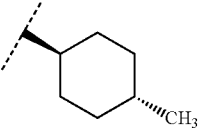 | | 7.8 | 571.2 | 6A |

TABLE 1-continued
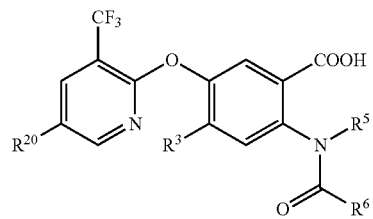
| Cpd | R20 | R3 | R5 | R6 | $t_R$ (min) | MS (M + H)+ | Method |
|---|---|---|---|---|---|---|---|
| 1012 | H | H | 2-isopropoxybenzyl | trans-4-methylcyclohexyl | 7.8 | 571.2 | 6A |
| 1013 | H | H | 4-phenoxybenzyl | trans-4-methylcyclohexyl | 8.0 | 605.2 | 6A |
| 1014 | H | H | (S)-2-methoxymethyl-propyl | trans-4-methylcyclohexyl | 6.9 | 495.2 | 10A |
| 1015 | H | H | (S)-1-(3-methoxyphenyl)ethyl | trans-4-methylcyclohexyl | 7.5 | 557.2 | 6A |
| 1016 | H | H | (R)-1-(3-methoxyphenyl)ethyl | trans-4-methylcyclohexyl | 7.5 | 557.2 | 6A |
| 1017 | H | H | 3-isopropoxypropyl | trans-4-methylcyclohexyl | 7.3 | 509.2 | 6A |

TABLE 1-continued
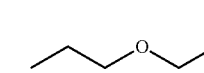
| Cpd | R20 | R3 | R5 | R6 | tR (min) | MS (M + H)+ | Method |
|---|---|---|---|---|---|---|---|
| 1018 | H | H | 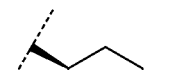 |  | 7.4 | 523.2 | 6A |
| 1019 | H | H | 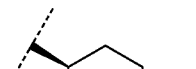 | 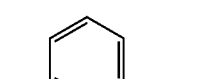 | 7.5 | 573.2 | 6A |
| 1020 | H | H | 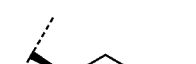 | 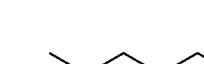 | 7.6 | 543.2 | 6A |
| 1021 | H | H | 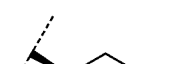 | 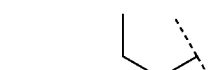 | 7.4 | 509.2 | 6A |
| 1022 | H | H | 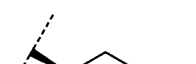 |  | 7.2 | 509.2 | 6A |
| 1023 | H | H |  |  | 7.7 | 537.3 | 6A |
| 1024 | H | H |  |  | 7.0 | 495.2 | 6A |
| 1025 | H | H |  | | 6.8 | 495.2 | 6A |

TABLE 1-continued
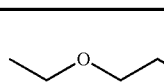
| Cpd | R[20] | R[3] | R[5] | R[6] | $t_R$ (min) | MS $(M + H)^+$ | Method |
|---|---|---|---|---|---|---|---|
| 1026 | H | H | 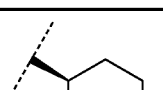 | 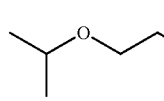 | 7.1 | 509.2 | 6A |
| 1027 | H | H | 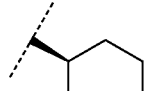 | 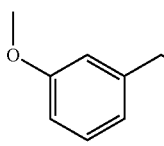 | 7.3 | 523.2 | 6A |
| 1028 | H | H | 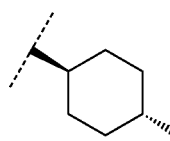 | 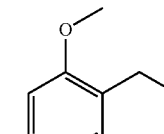 | 7.5 | 557.2 | 6A |
| 1029 | H | H | 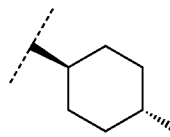 | 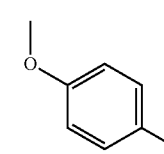 | 7.7 | 557.2 | 6A |
| 1030 | H | H | 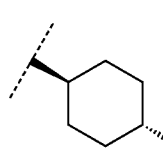 | 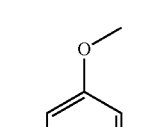 | 7.4 | 543.2 | 6A |
| 1031 | H | H | 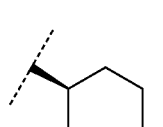 | 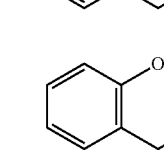 | 7.4 | 543.2 | 6A |
| 1032 | H | H | 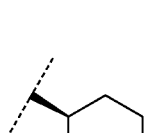 | 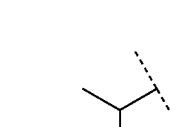 | 7.5 | 543.2 | 6A |
| 1033 | H | H | 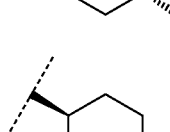 | | 6.9 | 495.2 | 6A |

TABLE 1-continued

| Cpd | R20 | R3 | R5 | R6 | $t_R$ (min) | MS $(M+H)^+$ | Method |
|---|---|---|---|---|---|---|---|
| 1034 | H | H | | | 7.9 | 611.3 | 6A |
| 1035 | H | H | | | 7.9 | 611.3 | 6A |
| 1036 | H | H | | | 7.1 | 573.2 | 6A |
| 1037 | H | H | | | 7.7 | 571.2 | 6A |
| 1038 | H | H | | | 7.3 | 557.2 | 6A |
| 1039 | H | H | | | 7.3 | 557.2 | 6A |

TABLE 1-continued

Structure: core scaffold with CF$_3$-pyridine-O-benzoic acid (COOH), with R$^{20}$ on pyridine, R$^3$ on benzene, and N(R$^5$)C(O)R$^6$ amide substituent.

| Cpd | R$^{20}$ | R$^3$ | R$^5$ | R$^6$ | t$_R$ (min) | MS (M+H)$^+$ | Method |
|---|---|---|---|---|---|---|---|
| 1040 | H | H | (S)-CH(CH$_3$)CH$_2$OCH$_3$ | 5-chloropyridin-2-yl | 5.3 | 508.1 | 10A |
| 1041 | H | H | (S)-CH(CH$_3$)CH$_2$OCH$_3$ | 5-bromopyridin-2-yl | 5.3 | 554.1 | 10A |
| 1042 | H | H | CH(CH$_2$OCH$_3$)$_2$ | trans-4-methylcyclohexyl | 7.3 | 525.2 | 11A |
| 1043 | 2H-1,2,3-triazol-2-ylmethyl | H | (S)-CH(CH$_3$)CH$_2$OCH$_3$ | 5-chloropyridin-2-yl | 5.3 | 591.1 | 12A |
| 1044 | 2H-1,2,3-triazol-2-ylmethyl | H | (S)-CH(CH$_3$)CH$_2$OCH$_3$ | trans-4-methylcyclohexyl | 5.9 | 576.3 | 13A |
| 1045 | (3,3-difluoropiperidin-1-yl)methyl | H | (S)-CH(CH$_3$)CH$_2$OCH$_3$ | trans-4-methylcyclohexyl | 5.9 | 628.2 | 19A |
| 1046 | 2-(2H-1,2,3-triazol-2-yl)ethyl | H | (S)-CH(CH$_3$)CH$_2$OCH$_3$ | trans-4-methylcyclohexyl | 6.4 | 590.3 | 14A |

TABLE 1-continued
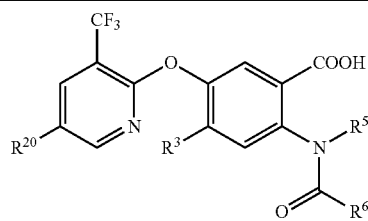
| Cpd | R20 | R3 | R5 | R6 | tR (min) | MS (M + H)+ | Method |
|---|---|---|---|---|---|---|---|
| 1047 | 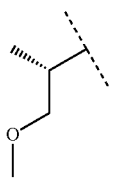 | F | 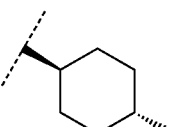 | 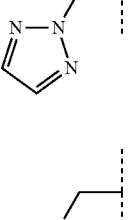 | 7.5 | 616.2 | 15A |
| 1048 | 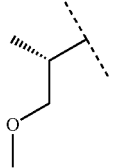 | F | 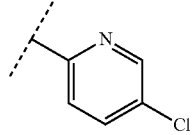 | 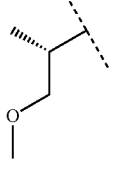 | 6.6 | 609.1 | 15A |
| 1049 | H | F | 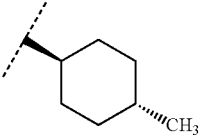 | 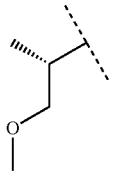 | 7.6 | 513.2 | 15A |
| 1050 | H | F | 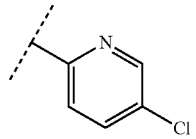 | 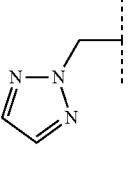 | 6.6 | 513.2 | 15A |
| 1051 | 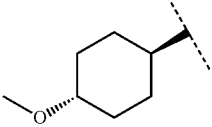 | F | 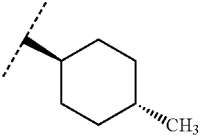 | 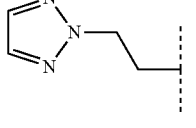 | 6.5 | 634.3 | 16A |
| 1052 | 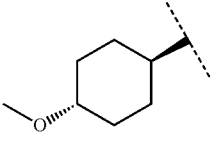 | F | 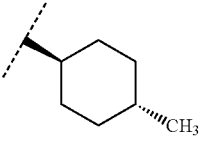 | 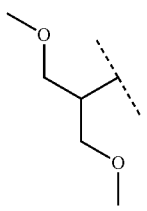 | 6.5 | 648.3 | 16A |
| 1053 | H | F | 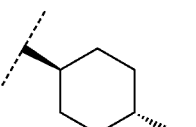 | | 7.6 | 543.3 | 17A |

TABLE 1-continued
| Cpd | R20 | R3 | R5 | R6 | tR (min) | MS (M + H)+ | Method |
|---|---|---|---|---|---|---|---|
| 1054 | 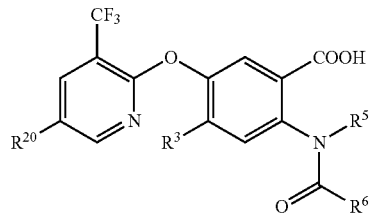 | F | 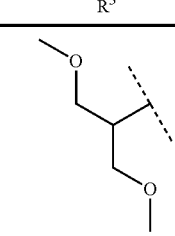 | 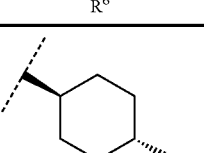 | 6.6 | 660.3 | 16A |
| 1055 | 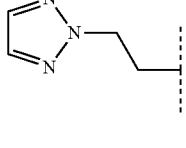 | F | 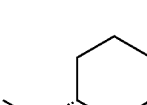 | 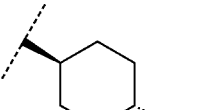 | | 686.3 | 16A |
| 1056 | 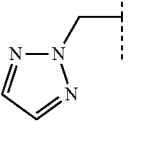 | F | 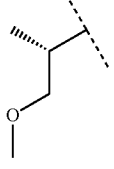 | 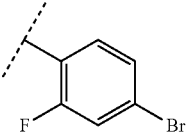 | 5.9 | 670.1 | 15A |
| 1057 | 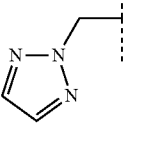 | F | 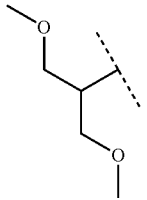 | 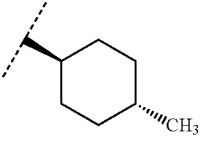 | 7.5 | 624.3 | 16A |
| 1058 | 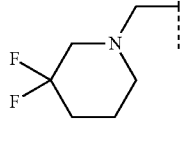 | F | 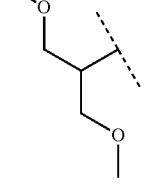 | 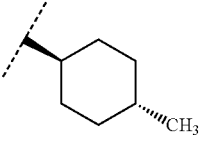 | 6.1 | 676.3 | 16A |
| 1059 | 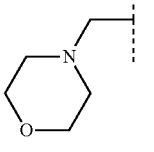 | H | 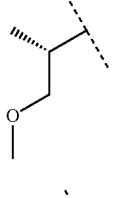 | 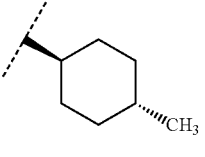 | 4.7 | 594.3 | 18A |
| 1060 | 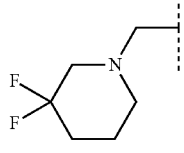 | F | 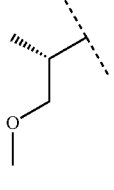 | 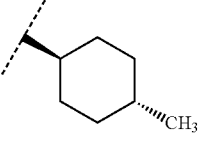 | | 644.3 | 19A |

TABLE 1-continued

| Cpd | R²⁰ | R³ | R⁵ | R⁶ | t_R (min) | MS (M + H)⁺ | Method |
|---|---|---|---|---|---|---|---|
| 1061 | 2-pyridyl-CH₂- | H | trans-4-methoxycyclohexyl | trans-4-methylcyclohexyl | 5.7 | 626.3 | 20A |
| 1062 | 2-pyridyl-CH₂- | H | (S)-1-methoxy-2-methylpropyl | trans-4-methylcyclohexyl | 4.9 | 586.3 | 20A |
| 1063 | (6-methyl-2-pyridyl)-CH₂- | H | (S)-1-methoxy-2-methylpropyl | trans-4-methylcyclohexyl | 4.9 | 600.3 | 20A |
| 1064 | thiazol-5-yl-CH₂- | H | (S)-1-methoxy-2-methylpropyl | trans-4-methylcyclohexyl | 6.2 | 592.2 | 20A |
| 1065 | pyrazin-2-yl-CH₂- | H | trans-4-methoxycyclohexyl | trans-4-methylcyclohexyl | 6.8 | 625.3 | 20A |
| 1066 | thiazol-5-yl-CH₂- | H | trans-4-methoxycyclohexyl | trans-4-methylcyclohexyl | 7.1 | 632.3 | 20A |
| 1067 | (2H-1,2,3-triazol-2-yl)-CH₂- | H | 1-methoxy-2-(methoxymethyl)propyl | trans-4-methylcyclohexyl | 7.3 | 606.3 | 19A |

TABLE 1-continued

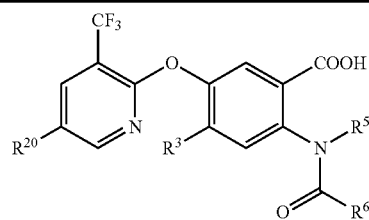

| Cpd | R20 | R3 | R5 | R6 | tR (min) | MS (M + H)+ | Method |
|---|---|---|---|---|---|---|---|
| 1068 | morpholinoethyl | F | CH2OCH(CH2OMe) | trans-4-methylcyclohexyl | 5.4 | 642.3 | 16A |
| 1069 | morpholinoethyl | F | (S)-CH(CH3)CH2OMe | trans-4-methylcyclohexyl | 5.3 | 612.3 | 19A |
| 1070 | 3-pyridylmethyl | H | (S)-CH(CH3)CH2OMe | trans-4-methylcyclohexyl | 4.9 | 586.3 | 20A |
| 1071 | (2H-1,2,3-triazol-2-yl)methyl | F | (S)-CH(CH3)CH2OMe | 5-bromopyridin-2-yl | 5.5 | 653.1 | 15A |
| 1072 | (2H-1,2,3-triazol-2-yl)ethyl | F | (S)-CH(CH3)CH2OMe | trans-4-methylcyclohexyl | 6.5 | 608.3 | 21A |
| 1073 | 2-pyridylmethyl | F | trans-4-methoxycyclohexyl | trans-4-methylcyclohexyl | 6.1 | 644.3 | 20A |
| 1074 | thiazol-5-ylmethyl | F | trans-4-methoxycyclohexyl | trans-4-methylcyclohexyl | 7.5 | 650.3 | 20A |

TABLE 1-continued

| Cpd | R20 | R3 | R5 | R6 | $t_R$ (min) | MS (M + H)+ | Method |
|---|---|---|---|---|---|---|---|
| 1075 | thiazol-2-ylmethyl | F | 4-methoxycyclohexyl | 4-methylcyclohexyl | 7.8 | 650.3 | 20A |
| 1076 | 2H-1,2,3-triazol-2-ylethyl | H | 1,3-dimethoxyprop-2-yl | 4-methylcyclohexyl | 6.4 | 620.3 | 16A |
| 1077 | 2H-1,2,3-triazol-2-ylmethyl | H | (S)-1-methoxyprop-2-yl | 4-bromo-2-fluorophenyl | 5.6 | 652.1 | 14A |
| 1078 | (3,3-difluoropiperidin-1-yl)methyl | H | 1,3-dimethoxyprop-2-yl | 4-methylcyclohexyl | 5.8 | 658.3 | 16A |
| 1079 | morpholin-4-ylmethyl | H | 1,3-dimethoxyprop-2-yl | 4-methylcyclohexyl | 5.1 | 624.3 | 16A |
| 1080 | 2-(morpholin-4-yl)ethyl | F | 1,3-dimethoxyprop-2-yl | 4-methylcyclohexyl | 4.9 | 656.4 | 16A |

TABLE 1-continued

| Cpd | R20 | R3 | R5 | R6 | $t_R$ (min) | MS (M + H)+ | Method |
|---|---|---|---|---|---|---|---|
| 1081 | 3,3-difluoropiperidin-1-yl-propyl | F | CH2OCH3, CH2OCH3 (branched) | trans-4-methylcyclohexyl | 5.2 | 690.4 | 16A |
| 1082 | H | F | CH2OCH3, CH2OCH3 (branched) | 4-bromo-2-fluorophenyl | 7.5 | 619.2 | 22A |
| 1083 | (6-methylpyridin-2-yl)methyl | H | CH2OCH3, CH2OCH3 (branched) | trans-4-methylcyclohexyl | 5.4 | 630.4 | 20A |
| 1084 | (thiazol-5-yl)methyl | H | CH2OCH3, CH2OCH3 (branched) | trans-4-methylcyclohexyl | 7.1 | 622.3 | 20A |
| 1085 | (2H-1,2,3-triazol-2-yl)methyl | F | CH2OCH3, ethyl (branched) | 5-chloropyridin-2-yl | 6.9 | 623.2 | 15A |
| 1086 | (2H-1,2,3-triazol-2-yl)methyl | H | CH2OCH3, methyl (branched) | 4-methylphenyl | 6.4 | 570.2 | 14A |

TABLE 1-continued

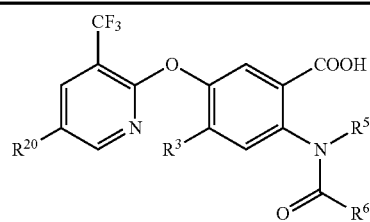

| Cpd | R20 | R3 | R5 | R6 | tR (min) | MS (M + H)+ | Method |
|---|---|---|---|---|---|---|---|
| 1087 | 2H-triazol-2-yl-CH2- | H | (S)-CH(CH3)CH2OCH3 | 4-chlorophenyl | 6.6 | 590.2 | 14A |
| 1088 | 2H-triazol-2-yl-CH2- | H | (S)-CH(CH3)CH2OCH3 | 4-bromophenyl | 6.7 | 634.1 | 14A |
| 1089 | 2H-triazol-2-yl-CH2- | H | (S)-CH(CH3)CH2OCH3 | 4-chloro-2-fluorophenyl | 6.7 | 608.2 | 14A |
| 1090 | 2H-triazol-2-yl-CH2- | H | (S)-CH(CH3)CH2OCH3 | 2-fluoro-4-methylphenyl | 6.5 | 588.2 | 14A |
| 1091 | 2H-triazol-2-yl-CH2- | H | (S)-CH(CH3)CH2OCH3 | 4-bromo-3-fluorophenyl | 6.8 | 652.1 | 14A |
| 1092 | vinyl | F | CH3OCH2CH(CH2OCH3)- | 5-chloropyridin-2-yl | 6.6 | 584.1 | 23A |
| 1093 | 2H-triazol-2-yl-CH2CH2- | F | CH3OCH2CH(CH2OCH3)- | 5-chloropyridin-2-yl | 6.2 | 653.2 | 23A |

TABLE 1-continued
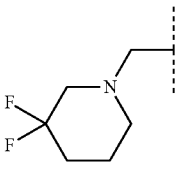
| Cpd | R20 | R3 | R5 | R6 | $t_R$ (min) | MS $(M+H)^+$ | Method |
|---|---|---|---|---|---|---|---|
| 1094 | 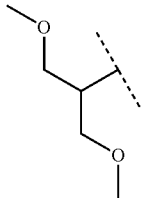 | H | 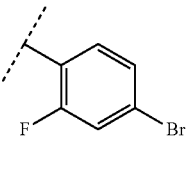 | 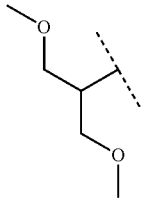 | 5.7 | 736.2 | 24A |
| 1095 | H | F | 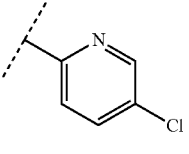 | 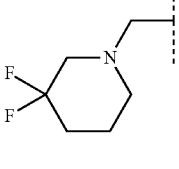 | 6.9 | 558.2 | 22A |
| 1096 | 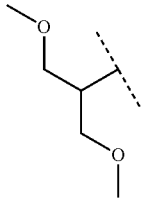 | H | 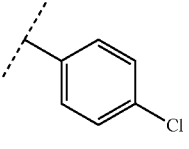 | 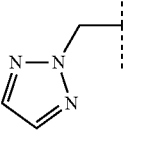 | 5.5 | 672.2 | 24A |
| 1097 | 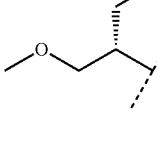 | F | 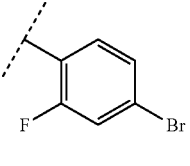 | 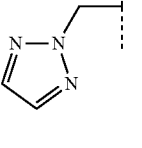 | 7.6 | 684.1 | 15A |
| 1098 | 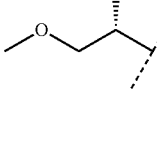 | H | 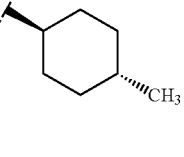 | 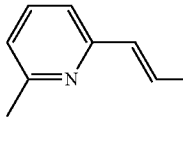 | 7.6 | 590.3 | 10A |
| 1099 | 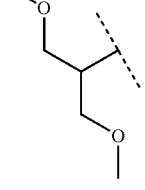 | F | 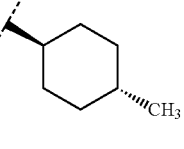 | | 5.3 | 660.3 | 25A |

TABLE 1-continued
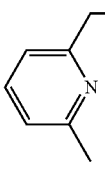
| Cpd | R²⁰ | R³ | R⁵ | R⁶ | t_R (min) | MS (M + H)⁺ | Method |
|---|---|---|---|---|---|---|---|
| 1100 | 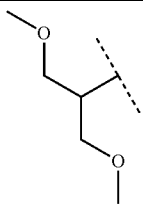 | F | 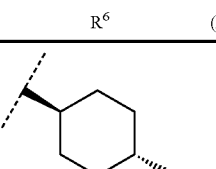 | 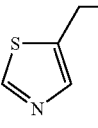 | 5.1 | 648.3 | 20A |
| 1101 | 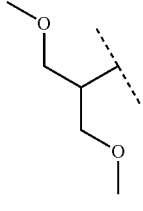 | F | 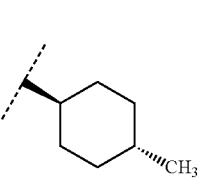 | 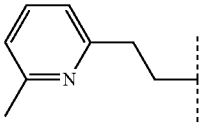 | 6.5 | 640.3 | 20A |
| 1102 | 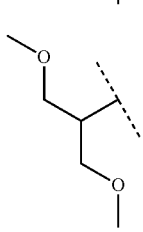 | F | 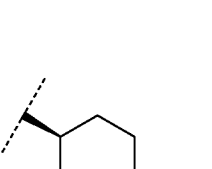 | 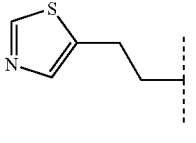 | 5.1 | 662.3 | 26A |
| 1103 | 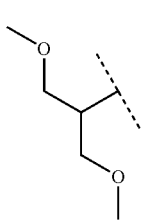 | F | 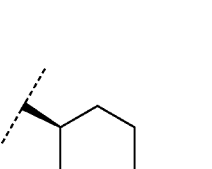 | 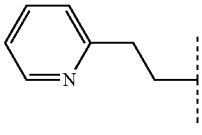 | 6.5 | 654.3 | 27A |
| 1104 | 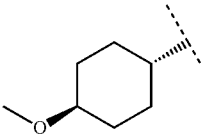 | F | 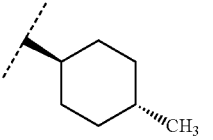 | 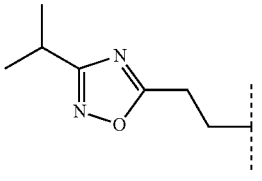 | 5.7 | 658.3 | 27A |
| 1105 | 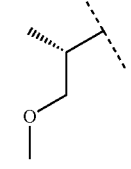 | H | 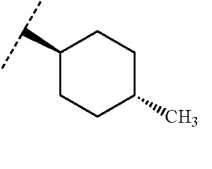 | 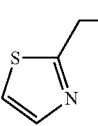 | 6.5 | 633.3 | 28A |
| 1106 | 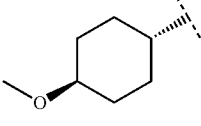 | H | 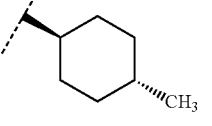 |  | 7.3 | 632.3 | 20A |

TABLE 1-continued
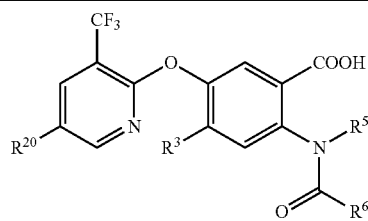
| Cpd | R²⁰ | R³ | R⁵ | R⁶ | t_R (min) | MS (M + H)⁺ | Method |
|---|---|---|---|---|---|---|---|
| 1107 | 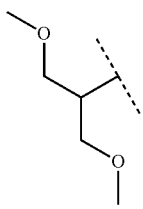 | H | 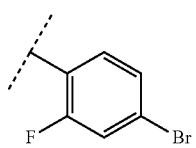 | 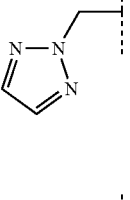 | 6.9 | 684.1 | 29A |
| 1108 | 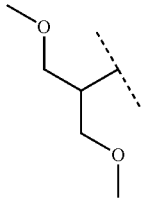 | H | 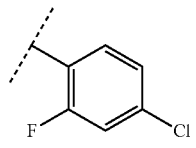 | 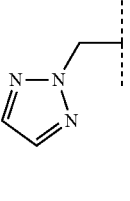 | 6.8 | 638.2 | 29A |
| 1109 | 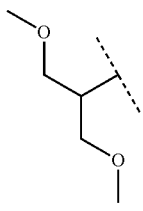 | H | 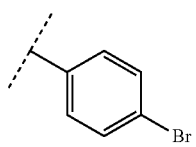 | 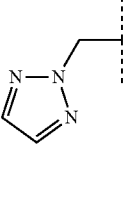 | 6.7 | 666.1 | 29A |
| 1110 | 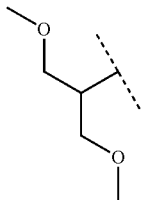 | F | 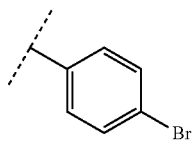 | 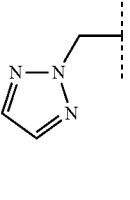 | 7.0 | 682.1 | 30A |
| 1111 | 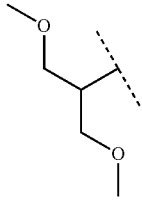 | F | 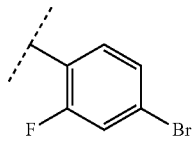 | 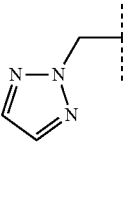 | 7.2 | 700.1 | 30A |
| 1112 | 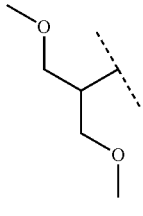 | F | 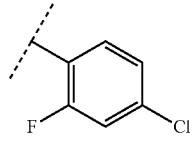 | | 7.2 | 656.2 | 30A |

TABLE 1-continued
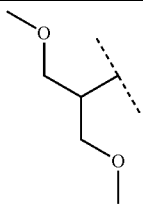
| Cpd | R20 | R3 | R5 | R6 | tR (min) | MS (M + H)+ | Method |
|---|---|---|---|---|---|---|---|
| 1113 | 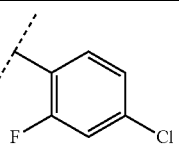 | H | 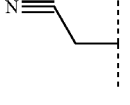 | 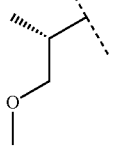 | 6.7 | 654.2 | 31A |
| 1114 | 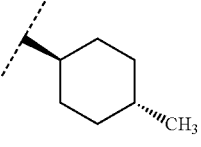 | H | 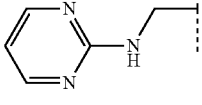 | 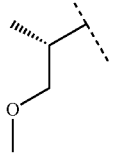 | 7.1 | 534.3 | 32A |
| 1115 | 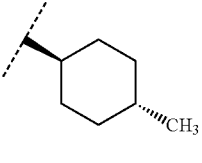 | H | 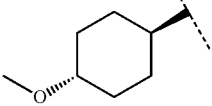 | 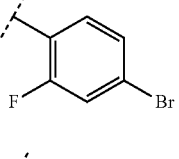 | 5.6 | 602.3 | 33A |
| 1116 | 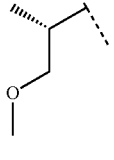 | F | 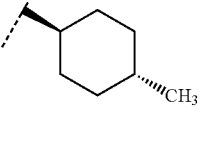 | 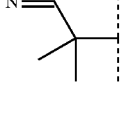 | 7.2 | 710.2 | 34A |
| 1117 | 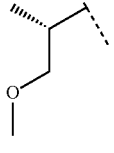 | H | | | 7.5 | 560.3 | 32A |
| 1118 | 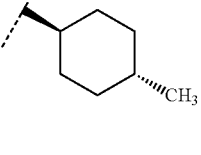 | H | | | 7.6 | 560.3 | 32A |
| 1119 | 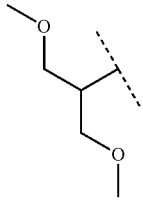 | F | 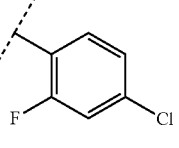 | | 5.8 | 680.2 | 31A |

TABLE 1-continued

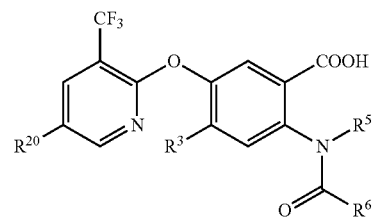

| Cpd | R20 | R3 | R5 | R6 | t_R (min) | MS (M + H)+ | Method |
|---|---|---|---|---|---|---|---|
| 1120 | thiazol-5-ylmethyl | F | 2-(methoxymethyl)-3-methoxypropyl | 2-fluoro-4-chlorophenyl | 7.0 | 672.1 | 31A |
| 1121 | (6-methylpyridin-2-yl)methyl | H | trans-4-methoxycyclohexyl | trans-4-methylcyclohexyl | 5.4 | 640.4 | 40A |
| 1122 | 2-(2H-1,2,3-triazol-2-yl)ethyl | F | 2-(methoxymethyl)-3-methoxypropyl | 2-fluoro-4-bromophenyl | 7.2 | 714.2 | 62A |
| 1123 | 2-(2H-1,2,3-triazol-2-yl)ethyl | F | 2-(methoxymethyl)-3-methoxypropyl | 2-fluoro-4-chlorophenyl | 7.2 | 670.2 | 62A |
| 1124 | (2-(dimethylamino)thiazol-4-yl)methyl | H | 2-(methoxymethyl)-3-methoxypropyl | trans-4-methylcyclohexyl | 5.2 | 665.4 | 49A |
| 1125 | 2-(2-(ethylamino)thiazol-4-yl)ethyl | H | 2-(methoxymethyl)-3-methoxypropyl | trans-4-methylcyclohexyl | 5.4 | 679.4 | 50A |

TABLE 1-continued

| Cpd | R20 | R3 | R5 | R6 | $t_R$ (min) | MS $(M+H)^+$ | Method |
|---|---|---|---|---|---|---|---|
| 1126 | isopropylamino-thiazole-propyl | H | methoxymethyl-methoxymethyl | trans-4-methylcyclohexyl | 5.5 | 693.4 | 50A |
| 1127 | dimethylamino-thiazole-propyl | H | methoxymethyl-methoxymethyl | trans-4-methylcyclohexyl | 5.3 | 679.4 | 50A |
| 1128 | ethylamino-thiazole-methyl | H | methoxymethyl-methoxymethyl | trans-4-methylcyclohexyl | 5.2 | 665.4 | 49A |
| 1129 | isopropylamino-thiazole-methyl | H | methoxymethyl-methoxymethyl | trans-4-methylcyclohexyl | 5.4 | 679.4 | 49A |
| 1130 | triazol-2-yl-ethyl | F | methoxymethyl | 4-bromophenyl | 6.9 | 652.2 | 15A |
| 1131 | triazol-2-yl-ethyl | F | methoxymethyl | 4-chloro-2-fluorophenyl | 7.0 | 626.2 | 15A |

TABLE 1-continued

| Cpd | R20 | R3 | R5 | R6 | $t_R$ (min) | MS (M + H)+ | Method |
|---|---|---|---|---|---|---|---|
| 1132 | 3,3-difluoropiperidin-1-yl-ethyl | F | 1,3-dimethoxyprop-2-yl | 5-chloropyridin-2-yl | 5.0 | 691.3 | 51B |
| 1133 | H | F | trans-4-methoxycyclohexyl | trans-4-methylcyclohexyl | 6.7 | 553.3 | 41A |
| 1134 | (6-methylpyridin-2-yl)methyl | F | 1,3-dimethoxyprop-2-yl | 5-chloropyridin-2-yl | 4.7 | 663.2 | 51C |
| 1135 | thiazol-5-ylmethyl | F | 1,3-dimethoxyprop-2-yl | 5-chloropyridin-2-yl | 6.0 | 655.2 | 51C |
| 1136 | 2-(2H-1,2,3-triazol-2-yl)ethyl | H | 1,3-dimethoxyprop-2-yl | 4-bromo-2-fluorophenyl | 6.9 | 698.2 | 63A |
| 1137 | 2-(2H-1,2,3-triazol-2-yl)ethyl | H | 1,3-dimethoxyprop-2-yl | 4-chloro-2-fluorophenyl | 6.8 | 652.2 | 63A |

TABLE 1-continued

| Cpd | R20 | R3 | R5 | R6 | tR (min) | MS (M + H)+ | Method |
|---|---|---|---|---|---|---|---|
| 1138 | 2-(2H-1,2,3-triazol-2-yl)ethyl | H | 2-(methoxymethyl)-3-methoxypropyl | 4-bromophenyl | 6.7 | 680.2 | 63A |
| 1139 | morpholin-4-yl | H | 2-(methoxymethyl)-3-methoxypropyl | trans-4-methylcyclohexyl | 7.3 | 610.3 | 42A |
| 1140 | 6,6-difluoro-4-methyl-1,4-diazepan-1-yl | H | 2-(methoxymethyl)-3-methoxypropyl | trans-4-methylcyclohexyl | 5.4 | 673.4 | 42A |
| 1141 | 4-(cyclopropyl(methyl)amino)piperidin-1-yl | H | 2-(methoxymethyl)-3-methoxypropyl | trans-4-methylcyclohexyl | 5.5 | 677.3 | 42A |
| 1142 | (3,3-difluoropiperidin-1-yl)methyl | F | 2-(methoxymethyl)-3-methoxypropyl | 4-chlorophenyl | 5.9 | 690.1 | 64A |
| 1143 | (3,3-difluoropiperidin-1-yl)methyl | F | 2-(methoxymethyl)-3-methoxypropyl | 4-bromophenyl | 5.9 | 734.1 | 64A |

TABLE 1-continued

| Cpd | R²⁰ | R³ | R⁵ | R⁶ | t_R (min) | MS (M + H)⁺ | Method |
|---|---|---|---|---|---|---|---|
| 1144 | 3,3-difluoropiperidin-1-yl-ethyl | F | bis(methoxymethyl) | 2-fluoro-4-bromophenyl | 6.0 | 752.1 | 64A |
| 1145 | morpholin-4-yl | F | bis(methoxymethyl) | trans-4-methylcyclohexyl | 7.7 | 628.3 | 42A |
| 1146 | 3-(dimethylamino)pyrrolidin-1-yl | F | bis(methoxymethyl) | trans-4-methylcyclohexyl | 5.5 | 655.4 | 42A |
| 1147 | 2-(isopropylamino)thiazol-4-yl-ethyl | F | bis(methoxymethyl) | trans-4-methylcyclohexyl | 5.6 | 711.3 | 52A |
| 1148 | 2-(ethylamino)thiazol-4-yl-ethyl | F | bis(methoxymethyl) | trans-4-methylcyclohexyl | 5.5 | 697.3 | 52A |
| 1149 | 2-(dimethylamino)thiazol-4-yl-ethyl | F | bis(methoxymethyl) | trans-4-methylcyclohexyl | 5.4 | 697.3 | 52A |

TABLE 1-continued

| Cpd | R20 | R3 | R5 | R6 | tR (min) | MS (M + H)+ | Method |
|---|---|---|---|---|---|---|---|
| 1150 | ethylamino-thiazolyl | F | CH2OCH3, CH2OCH3 branched | trans-4-methylcyclohexyl | 5.4 | 683.3 | 53A |
| 1151 | isopropylamino-thiazolyl | F | CH2OCH3, CH2OCH3 branched | trans-4-methylcyclohexyl | 5.6 | 697.3 | 53A |
| 1152 | dimethylamino-thiazolyl | F | CH2OCH3, CH2OCH3 branched | trans-4-methylcyclohexyl | 5.4 | 683.3 | 53A |
| 1153 | 4-(N-cyclopropyl-N-methylamino)piperidinyl | F | CH2OCH3, CH2OCH3 branched | trans-4-methylcyclohexyl | 5.8 | 695.3 | 42A |
| 1154 | 3,3-difluoropiperidinyl | F | CH2OCH3, CH2OCH3 branched | trans-4-methylcyclohexyl | 8.3 | 662.3 | 42A |
| 1155 | 3,3-difluoropyrrolidinyl | F | CH2OCH3, CH2OCH3 branched | trans-4-methylcyclohexyl | 8.2 | 648.3 | 42A |

TABLE 1-continued

| Cpd | R20 | R3 | R5 | R6 | t_R (min) | MS (M + H)+ | Method |
|---|---|---|---|---|---|---|---|
| 1156 | 3,3-difluoroazetidinyl | F | CH(CH2OMe)2 | trans-4-methylcyclohexyl | 8.1 | 634.3 | 42A |
| 1157 | N-methyl-N-(2-methoxyethyl)amino | F | CH(CH2OMe)2 | trans-4-methylcyclohexyl | 8.0 | 630.3 | 42A |
| 1158 | 2,6-dimethylmorpholinyl | F | CH(CH2OMe)2 | trans-4-methylcyclohexyl | 8.4 | 656.4 | 42A |
| 1159 | 1,2-oxazinan-2-yl | F | CH(CH2OMe)2 | trans-4-methylcyclohexyl | 8.6 | 628.3 | 42A |
| 1160 | H | H | CH(CH2OCH2CH=CH2)2 | trans-4-methylcyclohexyl | 8.3 | 577.3 | 43A |
| 1161 | H | H | CH(CH2OPr)2 | trans-4-methylcyclohexyl | 8.7 | 581.3 | 43A |

TABLE 1-continued

| Cpd | R20 | R3 | R5 | R6 | tR (min) | MS (M + H)+ | Method |
|---|---|---|---|---|---|---|---|
| 1162 | 3,3-difluoropiperidinylmethyl | H | 4-methoxycyclohexyl | 4-methylcyclohexyl | 6.1 | 668.3 | 65A |
| 1163 | 3,3-difluoropiperidinylmethyl | H | 4-ethoxycyclohexyl | 4-methylcyclohexyl | 6.3 | 682.3 | 66A |
| 1164 | 3,3-difluoropiperidinylmethyl | H | 4-cyclopropoxycyclohexyl | 4-methylcyclohexyl | 6.3 | 694.3 | 67A |
| 1165 | 7-azaindol-1-ylmethyl | H | 4-methoxycyclohexyl | 4-methylcyclohexyl | 6.6 | 665.3 | 54A |
| 1166 | 7-azaindol-1-ylmethyl | F | 2-methoxy-1-(methoxymethyl)ethyl | 4-methylcyclohexyl | 6.7 | 673.2 | 55A |
| 1167 | 4-cyclopropyl-2H-1,2,3-triazol-2-ylmethyl | F | 2-methoxy-1-(methoxymethyl)ethyl | 4-methylcyclohexyl | 8.2 | 662.2 [M − H] | 44B |
| 1168 | 7-azaindol-1-ylmethyl | F | 4-methoxycyclohexyl | 4-methylcyclohexyl | 6.7 | 683.3 | 56A |

TABLE 1-continued

| Cpd | R²⁰ | R³ | R⁵ | R⁶ | t_R (min) | MS (M + H)⁺ | Method |
|---|---|---|---|---|---|---|---|
| 1169 | 6-cyclopropylpyridazin-3-ylmethyl | F | 2-(methoxymethyl)-3-methoxypropyl | trans-4-methylcyclohexyl | 6.4 | 674.3 | 68B |
| 1170 | (4-methyl-2H-1,2,3-triazol-2-yl)methyl | F | 2-(methoxymethyl)-3-methoxypropyl | trans-4-methylcyclohexyl | 7.8 | 638.2 | 45A |
| 1171 | 3-hydroxy-2,2-dimethylpropyl | F | 2-(methoxymethyl)-3-methoxypropyl | trans-4-methylcyclohexyl | 7.5 | 615.2 | 81A |
| 1172 | (1-(methoxymethyl)cyclopropyl) | F | 2-(methoxymethyl)-3-methoxypropyl | trans-4-methylcyclohexyl | 8.4 | 627.2 | 69A |
| 1173 | (1-((2H-1,2,3-triazol-2-yl)methyl)cyclopropyl) | F | 2-(methoxymethyl)-3-methoxypropyl | trans-4-methylcyclohexyl | 8.0 | 664.2 | 69A |
| 1174 | (1-((1H-1,2,3-triazol-1-yl)methyl)cyclopropyl) | F | 2-(methoxymethyl)-3-methoxypropyl | trans-4-methylcyclohexyl | 7.2 | 664.2 | 69A |

TABLE 1-continued
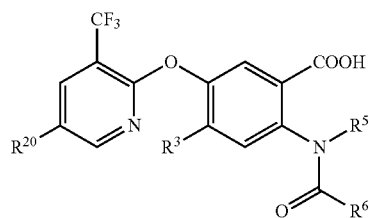
| Cpd | R20 | R3 | R5 | R6 | tR (min) | MS (M + H)+ | Method |
|---|---|---|---|---|---|---|---|
| 1175 | 2-methyl-triazolyl-methyl | F | CH(CH2OMe)2 | 4-methylcyclohexyl | 6.8 | 638.2 | 74A |
| 1176 | 4-cyclopropyl-2H-triazol-2-yl-methyl | F | 4-methoxycyclohexyl | 4-methylcyclohexyl | 8.1 | 674.3 | 44B |
| 1177 | 4-methyl-2H-triazol-2-yl-methyl | F | 4-methoxycyclohexyl | 4-methylcyclohexyl | 7.7 | 648.2 | 45A |
| 1178 | 4,5-dimethyl-1H-triazol-1-yl-methyl | F | 4-methoxycyclohexyl | 4-methylcyclohexyl | 7.9 | 662.2 | 45A |
| 1179 | H | H | 4-methoxyphenyl | 4-methylcyclohexyl | 7.3 | 529.2 | 6A |

TABLE 2

| Cpd | R20 | R3a | R3b | X | R5 | R6 | tR (min) | MS (M+H)+ | Method |
|---|---|---|---|---|---|---|---|---|---|
| 2001 | 2H-triazol-2-ylmethyl | H | F | N | (S)-CH2OMe methyl | trans-4-hydroxycyclohexyl | 7.6 | 594.3 | 35A |
| 2002 | 2H-triazol-2-ylmethyl | F | H | N | (S)-CH2OMe methyl | trans-4-hydroxycyclohexyl | 7.3 | 594.3 | 36A |
| 2003 | 2H-triazol-2-ylmethyl | Me | H | CH | bis(methoxymethyl) | trans-4-hydroxycyclohexyl | 7.8 | 619.2 | 70B |

TABLE 3

| Cpd | R20 | R3 | R5 | tR (min) | MS (M+H)+ | Synthetic Method |
|---|---|---|---|---|---|---|
| 3001 | 3,3-difluoropiperidin-1-ylmethyl | H | bis(methoxymethyl) | 5.2 | 657.4 | 37A |

TABLE 3-continued
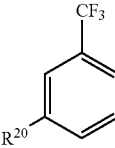
| Cpd | R[20] | R[3] | R[5] | $t_R$ (min) | MS (M + H)[+] | Synthetic Method |
|---|---|---|---|---|---|---|
| 3002 | 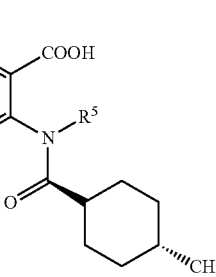 | H |  | 6.4 | 621.3 | 38A |
| 3003 | 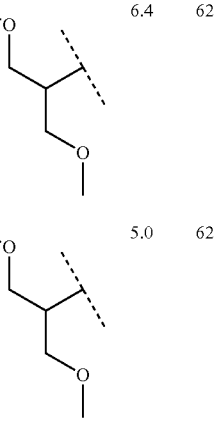 | H | 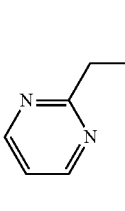 | 5.0 | 629.3 | 38A |
| 3004 | 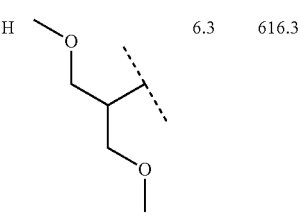 | H | 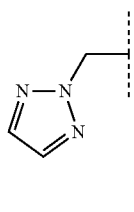 | 6.3 | 616.3 | 38A |
| 3005 | 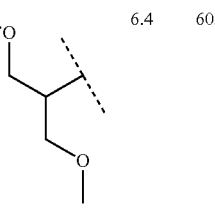 | H | 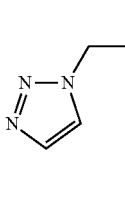 | 6.4 | 605.3 | 39A |
| 3006 | 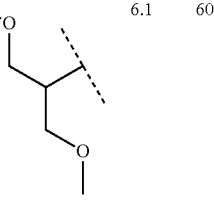 | H | 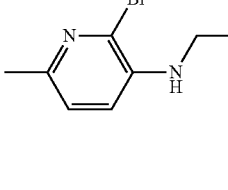 | 6.1 | 605.3 | 39A |
| 3007 | 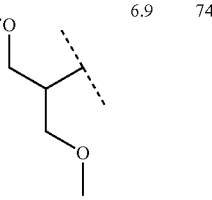 | F |  | 6.9 | 740.2 | 59A |

TABLE 3-continued
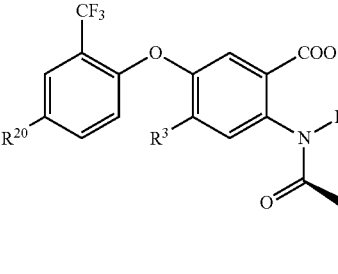
| Cpd | R[20] | R[3] | R[5] | t_R (min) | MS (M + H)[+] | Synthetic Method |
|---|---|---|---|---|---|---|
| 3008 | 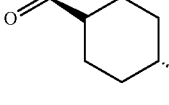 | F | 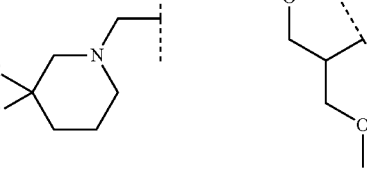 | 5.5 | 675.4 | 57B |
| 3009 | 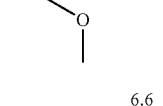 | F | | 6.6 | 623.3 | 57D |
| 3010 | 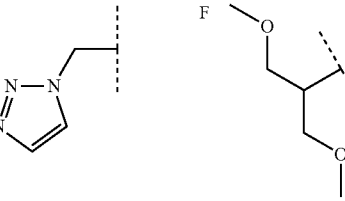 | F | | 6.3 | 623.3 | 57D |
| 3011 | 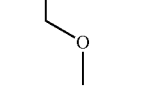 | F | | 6.5 | 639.3 | 58A |
| 3012 | 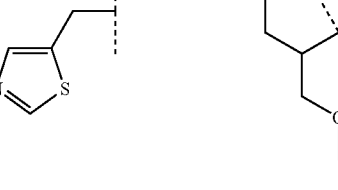 | F | | 6.1 | 667.3 | 58A |
| 3013 | 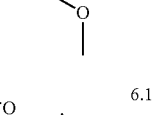 | F | | 5.5 | 647.2 | 58A |

TABLE 3-continued

| Cpd | R20 | R3 | R5 | t_R (min) | MS (M + H)+ | Synthetic Method |
|---|---|---|---|---|---|---|
| 3014 | pyrimidin-2-ylmethyl | F | (methoxymethyl)(methoxymethyl) | 6.5 | 634.2 | 58A |
| 3015 | (pyrimidin-2-ylthio)ethyl | F | (methoxymethyl)(methoxymethyl) | 6.8 | 666.2 | 59A |

TABLE 4

| Cpd | R2 | R3 | R5 | t_R (min) | MS (M + H)+ | Synthetic Method |
|---|---|---|---|---|---|---|
| 4001 | 6-methoxy-5-(trifluoromethyl)pyrimidin-4-yl | F | (methoxymethyl)(methoxymethyl) | 7.9 | 574.3 | 46A |
| 4002 | isoquinolin-1-yl | H | (methoxymethyl)(methoxymethyl) | 7.7 | 507.3 | 71A |

TABLE 4-continued

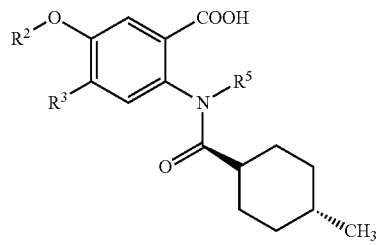

| Cpd | R² | R³ | R⁵ | t_R (min) | MS (M + H)⁺ | Synthetic Method |
|---|---|---|---|---|---|---|
| 4003 | quinolin-2-yl | H | 2-(methoxymethyl)-3-methoxypropyl | 7.5 | 507.3 | 72A |
| 4004 | 5-acetylthiophen-2-yl | H | 2-(methoxymethyl)-3-methoxypropyl | 6.1 | 504.3 | 60A |
| 4005 | thiazol-2-yl | H | 2-(methoxymethyl)-3-methoxypropyl | 5.8 | 463.3 | 60A |
| 4006 | naphthalen-1-yl | H | 2-(methoxymethyl)-3-methoxypropyl | 8.5 | 506.3 | 73A |
| 4007 | 4-methoxy-3-(trifluoromethyl)pyridin-2-yl | H | 2-(methoxymethyl)-3-methoxypropyl | 6.4 | 555.3 | 61 B |
| 4008 | tetrahydrofuran-3-yl | H | 2-(methoxymethyl)-3-methoxypropyl | 5.9 | 450.3 | 47A |

TABLE 4-continued
| Cpd | R² | R³ | R⁵ | $t_R$ (min) | MS (M + H)⁺ | Synthetic Method |
|---|---|---|---|---|---|---|
| 4009 | 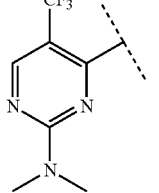 | F | 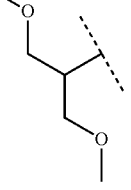 | 8.1 | 587.3 | 48A |
| 4010 | 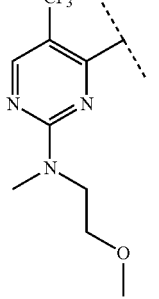 | F | 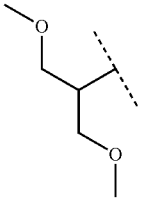 | 8.2 | 631.3 | 48A |
| 4011 | 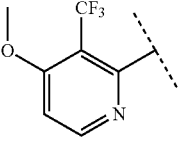 | F | 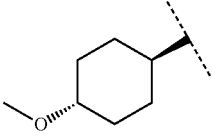 | 6.5 | 583.2 | 61B |
| 4012 | 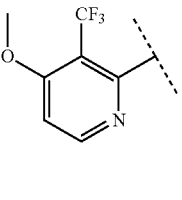 | F | 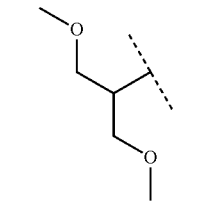 | 6.6 | 573.2 | 61B |
| 4013 | 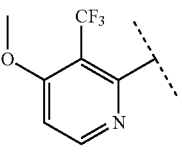 | H | 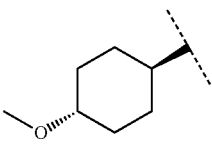 | 6.4 | 565.2 | 61B |
| 4014 | 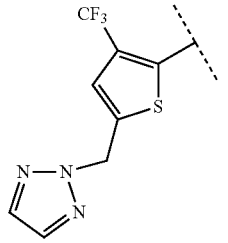 | H | 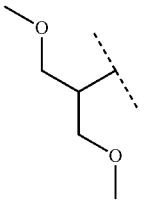 | 6.5 | 611.2 | 79A |

TABLE 4-continued
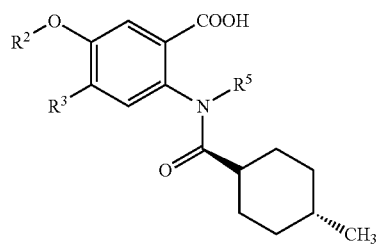
| Cpd | R² | R³ | R⁵ | $t_R$ (min) | MS (M + H)⁺ | Synthetic Method |
|---|---|---|---|---|---|---|
| 4015 | (4-CF₃-5-((1,2,3-triazol-1-yl)methyl)thiophen-2-yl) | H | (1,3-dimethoxyprop-2-yl) | 6.1 | 611.2 | 79A |
| 4016 | (4-CF₃-5-((3,3-difluoropiperidin-1-yl)methyl)thiophen-2-yl) | H | (1,3-dimethoxyprop-2-yl) | 5.6 | 663.2 | 75A |
| 4017 | (5-((3,3-difluoropiperidin-1-yl)methyl)thiophen-2-yl) | H | (1,3-dimethoxyprop-2-yl) | 4.9 | 595.2 | 76A |
| 4018 | (4-Br-5-((3,3-difluoropiperidin-1-yl)methyl)thiophen-2-yl) | H | (1,3-dimethoxyprop-2-yl) | 5.6 | 673.1 | 77A |

TABLE 4-continued

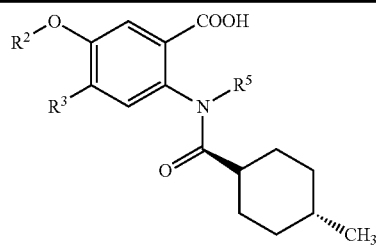

| Cpd | R² | R³ | R⁵ | $t_R$ (min) | MS (M + H)⁺ | Synthetic Method |
|---|---|---|---|---|---|---|
| 4019 | H₃C-thiophene-CH₂-(3,3-difluoropiperidine) | H | CH₃O-CH₂-CH(-)-CH₂-OCH₃ | 5.0 | 609.2 | 78A |
| 4020 | cyclopropyl-thiophene-CH₂-(3,3-difluoropiperidine) | H | CH₃O-CH₂-CH(-)-CH₂-OCH₃ | 5.3 | 635.2 | 78A |
| 4021 | CF₃-pyridine-morpholine | F | CH₃O-CH₂-CH(-)-CH₂-OCH₃ | 8.3 | 628.3 | 48B |

Each of the references, including all patents, patent applications and publications, listed in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:
1. A compound of formula (I):

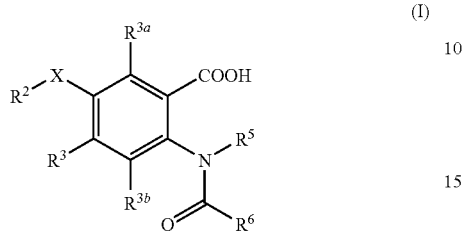

wherein:
X is O;
R² is pyridyl, optionally substituted with 1 to 5 R²⁰ substituents, wherein R²⁰ in each case is independently selected from:
a) halo, cyano or nitro;
b) R⁷, —C(=O)—R⁷, —C(=O)—O—R⁷, —O—R⁷, —S—R⁷, —SO—R⁷, —SO₂—R⁷, —($C_{1-6}$)alkylene-R⁷, —($C_{1-6}$)alkylene-C(=O)—R⁷, —($C_{1-6}$)alkylene-C(=O)—O—R⁷, —($C_{1-6}$)alkylene-O—R⁷, —($C_{1-6}$)alkylene-S—R⁷, —($C_{1-6}$)alkylene-SO—R⁷ or —($C_{1-6}$)alkylene-SO₂—R⁷;
  wherein R⁷ is in each instance independently selected from H, ($C_{1-6}$)alkyl, ($C_{2-6}$)alkenyl, ($C_{2-6}$)alkynyl, ($C_{1-6}$)haloalkyl, ($C_{3-7}$)cycloalkyl, ($C_{3-7}$)cycloalkyl-($C_{1-6}$)alkyl, aryl and Het;
  wherein the ($C_{1-6}$)alkyl, ($C_{2-6}$)alkenyl, ($C_{2-6}$)alkynyl, ($C_{1-6}$)haloalkyl, ($C_{3-7}$)cycloalkyl, ($C_{3-7}$)cycloalkyl-($C_{1-6}$)alkyl, and ($C_{1-6}$)alkylene are optionally substituted with 1 or 2 substituents each independently selected from —OH, —($C_{1-6}$)alkyl (optionally substituted with —O—($C_{1-6}$)alkyl), halo, —($C_{1-6}$)haloalkyl, ($C_{3-7}$)cycloalkyl, —O—($C_{1-6}$)alkyl, cyano, COOH, —NH₂, —NH($C_{1-4}$)alkyl, —NH($C_{3-7}$)cycloalkyl, —N(($C_{1-4}$)alkyl)($C_{3-7}$)cycloalkyl, —N(($C_{1-4}$)alkyl)₂, aryl, —($C_{1-6}$)alkyl-aryl, —($C_{1-6}$)alkyl-Het; and
  wherein each of the aryl and Het is optionally substituted with 1 to 3 substituents each independently selected from:
    i) halo, cyano, oxo, thioxo, imino, —OH, —O—($C_{1-6}$)alkyl, —O—($C_{1-6}$)haloalkyl, ($C_{3-7}$)cycloalkyl, ($C_{1-6}$)haloalkyl, —C(=O)—($C_{1-6}$)alkyl, —SO₂($C_{1-6}$)alkyl, —C(=O)—NH₂, —C(=O)—NH($C_{1-4}$)alkyl, —C(=O)—N(($C_{1-4}$)alkyl)₂, —C(=O)—NH($C_{3-7}$)cycloalkyl, —C(=O)—N(($C_{1-4}$)alkyl)($C_{3-7}$)cycloalkyl, —NH₂, —NH($C_{1-4}$)alkyl, —N(($C_{1-4}$)alkyl)₂, —NH($C_{3-7}$)cycloalkyl, —N(($C_{1-4}$)alkyl)($C_{3-7}$)cycloalkyl or —NH—C(=O)($C_{1-4}$)alkyl;
    ii) ($C_{1-6}$)alkyl optionally substituted with —OH, —O—($C_{1-6}$)haloalkyl, or —O—($C_{1-6}$)alkyl; and
    iii) aryl or Het, wherein each of the aryl and Het is optionally substituted with halo or ($C_{1-6}$)alkyl; and
c) —N(R⁸)R⁹, —C(=O)—N(R⁸)R⁹, —O—C(=O)—N(R⁸)R⁹, —SO₂—N(R⁸)R⁹, —($C_{1-6}$)alkylene-N(R⁸)R⁹, —($C_{1-6}$)alkylene-C(=O)—N(R⁸)R⁹, —($C_{1-6}$)alkylene-O—C(=O)—N(R⁸)R⁹, or —($C_{1-6}$)alkylene-SO₂—N(R⁸)R⁹; wherein the ($C_{1-6}$)alkylene is optionally substituted with 1 or 2 substituents each independently selected from —OH, —($C_{1-6}$)alkyl, halo, —($C_{1-6}$)haloalkyl, ($C_{3-7}$)cycloalkyl, —O—($C_{1-6}$)alkyl, cyano, COOH, —NH₂, —NH($C_{1-4}$)alkyl, —NH($C_{3-7}$)cycloalkyl, —N(($C_{1-4}$)alkyl)($C_{3-7}$)cycloalkyl and —N(($C_{1-4}$)alkyl)₂;
R⁸ is in each instance independently selected from H, ($C_{1-6}$)alkyl and ($C_{3-7}$)cycloalkyl; and
R⁹ is in each instance independently selected from R⁷, —O—($C_{1-6}$)alkyl, —($C_{1-6}$)alkylene-R⁷, —SO₂—R⁷, —C(=O)—R⁷, —C(=O)OR⁷ and —C(=O)N(R⁸)R⁷;
wherein R⁷ and R⁸ are as defined above;
  or R⁸ and R⁹, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO₂;
  wherein the heterocycle is optionally substituted with 1 to 3 substituents each independently selected from ($C_{1-6}$)alkyl, ($C_{1-6}$)haloalkyl, halo, oxo, —OH, SH, —O($C_{1-6}$)alkyl, —S($C_{1-6}$)alkyl, ($C_{3-7}$)cycloalkyl, —NH₂, —NH($C_{1-6}$)alkyl, —N(($C_{1-6}$)alkyl)₂, —NH($C_{3-7}$)cycloalkyl, —N(($C_{1-4}$)alkyl)($C_{3-7}$)cycloalkyl, —C(=O)($C_{1-6}$)alkyl and —NHC(=O)—($C_{1-6}$)alkyl;
R³, R³ᵃ and R³ᵇ are selected from H, halo, CN, ($C_{1-4}$)alkyl, —OH, —O—($C_{1-4}$)alkyl, —S—($C_{1-4}$)alkyl, —NH₂, —NH($C_{1-4}$)alkyl, —NH($C_{3-7}$)cycloalkyl, —N(($C_{1-4}$)alkyl)($C_{3-7}$)cycloalkyl) and —N(($C_{1-4}$)alkyl)₂;
R⁵ is R⁵¹ mono-, di-, or tri-substituted with O—R⁵²,
  wherein R⁵¹ is ($C_{1-6}$)alkyl, ($C_{3-7}$)cycloalkyl, ($C_{1-6}$)alkyl-($C_{3-7}$)cycloalkyl, aryl, ($C_{1-6}$)alkyl-aryl, Het or ($C_{1-6}$)alkyl-Het, each R⁵¹ being optionally substituted with ($C_{1-6}$)alkyl, ($C_{3-7}$)cycloalkyl or ($C_{1-6}$)alkyl-($C_{3-7}$)cycloalkyl; and
  R⁵² is ($C_{1-6}$)alkyl, ($C_{3-7}$)cycloalkyl, ($C_{1-6}$)alkyl-($C_{3-7}$)cycloalkyl, aryl, ($C_{1-6}$)alkyl-aryl, Het or ($C_{1-6}$)alkyl-Het, said aryl and Het being optionally substituted with ($C_{1-6}$)alkyl or O—($C_{1-6}$)alkyl;
R⁶ is ($C_{3-7}$)cycloalkyl, ($C_{1-6}$)alkyl-($C_{3-7}$)cycloalkyl, aryl, ($C_{1-6}$)alkyl-aryl, Het or ($C_{1-6}$)alkyl-Het; being optionally substituted with 1 to 5 substituents each independently selected from halo, ($C_{1-6}$)alkyl, ($C_{1-6}$)haloalkyl, ($C_{3-7}$)cycloalkyl, —OH, —SH, —O—($C_{1-4}$)alkyl, —S—($C_{1-4}$)alkyl and —N(R⁸)R⁹; wherein R⁸ and R⁹ are as defined above; and
Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO₂;
or a salt thereof.

2. The compound according to claim 1 or a pharmaceutically acceptable salt thereof, wherein $R^2$ is of the formula:

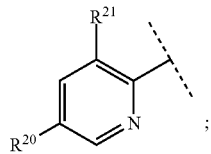

$R^{21}$ is selected from H, halo, $(C_{1-6})$alkyl, $(C_{1-6})$haloalkyl, $(C_{3-7})$cycloalkyl and —O—$(C_{1-6})$haloalkyl; and $R^{20}$ is as defined in claim 1.

3. The compound according to claim 2, or a pharmaceutically acceptable salt thereof, wherein $R^{21}$ is H or $CF_3$, and $R^{20}$ is selected from:

$R^7$ or —$(C_{1-6})$alkylene-$R^7$ wherein $R^7$ is in each instance independently selected from H, $(C_{1-6})$alkyl, $(C_{3-7})$cycloalkyl, $(C_{3-7})$cycloalkyl-$(C_{1-6})$alkyl, phenyl and Het;

wherein each of the phenyl and Het are optionally substituted with 1 to 3 substituents each independently selected from:

i) halo, $(C_{3-7})$cycloalkyl, $(C_{1-6})$haloalkyl, —C(=O)—$NH_2$, —C(=O)—NH$(C_{1-4})$alkyl, —C(=O)—N$((C_{1-4})$alkyl$)_2$, —C(=O)—NH$(C_{3-7})$cycloalkyl, —C(=O)—N$((C_{1-4})$alkyl$)(C_{3-7})$cycloalkyl, —$NH_2$, —NH$(C_{1-4})$alkyl, —N$((C_{1-4})$alkyl$)_2$, —NH$(C_{3-7})$cycloalkyl, —N$((C_{1-4})$alkyl$)(C_{3-7})$cycloalkyl or —NH—C(=O)$(C_{1-4})$alkyl; and ii) $(C_{1-6})$alkyl optionally substituted with —OH, —O—$(C_{1-6})$haloalkyl, or —O—$(C_{1-6})$alkyl;

wherein the Het is selected from:

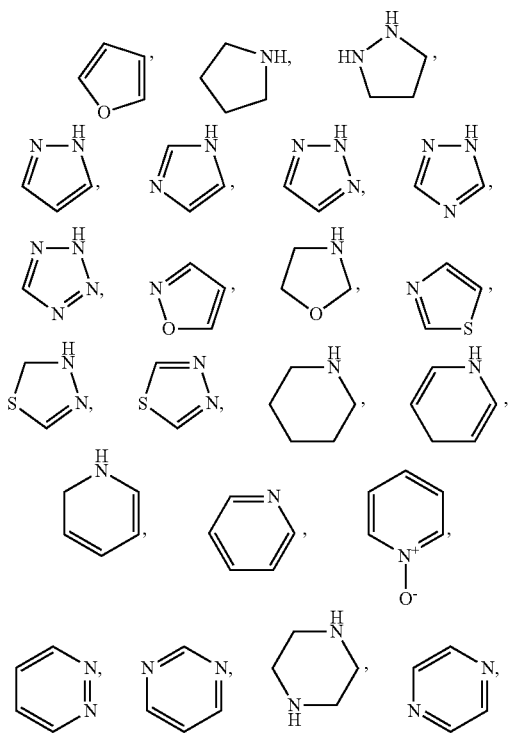

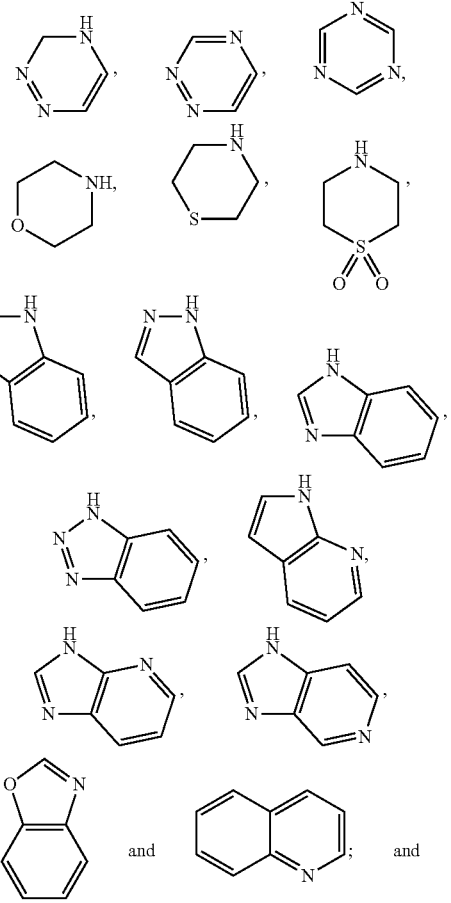

—N$(R^8)R^9$ or —$(C_{1-6})$alkylene-N$(R^8)R^9$;

$R^8$ is in each instance independently selected from H, $(C_{1-6})$alkyl and $(C_{3-7})$cycloalkyl; and $R^9$ is defined as $R^7$, wherein $R^7$ is as defined above.

4. The compound according to claim 2, or a pharmaceutically acceptable salt thereof, wherein $R^{21}$ is H or $CF_3$, and $R^{20}$ is selected from:

—$(C_{1-3})$alkylene-$R^7$;

wherein $R^7$ is Het; wherein the Het is a 5- or 6-membered heterocycle containing 1 to 4 heteroatoms, each independently selected from N, O and S, or Het is a 9- or 10-membered heteropolycycle containing 1 to 4 heteroatoms, each independently selected from N, O and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$;

wherein the Het is optionally substituted with 1 to 3 substituents each independently selected from halo, cyano, oxo, imino, —OH, —O—$(C_{1-6})$alkyl, —O—$(C_{1-6})$haloalkyl, $(C_{3-7})$cycloalkyl, —$NH_2$, —NH$(C_{1-4})$alkyl, —NH$(C_{3-7})$cycloalkyl, —N$((C_{1-4})$alkyl$)(C_{3-7})$cycloalkyl, —N$((C_{1-4})$alkyl$)_2$, —NH—C(=O)$(C_{1-4})$alkyl, $(C_{1-6})$alkyl and Het, wherein the Het is a 5- or 6-membered heterocycle containing 1 to 4 heteroatoms, each independently selected from N, O and S.

5. The compound according to claim 1 or a pharmaceutically acceptable salt thereof, wherein $R^3$ is selected from H, F, Cl and $CH_3$.

6. The compound according to claim 1, or a pharmaceutically acceptable salt thereof, wherein $R^{3a}$ is selected from H, F and $CH_3$.

7. The compound according to claim 1, or a pharmaceutically acceptable salt thereof, wherein $R^{3b}$ is selected from H, F, Cl, $CH_3$ and CN.

8. The compound according to claim 1, or a pharmaceutically acceptable salt thereof, wherein $R^5$ is $R^{51}$ being mono- or di-substituted with O—$R^{52}$, wherein $R^{51}$ is $(C_{1-6})$alkyl, $(C_{3-7})$cycloalkyl or $(C_{1-6})$alkyl-$(C_{3-7})$cycloalkyl, each $R^{51}$ being optionally substituted with $(C_{1-6})$alkyl, $(C_{3-7})$cycloalkyl or $(C_{1-6})$alkyl-$(C_{3-7})$cycloalkyl; and $R^{52}$ is $(C_{1-6})$alkyl, $(C_{3-7})$cycloalkyl, $(C_{1-6})$alkyl-$(C_{3-7})$cycloalkyl, aryl or $(C_{1-6})$alkyl-aryl, said aryl being optionally substituted with $(C_{1-6})$alkyl or O—$(C_{1-6})$alkyl.

9. The compound according to claim 1, or a pharmaceutically acceptable salt thereof, wherein $R^6$ is phenyl, cyclohexyl or pyridine optionally substituted with 1 to 3 substituents each independently selected from halo, $(C_{1-4})$alkyl and $(C_{1-4})$haloalkyl.

10. The compound according to claim 1 having the following formula:

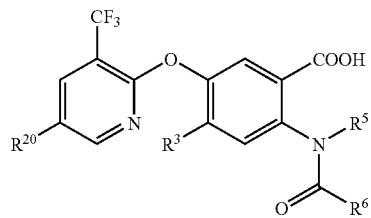

wherein $R^{20}$, $R^3$, $R^5$ and $R^6$ are defined as:

| Cpd | $R^{20}$ | $R^3$ | $R^5$ | $R^6$ |
|---|---|---|---|---|
| 1001 | H | H | 2-methoxyethyl | 5-bromopyridin-2-yl |
| 1002 | H | H | 2-methoxyethyl | trans-4-methylcyclohexyl |
| 1003 | H | H | (1S,2R)-2-(benzyloxy)cyclopentyl | trans-4-methylcyclohexyl |
| 1004 | H | H | (1S,2R)-2-(benzyloxy)cyclopentyl | trans-4-methylcyclohexyl |

-continued

| Cpd | R²⁰ | R³ | R⁵ | R⁶ |
|---|---|---|---|---|
| 1005 | H | H | (1R,2S)-2-(benzyloxy)cyclopentyl | 5-bromopyridin-2-yl |
| 1006 | H | H | (1S,2R)-2-(benzyloxy)cyclopentyl | 5-bromopyridin-2-yl; |
| 1007 | 2H-1,2,3-triazol-2-ylmethyl | H | 3-methoxypropyl | trans-4-methylcyclohexyl; |
| 1008 | 2H-1,2,3-triazol-2-ylmethyl | F | 3-methoxypropyl | trans-4-methylcyclohexyl; |
| 1009 | 1H-1,2,3-triazol-1-ylmethyl | H | trans-4-methoxycyclohexyl | trans-4-methylcyclohexyl; |
| 1010 | 2H-1,2,3-triazol-2-ylmethyl | H | trans-4-methoxycyclohexyl | trans-4-methylcyclohexyl; |
| 1011 | H | H | 4-isopropoxybenzyl | trans-4-methylcyclohexyl; |

-continued

| Cpd | R²⁰ | R³ | R⁵ | R⁶ |
|---|---|---|---|---|
| 1012 | H | H | 2-isopropoxybenzyl | trans-4-methylcyclohexyl |
| 1013 | H | H | 4-phenoxybenzyl | trans-4-methylcyclohexyl |
| 1014 | H | H | (S)-2-methyl-3-methoxypropyl | trans-4-methylcyclohexyl |
| 1015 | H | H | (S)-1-(3-methoxyphenyl)ethyl | trans-4-methylcyclohexyl |
| 1016 | H | H | (R)-1-(3-methoxyphenyl)ethyl | trans-4-methylcyclohexyl |
| 1017 | H | H | 3-isopropoxypropyl | trans-4-methylcyclohexyl |
| 1018 | H | H | 4-propoxybutyl | trans-4-methylcyclohexyl |

-continued
| Cpd | R²⁰ | R³ | R⁵ | R⁶ |
|---|---|---|---|---|
| 1019 | H | H | 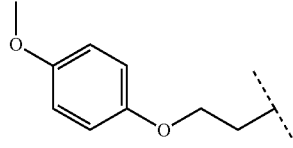 | 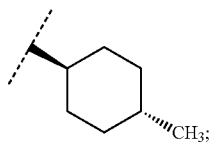 |
| 1020 | H | H | 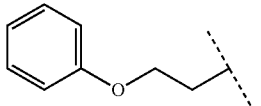 | 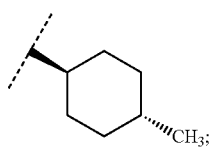 |
| 1021 | H | H | 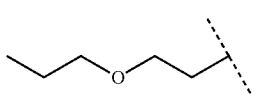 | 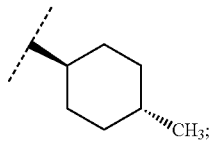 |
| 1022 | H | H | 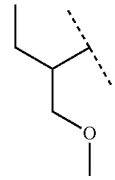 | 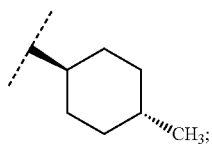 |
| 1023 | H | H | 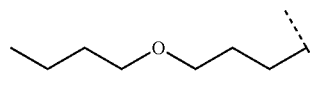 | 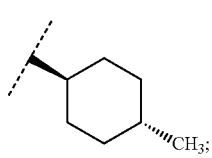 |
| 1024 | H | H | 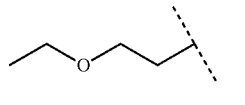 | 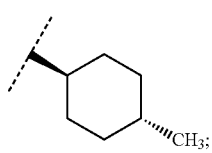 |
| 1025 | H | H | 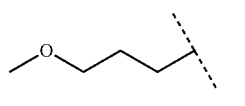 | 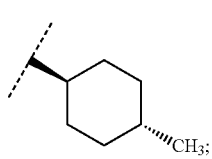 |
| 1026 | H | H | 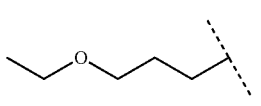 | 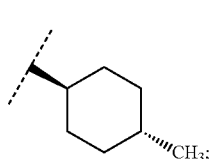 |
| 1027 | H | H | 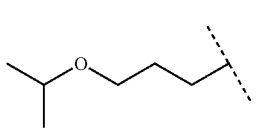 | 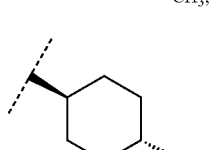 |
| 1028 | H | H | 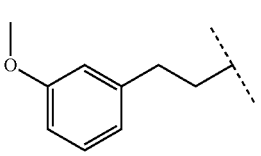 | 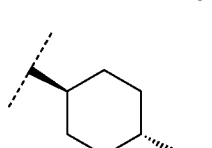 |

-continued
| Cpd | R²⁰ | R³ | R⁵ | R⁶ |
|---|---|---|---|---|
| 1029 | H | H | 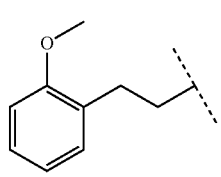 | 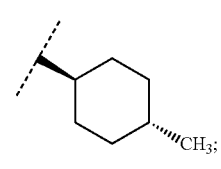 |
| 1030 | H | H | 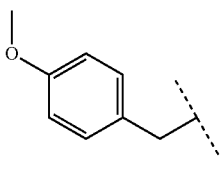 | 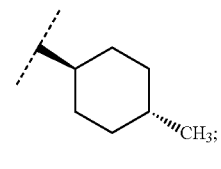 |
| 1031 | H | H | 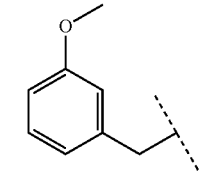 | 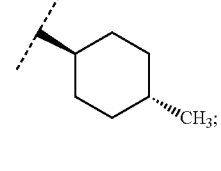 |
| 1032 | H | H | 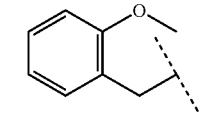 | 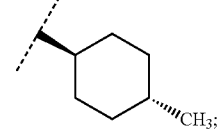 |
| 1033 | H | H | 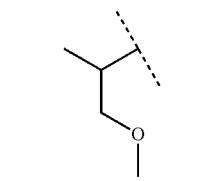 | 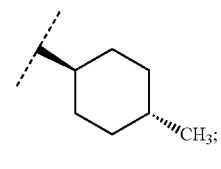 |
| 1034 | H | H | 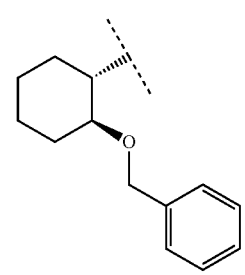 | 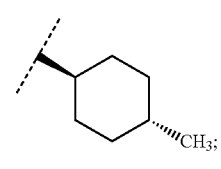 |
| 1035 | H | H | 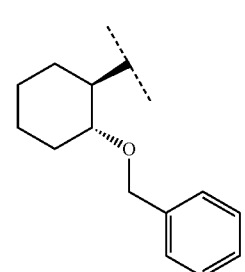 | 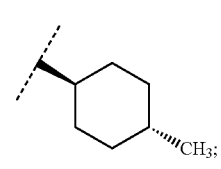 |
| 1036 | H | H | 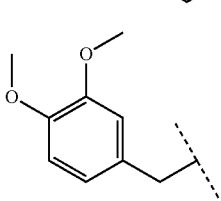 | 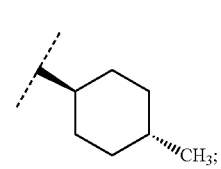 |

-continued

| Cpd | R²⁰ | R³ | R⁵ | R⁶ |
|---|---|---|---|---|
| 1037 | H | H | benzyl-CH(CH₃)-CH₂-OMe (S) | trans-4-methylcyclohexyl |
| 1038 | H | H | phenyl-CH(-)-CH₂-OMe | trans-4-methylcyclohexyl |
| 1039 | H | H | phenyl-CH(CH₃)-CH₂-OMe | trans-4-methylcyclohexyl |
| 1040 | H | H | (S)-CH(CH₃)-CH₂-OMe | 5-chloropyridin-2-yl |
| 1041 | H | H | (S)-CH(CH₃)-CH₂-OMe | 5-bromopyridin-2-yl |
| 1042 | H | H | MeO-CH₂-CH(-)-CH₂-OMe | trans-4-methylcyclohexyl |
| 1043 | 2H-1,2,3-triazol-2-yl-ethyl | H | (S)-CH(CH₃)-CH₂-OMe | 5-chloropyridin-2-yl |
| 1044 | 2H-1,2,3-triazol-2-yl-ethyl | H | (S)-CH(CH₃)-CH₂-OMe | trans-4-methylcyclohexyl |

-continued
| Cpd | R²⁰ | R³ | R⁵ | R⁶ |
|---|---|---|---|---|
| 1045 | 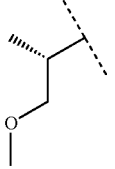 | H | 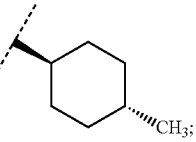 | 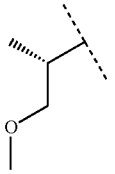 |
| 1046 | 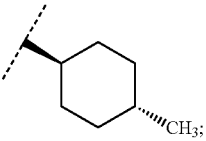 | H | 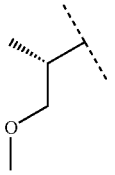 | 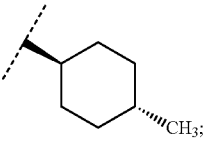 |
| 1047 | 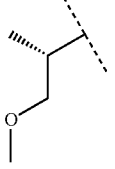 | F | 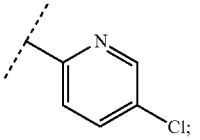 | 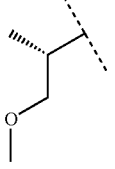 |
| 1048 | 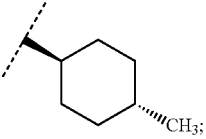 | F | 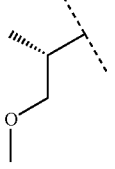 | 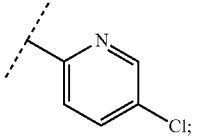 |
| 1049 | H | F | 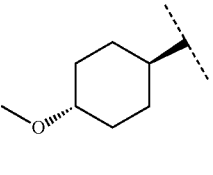 | 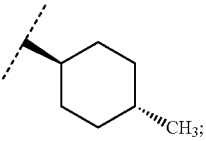 |
| 1050 | H | F | 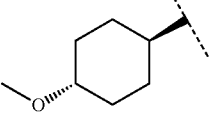 | 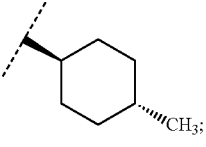 |
| 1051 |  | F |  |  |
| 1052 |  | F |  |  |

-continued
| Cpd | R²⁰ | R³ | R⁵ | R⁶ |
|---|---|---|---|---|
| 1053 | H | F | 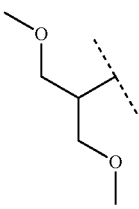 | 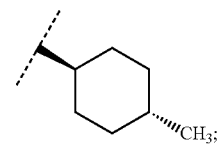 |
| 1054 | 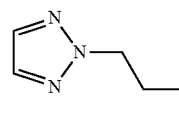 | F | 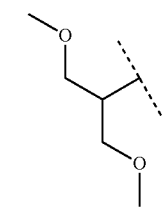 | 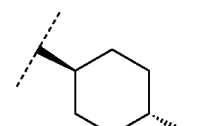 |
| 1055 | 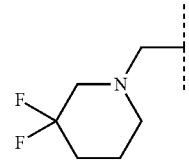 | F | 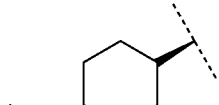 | 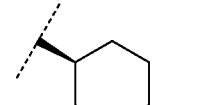 |
| 1056 | 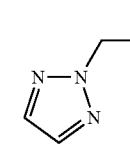 | F | 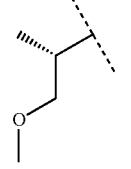 | 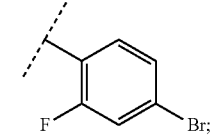 |
| 1057 | 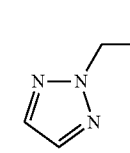 | F | 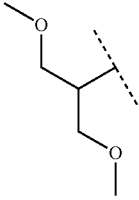 | 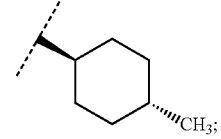 |
| 1058 | 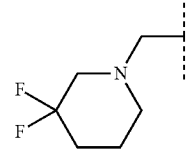 | F | 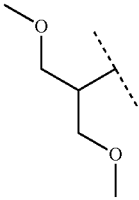 | 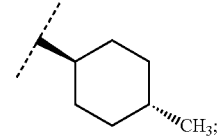 |
| 1059 | 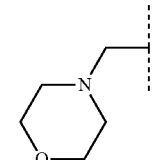 | H | 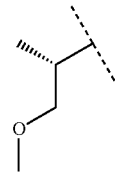 | 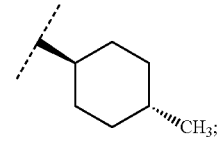 |
| 1060 | 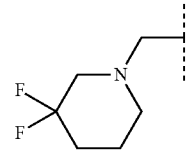 | F | 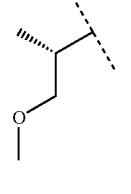 | 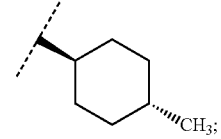 |

-continued

| Cpd | R²⁰ | R³ | R⁵ | R⁶ |
|---|---|---|---|---|
| 1061 | pyridin-2-ylmethyl | H | 4-methoxycyclohexyl | 4-methylcyclohexyl |
| 1062 | pyridin-2-ylmethyl | H | (S)-3-methoxy-2-methylpropyl | 4-methylcyclohexyl |
| 1063 | (6-methylpyridin-2-yl)methyl | H | (S)-3-methoxy-2-methylpropyl | 4-methylcyclohexyl |
| 1064 | thiazol-5-ylmethyl | H | (S)-3-methoxy-2-methylpropyl | 4-methylcyclohexyl |
| 1065 | pyrazin-2-ylmethyl | H | 4-methoxycyclohexyl | 4-methylcyclohexyl |
| 1066 | thiazol-5-ylmethyl | H | 4-methoxycyclohexyl | 4-methylcyclohexyl |
| 1067 | 2H-1,2,3-triazol-2-ylmethyl | H | 1,3-dimethoxypropan-2-yl | 4-methylcyclohexyl |
| 1068 | morpholin-4-ylmethyl | F | 1,3-dimethoxypropan-2-yl | 4-methylcyclohexyl |

-continued

| Cpd | R²⁰ | R³ | R⁵ | R⁶ |
| --- | --- | --- | --- | --- |
| 1069 | morpholine-CH₂CH₂- | F | (S)-CH(CH₃)CH₂OCH₃ | trans-cyclohexyl-CH₃ |
| 1070 | pyridin-3-yl-CH₂- | H | (S)-CH(CH₃)CH₂OCH₃ | trans-cyclohexyl-CH₃ |
| 1071 | 2H-1,2,3-triazol-2-yl-CH₂- | F | (S)-CH(CH₃)CH₂OCH₃ | 5-bromopyridin-2-yl |
| 1072 | 2H-1,2,3-triazol-2-yl-CH₂CH₂- | F | (S)-CH(CH₃)CH₂OCH₃ | trans-cyclohexyl-CH₃ |
| 1073 | pyridin-2-yl-CH₂- | F | trans-4-methoxycyclohexyl | trans-cyclohexyl-CH₃ |
| 1074 | thiazol-5-yl-CH₂- | F | trans-4-methoxycyclohexyl | trans-cyclohexyl-CH₃ |
| 1075 | thiazol-2-yl-CH₂- | F | trans-4-methoxycyclohexyl | trans-cyclohexyl-CH₃ |
| 1076 | 2H-1,2,3-triazol-2-yl-CH₂CH₂- | H | CH(CH₂OCH₃)₂ | trans-cyclohexyl-CH₃ |

-continued

| Cpd | R²⁰ | R³ | R⁵ | R⁶ |
|---|---|---|---|---|
| 1077 | 2H-1,2,3-triazol-2-ylethyl | H | (S)-methoxymethyl-CH(CH₃)- | 4-bromo-2-fluorophenyl; |
| 1078 | (3,3-difluoropiperidin-1-yl)ethyl | H | bis(methoxymethyl)CH- | trans-4-methylcyclohexyl; |
| 1079 | morpholin-4-ylethyl | H | bis(methoxymethyl)CH- | trans-4-methylcyclohexyl; |
| 1080 | morpholin-4-ylpropyl | F | bis(methoxymethyl)CH- | trans-4-methylcyclohexyl; |
| 1081 | (3,3-difluoropiperidin-1-yl)ethyl | F | bis(methoxymethyl)CH- | trans-4-methylcyclohexyl; |
| 1082 | H | F | bis(methoxymethyl)CH- | 4-bromo-2-fluorophenyl; |
| 1083 | (6-methylpyridin-2-yl)methyl | H | bis(methoxymethyl)CH- | trans-4-methylcyclohexyl; |

-continued
| Cpd | R20 | R3 | R5 | R6 |
|---|---|---|---|---|
| 1084 | 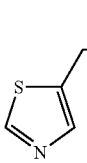 | H | 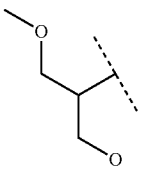 | 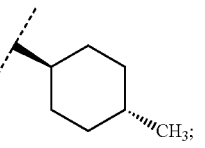 |
| 1085 | 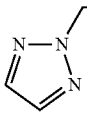 | F | 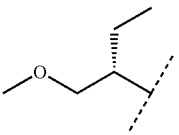 | 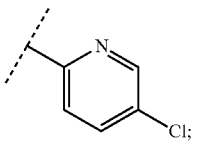 |
| 1086 | 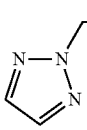 | H | 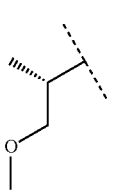 | 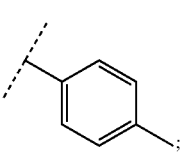 |
| 1087 | 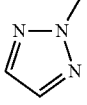 | H | 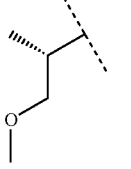 | 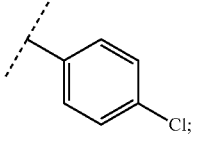 |
| 1088 | 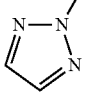 | H | 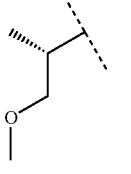 | 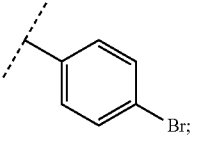 |
| 1089 | 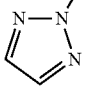 | H | 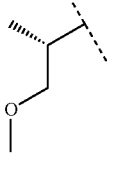 | 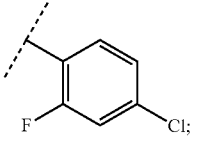 |
| 1090 | 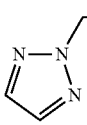 | H | 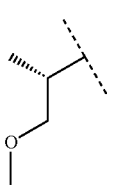 | 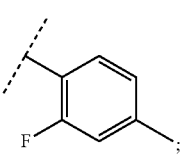 |
| 1091 | 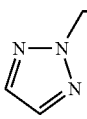 | H | 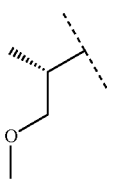 | 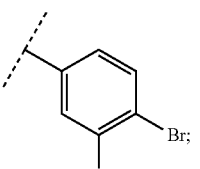 |

-continued

| Cpd | R²⁰ | R³ | R⁵ | R⁶ |
|---|---|---|---|---|
| 1092 | allyl | F | bis(methoxymethyl)methyl | 5-chloropyridin-2-yl; |
| 1093 | 2-(2H-1,2,3-triazol-2-yl)ethyl | F | bis(methoxymethyl)methyl | 5-chloropyridin-2-yl; |
| 1094 | (3,3-difluoropiperidin-1-yl)methyl | H | bis(methoxymethyl)methyl | 4-bromo-2-fluorophenyl; |
| 1095 | H | F | bis(methoxymethyl)methyl | 5-chloropyridin-2-yl; |
| 1096 | (3,3-difluoropiperidin-1-yl)methyl | H | bis(methoxymethyl)methyl | 4-chlorophenyl; |
| 1097 | 2-(2H-1,2,3-triazol-2-yl)ethyl | F | 1-(methoxymethyl)propyl | 4-bromo-2-fluorophenyl; |
| 1098 | 2-(2H-1,2,3-triazol-2-yl)ethyl | H | 1-(methoxymethyl)propyl | trans-4-methylcyclohexyl; |
| 1099 | (E)-2-(6-methylpyridin-2-yl)vinyl | F | bis(methoxymethyl)methyl | trans-4-methylcyclohexyl; |

-continued
| Cpd | R²⁰ | R³ | R⁵ | R⁶ |
|---|---|---|---|---|
| 1100 | 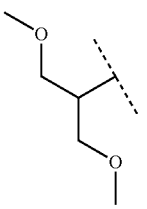 | F | 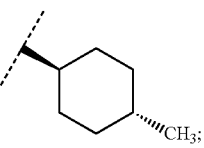 | 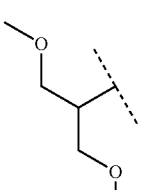 |
| 1101 | 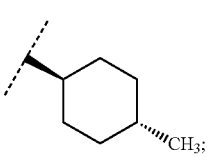 | F | 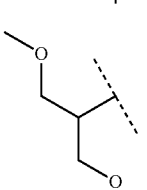 | 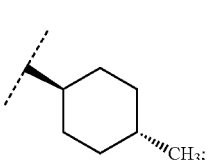 |
| 1102 | 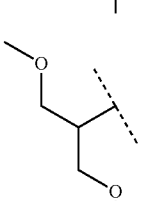 | F | 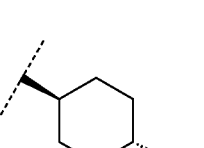 | 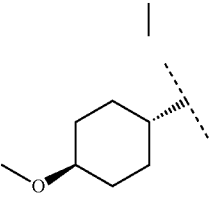 |
| 1103 | 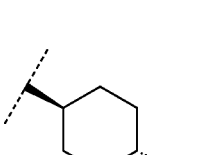 | F | 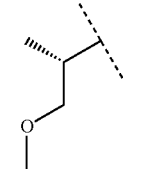 | 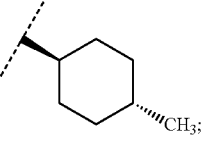 |
| 1104 | 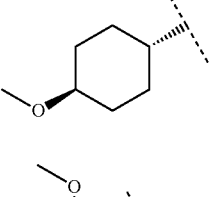 | F | 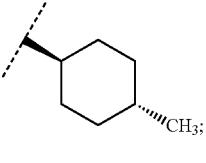 | 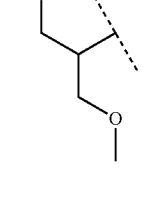 |
| 1105 | 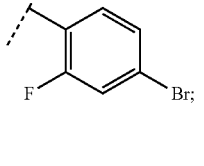 | H | | |
| 1106 | | H | | |
| 1107 | | H | | |

-continued

| Cpd | R²⁰ | R³ | R⁵ | R⁶ |
|---|---|---|---|---|
| 1108 | 2H-1,2,3-triazol-2-yl-CH₂- | H | -CH(CH₂OMe)₂ | 4-Cl-2-F-phenyl |
| 1109 | 2H-1,2,3-triazol-2-yl-CH₂- | H | -CH(CH₂OMe)₂ | 4-Br-phenyl |
| 1110 | 2H-1,2,3-triazol-2-yl-CH₂- | F | -CH(CH₂OMe)₂ | 4-Br-phenyl |
| 1111 | 2H-1,2,3-triazol-2-yl-CH₂- | F | -CH(CH₂OMe)₂ | 4-Br-2-F-phenyl |
| 1112 | 2H-1,2,3-triazol-2-yl-CH₂- | F | -CH(CH₂OMe)₂ | 4-Cl-2-F-phenyl |
| 1113 | thiazol-5-yl-CH₂- | H | -CH(CH₂OMe)₂ | 4-Cl-2-F-phenyl |
| 1114 | N≡C-CH₂-CH₂- | H | (S)-CH(CH₃)CH₂OMe | trans-4-methylcyclohexyl |

-continued

| Cpd | R²⁰ | R³ | R⁵ | R⁶ |
|---|---|---|---|---|
| 1115 | pyrimidin-2-ylamino-ethyl | H | (S)-methoxymethyl-methyl | trans-4-methylcyclohexyl |
| 1116 | 2H-1,2,3-triazol-2-yl-ethyl | F | trans-4-methoxycyclohexyl | 4-bromo-2-fluorophenyl |
| 1117 | 1-cyanocyclopropyl-methyl | H | (S)-methoxymethyl-methyl | trans-4-methylcyclohexyl |
| 1118 | 2-cyano-2-methylpropyl | H | (S)-methoxymethyl-methyl | trans-4-methylcyclohexyl |
| 1119 | (6-methylpyridin-2-yl)methyl | F | bis(methoxymethyl)methyl | 4-chloro-2-fluorophenyl |
| 1120 | thiazol-5-ylmethyl | F | bis(methoxymethyl)methyl | 4-chloro-2-fluorophenyl |
| 1121 | (6-methylpyridin-2-yl)methyl | H | trans-4-methoxycyclohexyl | trans-4-methylcyclohexyl |
| 1122 | 2H-1,2,3-triazol-2-yl-ethyl | F | bis(methoxymethyl)methyl | 4-bromo-2-fluorophenyl |

-continued

| Cpd | R²⁰ | R³ | R⁵ | R⁶ |
|---|---|---|---|---|
| 1123 | 2H-1,2,3-triazol-2-yl-CH₂CH₂– | F | –CH(CH₂OCH₃)₂ | 2-fluoro-4-chlorophenyl |
| 1124 | 2-(dimethylamino)thiazol-4-yl-CH₂– | H | –CH(CH₂OCH₃)₂ | trans-4-methylcyclohexyl |
| 1125 | 2-(ethylamino)thiazol-4-yl-CH₂CH₂– | H | –CH(CH₂OCH₃)₂ | trans-4-methylcyclohexyl |
| 1126 | 2-(isopropylamino)thiazol-4-yl-CH₂CH₂– | H | –CH(CH₂OCH₃)₂ | trans-4-methylcyclohexyl |
| 1127 | 2-(dimethylamino)thiazol-4-yl-CH₂CH₂– | H | –CH(CH₂OCH₃)₂ | trans-4-methylcyclohexyl |
| 1128 | 2-(ethylamino)thiazol-4-yl-CH₂– | H | –CH(CH₂OCH₃)₂ | trans-4-methylcyclohexyl |
| 1129 | 2-(isopropylamino)thiazol-4-yl-CH₂– | H | –CH(CH₂OCH₃)₂ | trans-4-methylcyclohexyl |

-continued
| Cpd | R²⁰ | R³ | R⁵ | R⁶ |
|---|---|---|---|---|
| 1130 | 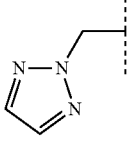 | F | 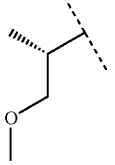 | 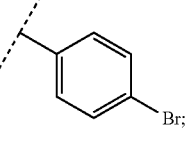 |
| 1131 | 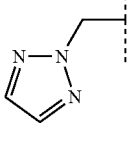 | F | 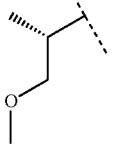 | 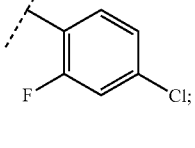 |
| 1132 | 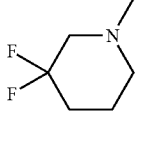 | F | 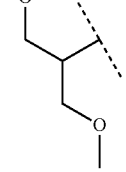 | 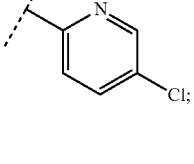 |
| 1133 | H | F | 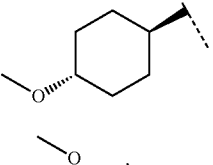 | 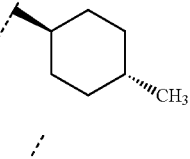 |
| 1134 | 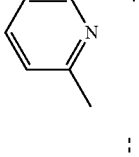 | F | 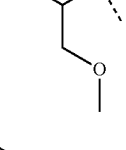 | 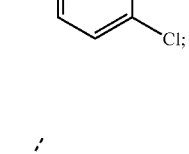 |
| 1135 | 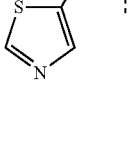 | F | 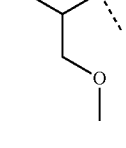 | 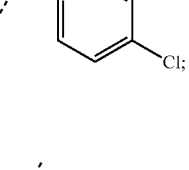 |
| 1136 | 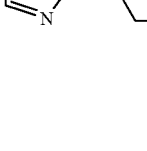 | H | 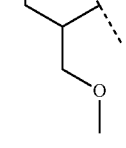 | 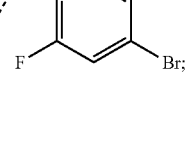 |
| 1137 | 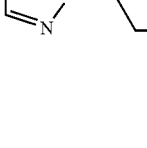 | H | 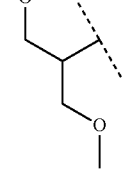 | 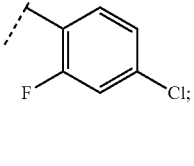 |

-continued

| Cpd | R²⁰ | R³ | R⁵ | R⁶ |
|---|---|---|---|---|
| 1138 | 2H-1,2,3-triazol-2-yl-ethyl | H | 2-(methoxymethyl)-3-methoxypropyl | 4-bromophenyl |
| 1139 | morpholin-4-yl | H | 2-(methoxymethyl)-3-methoxypropyl | trans-4-methylcyclohexyl |
| 1140 | 5,5-difluoro-1-methyl-1,4-diazepan-4-yl | H | 2-(methoxymethyl)-3-methoxypropyl | trans-4-methylcyclohexyl |
| 1141 | 4-[cyclopropyl(methyl)amino]piperidin-1-yl | H | 2-(methoxymethyl)-3-methoxypropyl | trans-4-methylcyclohexyl |
| 1142 | (3,3-difluoropiperidin-1-yl)methyl | F | 2-(methoxymethyl)-3-methoxypropyl | 4-chlorophenyl |
| 1143 | (3,3-difluoropiperidin-1-yl)methyl | F | 2-(methoxymethyl)-3-methoxypropyl | 4-bromophenyl |
| 1144 | (3,3-difluoropiperidin-1-yl)methyl | F | 2-(methoxymethyl)-3-methoxypropyl | 4-bromo-2-fluorophenyl |

-continued

| Cpd | R²⁰ | R³ | R⁵ | R⁶ |
|---|---|---|---|---|
| 1145 | morpholin-4-yl | F | CH(CH₂OCH₃)₂ | trans-4-methylcyclohexyl; |
| 1146 | 3-(dimethylamino)pyrrolidin-1-yl | F | CH(CH₂OCH₃)₂ | trans-4-methylcyclohexyl; |
| 1147 | 2-(isopropylamino)thiazol-4-yl-CH₂CH₂- | F | CH(CH₂OCH₃)₂ | trans-4-methylcyclohexyl; |
| 1148 | 2-(ethylamino)thiazol-4-yl-CH₂- | F | CH(CH₂OCH₃)₂ | trans-4-methylcyclohexyl; |
| 1149 | 2-(dimethylamino)thiazol-4-yl-CH₂CH₂- | F | CH(CH₂OCH₃)₂ | trans-4-methylcyclohexyl; |
| 1150 | 2-(ethylamino)thiazol-4-yl-CH₂- | F | CH(CH₂OCH₃)₂ | trans-4-methylcyclohexyl; |
| 1151 | 2-(isopropylamino)thiazol-4-yl-CH₂- | F | CH(CH₂OCH₃)₂ | trans-4-methylcyclohexyl; |

-continued

| Cpd | R²⁰ | R³ | R⁵ | R⁶ |
|---|---|---|---|---|
| 1152 | 4-[(dimethylamino)thiazol-4-yl]methyl | F | 2-(methoxymethyl)-3-methoxypropyl | trans-4-methylcyclohexyl |
| 1153 | 4-[cyclopropyl(methyl)amino]piperidin-1-yl | F | 2-(methoxymethyl)-3-methoxypropyl | trans-4-methylcyclohexyl |
| 1154 | 3,3-difluoropiperidin-1-yl | F | 2-(methoxymethyl)-3-methoxypropyl | trans-4-methylcyclohexyl |
| 1155 | 3,3-difluoropyrrolidin-1-yl | F | 2-(methoxymethyl)-3-methoxypropyl | trans-4-methylcyclohexyl |
| 1156 | 3,3-difluoroazetidin-1-yl | F | 2-(methoxymethyl)-3-methoxypropyl | trans-4-methylcyclohexyl |
| 1157 | N-(2-methoxyethyl)-N-methyl | F | 2-(methoxymethyl)-3-methoxypropyl | trans-4-methylcyclohexyl |
| 1158 | 2,6-dimethylmorpholin-4-yl | F | 2-(methoxymethyl)-3-methoxypropyl | trans-4-methylcyclohexyl |

-continued
| Cpd | R²⁰ | R³ | R⁵ | R⁶ |
|---|---|---|---|---|
| 1159 |  | F | 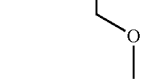 |  |
| 1161 | H | H |  | 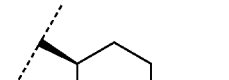 |
| 1162 |  | H | 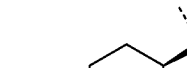 | 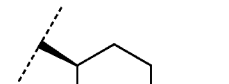 |
| 1163 | 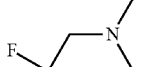 | H | 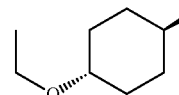 | 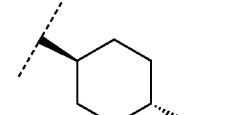 |
| 1164 |  | H | 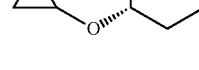 | 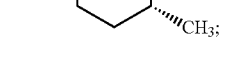 |
| 1165 | 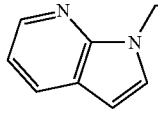 | H | 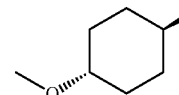 |  |
| 1166 | 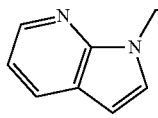 | F | 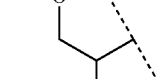 | 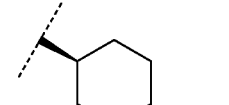 |
| 1167 | 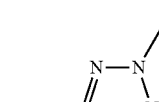 | F | 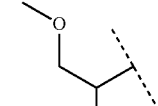 | 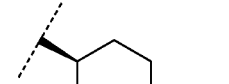 |

-continued

| Cpd | R²⁰ | R³ | R⁵ | R⁶ |
|---|---|---|---|---|
| 1168 | pyrrolopyridazine-CH₂– | F | 4-methoxycyclohexyl | 4-methylcyclohexyl |
| 1169 | (6-cyclopropylpyridin-2-yl)-CH₂– | F | CH(CH₂OCH₃)₂ | 4-methylcyclohexyl |
| 1170 | (4-methyl-2H-1,2,3-triazol-2-yl)-CH₂– | F | CH(CH₂OCH₃)₂ | 4-methylcyclohexyl |
| 1171 | HOCH₂C(CH₃)₂– | F | CH(CH₂OCH₃)₂ | 4-methylcyclohexyl |
| 1172 | 1-(methoxymethyl)cyclopropyl– | F | CH(CH₂OCH₃)₂ | 4-methylcyclohexyl |
| 1173 | 1-((2H-1,2,3-triazol-2-yl)methyl)cyclopropyl– | F | CH(CH₂OCH₃)₂ | 4-methylcyclohexyl |
| 1174 | 1-((1H-1,2,3-triazol-1-yl)methyl)cyclopropyl– | F | CH(CH₂OCH₃)₂ | 4-methylcyclohexyl |

-continued

| Cpd | $R^{20}$ | $R^3$ | $R^5$ | $R^6$ |
|---|---|---|---|---|
| 1175 | methyltriazolylmethyl | F | CH(CH2OMe)2 | trans-4-methylcyclohexyl |
| 1176 | cyclopropyltriazolylmethyl | F | trans-4-methoxycyclohexyl | trans-4-methylcyclohexyl |
| 1177 | methyltriazolylmethyl | F | trans-4-methoxycyclohexyl | trans-4-methylcyclohexyl |
| 1178 | dimethyltriazolylmethyl | F | trans-4-methoxycyclohexyl | trans-4-methylcyclohexyl |
| 1179 | H | H | 4-methoxybenzyl | trans-4-methylcyclohexyl or | a pharmaceutically acceptable salt thereof.

11. A pharmaceutical composition comprising a compound according to claim 1 or a pharmaceutically acceptable salt thereof, and one or more pharmaceutically acceptable carriers.

12. The pharmaceutical composition according to claim 11 additionally comprising at least one other antiviral agent.

13. A method of alleviating symptoms of HCV disease and or reducing viral load in a patient, said method comprised of the step of adminstering to a patient in need thereof a compound according to claim 1.

14. A compound having the structure

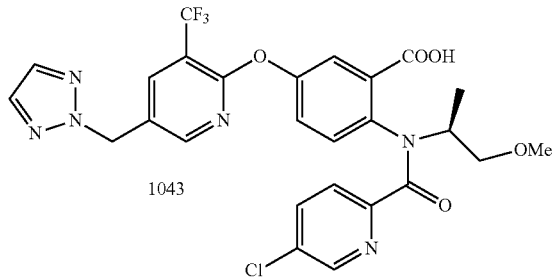 [SMILES: COC[C@H](C)N(C(=O)c1ccc(Cl)cn1)c1ccc(Oc2ncc(Cn3nccn3)cc2C(F)(F)F)cc1C(=O)O]

1043 or a pharmaceutically acceptable salt thereof.

15. A compound having the structure

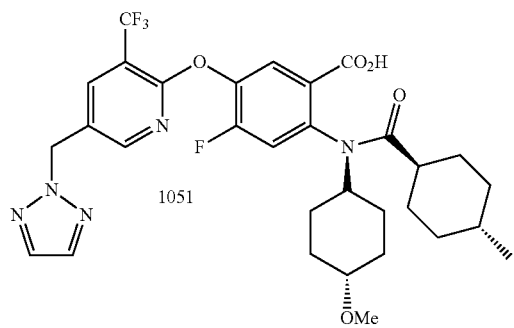

or a pharmaceutically acceptable salt thereof.

16. A compound having the structure

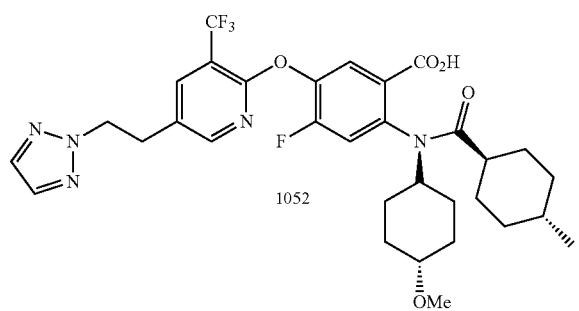

or a pharmaceutically acceptable salt thereof.

17. A compound having the structure

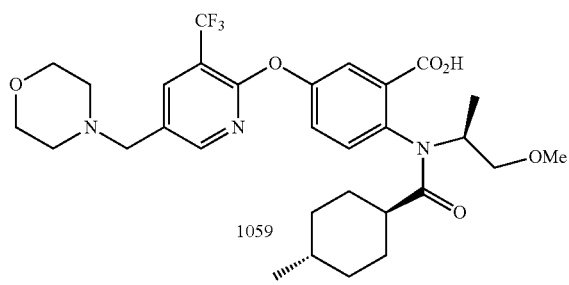 [SMILES: COC[C@H](C)N(c1ccc(Oc2ncc(CN3CCOCC3)cc2C(F)(F)F)cc1C(=O)O)C(=O)[C@H]1CC[C@H](C)CC1]

or a pharmaceutically acceptable salt thereof.

18. A compound having the structure

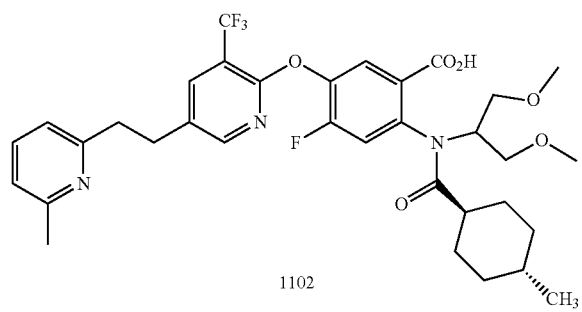 [SMILES: COCC(COC)N(c1cc(F)c(Oc2ncc(CCc3cccc(C)n3)cc2C(F)(F)F)cc1C(=O)O)C(=O)[C@H]1CC[C@H](C)CC1]

or a pharmaceutically acceptable salt thereof.

19. A compound having the structure

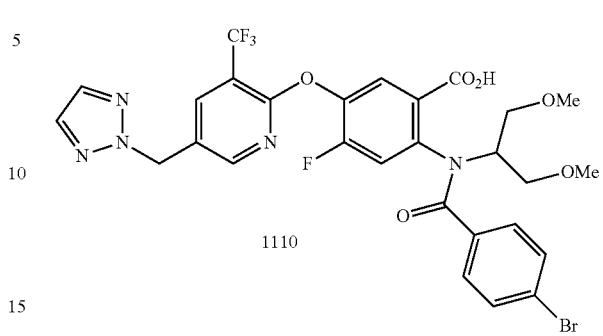

or a pharmaceutically acceptable salt thereof.

20. A compound having the structure

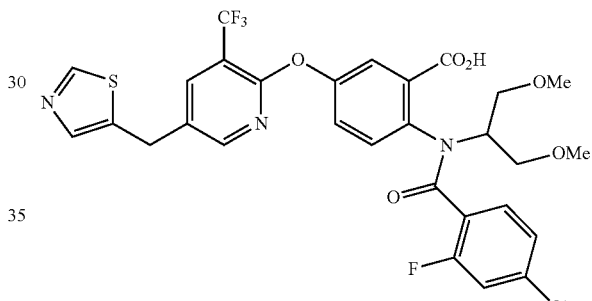

or a pharmaceutically acceptable salt thereof.

21. A compound having the structure

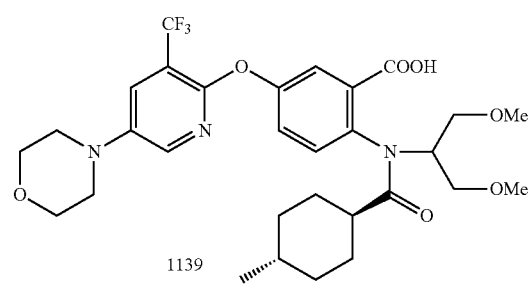 [SMILES: COCC(COC)N(c1ccc(Oc2ncc(N3CCOCC3)cc2C(F)(F)F)cc1C(=O)O)C(=O)[C@H]1CC[C@H](C)CC1]

or a pharmaceutically acceptable salt thereof.

22. A compound having the structure

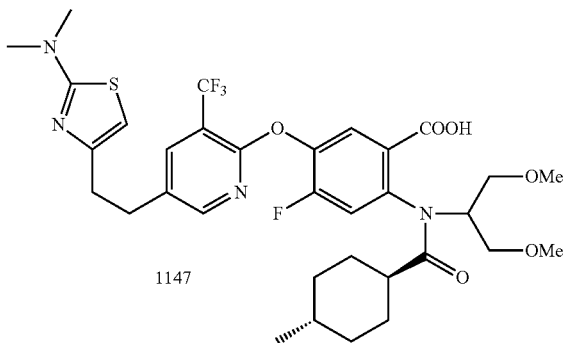 [SMILES: COCC(COC)N(c1cc(F)c(Oc2ncc(CCc3csc(N(C)C)n3)cc2C(F)(F)F)cc1C(=O)O)C(=O)[C@H]1CC[C@H](C)CC1]

1147 or a pharmaceutically acceptable salt thereof.

23. A compound having the structure

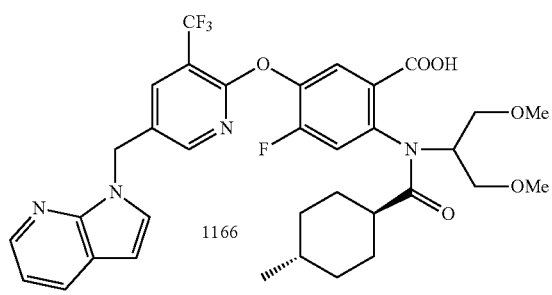 [SMILES: COCC(COC)N(c1cc(F)c(Oc2ncc(Cn3ccc4cccnc43)cc2C(F)(F)F)cc1C(=O)O)C(=O)[C@H]1CC[C@H](C)CC1]

1166 or a pharmaceutically acceptable salt thereof.

24. A compound having the structure

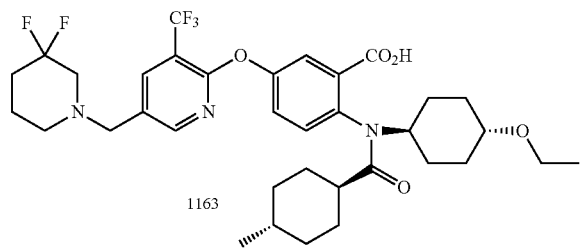 [SMILES: CCO[C@H]1CC[C@H](N(c2ccc(Oc3ncc(CN4CCCC(F)(F)C4)cc3C(F)(F)F)cc2C(=O)O)C(=O)[C@H]2CC[C@H](C)CC2)CC1]

1163 or a pharmaceutically acceptable salt thereof.

25. A method of alleviating symptoms of HCV disease and or reducing viral load in a patient, said method comprised of the step of administering to a patient in need thereof a compound according to claim 14.

26. A method of alleviating symptoms of HCV disease and or reducing viral load in a patient, said method comprised of the step of administering to a patient in need thereof a compound according to claim 15.

27. A method of alleviating symptoms of HCV disease and or reducing viral load in a patient, said method comprised of the step of administering to a patient in need thereof a compound according to claim 16.

28. A method of alleviating symptoms of HCV disease and or reducing viral load in a patient, said method comprised of the step of administering to a patient in need thereof a compound according to claim 17.

29. A method of alleviating symptoms of HCV disease and or reducing viral load in a patient, said method comprised of the step of administering to a patient in need thereof a compound according to claim 18.

30. A method of alleviating symptoms of HCV disease and or reducing viral load in patient, said method comprised of the step of administering to a patient in need thereof a compound according to claim 19.

31. A method of alleviating symptoms of HCV disease and or reducing viral load in patient, said method comprised of the step of administering to a patient in need thereof a compound according to claim 20.

32. A method of alleviating symptoms of HCV disease and or reducing viral load in patient, said method comprised of the step of administering to a patient in need thereof a compound according to claim 21.

33. A method of alleviating symptoms of HCV disease and or reducing viral load in patient, said method comprised of the step of administering to a patient in need thereof of a compound according to claim 22.

34. A method of alleviating symptoms of HCV disease and or reducing viral load in patient, said method comprised of the step of administering to a patient in need thereof a compound according to claim 23.

35. A method of alleviating symptoms of HCV disease and or reducing viral load in patient, said method comprised of the step of administering to a patient in need thereof a compound according to claim 24.

* * * * *